United States Patent
Taylor et al.

(10) Patent No.: US 11,486,874 B2
(45) Date of Patent: *Nov. 1, 2022

(54) METHODS FOR QUANTITATION OF INSULIN LEVELS BY MASS SPECTROMETRY

(71) Applicant: QUEST DIAGNOSTICS INVESTMENTS LLC, Secaucus, NJ (US)

(72) Inventors: Steven W. Taylor, Laguna Niguel, CA (US); Michael McPhaul, Dana Point, CA (US); Richard E. Reitz, Las Vegas, NV (US); Zhaohui Chen, Las Flores, CA (US); Nigel Clarke, Oceanside, CA (US)

(73) Assignee: Quest Diagnostics Investments LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/442,894

(22) Filed: Jun. 17, 2019

(65) Prior Publication Data

US 2019/0302095 A1 Oct. 3, 2019

Related U.S. Application Data

(63) Continuation of application No. 15/059,247, filed on Mar. 2, 2016, now Pat. No. 10,324,082.

(60) Provisional application No. 62/128,236, filed on Mar. 4, 2015, provisional application No. 62/127,770, filed on Mar. 3, 2015.

(51) Int. Cl.
*G01N 33/49* (2006.01)
*G01N 33/74* (2006.01)
*G01N 33/68* (2006.01)
*G01N 30/72* (2006.01)
*G01N 30/88* (2006.01)

(52) U.S. Cl.
CPC ......... *G01N 33/49* (2013.01); *G01N 33/6848* (2013.01); *G01N 33/74* (2013.01); *G01N 30/72* (2013.01); *G01N 2030/8813* (2013.01); *G01N 2333/47* (2013.01); *G01N 2333/62* (2013.01); *G01N 2800/042* (2013.01)

(58) Field of Classification Search
CPC ....... G01N 2030/8813; G01N 2333/47; G01N 2333/62; G01N 2800/042; G01N 30/72; G01N 33/49; G01N 33/6848; G01N 33/72; G01N 33/74
See application file for complete search history.

(56) References Cited

U.S. PATENT DOCUMENTS

| | | | |
|---|---|---|---|
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koester | |
| 6,995,364 B2 | 2/2006 | Makarov et al. | |
| 10,324,082 B2 * | 6/2019 | Taylor | G01N 33/49 |
| 10,436,803 B2 * | 10/2019 | Chen | G01N 33/49 |
| 2005/0103991 A1 | 5/2005 | Walk et al. | |
| 2006/0219558 A1 | 10/2006 | Hafeman et al. | |
| 2008/0118932 A1 | 5/2008 | Toler et al. | |
| 2009/0035807 A1 | 2/2009 | McCellan et al. | |
| 2009/0090856 A1 | 4/2009 | Grant et al. | |
| 2011/0166132 A1 | 7/2011 | Hitchcock et al. | |
| 2012/0100071 A1 | 4/2012 | Valliant et al. | |
| 2012/0164741 A1 * | 6/2012 | Chen | G01N 33/49 436/86 |

FOREIGN PATENT DOCUMENTS

| | | |
|---|---|---|
| CN | 103392219 A | 11/2013 |
| CN | 103454433 A | 12/2013 |
| JP | 2004503749 A | 2/2004 |
| JP | 2005526962 A | 9/2005 |
| JP | 2008540573 A | 11/2008 |
| JP | 2009540856 A | 11/2009 |
| JP | 6092890 B2 | 3/2017 |
| WO | 0204957 A2 | 1/2002 |
| WO | 2006124713 A2 | 11/2006 |
| WO | 2008001079 A1 | 1/2008 |

(Continued)

OTHER PUBLICATIONS

Thevis et al. Mass Spectrometric Determination of Insulins and Their Degradation Products in Sports Drug Testing. Volume 27, Issue 1. pp. 35-50 (Year: 2008).*
Darby et al. J Anal Toxicol. A Mass Spectrometric Method for Quantitation of Intact Insulin in Blood Samples, vol. 25, No. 1, pp. 8-14. (Year: 2001).*
Van Uytfanghe et al Rapid Commun Mass Spectrom New liquid chromatography/electrospray ionisation tandem mass spectrometry measurement procedure for quantitative analysis of human insulin in serum. Vol. 21, No. 5, pp. 819-821. (Year: 2007).*
Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

(Continued)

*Primary Examiner* — Marcela M Cordero Garcia
(74) *Attorney, Agent, or Firm* — Quest Diagnostics, Inc.

(57) ABSTRACT

Methods are described for determining the amount of insulin in a sample. Provided herein are mass spectrometric methods for detecting and quantifying insulin and C-peptide in a biological sample utilizing enrichment and/or purification methods coupled with tandem mass spectrometric or high resolution/high accuracy mass spectrometric techniques. Also provided herein are mass spectrometric methods for detecting and quantifying insulin and b-chain in a biological sample utilizing enrichment and/or purification methods coupled with tandem mass spectrometric or high resolution/high accuracy mass spectrometric techniques.

50 Claims, 58 Drawing Sheets

(56) References Cited

FOREIGN PATENT DOCUMENTS

| WO | 2009133152 A1 | 11/2009 |
|---|---|---|
| WO | 2012092281 A2 | 7/2012 |
| WO | 2014105858 A1 | 7/2014 |

OTHER PUBLICATIONS

Bredehoft M., et al., "Quantification of Human Insulin-Like Growth Factor-1 and Qualitative Detection of Its Analogues in Plasma Using Liquid Chromatography/Electrospray Ionisation Tandem Mass Spectrometry," Rapid Communications in Mass Spectrometry, 2008, vol. 22 (4), pp. 477-485.
Cham B.E., et al., "A Solvent System for Delipidation of Plasma or Serum Without Protein Precipitation," Journal of Lipid Research, Mar. 1976, vol. 17 (2), pp. 176-181.
Darby S.M., et al., "A Mass Spectrometric Method for Quantitation of Intact Insulin in Blood Samples," Journal of Analytical Toxicology, 2001, vol. 25 (1), pp. 8-14.
European Search Report for Application No. 16759509.9 dated Jul. 13, 2018.
European Search Report for Application No. 17189034.6 dated Oct. 19, 2017.
Ewing N.P., et al., "Effects of Cysteic Acid Groups on the Gas-Phase Reactivity and Dissociation of [M+4H](4+) Ions From Insulin Chain B," Journal of the American Society for Mass Spectrometry, Oct. 1999, vol. 10 (10), pp. 928-940.
Extended European Search Report for Application No. EP18209927.5, dated Apr. 17, 2019, 8 pages.
Extended European Search Report for Application No. 11852467.7, dated Mar. 14, 2014, 6 pages.
Extended European Search Report for Application No. EP16176190.3, dated Sep. 29, 2016, 7 pages.
Fierens C., et al., "Strategies for Determination of Insulin with Tandem Electrospray Mass Spectrometry: Implications for Other Analyte Proteins?," Rapid Communications in Mass Spectrometry, 2001, vol. 15 (16), pp. 1433-1441.
Final Office Action dated Aug. 3, 2016 for U.S. Appl. No. 13/338,123, filed Dec. 27, 2011.
Final Office Action dated Oct. 12, 2018 for U.S. Appl. No. 13/338,123, filed Dec. 27, 2011.
Fung, Y.M.E., et al., "Facile Disulfide Bond Cleavage in Gaseous Peptide and Protein Cations by Ultraviolet Photodissociation at 157nm," Angewandte Chemie International Edition, 2005, vol. 44(39), pp. 6399-6403.
Guedes S., et al., "Mass Spectrometry Characterization of the Glycation Sites of Bovine Insulin by Tnadem Mass Spectrometry," Journal of the American Society for Mass Spectrometry, 2009, vol. 20 (7), pp. 1319-1326.
Ho E.N.M., et al., "Doping Control Analysis of Insulin and Its Analogues in Equine Plasma by Liquid Chromatography-Tandem Mass Spectrometry," Journal of Chromatography A, 2008, vol. 1201, pp. 183-190.
International Preliminary Report and Written Opinion on Patentability for Application No. PCT/US2016/020723, dated Sep. 14, 2017.
International Preliminary Report on Patentability for Application No. PCT/US2011/067397, dated Jul. 11, 2013.
International Search Report and Written Opinion for Application No. PCT/US2016/020723, dated Jul. 25, 2016, 19 pages.
International Search Report for Application No. PCT/US11/67397, dated Jun. 28, 2012, 6 Pages.
Jespersen S., et al., "Optimization of Sample Recovery From the Nitrocellulose Support Used in Plasma Desorption Mass Spectrometry and Its Use for Multiple Analyses of Insulin," Biological Mass Spectrometry, Jan. 1993, vol. 22 (1), pp. 77-83.
Jia X., et al., "Structural and Functional Changes in Human Insulin Induced by Methylglyoxal," FASEB Journal, 2006, vol. 20 (9), pp. E871-E879.
Jonassen P., et al., "Single-Step Trypsin Cleavage of a Fusion Protein to Obtain Human Insulin and Its C Peptide," European Journal of Biochemistry, Mar. 1996, vol. 236 (2), pp. 656-661.
Kippen A.D., et al., "Development of an Isotope Dilution Assay for Precise Determination of Insulin, C-Peptide, and Proinsulin Levels in Non-diabetic and Type II Diabetic Individuals With Comparison to Immunoassay," The Journal of Biological Chemistry, May 1997, vol. 272 (19), pp. 12513-12522.
Kuuranne T., et al., "Insulins in Equine Urine: Qualitative Analysis by Immunoaffinity Purification and Liquid Chromatography/Tandem Mass Spectrometry for Doping Control Purposes in Horse-Racing," Rapid Communications in Mass Spectrometry, 2008, vol. 22 (3), pp. 355-362.
Landreh M., et al., "Proinsulin C-Peptide Interferes With Insulin Fibril Formation," Biochemical and Biophysical Research Communications, Feb. 2012, vol. 418 (3), pp. 489-493.
Landreh M., et al., "Insulin, Islet Amyloid Polypeptide and C-Peptide Interactions Evaluated by Mass Spectrometric Analysis," Rapid Communications in Mass Spectrometry, 2014, vol. 28 (2), pp. 178-184.
Le-Breton M.H., et al., "Direct Determination of Recombinant Bovine Somatotropin in Plasma from A Treated Goat by Liquid Chromatography/High-Resolution Mass Spectrometry," Rapid Communications in Mass Spectrometry, 2008, vol. 22 (20), pp. 3130-3136.
Loo J.A., et al., "Tandem Mass Spectrometry of Very Large Molecules: Serum Albumin Sequence Information From Multiply Charged Ions Formed by Electrospray Ionization," Analytical Chemistry, 1991, vol. 63 (21), pp. 2488-2499.
Manley S., et al., "Comparison of II Human Insulin Assays: Implications for Clinical Investigation and Research," Clinical Chemistry, 2007, vol. 53 (5), pp. 922-932.
Mannering S.I., et al., "The Insulin A-Chain Epitope Recognized by Human T Cells is Posttranslationally Modified," The Journal of Experimental Medicine, 2005, vol. 202 (9), pp. 1191-1197.
Merchant M., et al., "Recent Advancements in Surface-Enhanced Laser Desorption/Ionization-Time of Flight-Mass Spectrometry," Electrophoresis, 2000, vol. 21 (6), pp. 1164-1167.
Non-Final Office Action dated May 23, 2018 for U.S. Appl. No. 15/059,247, filed Mar. 2, 2016.
Non-Final Office Action dated Dec. 22, 2017 for U.S. Appl. No. 13/338,123, filed Dec. 27, 2011.
Non-Final Office Action dated Jan. 22, 2016 for U.S. Appl. No. 14/063,956, filed Oct. 25, 2013.
Non-Final Office Action dated Dec. 24, 2014 for U.S. Appl. No. 13/338,123, filed Dec. 27, 2011.
Non-Final Office Action dated Dec. 24, 2015 for U.S. Appl. No. 13/338,123, filed Dec. 27, 2011.
Olsen J.V., et al., "Higher-Energy C-Trap Dissociation for Peptide Modification Analysis," Nature Methods, 2007, vol. 4 (9), pp. 709-712.
Peng, I.X., et al., "Reactive-Electrospray-Assisted Laser Desorption/Ionization for Characterization of Peptides and Proteins," Analytical chemistry, ACS Publications, Aug. 2008, vol. 80(18), pp. 6995-7003.
Regnier F., et al., "Future Potential of Targeted Component Analysis by Multidimensional Liquid Chromatography-Mass Spectrometry," Journal of Chromatography A, 1996, vol. 750, pp. 3-10.
Requirement for Restriction dated Nov. 5, 2015 for U.S. Appl. No. 13/338,123, filed Dec. 27, 2011.
Robb D.B., et al., "Atmospheric Pressure Photoionization: An Ionization Method for Liquid Chromatography-Mass Spectrometry," Analytical Chemistry, 2000, vol. 72 (15), pp. 3653-3659.
Rodriguez-Cabaleiro D., et al., "Pilot Study for the Standardization of Insulin Immunoassays with Isotope Dilution-Liquid Chromatography/Tandem Mass Spectrometry," Clinical Chemistry, 2007, vol. 53 (8), pp. 1462-1469.
Schenk S., et al., "A High Confidence, Manually Validated Human Blood Plasma Protein Reference Set," BMC Medical Geonomics, 2008, vol. 1, pp. 41.
Sinner et al., "A Robust and Easy Method for Simultaneous Quantitation of Glucose and [6,6-d2]Glucose in Human Plasma Using

(56) References Cited

OTHER PUBLICATIONS

GC-MS," Proceedings of the 52nd ASMS Conference on Mass Spectrometry and Allied Topics, Nashville, Tennessee, May 23-27, 2004, 5 pages.

Stephenson J. L., et al., "Ion Trap Collisional Activation of Disulfide Linkage Intact and Reduced Multiply Protonated Polypeptides," Rapid communications in Mass Spectrometry, 1999, vol. 13 (20), pp. 2040-2048.

Stewart K.W., et al., "A Simple and Rapid Method for Identifying and Semi-quantifying Peptide Hormones in Isolated Pancreatic Islets by Direct-Tissue Matrix-Assisted Laser Desorption Ionization Time-of-Flight Mass Spectrometry," Rapid Communications in Mass Spectrometry, 2011, vol. 25 (22), pp. 3387-3395.

Stocklin R., et al., "A Stable Isotope Dilution Assay for the in Vivo Determination of Insulin Levels in Humans by Mass Spectrometry," Diabetes, 1997, vol. 46 (1), pp. 44-50.

Thevis M., et al., "Current Role of LC-MS(/MS) in Doping Control," Analytical and Bioanalytical Chemistry, 2007, vol. 388 (7), pp. 1351-1358.

Thevis M., et al., "Doping Control Analysis of Intact Rapid-Acting Insulin Analogues in Human Urine by Liquid Chromatography-Tandem Mass Spectrometry," Analytical Chemistry, 2006, vol. 78 (6), pp. 1897-1903.

Thevis M., et al., "Mass Spectrometric Determination of Insulins and Their Degradation Products in Sports Drug Testing," Mass Spectrometry Reviews, 2008, vol. 27 (1), pp. 35-50.

Thevis M., et al., "Qualitative Determination of Synthetic Analogues of Insulin in Human Plasma by Immunoaffinity Purification and Liquid Chromatography-Tandem Mass Spectrometry for Doping Control Purposes," Analytical Chemistry, Jun. 2005, vol. 77 (11), pp. 3579-3585.

Thevis M., et al., "Recommended Criteria for the Mass Spectrometric Identification of Target Peptides and Proteins ( 8 kDa) in Sports Drug Testing," Rapid Communications in Mass Spectrometry, 2007, vol. 21, pp. 297-304.

Thomas A., et al., "Identification and Determination of Human Insulin, Synthetic Insulin Analogues, Their Degradation Products and C-peptide in Human Urine and Human Plasma for Doping Control Purposes by Means of Liquid Chromatography / Mass Spectrometry", University and State Library Bonn, 2008, pp. 1-154—English Translation Available.

Thomas A., et al., "Mass Spectrometric Determination of Gonadotrophin-Releasing Hormone (Gnrh) In Human Urine for Doping Control Purposes by Means of LC-ESI-MS/MS," Journal of Mass Spectrometry, 2008, vol. 43 (7), pp. 908-915.

Thomas A., et al., "Mass Spectrometric Identification of Degradation Products of Insulin and Its Long-Acting Analogues in Human Urine for Doping Control Purposes," Analytical Chemistry, 2007, vol. 79 (6), pp. 2518-2524.

Van-Uytfanghe K., et al., "New Liquid Chromatography/Electrospray Ionization Tandem Mass Spectrometry Measurement Procedure for Quantitative Analysis of Human Insulin In Serum," Rapid Communications in Mass Spectrometry, 2007, vol. 21 (5), pp. 819-821.

Waters QTOF Ultima ESI, Mass Spectrometry Lab, School of Chemical Sciences, 2002, 2 pages, [retrieved on May 18, 2018]. Retrieved from the Internet:[URL: http://www.scs.illinois.edu/massSpec/instrum/qtof.php].

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Written Opinion for Application No. PCT/US11/67397, dated Jun. 28, 2012, 6 Pages.

Zhang X., et al., "Apparent Gas-Phase Acidities of Multiply Protonated Peptide Ions: Ubiquitin, Insulin B, and Renin Substrate," Journal of the American Society for Mass Spectrometry, Dec. 1996, vol. 7 (12), pp. 1211-1218.

Zimmer D., et al., "Comparison of Turbulent-Flow Chromatography with Automated Solid-Phase Extraction in 96-Well Plates and Liquid-Liquid Extraction Used As Plasma Sample Preparation Techniques for Liquid Chromatography-Tandem Mass Spectrometry," Journal of Chromatography A, 1999, vol. 854, pp. 23-35.

Extended European Search Report for Application No. 20206370.7, dated Jan. 22, 2021, 8 pages.

Non-Final Office Action dated Jan. 14, 2020 for U.S. Appl. No. 15/942,188, filed Mar. 30, 2018.

Hauser N.J., and Basile F., "Online Microwave D-Cleavage LC-ESI-MS/MS of Intact Proteins: Site-specific Cleavages at Aspartic Acid Residues and Disulfide Bonds," Journal of Proteome Research, Jan. 2008, vol. 7(3), pp. 1012-1026.

Huang F., and Murray K., "Continuous Flow Infrared Matrix-Assisted Laser Desorption Electrospray Ionization Mass Spectrometry," Rapid Communications in Mass Spectrometry, 2010, vol. 24(19), pp. 2799-2804.

Javahery G., and Thomson B., "A Segmented Radiofrequency-only Quadrupole Collision Cell for Measurements of Ion Collision Cross Section on a Triple Quadrupole Mass Spectrometer," Journal of the American Society for Mass Spectrometry, Jul. 1997, vol. 8(7), pp. 697-702.

Li J., et al., "Online Coupling of Electrochemical Reactions with Liquid Sample Desorption Electrospray Ionization-Mass Spectrometry," Analytical Chemistry, Oct. 2009, vol. 81, pp. 9716-9722.

\* cited by examiner

Insulin

Lantus

Levemir

Humalog

Novalog

Apidra

Immunocapture-mass spectrometry vs Beckman immunoassay

Immunocapture-mass spectrometry vs B chain LC-MS/MS

Immunocapture-mass spectrometry cals by Beckman immunoassay

Beckman cals by Immunocapture-mass spectrometry

METHODS FOR QUANTITATION OF INSULIN LEVELS BY MASS SPECTROMETRY

CROSS REFERENCE TO RELATED PATENT APPLICATIONS

This is a continuation application of U.S. Non-Provisional application Ser. No. 15/059,247, filed Mar. 2, 2016, which claims benefit of U.S. Provisional Application No. 62/127,770, filed Mar. 3, 2015 and U.S. Provisional Application No. 62/128,236, filed Mar. 4, 2015, each of which is incorporated by reference herein in its entirety.

BACKGROUND OF THE INVENTION

Insulin is a hormone that is central to regulating carbohydrate and fat metabolism in the body. Aberrant levels of insulin indicate glycemic disorders and/or insulin resistant syndromes such as diabetes. Diabetes and its complications represent a major public health issue. Thus, quantitation of insulin in diabetic and pre-diabetic patients is important both as a diagnostic tool and for monitoring treatment in patients.

Immunological techniques have been widely used for insulin quantitation, initially through radioimmunoassay (RIA), and more recently by commercially available immunochemiluminometric assays (ICMA) on automated platforms. However, no international reference method for insulin has yet been established. The major hurdle in establishing such a method stems from the variability in insulin values measured across different immunoassays and platforms, which are likely caused by differing cross-reactivities of the assay antibodies utilized.

A reliable and accurate method for measuring insulin levels is needed.

SUMMARY OF THE INVENTION

In one aspect, provided herein are methods for measuring insulin levels in a patient by determining the amount of insulin and C-peptide in a sample using mass spectrometry.

In certain embodiments, the methods provided herein comprise multiplexed assays that simultaneously measure the amount of insulin and C-peptide in a sample by mass spectrometry. In some embodiments, methods comprise (a) subjecting insulin and C-peptide from a sample to an ionization source under conditions suitable to generate one or more insulin and C-peptide ions detectable by mass spectrometry; and (b) determining the amount of one or more insulin and C-peptide ions by mass spectrometry.

In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient.

In some embodiments, methods comprise (a) subjecting a sample to an enrichment process to obtain a fraction enriched in insulin and C-peptide, (b) subjecting the enriched insulin and C-peptide to an ionization source under conditions suitable to generate one or more insulin and C-peptide ions detectable by mass spectrometry; (c) determining the amount of one or more insulin and C-peptide ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient.

In some embodiments, the enrichment process provided herein comprises immunocapture of insulin and C-peptide using antibodies. In some embodiments, methods comprise (a) immunocapturing insulin and C-peptide, (b) subjecting the immunocaptured insulin and C-peptide to an ionization source under conditions suitable to generate one or more insulin and C-peptide ions detectable by mass spectrometry; (c) determining the amount of one or more insulin and C-peptide ions by mass spectrometry.

In some embodiments, immunocapturing provided herein comprises using anti-insulin antibodies and anti-C-peptide antibodies. In some embodiments, the antibodies provided herein are monoclonal antibodies. In some embodiments, the antibodies provided herein are mouse monoclonal antibodies. In some embodiments, the antibodies provided herein are monoclonal IgG antibodies. In some embodiments, the antibodies provided herein are polyclonal antibodies.

In some embodiments, the anti-insulin antibodies and anti-C-peptide antibodies are immobilized on magnetic beads. In some embodiments, insulin and C-peptide immunocaptured on magnetic beads are washed and eluted.

In some embodiments, serum is delipidated prior to quantitation by mass spectrometry. In some embodiments, one or more delipidation reagent is used to remove lipids from the sample. In some embodiments, the delipidation reagent is CLEANASCITE®.

In some embodiments, the methods provided herein comprise purifying the samples prior to mass spectrometry. In some embodiments, the methods comprise purifying the samples using liquid chromatography. In some embodiments, liquid chromatography comprise high performance liquid chromatography (HPLC) or high turbulence liquid chromatograph (HTLC). In some embodiments, the methods comprise subjecting a sample to solid phase extraction (SPE).

In some embodiments, mass spectrometry comprises tandem mass spectrometry. In some embodiments, mass spectrometry is high resolution mass spectrometry. In some embodiments, mass spectrometry is high resolution/high accuracy mass spectrometry.

In some embodiments, ionization is by electrospray ionization (ESI). In some embodiments, ionization is by atmospheric pressure chemical ionization (APCI). In some embodiments, said ionization is in positive ion mode.

In some embodiments, methods provided herein comprise adding internal standards to the sample. In some embodiments, the internal standard for insulin is bovine insulin. In some embodiments, the internal standard for C-peptide is C-peptide heavy internal standard. In some embodiments, the internal standard is labeled. In some embodiments, the internal standard is deuterated or isotopically labeled.

In some embodiments, the patient sample is a serum sample. In some embodiments, the patient sample is a plasma sample. In some embodiments, the patient sample is a blood, saliva, or urine sample.

In some embodiments, the sample is subjected to acidic conditions prior to ionization. In some embodiments, subjecting the sample to acidic conditions comprises subjecting enriched insulin and C-peptide to formic acid.

In some embodiments, the sample is subjected to basic conditions prior to mass spectrometry. In some embodiments, subjecting the sample to basic conditions comprises subjecting the sample to trizma. In some embodiments, subjecting the sample to basic conditions comprises subjecting the sample to trizma and ethanol.

In some embodiments, one or more ions comprise an insulin precursor ion with a mass to charge ratio (m/z) of 968.7±0.5. In some embodiments, one or more ions comprise one or more fragment ions selected from the group consisting of ions with m/z of 136.0±0.5, 226.1±0.5, and 345.2±0.5. In some embodiments, the insulin fragment ion with m/z of 226.1±0.5 is the quantifier ion. In some embodiments, one or more ions comprise a bovine insulin precursor ion with a mass to charge ratio (m/z) of 956.8±0.5. In some embodiments, one or more ions comprise one or more fragment ions selected from the group consisting of ions with m/z of 136.0±0.5, 226.1±0.5, and 315.2±0.5. In some embodiments, the bovine insulin fragment ion with m/z of 136.0±0.5 is the quantifier ion.

In some embodiments, one or more ions comprise a C-peptide precursor ion with a mass to charge ratio (m/z) of 1007.7±0.5. In some embodiments, one or more ions comprise one or more fragment ions selected from the group consisting of ions with m/z of 533.3±0.5, 646.4±0.5, and 927.5±0.5. In some embodiments, any of the C-peptide fragment ion with m/z of 533.3±0.5, 646.4±0.5, and 927.5±0.5 or their summed intensity can be used for quantification. In some embodiments, one or more ions comprise a C-peptide heavy internal standard precursor ion with a mass to charge ratio (m/z) of 1009.5±0.5. In some embodiments, one or more ions comprise one or more fragment ions selected from the group consisting of ions with m/z of 540.3±0.5, 653.4±0.5, and 934.5±0.5. In some embodiments, any of the C-peptide heavy internal standard fragment ion with m/z of 540.3±0.5, 653.4±0.5, and 934.5±0.5 or their summed intensity can be used for quantification.

In some embodiments, provided herein is utilizing mass spectrometry for determining the amount of insulin and C-peptide in a sample, the methods include: (a) enriching insulin and C-peptide and in a sample by an extraction technique; (b) subjecting the purified insulin and C-peptide from step (a) to liquid chromatography to obtain a fraction enriched in insulin and C-peptide from the sample; (c) subjecting the enriched insulin to an ionization source under conditions suitable to generate an insulin precursor ion detectable by mass spectrometry; and (d) determining the amount of one or more of the fragment ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient.

In some embodiments, the extraction technique provided herein comprises immunocapture of insulin and C-peptide using antibodies. In some embodiments, the extraction technique provided herein comprises solid phase extraction (SPE).

In some embodiments, the collision energy is within the range of about 40 to 60 V. In some embodiments, the collision energy is within the range of about 40 to 50 V.

In another aspect, provided herein are methods for determining the amount of insulin or C-peptide in a sample by mass spectrometry comprising (a) immunocapturing insulin or C-peptide, (b) subjecting the immunocaptured insulin or C-peptide to an ionization source under conditions suitable to generate one or more insulin or C-peptide ions detectable by mass spectrometry; (c) determining the amount of one or more insulin or C-peptide ions by mass spectrometry. In some embodiments, provided herein are methods for determining the amount of insulin in a sample by mass spectrometry comprising (a) immunocapturing insulin, (b) subjecting the immunocaptured insulin to an ionization source under conditions suitable to generate one or more insulin ions detectable by mass spectrometry; (c) determining the amount of one or more insulin ions by mass spectrometry. In some embodiments, provided herein are methods for determining the amount of C-peptide in a sample by mass spectrometry comprising (a) immunocapturing C-peptide, (b) subjecting the immunocaptured C-peptide to an ionization source under conditions suitable to generate one or more C-peptide ions detectable by mass spectrometry; (c) determining the amount of one or more C-peptide ions by mass spectrometry. In some embodiments, immunocapturing comprises using anti-insulin antibodies or anti-C-peptide antibodies. In some embodiments, the anti-insulin antibodies or anti-C-peptide antibodies are immobilized on magnetic beads. In some embodiments, insulin or C-peptide immunocaptured on magnetic beads are washed and eluted.

In another aspect, provided herein are methods for determining the amount of insulin analog in a sample by mass spectrometry comprising (a) immunocapturing insulin analog, (b) subjecting the immunocaptured insulin analog to an ionization source under conditions suitable to generate one or more insulin analog ions detectable by mass spectrometry; (c) determining the amount of one or more insulin analog ions by mass spectrometry.

In another aspect, provided herein are methods for determining the amount of insulin analog and C peptide simultaneously in a sample by mass spectrometry comprising (a) immunocapturing insulin analog, (b) subjecting the immunocaptured insulin analog and C peptide to an ionization source under conditions suitable to generate one or more insulin analog and C peptide ions detectable by mass spectrometry; (c) determining the amount of one or more insulin analog and C peptide ions by mass spectrometry.

In some embodiments, the insulin analog is selected from aspart (NOVOLOG®), lispro (HUMALOG®), glulisine (APIDRA®), detemir (LEVEMIR®), degludec (TRESIBA®), glargine (LANTUS®), and NPH (HUMULIN R®/NOVOLIN N®). In some embodiments, the insulin analog is a rapid acting or long acting insulin analog.

In some embodiments, one or more ions comprise an insulin analog precursor ion with a mass to charge ratio (m/z) of 1011.2±0.5. In some embodiments, one or more ions comprise one or more fragment ions selected from the group consisting of ions with m/z of 136.0±0.5, 1179.0±0.5, and 175.0±0.5. In some embodiments, one or more ions comprise an insulin analog precursor ion with a mass to charge ratio (m/z) of 987.2±0.5. In some embodiments, one or more ions comprise one or more fragment ions selected from the group consisting of ions with m/z of 454.4±0.5 and 357.2±0.5. In some embodiments, one or more ions comprise an insulin analog precursor ion with a mass to charge ratio (m/z) of 971.5±0.5. In some embodiments, one or more ions comprise one or more fragment ions selected from the group consisting of ions with m/z of 219.0±0.5, 226.0±0.5, and 660.8±0.5. In some embodiments, one or more ions comprise an insulin analog precursor ion with a mass to charge ratio (m/z) of 971.5±0.5. In some embodiments, one or more ions comprise one or more fragment ions selected from the group consisting of ions with m/z of 199.0±0.5, 346.2±0.5, and 328.2±0.5. In some embodiments, one or more ions comprise an insulin analog precursor ion with a mass to charge ratio (m/z) of 1162.4±0.5. In some embodiments, one or more ions comprise one or more fragment ions with m/z of 217.3±0.5. In some embodiments, one or more ions comprise an insulin analog precursor ion with a mass to charge ratio (m/z) of 968.7±0.5. In some embodiments, one or more ions comprise one or more fragment ions with m/z of 217.3±0.5. In some embodiments, one or more ions comprise a bovine insulin precursor ion with a mass to charge ratio (m/z) of 956.8±0.5. In some embodiments, one or more ions comprise one or more fragment ions selected from the group consisting of ions with m/z of 136.0±0.5, 226.1±0.5, and 315.2±0.5.

In some embodiments, the sample is delipidated prior to quantitation by mass spectrometry. In some embodiments, the insulin analog is extracted by a base extraction. In some embodiments, mass spectrometry comprises tandem mass spectrometry. In some embodiments, mass spectrometry is high resolution mass spectrometry. In some embodiments, mass spectrometry is high resolution/high accuracy mass spectrometry.

In another aspect, provided herein are methods for diagnosis of glycemic disorders or insulin resistant syndromes in diabetic and pre-diabetic patients. In some embodiments, the methods of quantitation of endogenous insulin and C-peptide provided herein are used for diagnosing diabetes. In some embodiments, the methods of quantitation of endogenous insulin and C-peptide provided herein are used for distinguishing insulin-secreting tumors from exogenous insulin administration as a cause for hypoglycemia. In some embodiments, the methods of quantitation of endogenous insulin and C-peptide provided herein are used for distinguishing type 1 diabetes from type 2 diabetes. In some embodiments, the methods of quantitation of endogenous insulin and C-peptide provided herein are used for assessing the risk of diabetes in pre-diabetic patients.

In another aspect, provided herein are methods for diagnosis or prognosis of glycemic disorders or insulin resistant syndromes in diabetic and pre-diabetic patients comprising comparing the relative amount of intact insulin and insulin B chain. In another aspect, provided herein are methods for diagnosis or prognosis of glycemic disorders or insulin resistant syndromes in diabetic and pre-diabetic patients comprising determining the ratio of intact insulin and insulin B chain. In some embodiments, the methods comprise determining the amount of intact insulin and insulin B chain. In some embodiments, the amount of intact insulin and insulin B chain are determined simultaneously in a single assay. In some embodiments, the amount of intact insulin and insulin B chain are determined separately. In some embodiments, an aberrant or abnormal amount or ratio of intact insulin or insulin B chain relative to each other indicates glycemic disorders or insulin resistant syndromes. In some embodiments, a higher level of insulin B chain relative to intact insulin indicates glycemic disorders or insulin resistant syndromes. In some embodiments, a higher level of intact insulin relative to insulin B chain indicates glycemic disorders or insulin resistant syndromes.

In some embodiments, provided herein are methods for diagnosis or prognosis of glycemic disorders or insulin resistant syndromes in diabetic and pre-diabetic patients comprising determining the amount of intact insulin and insulin B-chain in a sample by mass spectrometry. In some embodiments, provided herein are methods for diagnosis or prognosis of glycemic disorders or insulin resistant syndromes in diabetic and pre-diabetic patients comprising determining the ratio of intact insulin and insulin B-chain in a sample by mass spectrometry. In some embodiments, methods comprise (a) subjecting intact insulin and insulin B-chain from a sample to an ionization source under conditions suitable to generate one or more intact insulin and insulin B-chain ions detectable by mass spectrometry; and (b) determining the amount of one or more intact insulin and insulin B-chain ions by mass spectrometry. In some embodiments, an aberrant or abnormal amount or ratio of intact insulin or insulin B chain relative to each other indicates glycemic disorders or insulin resistant syndromes. In some embodiments, a higher level of insulin B chain relative to intact insulin indicates glycemic disorders or insulin resistant syndromes. In some embodiments, a higher level of intact insulin relative to insulin B chain indicates glycemic disorders or insulin resistant syndromes.

In some embodiments, provided herein are methods for diagnosis or prognosis of glycemic disorders or insulin resistant syndromes in diabetic and pre-diabetic patients comprising determining the amount of intact insulin and insulin B-chain in a sample by an immunoassay. In some embodiments, provided herein are methods for diagnosis or prognosis of glycemic disorders or insulin resistant syndromes in diabetic and pre-diabetic patients comprising determining the ratio of intact insulin and insulin B-chain in a sample by an immunoassay. In some embodiments, an aberrant or abnormal amount or ratio of intact insulin or insulin B chain relative to each other indicates glycemic disorders or insulin resistant syndromes. In some embodiments, a higher level of insulin B chain relative to intact insulin indicates glycemic disorders or insulin resistant syndromes. In some embodiments, a higher level of intact insulin relative to insulin B chain indicates glycemic disorders or insulin resistant syndromes.

In some embodiments, provided herein are methods for diagnosis or prognosis of diabetes in a human comprising comparing the relative amount of intact insulin and insulin B chain. In some embodiments, provided herein are methods for diagnosis or prognosis of diabetes in a human comprising determining the ratio of intact insulin and insulin B chain. In some embodiments, the methods comprise determining the amount of intact insulin and insulin B chain. In some embodiments, the amount of intact insulin and insulin B chain are determined simultaneously in a single assay. In some embodiments, the amount of intact insulin and insulin B chain are determined separately. In some embodiments, an aberrant or abnormal amount or ratio of intact insulin or insulin B chain relative to each other indicates diabetes or prediabetes. In some embodiments, a higher level of insulin B chain relative to intact insulin indicates diabetes or prediabetes. In some embodiments, a higher level of intact insulin relative to insulin B chain indicates diabetes or prediabetes.

In some embodiments, provided herein are methods for diagnosis or prognosis of diabetes in a human comprising determining the amount of intact insulin and insulin B-chain in a sample by mass spectrometry. In some embodiments, provided herein are methods for diagnosis or prognosis of diabetes in a human comprising determining the ratio of intact insulin and insulin B-chain in a sample by mass spectrometry. In some embodiments, methods comprise (a) subjecting intact insulin and insulin B-chain from a sample to an ionization source under conditions suitable to generate one or more intact insulin and insulin B-chain ions detectable by mass spectrometry; and (b) determining the amount of one or more intact insulin and insulin B-chain ions by mass spectrometry. In some embodiments, an aberrant or abnormal amount or ratio of intact insulin or insulin B chain relative to each other indicates diabetes or prediabetes. In some embodiments, a higher level of insulin B chain relative to intact insulin indicates diabetes or prediabetes. In some embodiments, a higher level of intact insulin relative to insulin B chain indicates diabetes or prediabetes.

In some embodiments, provided herein are methods for diagnosis or prognosis of diabetes in a human comprising determining the amount of intact insulin and insulin B-chain in a sample by an immunoassay. In some embodiments, an aberrant or abnormal amount or ratio of intact insulin or insulin B chain relative to each other indicates diabetes or prediabetes. In some embodiments, a higher level of insulin B chain relative to intact insulin indicates diabetes or prediabetes. In some embodiments, a higher level of intact insulin relative to insulin B chain indicates diabetes or prediabetes.

In some embodiments, the methods of quantitation of endogenous intact insulin and insulin B chain provided herein are used for distinguishing insulin-secreting tumors from exogenous insulin administration as a cause for hypoglycemia. In some embodiments, the methods of quantitation of endogenous intact insulin and insulin B chain provided herein are used for distinguishing type 1 diabetes from type 2 diabetes. In some embodiments, the methods of quantitation of endogenous intact insulin and insulin B chain provided herein are used for assessing the risk of diabetes in pre-diabetic patients. In some embodiments, a higher level of insulin B chain relative to intact insulin indicates diabetes or prediabetes. In some embodiments, a higher level of intact insulin relative to insulin B chain indicates diabetes or prediabetes.

In another aspect, provided herein are methods for assessing the insulin degrading enzyme (IDE) activity comprising determining the ratio of intact insulin to insulin B chain.

In some embodiments, provided herein are methods for measuring insulin levels in a patient by determining the amount of intact insulin and insulin B-chain in a sample using mass spectrometry.

In certain embodiments, the methods provided herein comprise multiplexed assays that simultaneously measure the amount of intact insulin and insulin B-chain in a sample by mass spectrometry. In some embodiments, methods comprise (a) subjecting intact insulin and insulin B-chain from a sample to an ionization source under conditions suitable to generate one or more intact insulin and insulin B-chain ions detectable by mass spectrometry; and (b) determining the amount of one or more intact insulin and insulin B-chain ions by mass spectrometry.

In some embodiments, the amount of the one or more ions determined is used to determine the amount of intact insulin and insulin B-chain in the sample. In some embodiments, the amount of intact insulin and insulin B-chain in the sample is related to the amount of insulin in the patient. In some embodiments, the amount of intact insulin and insulin B-chain in the sample is used to determine the ratio of intact insulin and insulin B-chain in the patient.

In some embodiments, methods comprise (a) subjecting a sample to an enrichment process to obtain a fraction enriched in intact insulin and insulin B-chain, (b) subjecting the enriched intact insulin and insulin B-chain to an ionization source under conditions suitable to generate one or more intact insulin and insulin B-chain ions detectable by mass spectrometry; (c) determining the amount of one or more intact insulin and insulin B-chain ions by mass spectrometry. In some embodiments, the amount of the one or more ions determined is used to determine the amount of intact insulin and insulin B-chain in the sample. In some embodiments, the amount of intact insulin and insulin B-chain in the sample is related to the amount of insulin in the patient. In some embodiments, the amount of intact insulin and insulin B-chain in the sample is used to determine the ratio of intact insulin and insulin B-chain in the patient.

In some embodiments, the enrichment process provided herein comprises immunocapture of intact insulin and insulin B-chain using antibodies. In some embodiments, methods comprise (a) immunocapturing intact insulin and insulin B-chain, (b) subjecting the immunocaptured intact insulin and insulin B-chain to an ionization source under conditions suitable to generate one or more intact insulin and insulin B-chain ions detectable by mass spectrometry; (c) determining the amount of one or more intact insulin and insulin B-chain ions by mass spectrometry.

In some embodiments, immunocapturing provided herein comprises using anti-insulin antibodies and anti-insulin B-chain antibodies. In some embodiments, the antibodies provided herein are monoclonal antibodies. In some embodiments, the antibodies provided herein are mouse monoclonal antibodies. In some embodiments, the antibodies provided herein are monoclonal IgG antibodies. In some embodiments, the antibodies provided herein are polyclonal antibodies.

In some embodiments, the anti-insulin antibodies and anti-insulin B-chain antibodies are immobilized on magnetic beads. In some embodiments, insulin and insulin B-chain immunocaptured on magnetic beads are washed and eluted.

In some embodiments, one or more ions comprise an insulin B chain precursor ion selected from the group consisting of ions with m/z of $1144.2\pm0.5$, $858.3\pm0.5$, and $686.8\pm0.5$. In some embodiments, one or more ions comprise one or more fragment ions selected from the group consisting of ions with m/z of $824.9\pm0.5$, $768.4\pm0.5$, $752.8\pm0.5$, $345.0\pm0.5$, and $226.2\pm0.5$, such as the group consisting of ions with m/z of $345.0\pm0.5$ and $226.2\pm0.5$. In some embodiments, one or more ions comprise two or more fragment ions selected from the group consisting of a fragment ion from an insulin B chain precursor ion with m/z of $1144.2\pm0.5$, a fragment ion from an insulin B chain precursor ion with m/z of $858.3\pm0.5$, and a fragment ion from an insulin B chain precursor ion with m/z of $686.8\pm0.5$. In some embodiments, one or more fragment ions from each precursor ion comprise one or more fragment ions selected from the group consisting of ions with m/z of $824.9\pm0.5$, $768.4\pm0.5$, $752.8\pm0.5$, $345.0\pm0.5$, and $226.2\pm0.5$, such as the group consisting of ions with m/z of $345.0\pm0.5$ and $226.2\pm0.5$.

In alternative embodiments, the insulin B chains are chemically modified prior to ionization. In some embodiments, chemical modification comprises alkylating said insulin B chains. In some embodiments, one or more ions comprise an alkylated insulin B chain precursor ion selected from the group consisting of ions with m/z of $1181.9\pm0.5$, $886.9\pm0.5$, and $709.8\pm0.5$. In some embodiments, one or more ions comprise one or more fragment ions selected from the group of ions with m/z of $345.0\pm0.5$ and $226.2\pm0.5$. In some embodiments, one or more ions comprise two or more fragment ions selected from the group consisting of a fragment ion from an alkylated insulin B chain precursor ion with a mass to charge ratio (m/z) of $1181.9\pm0.5$, a fragment ion from an alkylated insulin B chain precursor ion with m/z of $886.9\pm0.5$, and a fragment ion from an alkylated insulin B chain precursor ion with m/z of $709.8\pm0.5$. In some related embodiments, the fragment ion from each precursor ion comprises an ion selected from the group consisting of ions with m/z of $345.0\pm0.5$ and $226.2\pm0.5$.

In another aspect, provided herein are methods for diagnosis or prognosis of glycemic disorders or insulin resistant syndromes in diabetic and pre-diabetic patients comprising comparing the relative amount of intact insulin and insulin A chain. In another aspect, provided herein are methods for diagnosis or prognosis of glycemic disorders or insulin resistant syndromes in diabetic and pre-diabetic patients comprising determining the ratio of intact insulin and insulin A chain. In some embodiments, the methods comprise determining the amount of intact insulin and insulin A chain. In some embodiments, the amount of intact insulin and insulin A chain are determined simultaneously in a single assay. In some embodiments, the amount of intact insulin and insulin A chain are determined separately. In some embodiments, an aberrant or abnormal amount or ratio of intact insulin or insulin A chain relative to each other indicates glycemic disorders or insulin resistant syndromes. In some embodiments, a higher level of insulin A chain relative to intact insulin indicates glycemic disorders or insulin resistant syndromes. In some embodiments, a higher level of intact insulin relative to insulin A chain indicates glycemic disorders or insulin resistant syndromes.

In some embodiments, provided herein are methods for diagnosis or prognosis of glycemic disorders or insulin resistant syndromes in diabetic and pre-diabetic patients comprising determining the amount of intact insulin and insulin A-chain in a sample by mass spectrometry. In some embodiments, provided herein are methods for diagnosis or prognosis of glycemic disorders or insulin resistant syndromes in diabetic and pre-diabetic patients comprising determining the ratio of intact insulin and insulin A-chain in a sample by mass spectrometry. In some embodiments, methods comprise (a) subjecting intact insulin and insulin A-chain from a sample to an ionization source under conditions suitable to generate one or more intact insulin and insulin A-chain ions detectable by mass spectrometry; and (b) determining the amount of one or more intact insulin and insulin A-chain ions by mass spectrometry. In some embodiments, an aberrant or abnormal amount or ratio of intact insulin or insulin A chain relative to each other indicates glycemic disorders or insulin resistant syndromes. In some embodiments, a higher level of insulin A chain relative to intact insulin indicates glycemic disorders or insulin resistant syndromes. In some embodiments, a higher level of intact insulin relative to insulin A chain indicates glycemic disorders or insulin resistant syndromes.

In some embodiments, provided herein are methods for diagnosis or prognosis of glycemic disorders or insulin resistant syndromes in diabetic and pre-diabetic patients comprising determining the amount of intact insulin and insulin A-chain in a sample by an immunoassay. In some embodiments, provided herein are methods for diagnosis or prognosis of glycemic disorders or insulin resistant syndromes in diabetic and pre-diabetic patients comprising determining the ratio of intact insulin and insulin A-chain in a sample by an immunoassay. In some embodiments, an aberrant or abnormal amount or ratio of intact insulin or insulin A chain relative to each other indicates glycemic disorders or insulin resistant syndromes. In some embodiments, a higher level of insulin A chain relative to intact insulin indicates glycemic disorders or insulin resistant syndromes. In some embodiments, a higher level of intact insulin relative to insulin A chain indicates glycemic disorders or insulin resistant syndromes.

In some embodiments, provided herein are methods for diagnosis or prognosis of diabetes in a human comprising comparing the relative amount of intact insulin and insulin A chain. In some embodiments, provided herein are methods for diagnosis or prognosis of diabetes in a human comprising determining the ratio of intact insulin and insulin A chain. In some embodiments, the methods comprise determining the amount of intact insulin and insulin A chain. In some embodiments, the amount of intact insulin and insulin A chain are determined simultaneously in a single assay. In some embodiments, the amount of intact insulin and insulin A chain are determined separately. In some embodiments, an aberrant or abnormal amount or ratio of intact insulin or insulin A chain relative to each other indicates diabetes or prediabetes. In some embodiments, a higher level of insulin A chain relative to intact insulin indicates diabetes or prediabetes. In some embodiments, a higher level of intact insulin relative to insulin A chain indicates diabetes or prediabetes.

In some embodiments, provided herein are methods for diagnosis or prognosis of diabetes in a human comprising determining the amount of intact insulin and insulin A-chain in a sample by mass spectrometry. In some embodiments, provided herein are methods for diagnosis or prognosis of diabetes in a human comprising determining the ratio of intact insulin and insulin A-chain in a sample by mass spectrometry. In some embodiments, methods comprise (a) subjecting intact insulin and insulin A-chain from a sample to an ionization source under conditions suitable to generate one or more intact insulin and insulin A-chain ions detectable by mass spectrometry; and (b) determining the amount of one or more intact insulin and insulin A-chain ions by mass spectrometry. In some embodiments, an aberrant or abnormal amount or ratio of intact insulin or insulin A chain relative to each other indicates diabetes or prediabetes. In some embodiments, a higher level of insulin A chain relative to intact insulin indicates diabetes or prediabetes. In some embodiments, a higher level of intact insulin relative to insulin A chain indicates diabetes or prediabetes.

In some embodiments, provided herein are methods for diagnosis or prognosis of diabetes in a human comprising determining the amount of intact insulin and insulin A-chain in a sample by an immunoassay. In some embodiments, an aberrant or abnormal amount or ratio of intact insulin or insulin A chain relative to each other indicates diabetes or prediabetes. In some embodiments, a higher level of insulin A chain relative to intact insulin indicates diabetes or prediabetes. In some embodiments, a higher level of intact insulin relative to insulin A chain indicates diabetes or prediabetes.

In some embodiments, the methods of quantitation of endogenous intact insulin and insulin A chain provided herein are used for distinguishing insulin-secreting tumors from exogenous insulin administration as a cause for hypoglycemia. In some embodiments, the methods of quantitation of endogenous intact insulin and insulin A chain provided herein are used for distinguishing type 1 diabetes from type 2 diabetes. In some embodiments, the methods of quantitation of endogenous intact insulin and insulin A chain provided herein are used for assessing the risk of diabetes in pre-diabetic patients. In some embodiments, a higher level of insulin A chain relative to intact insulin indicates diabetes or prediabetes. In some embodiments, a higher level of intact insulin relative to insulin A chain indicates diabetes or prediabetes.

In another aspect, provided herein are methods for assessing the insulin degrading enzyme (IDE) activity comprising determining the ratio of intact insulin to insulin A chain.

In some embodiments, provided herein are methods for measuring insulin levels in a patient by determining the amount of intact insulin and insulin A-chain in a sample using mass spectrometry.

In certain embodiments, the methods provided herein comprise multiplexed assays that simultaneously measure the amount of intact insulin and insulin A-chain in a sample by mass spectrometry. In some embodiments, methods comprise (a) subjecting intact insulin and insulin A-chain from a sample to an ionization source under conditions suitable to generate one or more intact insulin and insulin A-chain ions detectable by mass spectrometry; and (b) determining the amount of one or more intact insulin and insulin A-chain ions by mass spectrometry.

In some embodiments, the amount of the one or more ions determined is used to determine the amount of intact insulin and insulin A-chain in the sample. In some embodiments, the amount of intact insulin and insulin A-chain in the sample is related to the amount of insulin in the patient. In some embodiments, the amount of intact insulin and insulin A-chain in the sample is used to determine the ratio of intact insulin and insulin A-chain in the patient.

In some embodiments, methods comprise (a) subjecting a sample to an enrichment process to obtain a fraction enriched in intact insulin and insulin A-chain, (b) subjecting the enriched intact insulin and insulin A-chain to an ionization source under conditions suitable to generate one or more intact insulin and insulin A-chain ions detectable by mass spectrometry; (c) determining the amount of one or more intact insulin and insulin A-chain ions by mass spectrometry. In some embodiments, the amount of the one or more ions determined is used to determine the amount of intact insulin and insulin A-chain in the sample. In some embodiments, the amount of intact insulin and insulin A-chain in the sample is related to the amount of insulin in the patient. In some embodiments, the amount of intact insulin and insulin A-chain in the sample is used to determine the ratio of intact insulin and insulin A-chain in the patient.

In some embodiments, the enrichment process provided herein comprises immunocapture of intact insulin and insulin A-chain using antibodies. In some embodiments, methods comprise (a) immunocapturing intact insulin and insulin A-chain, (b) subjecting the immunocaptured intact insulin and insulin A-chain to an ionization source under conditions suitable to generate one or more intact insulin and insulin A-chain ions detectable by mass spectrometry; (c) determining the amount of one or more intact insulin and insulin B-chain ions by mass spectrometry.

In some embodiments, immunocapturing provided herein comprises using anti-insulin antibodies and anti-insulin A-chain antibodies. In some embodiments, the antibodies provided herein are monoclonal antibodies. In some embodiments, the antibodies provided herein are mouse monoclonal antibodies. In some embodiments, the antibodies provided herein are monoclonal IgG antibodies. In some embodiments, the antibodies provided herein are polyclonal antibodies.

In some embodiments, the anti-insulin antibodies and anti-insulin A-chain antibodies are immobilized on magnetic beads. In some embodiments, insulin and insulin A-chain immunocaptured on magnetic beads are washed and eluted.

In embodiments where insulin A-chains are subject to tandem mass spectrometric analysis, Q1 may select for one or more insulin A-chain precursor ions with an m/z of about 1192.0±0.5 and 795.0±0.5. Fragmentation of either of these insulin A-chain precursor ions may generate fragment ions with m/z of about 513.0±0.5, 399.0±0.5, 236.0±0.5, and 133.0±0.5. Thus, in embodiments where Q1 selects for one or more insulin A-chain precursor ions selected from the group consisting of ions with m/z of about 1192.0±0.5 and 795.0±0.5, Q3 may select one or more fragment ions selected from the group of ions with m/z of about 513.0±0.5, 399.0±0.5, 236.0±0.5, and 133.0±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

In some embodiments, serum is delipidated prior to quantitation by mass spectrometry. In some embodiments, one or more delipidation reagent is used to remove lipids from the sample. In some embodiments, the delipidation reagent is CLEANASCITE®.

In some embodiments, the methods provided herein comprise purifying the samples prior to mass spectrometry. In some embodiments, the methods comprise purifying the samples using liquid chromatography. In some embodiments, liquid chromatography comprise high performance liquid chromatography (HPLC) or high turbulence liquid chromatograph (HTLC). In some embodiments, the methods comprise subjecting a sample to solid phase extraction (SPE).

In some embodiments, mass spectrometry comprises tandem mass spectrometry. In some embodiments, mass spectrometry is high resolution mass spectrometry. In some embodiments, mass spectrometry is high resolution/high accuracy mass spectrometry.

In some embodiments, ionization is by electrospray ionization (ESI). In some embodiments, ionization is by atmospheric pressure chemical ionization (APCI). In some embodiments, said ionization is in positive ion mode.

In some embodiments, methods provided herein comprise adding internal standards to the sample. In some embodiments, the internal standard is labeled. In some embodiments, the internal standard is deuterated or isotopically labeled.

In some embodiments, the patient sample is a serum sample. In some embodiments, the patient sample is a plasma sample. In some embodiments, the patient sample is a blood, saliva, or urine sample.

In some embodiments, the sample is subjected to acidic conditions prior to ionization. In some embodiments, subjecting the sample to acidic conditions comprises subjecting enriched insulin and insulin B-chain to formic acid.

In some embodiments, the sample is subjected to basic conditions prior to. In some embodiments, subjecting the sample to basic conditions comprises subjecting the sample to trizma. In some embodiments, subjecting the sample to basic conditions comprises subjecting the sample to trizma and ethanol.

In some embodiments, one or more ions comprise an insulin precursor ion with a mass to charge ratio (m/z) of 968.7±0.5. In some embodiments, one or more ions comprise one or more fragment ions selected from the group consisting of ions with m/z of 136.0±0.5, 226.1±0.5, and 345.2±0.5. In some embodiments, the insulin fragment ion with m/z of 226.1±0.5 is the quantifier ion.

In another aspect, provided herein are methods for diagnosis or prognosis of glycemic disorders or insulin resistant syndromes in diabetic and pre-diabetic patients comprising comparing the relative amount of insulin B chain and insulin A chain. In another aspect, provided herein are methods for diagnosis or prognosis of glycemic disorders or insulin resistant syndromes in diabetic and pre-diabetic patients comprising determining the ratio of insulin B chain and insulin A chain. In some embodiments, the methods comprise determining the amount of insulin B chain and insulin A chain. In some embodiments, the amount of insulin B chain and insulin A chain are determined simultaneously in a single assay. In some embodiments, the amount of insulin B chain and insulin A chain are determined separately. In some embodiments, an aberrant or abnormal amount or ratio of insulin B chain or insulin A chain relative to each other indicates glycemic disorders or insulin resistant syndromes. In some embodiments, a higher level of insulin A chain relative to insulin B chain indicates glycemic disorders or insulin resistant syndromes. In some embodiments, a higher level of insulin B chain relative to insulin A chain indicates glycemic disorders or insulin resistant syndromes.

In some embodiments, provided herein are methods for diagnosis or prognosis of glycemic disorders or insulin resistant syndromes in diabetic and pre-diabetic patients comprising determining the amount of insulin A chain and insulin B-chain in a sample by mass spectrometry. In some embodiments, provided herein are methods for diagnosis or prognosis of glycemic disorders or insulin resistant syndromes in diabetic and pre-diabetic patients comprising determining the ratio of insulin A chain and insulin B-chain in a sample by mass spectrometry. In some embodiments, methods comprise (a) subjecting insulin A chain and insulin B-chain from a sample to an ionization source under conditions suitable to generate one or more insulin A chain and insulin B-chain ions detectable by mass spectrometry; and (b) determining the amount of one or more insulin A chain and insulin B-chain ions by mass spectrometry. In some embodiments, an aberrant or abnormal amount or ratio of insulin A chain or insulin B chain relative to each other indicates glycemic disorders or insulin resistant syndromes. In some embodiments, a higher level of insulin B chain relative to insulin A chain indicates glycemic disorders or insulin resistant syndromes. In some embodiments, a higher level of insulin A chain relative to insulin B chain indicates glycemic disorders or insulin resistant syndromes.

In some embodiments, provided herein are methods for diagnosis or prognosis of diabetes in a human comprising comparing the relative amount of insulin B chain and insulin A chain. In some embodiments, provided herein are methods for diagnosis or prognosis of diabetes in a human comprising determining the ratio of insulin B chain and insulin A chain. In some embodiments, the methods comprise determining the amount of insulin B chain and insulin A chain. In some embodiments, the amount of insulin B chain and insulin A chain are determined simultaneously in a single assay. In some embodiments, the amount of insulin B chain and insulin A chain are determined separately. In some embodiments, an aberrant or abnormal amount or ratio of insulin B chain or insulin A chain relative to each other indicates diabetes or prediabetes. In some embodiments, a higher level of insulin A chain relative to insulin B chain indicates diabetes or prediabetes. In some embodiments, a higher level of insulin B chain relative to insulin A chain indicates diabetes or prediabetes.

In some embodiments, provided herein are methods for diagnosis or prognosis of diabetes in a human comprising determining the amount of insulin B chain and insulin A-chain in a sample by mass spectrometry. In some embodiments, provided herein are methods for diagnosis or prognosis of diabetes in a human comprising determining the ratio of insulin B chain and insulin A-chain in a sample by mass spectrometry. In some embodiments, methods comprise (a) subjecting insulin B chain and insulin A-chain from a sample to an ionization source under conditions suitable to generate one or more insulin B chain and insulin A-chain ions detectable by mass spectrometry; and (b) determining the amount of one or more insulin B chain and insulin A-chain ions by mass spectrometry. In some embodiments, an aberrant or abnormal amount or ratio of insulin B chain or insulin A chain relative to each other indicates diabetes or prediabetes. In some embodiments, a higher level of insulin A chain relative to insulin B chain indicates diabetes or prediabetes. In some embodiments, a higher level of insulin B chain relative to insulin A chain indicates diabetes or prediabetes.

In another aspect, certain methods presented herein utilize high resolution/high accuracy mass spectrometry to determine the amount of insulin in a sample. In some embodiments utilizing high accuracy/high resolution mass spectrometry, the methods include: (a) subjecting insulin from a sample to an ionization source under conditions suitable to generate multiply charged insulin ions, wherein the insulin ions are detectable by mass spectrometry; and (b) determining the amount of one or more multiply charged insulin ions by high resolution/high accuracy mass spectrometry. In these embodiments, the amount of one or more ions determined in step (b) is related to the amount of insulin in the sample. In some embodiments, high resolution/high accuracy mass spectrometry is conducted at a FWHM of 10,000 and a mass accuracy of 50 ppm. In some embodiments, high resolution/high accuracy mass spectrometry is conducted with a high resolution/high accuracy time-of-flight (TOF) mass spectrometer. In some embodiments, the ionization conditions comprise ionization of insulin under acidic conditions. In some related embodiments, the acidic conditions comprise treatment of said sample with formic acid prior to ionization. In some embodiments, the multiply charged insulin ions are selected from the group consisting of 4+, 5+, and 6+ charged insulin ions.

In some embodiments, one or more insulin ions in a 6+ charge state comprise one or more ions with m/z within the range of about 968.8±1.5. In some embodiments, one or more insulin ions in a 6+ charge state comprise one or more ions selected from the group consisting of ions with m/z of 968.28±0.1, 968.45±0.1, 968.62±0.1, 968.79±0.1, 968.95±0.1, 969.12±0.1, 969.28±0.1, 969.45±0.1, 969.61±0.1; such as an ions with m/z of 968.95±0.1.

In some embodiments, one or more insulin ions in a 5+ charge state comprise one or more ions with m/z within the range of about 1162.5±1.0. In some embodiments, one or more insulin ions in a 5+ charge state comprise one or more ions selected from the group consisting of ions with m/z of 1161.72±0.1, 1161.92±0.1, 1162.12±0.1, 1162.32±0.1, 1162.52±0.1, 1162.72±0.1, 1162.92±0.1, 1163.12±0.1, 1163.32±0.1; such as an ion with m/z of 1162.54±0.1.

In some embodiments, one or more insulin ions in a 4+ charge state comprise one or more ions with m/z within the range of about 1452.9±0.8.

In any of the methods described herein, the sample may comprise a biological sample. In some embodiments, the biological sample may comprise a biological fluid such as urine, plasma, or serum. In some embodiments, the biological sample may comprise a sample from a human; such as from an adult male or female, or juvenile male or female, wherein the juvenile is under age 18, under age 15, under age 12, or under age 10. The human sample may be analyzed to diagnose or monitor a disease state or condition, or to monitor therapeutic efficacy of treatment of a disease state or condition. In some related embodiments, the methods described herein may be used to determine the amount of insulin in a biological sample when taken from a human.

In embodiments utilizing tandem mass spectrometry, tandem mass spectrometry may be conducted by any method known in the art, including for example, multiple reaction monitoring, precursor ion scanning, or product ion scanning.

In some embodiments, tandem mass spectrometry comprises fragmenting a precursor ion into one or more fragment ions. In embodiments where the amounts of two or more fragment ions are determined, the amounts may be subject to any mathematical manipulation known in the art in order to relate the measured ion amounts to the amount of insulin in the sample. For example, the amounts of two or more fragment ions may be summed as part of determining the amount of insulin in the sample.

In any of the methods described herein, the analyte of interest (e.g., insulin, or chemically modified or unmodified insulin B chains) may be purified from a sample by high performance liquid chromatography (HPLC) prior to ionization. In any of the methods described herein, the analyte of interest may be purified from a sample by an extraction technique, such as subjecting the sample to a solid phase extraction (SPE) column. In some embodiments, the extraction technique is not an immunopurification technique. Specifically, in some embodiments, the SPE column is not an immunoaffinity column. In some embodiments, immunopurification is not used at any point in the method. In some embodiments; an extraction technique and HPLC may be performed in an on-line fashion to allow for automated sample processing and analysis.

In some embodiments, the high resolution/high accuracy mass spectrometry is conducted at a resolving power (FWHM) of greater than or equal to about 10,000, such as greater than or equal to about 15,000, such as greater than or equal to about 20,000, such as greater than or equal to about 25,000. In some embodiments, the high resolution/high accuracy mass spectrometry is conducted at an accuracy of less than or equal to about 50 ppm, such as less than or equal to about 20 ppm, such as less than or equal to about 10 ppm, such as less than or equal to about 5 ppm; such as less than or equal to about 3 ppm. In some embodiments, high resolution/high accuracy mass spectrometry is conducted at a resolving power (FWHM) of greater than or equal to about 10,000 and an accuracy of less than or equal to about 50 ppm. In some embodiments, the resolving power is greater than about 15,000 and the accuracy is less than or equal to about 20 ppm. In some embodiments, the resolving power is greater than or equal to about 20,000 and the accuracy is less than or equal to about 10 ppm; preferably resolving power is greater than or equal to about 20,000 and accuracy is less than or equal to about 5 ppm, such as less than or equal to about 3 ppm.

In some embodiments, the high resolution/high accuracy mass spectrometry may be conducted with an orbitrap mass spectrometer, a time of flight (TOF) mass spectrometer, or a Fourier transform ion cyclotron resonance mass spectrometer (sometimes known as a Fourier transform mass spectrometer).

In some embodiments, the one or more insulin ions detectable by high resolution/high accuracy mass spectrometry are one or more ions selected from the group consisting of ions with m/z within the ranges of about 1452.9±0.8, 1162.5±1 and 968.8±1.5. Ions within these ranges correspond to insulin ions with charges of 4+, 5+, and 6+, respectively. Monoisotopic ions with these charges predominantly fall within the cited m/z ranges. However, lower abundance naturally occurring isotopic variants may occur outside of these ranges. Insulin ions within the range of 1162.5±1 preferably comprise an insulin ion with m/z of about 1161.72±0.1, 1161.92±0.1, 1162.12±0.1, 1162.32±0.1, 1162.52±0.1, 1162.72±0.1, 1162.92±0.1, 1163.12±0.1, 1163.32±0.1; such as an ion with m/z of 1162.54±0.1. Insulin ions within the range of 968.8±1.5 preferably comprise an insulin ion with m/z of about 968.28±0.1, 968.45±0.1, 968.62±0.1, 968.79±0.1, 968.95±0.1, 969.12±0.1, 969.28±0.1, 969.45±0.1, 969.61±0.1; such as an ions with m/z of 968.95±0.1. In some embodiments, relating the amount of one or more insulin ions detected by mass spectrometry to the amount of an insulin protein in the sample includes comparison to an internal standard; such as a human or non-human insulin protein. The internal standard may optionally be isotopically labeled.

In any of the methods presented herein, the sample may comprise a biological sample; preferably a body fluid sample, including, for example, plasma or serum.

Mass spectrometry (either tandem or high resolution/high accuracy) may be performed in positive ion mode. Alternatively, mass spectrometry may be performed in negative ion mode. Various ionization sources, including for example atmospheric pressure chemical ionization (APCI) or electrospray ionization (ESI), may be used to ionize insulin. In some embodiments, insulin, and/or chemically modified or unmodified insulin B chain are ionized by ESI in positive ion mode.

In any method presented herein, a separately detectable internal standard may be provided in the sample, the amount of which is also determined in the sample. In embodiments utilizing a separately detectable internal standard, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample by comparison to the amount of internal standard ions detected.

Alternatively, the amount of insulin in a sample may be determined by comparison to one or more external reference standards. Exemplary external reference standards include blank plasma or serum spiked with human or non-human insulin, a synthetic insulin analogue, or an isotopically labeled variant thereof.

In some embodiments, the methods are capable of determining the amount of insulin in a sample at levels within the range of about 10 µIU/mL to 500 µIU/mL.

The summary of the invention described above is non-limiting and other features and advantages of the invention will be apparent from the following detailed description of the invention, and from the claims.

BRIEF DESCRIPTION OF THE DRAWINGS

FIG. 21A shows the results of 3 assays of Siemens values 30 uIU/mL and greater, and FIG. 21B shows the results of 3 assays of Siemens values 10-30 uIU/mL. Y-axis represents the ratio of measured insulin value method/Beckman.

DETAILED DESCRIPTION OF THE INVENTION

Figure 1A:
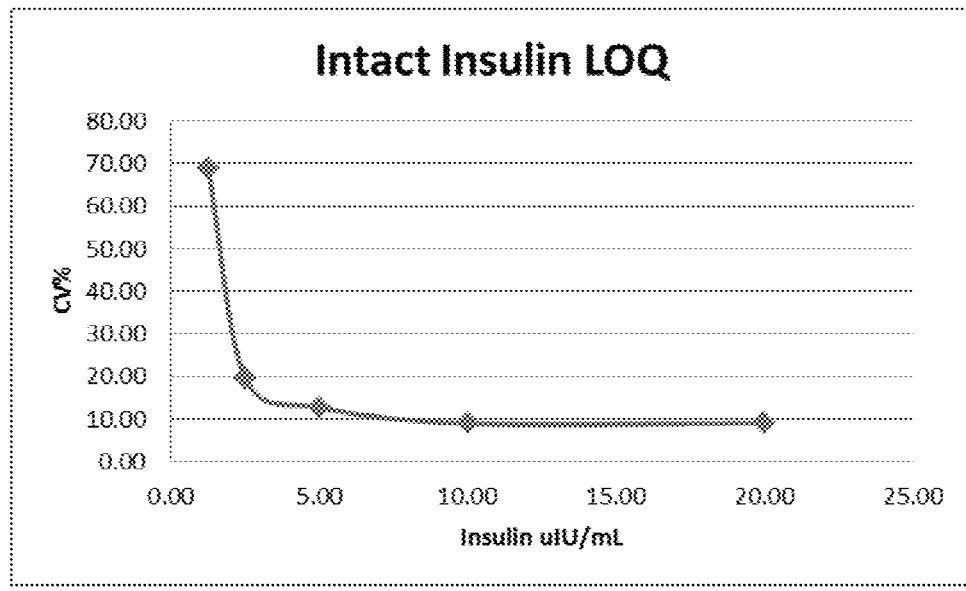
FIGS. 1A-1B show limit of quantitation for insulin (FIG. 1A) and C-peptide (FIG. 1B).

As used herein, unless otherwise stated, the singular forms "a," "an," and "the" include plural reference. Thus, for example, a reference to "a protein" includes a plurality of protein molecules.

As used herein, the terms "purification", "purifying", and "enriching" do not refer to removing all materials from the sample other than the analyte(s) of interest. Instead, these terms refer to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "immunopurification" or "immunopurify" refers to a purification procedure that utilizes antibodies, including polyclonal or monoclonal antibodies, to enrich the one or more analytes of interest. Immunopurification can be performed using any of the immunopurification methods well known in the art. Often the immunopurification procedure utilizes antibodies bound, conjugated or otherwise attached to a solid support, for example a column, well, tube, gel, capsule, particle or the like. Immunopurification as used herein includes without limitation procedures often referred to in the art as immunoprecipitation, as well as procedures often referred to in the art as affinity chromatography or immunoaffinity chromatography.

As used herein, the term "immunoparticle" refers to a capsule, bead, gel particle or the like that has antibodies bound, conjugated or otherwise attached to its surface (either on and/or in the particle). In certain preferred embodiments, immunoparticles are sepharose or agarose beads. In alternative preferred embodiments, immunoparticles comprise glass, plastic or silica beads, or silica gel.

As used herein, the term "anti-insulin antibody" refers to any polyclonal or monoclonal antibody that has an affinity for insulin. In various embodiments the specificity of insulin antibodies to chemical species other than insulin may vary; for example in certain preferred embodiments the anti-insulin antibodies are specific for insulin and thus have little or no affinity for chemical species other than insulin, whereas in other preferred embodiments the anti-insulin antibodies are non-specific and thus bind certain chemical species other than insulin.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. In preferred embodiments, the sample comprises a body fluid sample from human; preferably plasma or serum.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit strong cation exchange and hydrophobic retention.

Generally, the affinity of a SPE column packing material for an analyte may be due to any of a variety of mechanisms, such as one or more chemical interactions or an immuno-affinity interaction. In some embodiments, SPE of insulin is conducted without the use of an immunoaffinity column packing material. That is, in some embodiments, insulin is purified from a sample by a SPE column that is not an immunoaffinity column.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in substantially straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 5 µm in diameter.

As used herein, the terms "on-line" and "inline", for example as used in "on-line automated fashion" or "on-line extraction", refers to a procedure performed without the need for operator intervention. In contrast, the term "off-line" as used herein refers to a procedure requiring manual intervention of an operator. Thus, if samples are subjected to precipitation and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer, a mass analyzer, and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;" 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, "high resolution/high accuracy mass spectrometry" refers to mass spectrometry conducted with a mass analyzer capable of measuring the mass to charge ratio of a charged species with sufficient precision and accuracy to confirm a unique chemical ion. Confirmation of a unique chemical ion is possible for an ion when individual isotopic peaks from that ion are readily discernable. The particular resolving power and mass accuracy necessary to confirm a unique chemical ion varies with the mass and charge state of the ion.

Figure 1B:
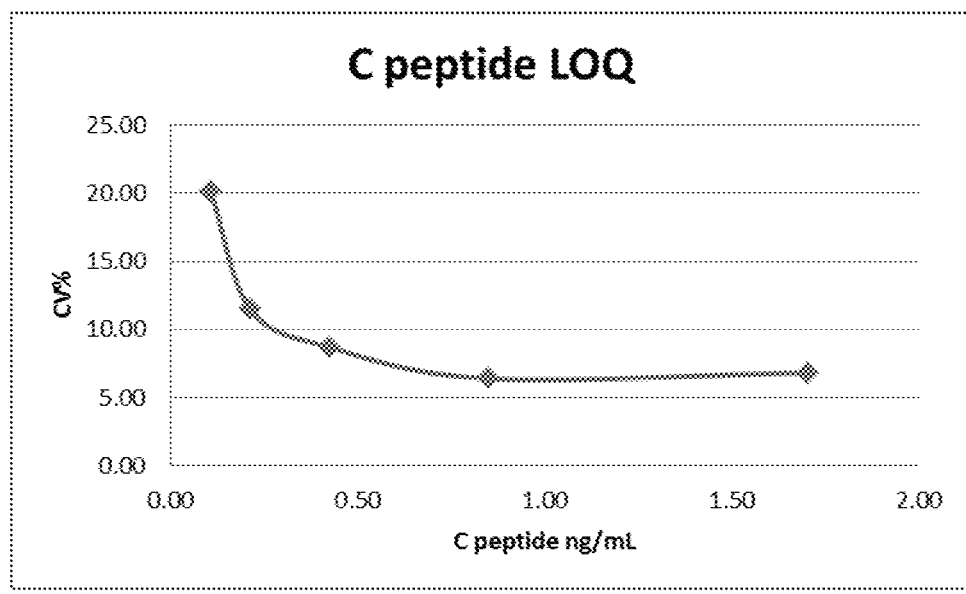

As used herein, the term "resolving power" or "resolving power (FWHM)" (also known in the art as "m/$\Delta m_{50\%}$") refers to an observed mass to charge ratio divided by the width of the mass peak at 50% maximum height (Full Width Half Maximum, "FWHM"). The effect of differences in resolving power is illustrated in FIGS. 1A-C, which show theoretical mass spectra of an ion with a m/z of about 1093. FIG. 1A shows a theoretical mass spectrum from a mass analyzer with resolving power of about 3000 (a typical operating condition for a conventional quadrupole mass analyzer). As seen in FIG. 1A, no individual isotopic peaks are discernable. By comparison, FIG. 1B shows a theoretical mass spectrum from a mass analyzer with resolving power of about 10,000, with clearly discernable individual isotopic peaks. FIG. 1C shows a theoretical mass spectrum from a mass analyzer with resolving power of about 12,000. At this highest resolving power, the individual isotopic peaks contain less than 1% contribution from baseline.

As used herein a "unique chemical ion" with respect to mass spectrometry refers a single ion with a single atomic makeup. The single ion may be singly or multiply charged.

Figure 2A:
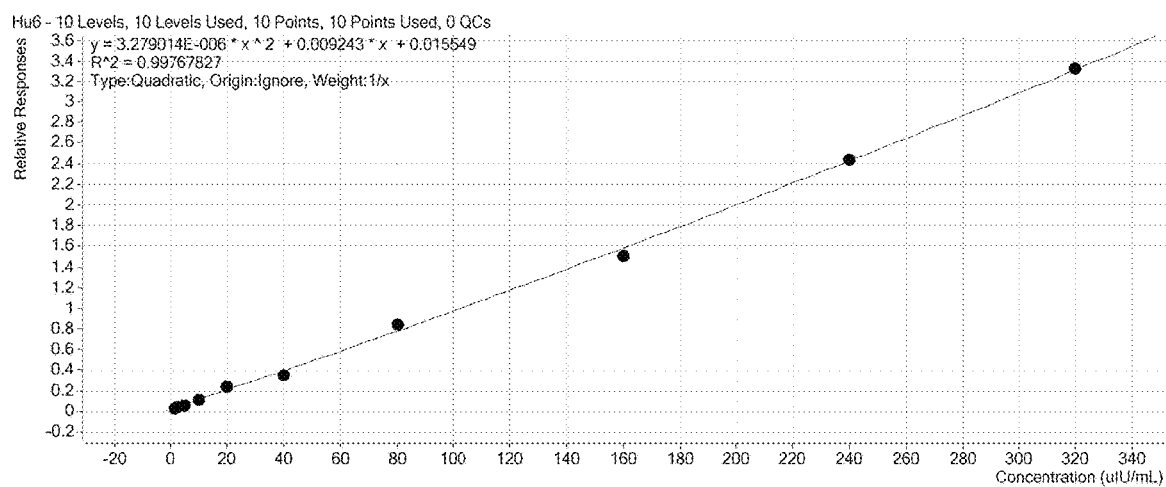
FIGS. 2A-2B show example calibration curve for insulin (FIG. 2A), and an expanded view of the low concentration region (FIG. 2B).
Figure 2B:
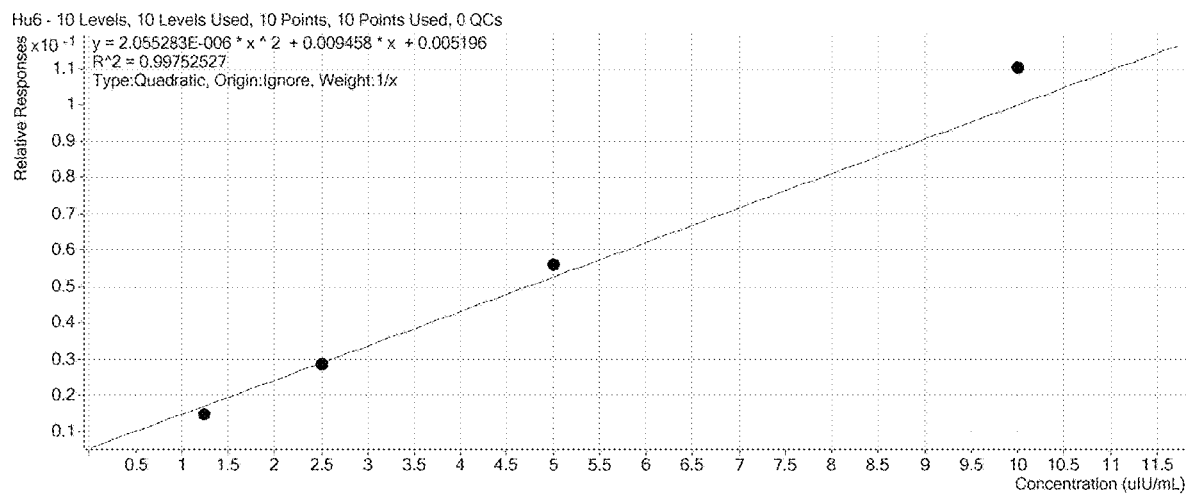
Figure 2C:
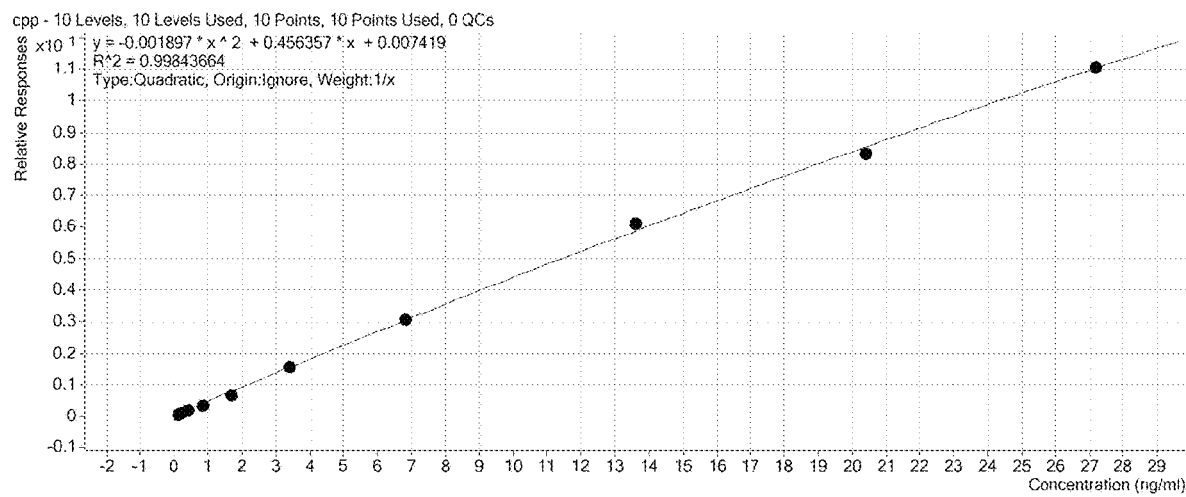
FIGS. 2C-2D show example calibration curve for C-peptide (FIG. 2C), and an expanded view of the low concentration region (FIG. 2D).
Figure 2D:
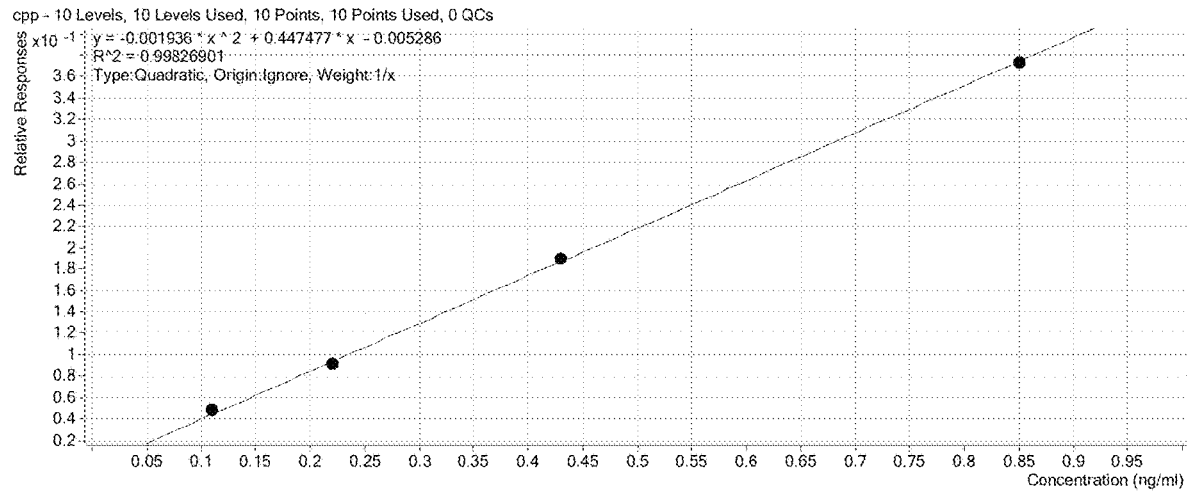

As used herein, the term "accuracy" (or "mass accuracy") with respect to mass spectrometry refers to potential deviation of the instrument response from the true m/z of the ion investigated. Accuracy is typically expressed in parts per million (ppm). The effect of differences in mass accuracy is illustrated in FIGS. 2A-D, which show the boundaries of potential differences between a detected m/z and the actual m/z for a theoretical peak at m/z of 1093.52094. FIG. 2A shows the potential range of detected m/z at an accuracy of 120 ppm. By contrast, FIG. 2B shows the potential range of detected m/z at an accuracy of 50 ppm. FIGS. 2C and 2D show the even narrower potential ranges of detected m/z at accuracies of 20 ppm and 10 ppm.

High resolution/high accuracy mass spectrometry methods of the present invention may be conducted on instruments capable of performing mass analysis with FWHM of greater than 10,000, 15,000, 20,000, 25,000, 50,000, 100,000, or even more. Likewise, methods of the present invention may be conducted on instruments capable of performing mass analysis with accuracy of less than 50 ppm, 20 ppm, 15 ppm, 10 ppm, 5 ppm, 3 ppm, or even less. Instruments capable of these performance characteristics may incorporate certain orbitrap mass analyzers, time-of-flight ("TOF") mass analyzers, or Fourier-transform ion cyclotron resonance mass analyzers. In preferred embodiments, the methods are carried out with an instrument which includes an orbitrap mass analyzer or a TOF mass analyzer.

The term "orbitrap" describes an ion trap consisting of an outer barrel-like electrode and a coaxial inner electrode. Ions are injected tangentially into the electric field between the electrodes and trapped because electrostatic interactions between the ions and electrodes are balanced by centrifugal forces as the ions orbit the coaxial inner electrode. As an ion orbits the coaxial inner electrode, the orbital path of a trapped ion oscillates along the axis of the central electrode at a harmonic frequency relative to the mass to charge ratio of the ion. Detection of the orbital oscillation frequency allows the orbitrap to be used as a mass analyzer with high accuracy (as low as 1-2 ppm) and high resolving power (FWHM) (up to about 200,000). A mass analyzer based on an orbitrap is described in detail in U.S. Pat. No. 6,995,364, incorporated by reference herein in its entirety. Use of orbitrap analyzers has been reported for qualitative and quantitative analyses of various analytes. See, e.g., U.S. Patent Application Pub. No. 2008/0118932 (filed Nov. 9, 2007); Bredehoft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

As used herein, the term "operating in negative ion mode" refers to those mass spectrometry methods where negative ions are generated and detected. The term "operating in positive ion mode" as used herein, refers to those mass spectrometry methods where positive ions are generated and detected. In preferred embodiments, mass spectrometry is conducted in positive ion mode.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the ionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about"

in the context of the mass of an ion or the mass/charge ratio of an ion refers to +/−0.50 atomic mass unit.

The determination of insulin in serum is primarily used for the diagnosis of glycemic disorders in diabetic and pre-diabetic patients in the assessment of insulin resistant syndromes. C-peptide is a peptide that connects insulin's 2 peptide chains and is released from proinsulin during processing and subsequently co-secreted from the pancreatic beta cell. Because of differences in half-life and hepatic clearance, peripheral blood levels of C-peptide and insulin are no longer equimolar but remain highly correlated. In the present embodiments, methods provided herein measure endogenous insulin and C-peptide for distinguishing (1) insulin-secreting tumors from exogenous insulin administration as a cause for hypoglycemia and (2) type 1 from type 2 diabetes.

In one aspect, provided herein are methods for measuring insulin levels in a patient by determining the amount of insulin and C-peptide in a sample using mass spectrometry. In some embodiments, the methods provided herein comprise multiplexed assays that simultaneously measure the amount of insulin and C-peptide in a sample by mass spectrometry. In some embodiments, methods comprise (a) subjecting insulin and C-peptide from a sample to an ionization source under conditions suitable to generate one or more insulin and C-peptide ions detectable by mass spectrometry; and (b) determining the amount of one or more insulin and C-peptide ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient.

In some embodiments, methods comprise (a) subjecting a sample to an enrichment process to obtain a fraction enriched in insulin and C-peptide, (b) subjecting the enriched insulin and C-peptide to an ionization source under conditions suitable to generate one or more insulin and C-peptide ions detectable by mass spectrometry; (c) determining the amount of one or more insulin and C-peptide ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient. In some embodiments, the enrichment process provided herein comprises immunocapture of insulin and C-peptide using antibodies. In some embodiments, methods comprise (a) immunocapturing insulin and C-peptide, (b) subjecting the immunocaptured insulin and C-peptide to an ionization source under conditions suitable to generate one or more insulin and C-peptide ions detectable by mass spectrometry; (c) determining the amount of one or more insulin and C-peptide ions by mass spectrometry. In some embodiments, immunocapturing provided herein comprises using anti-insulin antibodies and anti-C-peptide antibodies. In some embodiments, the antibodies provided herein are monoclonal antibodies. In some embodiments, the antibodies provided herein are mouse monoclonal antibodies. In some embodiments, the antibodies provided herein are monoclonal IgG antibodies. In some embodiments, the antibodies provided herein are polyclonal antibodies. In some embodiments, the anti-insulin antibodies and anti-C-peptide antibodies are immobilized on magnetic beads. In some embodiments, insulin and C-peptide immunocaptured on magnetic beads are washed and eluted.

In some embodiments, serum is delipidated prior to quantitation by mass spectrometry. In some embodiments, one or more delipidation reagent is used to remove lipids from the sample. In some embodiments, the delipidation reagent is CLEANASCITE®.

In some embodiments, the methods provided herein comprise purifying the samples prior to mass spectrometry. In some embodiments, the methods comprise purifying the samples using liquid chromatography. In some embodiments, liquid chromatography comprise high performance liquid chromatography (HPLC) or high turbulence liquid chromatograph (HTLC). In some embodiments, the methods comprise subjecting a sample to solid phase extraction (SPE).

In some embodiments, mass spectrometry comprises tandem mass spectrometry. In some embodiments, mass spectrometry is high resolution mass spectrometry. In some embodiments, mass spectrometry is high resolution/high accuracy mass spectrometry. In some embodiments, ionization is by electrospray ionization (ESI). In some embodiments, ionization is by atmospheric pressure chemical ionization (APCI). In some embodiments, said ionization is in positive ion mode.

In some embodiments, methods provided herein comprise adding internal standards to the sample. In some embodiments, the internal standard for insulin is bovine insulin. In some embodiments, the internal standard for C-peptide is C-peptide heavy internal standard. In some embodiments, the internal standard is labeled. In some embodiments, the internal standard is deuterated or isotopically labeled.

In some embodiments, the patient sample is a serum sample. In some embodiments, the patient sample is a plasma sample. In some embodiments, the patient sample is a blood, saliva, or urine sample.

In some embodiments, the sample is subjected to acidic conditions prior to ionization. In some embodiments, subjecting the sample to acidic conditions comprises subjecting enriched insulin and C-peptide to formic acid. In some embodiments, the sample is subjected to basic conditions prior to. In some embodiments, subjecting the sample to basic conditions comprises subjecting the sample to trizma. In some embodiments, subjecting the sample to basic conditions comprises subjecting the sample to trizma and ethanol.

In some embodiments, one or more ions comprise an insulin precursor ion with a mass to charge ratio (m/z) of 968.7±0.5. In some embodiments, one or more ions comprise one or more fragment ions selected from the group consisting of ions with m/z of 136.0±0.5, 226.1±0.5, and 345.2±0.5. In some embodiments, the insulin fragment ion with m/z of 226.1±0.5 is the quantifier ion. In some embodiments, one or more ions comprise a bovine insulin precursor ion with a mass to charge ratio (m/z) of 956.8±0.5. In some embodiments, one or more ions comprise one or more fragment ions selected from the group consisting of ions with m/z of 136.0±0.5, 226.1±0.5, and 315.2±0.5. In some embodiments, the bovine insulin fragment ion with m/z of 136.0±0.5 is the quantifier ion. In some embodiments, one or more ions comprise a C-peptide precursor ion with a mass to charge ratio (m/z) of 1007.7±0.5. In some embodiments, one or more ions comprise one or more fragment ions selected from the group consisting of ions with m/z of 533.3±0.5, 646.4±0.5, and 927.5±0.5. In some embodiments, any of the C-peptide fragment ion with m/z of 533.3±0.5, 646.4±0.5, and 927.5±0.5 can be used as the quantifier ion. In some embodiments, one or more ions comprise a C-peptide heavy internal standard precursor ion with a mass to charge ratio (m/z) of 1009.5±0.5. In some embodiments, one or more ions comprise one or more fragment ions selected from the group consisting of ions with m/z of 540.3±0.5, 653.4±0.5, and 934.5±0.5. In some embodiments, any of the C-peptide heavy internal standard fragment ion with m/z of 540.3±0.5, 653.4±0.5, and 934.5±0.5 can be used as the quantifier ion.

In some embodiments, provided herein is utilizing mass spectrometry for determining the amount of insulin and C-peptide in a sample, the methods include: (a) enriching insulin and C-peptide and in a sample by an extraction technique; (b) subjecting the purified insulin and C-peptide from step (a) to liquid chromatography to obtain a fraction enriched in insulin and C-peptide from the sample; (c) subjecting the enriched insulin to an ionization source under conditions suitable to generate an insulin precursor ion detectable by mass spectrometry; and (d) determining the amount of one or more of the fragment ions by mass spectrometry. In some embodiments, the amount of the one or more ions determined is used to determine the amount of insulin and C-peptide in the sample. In some embodiments, the amount of insulin and C-peptide in the sample is related to the amount of insulin in the patient. In some embodiments, the amount of insulin and C-peptide in the sample is used to determine the ratio of insulin to C-peptide in the patient. In some embodiments, the extraction technique provided herein comprises immunocapture of insulin and C-peptide using antibodies. In some embodiments, the extraction technique provided herein comprises solid phase extraction (SPE).

In some embodiments, the collision energy is within the range of about 40 to 60 eV. In some embodiments, the collision energy is within the range of about 40 to 50 eV.

In another aspect, provided herein are methods for determining the amount of insulin or C-peptide in a sample by mass spectrometry comprising (a) immunocapturing insulin or C-peptide, (b) subjecting the immunocaptured insulin or C-peptide to an ionization source under conditions suitable to generate one or more insulin or C-peptide ions detectable by mass spectrometry; (c) determining the amount of one or more insulin or C-peptide ions by mass spectrometry. In some embodiments, provided herein are methods for determining the amount of insulin in a sample by mass spectrometry comprising (a) immunocapturing insulin, (b) subjecting the immunocaptured insulin to an ionization source under conditions suitable to generate one or more insulin ions detectable by mass spectrometry; (c) determining the amount of one or more insulin ions by mass spectrometry. In some embodiments, provided herein are methods for determining the amount of C-peptide in a sample by mass spectrometry comprising (a) immunocapturing C-peptide, (b) subjecting the immunocaptured C-peptide to an ionization source under conditions suitable to generate one or more C-peptide ions detectable by mass spectrometry; (c) determining the amount of one or more C-peptide ions by mass spectrometry. In some embodiments, immunocapturing comprises using anti-insulin antibodies or anti-C-peptide antibodies. In some embodiments, the anti-insulin antibodies or anti-C-peptide antibodies are immobilized on magnetic beads. In some embodiments, insulin or C-peptide immunocaptured on magnetic beads are washed and eluted.

In another aspect, provided herein are methods for determining the amount of insulin analog in a sample by mass spectrometry comprising (a) immunocapturing insulin analog, (b) subjecting the immunocaptured insulin analog to an ionization source under conditions suitable to generate one or more insulin analog ions detectable by mass spectrometry; (c) determining the amount of one or more insulin analog ions by mass spectrometry. In some embodiments, the insulin analog is selected from aspart (NOVOLOG®), lispro (HUMALOG®), glulisine (APIDRA®), detemir (LEVEMIR®), degludec (TRESIBA®), glargine (LANTUS®), and NPH (HUMULIN R®/NOVOLIN N®). In some embodiments, the insulin analog is a rapid acting or long acting insulin analog.

In some embodiments, one or more ions comprise an insulin analog precursor ion with a mass to charge ratio (m/z) of 1011.2±0.5. In some embodiments, one or more ions comprise one or more fragment ions selected from the group consisting of ions with m/z of 136.0±0.5, 1179.0±0.5, and 175.0±0.5. In some embodiments, one or more ions comprise an insulin analog precursor ion with a mass to charge ratio (m/z) of 987.2±0.5. In some embodiments, one or more ions comprise one or more fragment ions selected from the group consisting of ions with m/z of 454.4±0.5 and 357.2±0.5. In some embodiments, one or more ions comprise an insulin analog precursor ion with a mass to charge ratio (m/z) of 971.5±0.5. In some embodiments, one or more ions comprise one or more fragment ions selected from the group consisting of ions with m/z of 219.0±0.5, 226.0±0.5, and 660.8±0.5. In some embodiments, one or more ions comprise an insulin analog precursor ion with a mass to charge ratio (m/z) of 971.5±0.5. In some embodiments, one or more ions comprise one or more fragment ions selected from the group consisting of ions with m/z of 199.0±0.5, 346.2±0.5, and 328.2±0.5. In some embodiments, one or more ions comprise an insulin analog precursor ion with a mass to charge ratio (m/z) of 1162.4±0.5. In some embodiments, one or more ions comprise one or more fragment ions with m/z of 217.3±0.5. In some embodiments, one or more ions comprise an insulin analog precursor ion with a mass to charge ratio (m/z) of 968.7±0.5. In some embodiments, one or more ions comprise one or more fragment ions with m/z of 217.3±0.5. In some embodiments, one or more ions comprise a bovine insulin precursor ion with a mass to charge ratio (m/z) of 956.8±0.5. In some embodiments, one or more ions comprise one or more fragment ions selected from the group consisting of ions with m/z of 136.0±0.5, 226.1±0.5, and 315.2±0.5.

In some embodiments, the sample is delipidated prior to quantitation by mass spectrometry. In some embodiments, the insulin analog is extracted by a base extraction. In some embodiments, mass spectrometry comprises tandem mass spectrometry. In some embodiments, mass spectrometry is high resolution mass spectrometry. In some embodiments, mass spectrometry is high resolution/high accuracy mass spectrometry.

In another aspect, provided herein are methods for diagnosis of glycemic disorders or insulin resistant syndromes in diabetic and pre-diabetic patients. In some embodiments, the methods of quantitation of endogenous insulin and C-peptide provided herein are used for diagnosing diabetes. In some embodiments, the methods of quantitation of endogenous insulin and C-peptide provided herein are used for distinguishing insulin-secreting tumors from exogenous insulin administration as a cause for hypoglycemia. In some embodiments, the methods of quantitation of endogenous insulin and C-peptide provided herein are used for distinguishing type 1 diabetes from type 2 diabetes. In some embodiments, the methods of quantitation of endogenous insulin and C-peptide provided herein are used for assessing the risk of diabetes in pre-diabetic patients.

In another aspect, provided herein are methods for diagnosis or prognosis of glycemic disorders or insulin resistant syndromes in diabetic and pre-diabetic patients comprising comparing the relative amount of intact insulin and insulin B chain. In another aspect, provided herein are methods for diagnosis or prognosis of glycemic disorders or insulin resistant syndromes in diabetic and pre-diabetic patients comprising determining the ratio of intact insulin and insulin B chain. In some embodiments, the methods comprise determining the amount of intact insulin and insulin B chain. In some embodiments, the amount of intact insulin and insulin B chain are determined simultaneously in a single assay. In some embodiments, the amount of intact insulin and insulin B chain are determined separately. In some embodiments, an aberrant or abnormal amount or ratio of intact insulin or insulin B chain relative to each other indicates glycemic disorders or insulin resistant syndromes.

In some embodiments, provided herein are methods for diagnosis or prognosis of glycemic disorders or insulin resistant syndromes in diabetic and pre-diabetic patients comprising determining the amount of intact insulin and insulin B-chain in a sample by mass spectrometry. In some embodiments, provided herein are methods for diagnosis or prognosis of glycemic disorders or insulin resistant syndromes in diabetic and pre-diabetic patients comprising determining the ratio of intact insulin and insulin B-chain in a sample by mass spectrometry. In some embodiments, methods comprise (a) subjecting intact insulin and insulin B-chain from a sample to an ionization source under conditions suitable to generate one or more intact insulin and insulin B-chain ions detectable by mass spectrometry; and (b) determining the amount of one or more intact insulin and insulin B-chain ions by mass spectrometry. In some embodiments, an aberrant or abnormal amount or ratio of intact insulin or insulin B chain relative to each other indicates glycemic disorders or insulin resistant syndromes.

In some embodiments, provided herein are methods for diagnosis or prognosis of glycemic disorders or insulin resistant syndromes in diabetic and pre-diabetic patients comprising determining the amount of intact insulin and insulin B-chain in a sample by an immunoassay. In some embodiments, provided herein are methods for diagnosis or prognosis of glycemic disorders or insulin resistant syndromes in diabetic and pre-diabetic patients comprising determining the ratio of intact insulin and insulin B-chain in a sample by an immunoassay. In some embodiments, an aberrant or abnormal amount or ratio of intact insulin or insulin B chain relative to each other indicates glycemic disorders or insulin resistant syndromes.

In some embodiments, provided herein are methods for diagnosis or prognosis of diabetes in a human comprising comparing the relative amount of intact insulin and insulin B chain. In some embodiments, provided herein are methods for diagnosis or prognosis of diabetes in a human comprising determining the ratio of intact insulin and insulin B chain. In some embodiments, the methods comprise determining the amount of intact insulin and insulin B chain. In some embodiments, the amount of intact insulin and insulin B chain are determined simultaneously in a single assay. In some embodiments, the amount of intact insulin and insulin B chain are determined separately. In some embodiments, an aberrant or abnormal amount or ratio of intact insulin or insulin B chain relative to each other indicates diabetes or prediabetes.

In some embodiments, provided herein are methods for diagnosis or prognosis of diabetes in a human comprising determining the amount of intact insulin and insulin B-chain in a sample by mass spectrometry. In some embodiments, provided herein are methods for diagnosis or prognosis of diabetes in a human comprising determining the ratio of intact insulin and insulin B-chain in a sample by mass spectrometry. In some embodiments, methods comprise (a) subjecting intact insulin and insulin B-chain from a sample to an ionization source under conditions suitable to generate one or more intact insulin and insulin B-chain ions detectable by mass spectrometry; and (b) determining the amount of one or more intact insulin and insulin B-chain ions by mass spectrometry. In some embodiments, an aberrant or abnormal amount or ratio of intact insulin or insulin B chain relative to each other indicates diabetes or prediabetes.

In some embodiments, provided herein are methods for diagnosis or prognosis of diabetes in a human comprising determining the amount of intact insulin and insulin B-chain in a sample by an immunoassay. In some embodiments, an aberrant or abnormal amount or ratio of intact insulin or insulin B chain relative to each other indicates diabetes or prediabetes.

In some embodiments, the methods of quantitation of endogenous intact insulin and insulin B chain provided herein are used for distinguishing insulin-secreting tumors from exogenous insulin administration as a cause for hypoglycemia. In some embodiments, the methods of quantitation of endogenous intact insulin and insulin B chain provided herein are used for distinguishing type 1 diabetes from type 2 diabetes. In some embodiments, the methods of quantitation of endogenous intact insulin and insulin B chain provided herein are used for assessing the risk of diabetes in pre-diabetic patients.

In another aspect, provided herein are methods for assessing the insulin degrading enzyme (IDE) activity comprising determining the ratio of intact insulin to insulin B chain.

In some embodiments, provided herein are methods for measuring insulin levels in a patient by determining the amount of intact insulin and insulin B-chain in a sample using mass spectrometry.

In some embodiments, provided herein are methods for measuring insulin levels in a patient by determining the amount of intact insulin and insulin B-chain in a sample using mass spectrometry. In certain embodiments, the methods provided herein comprise multiplexed assays that simultaneously measure the amount of intact insulin and insulin B-chain in a sample by mass spectrometry. In some embodiments, methods comprise (a) subjecting intact insulin and insulin B-chain from a sample to an ionization source under conditions suitable to generate one or more intact insulin and insulin B-chain ions detectable by mass spectrometry; and (b) determining the amount of one or more intact insulin and insulin B-chain ions by mass spectrometry. In some embodiments, the amount of the one or more ions determined is used to determine the amount of intact insulin and insulin B-chain in the sample. In some embodiments, the amount of intact insulin and insulin B-chain in the sample is related to the amount of insulin in the patient. In some embodiments, the amount of intact insulin and insulin B-chain in the sample is used to determine the ratio of intact insulin and insulin B-chain in the patient.

In some embodiments, methods comprise (a) subjecting a sample to an enrichment process to obtain a fraction enriched in intact insulin and insulin B-chain, (b) subjecting the enriched intact insulin and insulin B-chain to an ionization source under conditions suitable to generate one or more intact insulin and insulin B-chain ions detectable by mass spectrometry; (c) determining the amount of one or more intact insulin and insulin B-chain ions by mass spectrometry. In some embodiments, the amount of the one or more ions determined is used to determine the amount of intact insulin and insulin B-chain in the sample. In some embodiments, the amount of intact insulin and insulin B-chain in the sample is related to the amount of insulin in the patient. In some embodiments, the amount of intact insulin and insulin B-chain in the sample is used to determine the ratio of intact insulin and insulin B-chain in the patient. In some embodiments, the enrichment process provided herein comprises immunocapture of intact insulin and insulin B-chain using antibodies. In some embodiments, methods comprise (a) immunocapturing intact insulin and insulin B-chain, (b) subjecting the immunocaptured intact insulin and insulin B-chain to an ionization source under conditions suitable to generate one or more intact insulin and insulin B-chain ions detectable by mass spectrometry; (c) determining the amount of one or more intact insulin and insulin B-chain ions by mass spectrometry. In some embodiments, immunocapturing provided herein comprises using anti-insulin antibodies and anti-insulin B-chain antibodies. In some embodiments, the antibodies provided herein are monoclonal antibodies. In some embodiments, the antibodies provided herein are mouse monoclonal antibodies. In some embodiments, the antibodies provided herein are monoclonal IgG antibodies. In some embodiments, the antibodies provided herein are polyclonal antibodies. In some embodiments, the anti-insulin antibodies and anti-insulin B-chain antibodies are immobilized on magnetic beads. In some embodiments, insulin and insulin B-chain immunocaptured on magnetic beads are washed and eluted.

In some embodiments, serum is delipidated prior to quantitation by mass spectrometry. In some embodiments, one or more delipidation reagent is used to remove lipids from the sample. In some embodiments, the delipidation reagent is CLEANASCITE®.

In some embodiments, the methods provided herein comprise purifying the samples prior to mass spectrometry. In some embodiments, the methods comprise purifying the samples using liquid chromatography. In some embodiments, liquid chromatography comprise high performance liquid chromatography (HPLC) or high turbulence liquid chromatograph (HTLC). In some embodiments, the methods comprise subjecting a sample to solid phase extraction (SPE).

In some embodiments, mass spectrometry comprises tandem mass spectrometry. In some embodiments, mass spectrometry is high resolution mass spectrometry. In some embodiments, mass spectrometry is high resolution/high accuracy mass spectrometry. In some embodiments, ionization is by electrospray ionization (ESI). In some embodiments, ionization is by atmospheric pressure chemical ionization (APCI). In some embodiments, said ionization is in positive ion mode. In some embodiments, methods provided herein comprise adding internal standards to the sample. In some embodiments, the internal standard is labeled. In some embodiments, the internal standard is deuterated or isotopically labeled.

In some embodiments, the patient sample is a serum sample. In some embodiments, the patient sample is a plasma sample. In some embodiments, the patient sample is a blood, saliva, or urine sample.

In some embodiments, the sample is subjected to acidic conditions prior to ionization. In some embodiments, subjecting the sample to acidic conditions comprises subjecting enriched insulin and insulin B-chain to formic acid. In some embodiments, the sample is subjected to basic conditions prior to. In some embodiments, subjecting the sample to basic conditions comprises subjecting the sample to trizma. In some embodiments, subjecting the sample to basic conditions comprises subjecting the sample to trizma and ethanol.

In some embodiments, one or more ions comprise an insulin precursor ion with a mass to charge ratio (m/z) of 968.7±0.5. In some embodiments, one or more ions comprise one or more fragment ions selected from the group consisting of ions with m/z of 136.0±0.5, 226.1±0.5, and 345.2±0.5. In some embodiments, the insulin fragment ion with m/z of 226.1±0.5 is the quantifier ion. In some embodiments, one or more ions comprise an insulin B chain precursor ion selected from the group consisting of ions with m/z of 1144.2±0.5, 858.3±0.5, and 686.8±0.5. In some embodiments, one or more ions comprise one or more fragment ions selected from the group consisting of ions with m/z of 824.9±0.5, 768.4±0.5, 752.8±0.5, 345.0±0.5, and 226.2±0.5, such as the group consisting of ions with m/z of 345.0±0.5 and 226.2±0.5. In some embodiments, one or more ions comprise two or more fragment ions selected from the group consisting of a fragment ion from an insulin B chain precursor ion with m/z of 1144.2±0.5, a fragment ion from an insulin B chain precursor ion with m/z of 858.3±0.5, and a fragment ion from an insulin B chain precursor ion with m/z of 686.8±0.5. In some embodiments, one or more fragment ions from each precursor ion comprise one or more fragment ions selected from the group consisting of ions with m/z of 824.9±0.5, 768.4±0.5, 752.8±0.5, 345.0±0.5, and 226.2±0.5, such as the group consisting of ions with m/z of 345.0±0.5 and 226.2±0.5.

In alternative embodiments, the insulin B chains are chemically modified prior to ionization. In some embodiments, chemical modification comprises alkylating said insulin B chains. In some embodiments, one or more ions comprise an alkylated insulin B chain precursor ion selected from the group consisting of ions with m/z of 1181.9±0.5, 886.9±0.5, and 709.8±0.5. In some embodiments, one or more ions comprise one or more fragment ions selected from the group of ions with m/z of 345.0±0.5 and 226.2±0.5. In some embodiments, one or more ions comprise two or more fragment ions selected from the group consisting of a fragment ion from an alkylated insulin B chain precursor ion with a mass to charge ratio (m/z) of 1181.9±0.5, a fragment ion from an alkylated insulin B chain precursor ion with m/z of 886.9±0.5, and a fragment ion from an alkylated insulin B chain precursor ion with m/z of 709.8±0.5. In some related embodiments, the fragment ion from each precursor ion comprises an ion selected from the group consisting of ions with m/z of 345.0±0.5 and 226.2±0.5.

In another aspect, provided herein are methods for diagnosis of glycemic disorders or insulin resistant syndromes in diabetic and pre-diabetic patients. In some embodiments, the methods of quantitation of endogenous intact insulin and insulin B chain provided herein are used for diagnosing diabetes. In some embodiments, the methods of quantitation of endogenous insulin and insulin B chain provided herein are used for diagnosing glycemic disorders or insulin resistant syndromes in diabetic and pre-diabetic patients. In some embodiments, the methods of quantitation of endogenous intact insulin and insulin B chain provided herein are used for distinguishing insulin-secreting tumors from exogenous insulin administration as a cause for hypoglycemia. In some embodiments, the methods of quantitation of endogenous intact insulin and insulin B chain provided herein are used for distinguishing type 1 diabetes from type 2 diabetes. In some embodiments, the methods of quantitation of endogenous intact insulin and insulin B chain provided herein are used for assessing the risk of diabetes in pre-diabetic patients.

In another aspect, provided herein are methods for assessing the insulin degrading enzyme (IDE) activity comprising determining the ratio of intact insulin to insulin B chain by mass spectrometry as described herein.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma and serum. Such samples may be obtained, for example, from a patient; that is, a living person, male or female, presenting oneself in a clinical setting for diagnosis, prognosis, or treatment of a disease or condition. In embodiments where the sample comprises a biological sample, the methods may be used to determine the amount of insulin in the sample when the sample was obtained from the biological source.

Insulin is a small peptide consisting of fifty-one amino acids. Insulin is composed of two chains, the A chain and the B chain, linked by disulfide bridges between cysteine residues. The A chain has twenty one amino acids and the B chain has thirty amino acids.

The present invention also contemplates kits for an insulin quantitation assay. A kit for an insulin quantitation assay may include a kit comprising the compositions provided herein. For example, a kit may include packaging material and measured amounts of an isotopically labeled internal standard, in amounts sufficient for at least one assay. Typically, the kits will also include instructions recorded in a tangible form (e.g., contained on paper or an electronic medium) for using the packaged reagents for use in an insulin quantitation assay.

Calibration and QC pools for use in embodiments of the present invention are preferably prepared using a matrix similar to the intended sample matrix, provided that insulin is essentially absent.

Sample Preparation for Mass Spectrometric Analysis

In preparation for mass spectrometric analysis, insulin may be enriched relative to one or more other components in the sample by various methods known in the art, including for example, immunocapture, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

One method of sample purification that may be used prior to mass spectrometry is applying a sample to a solid-phase extraction (SPE) column under conditions where the analyte of interest is reversibly retained by the column packing material, while one or more other materials are not retained. In this technique, a first mobile phase condition can be employed where the analyte of interest is retained by the column, and a second mobile phase condition can subsequently be employed to remove retained material from the column, once the non-retained materials are washed through.

In some embodiments, insulin in a sample may be reversibly retained on a SPE column with a packing material comprising an alkyl bonded surface. For example, in some embodiments, a C-8 on-line SPE column (such as an Oasis HLB on-line SPE column/cartridge (2.1 mm×20 mm) from Phenomenex, Inc. or equivalent) may be used to enrich insulin prior to mass spectrometric analysis. In some embodiments, use of an SPE column is conducted with HPLC Grade 0.2% aqueous formic acid as a wash solution, and use of 0.2% formic acid in acetonitrile as an elution solution.

In other embodiments, the methods include immunopurifying insulin prior to mass spectrometry analysis. The immunopurification step may be performed using any of the immunopurification methods well known in the art. Often the immunopurification procedure utilizes antibodies bound, conjugated, immobilized or otherwise attached to a solid support, for example a column, well, tube, capsule, particle or the like. Generally, immunopurification methods involve (1) incubating a sample containing the analyte of interest with antibodies such that the analyte binds to the antibodies, (2) performing one or more washing steps, and (3) eluting the analyte from the antibodies.

In certain embodiments the incubation step of the immunopurification is performed with the antibodies free in solution and the antibodies are subsequently bound or attached to a solid surface prior to the washing steps. In certain embodiments this can be achieved using a primary antibody that is an anti-insulin antibody and a secondary antibody attached to a solid surface that has an affinity to the primary anti-insulin antibody. In alternative embodiments, the primary antibody is bound to the solid surface prior to the incubation step.

Appropriate solid supports include without limitation tubes, slides, columns, beads, capsules, particles, gels, and the like. In some preferred embodiments, the solid support is a multi-well plate, such as, for example, a 96 well plate, a 384-well plate or the like. In some embodiments the solid support are sepharose or agarose beads or gels. There are numerous methods well known in the art by which antibodies (for example, an insulin antibody or a secondary antibody) may be bound, attached, immobilized or coupled to a solid support, e.g., covalent or non-covalent linkages adsorption, affinity binding, ionic linkages and the like. In some embodiments antibodies are coupled using CNBr, for example the antibodies may be coupled to CNBr activated sepharose. In other embodiments, the antibody is attached to the solid support through an antibody binding protein such as protein A, protein G, protein A/G, or protein L.

The washing step of the immunopurification methods generally involve washing the solid support such that the insulin remain bound to the anti-insulin antibodies on the solid support. The elution step of the immunopurification generally involves the addition of a solution that disrupts the binding of insulin to the anti-insulin antibodies. Exemplary elution solutions include organic solutions, salt solutions, and high or low pH solutions.

Another method of sample purification that may be used prior to mass spectrometry is liquid chromatography (LC). In liquid chromatography techniques, an analyte may be purified by applying a sample to a chromatographic analytical column under mobile phase conditions where the analyte of interest elutes at a differential rate in comparison to one or more other materials. Such procedures may enrich the amount of one or more analytes of interest relative to one or more other components of the sample.

Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a partition process and may select LC, including HPLC, instruments and columns that are suitable for use with C peptide. The chromatographic analytical column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In some embodiments, the chromatographic analytical column is a monolithic C-18 column. The chromatographic analytical column includes an inlet port for receiving a sample and an outlet port for discharging an effluent that includes the fractionated sample. The sample may be supplied to the inlet port directly, or from a SPE column, such as an on-line SPE column or a TFLC column. In some embodiments, an on-line filter may be used ahead of the SPE column and or HPLC column to remove particulates and phospholipids in the samples prior to the samples reaching the SPE and/or TFLC and/or HPLC columns.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytypic (i.e. mixed) mode. During chromatography, the separation of materials is effected by variables such as choice of eluent (also known as a "mobile phase"), elution mode, gradient conditions, temperature, etc.

In some embodiments, insulin in a sample is enriched with HPLC. This HPLC may be conducted with a monolithic C-18 column chromatographic system, for example, an Onyx Monolithic C-18 column from Phenomenex Inc. (50× 2.0 mm), or equivalent. In certain embodiments, HPLC is performed using HPLC Grade 0.2% aqueous formic acid as solvent A, and 0.2% formic acid in acetonitrile as solvent B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of insulin prior to mass spectrometry. In such embodiments, samples may be extracted using a TFLC column which captures the analyte. The analyte is then eluted and transferred on-line to an analytical HPLC column. For example, sample extraction may be accomplished with a TFLC extraction cartridge with a large particle size (50 μm) packing. Sample eluted off of this column may then be transferred on-line to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, one or more of the above purification techniques may be used in parallel for purification of insulin to allow for simultaneous processing of multiple samples. In some embodiments, the purification techniques employed exclude immunopurification techniques, such as immunoaffinity chromatography.

Detection and Quantitation of Insulin by Mass Spectrometry

Mass spectrometry is performed using a mass spectrometer, which includes an ion source for ionizing the fractionated sample and creating charged molecules for further analysis. In various embodiments, insulin may be ionized by any method known to the skilled artisan. For example, ionization of insulin may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. insulin may be ionized in positive or negative mode. In preferred embodiments, insulin is ionized by ESI in positive ion mode.

In mass spectrometry techniques generally, after the sample has been ionized, the positively or negatively charged ions thereby created may be analyzed to determine a mass to charge ratio (m/z). Various analyzers for determining m/z include quadrupole analyzers, ion traps analyzers, time-of-flight analyzers, Fourier transform ion cyclotron resonance mass analyzers, and orbitrap analyzers. Some exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). In some embodiments, the mass-to-charge ratio is determined using a quadrupole analyzer. In a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of insulin. The relative abundance of a given ion may be converted into an absolute amount of the original analyte using calibration standard curves based on peaks of one or more ions of an internal or external molecular standard.

One may enhance the resolution of MS techniques employing certain mass spectrometric analyzers through "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples. In certain embodiments, a mass spectrometric instrument with multiple quadrupole analyzers (such as a triple quadrupole instrument) is employed to conduct tandem mass spectrometric analysis.

In certain embodiments using a MS/MS technique, precursor ions are isolated for further fragmentation, and collision activated dissociation (CAD) is used to generate fragment ions from the precursor ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In some embodiments, insulin in a sample is detected and/or quantified using MS/MS as follows. Insulin is enriched in a sample by first subjecting the sample to SPE, then to liquid chromatography, preferably HPLC; the flow of liquid solvent from a chromatographic analytical column enters the heated nebulizer interface of an MS/MS analyzer; and the solvent/analyte mixture is converted to vapor in the heated charged tubing of the interface. During these processes, the analyte (i.e., insulin) is ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the m/z of an insulin ion. Precursor ions with the correct m/z are allowed to pass into the collision chamber (Q2), while unwanted ions with any other m/z collide with the sides of the quadrupole and are eliminated. Precursor ions entering Q2 collide with neutral gas molecules (such as Argon molecules) and fragment. The fragment ions generated are passed into quadrupole 3 (Q3), where the fragment ions are selected for detection.

Ionization of insulin may result in multiply charged precursor ions (such as precursor ions of 4+, 5+, 6+, etc.). Ionization conditions, particularly the pH of the buffer utilized in electrospray techniques, greatly influence the identity and quantity of insulin precursor ions generated. For example, under acidic conditions, positive electrospray ionization may predominately generate 5+ and 6+ charged insulin precursor ions with m/z of 1162.5±0.5 and 968.5±0.5, respectively. However, under basic conditions, positive electrospray ionization may predominately generate 4+ and 5+ charged insulin precursor ions with m/z of 1453.75±0.5 and 1162.94±0.5, respectively. The methods may utilize either acidic or basic conditions; preferably acidic conditions.

The methods may involve MS/MS performed in either positive or negative ion mode; preferably positive ion mode. In certain embodiments, the electrospray buffer is acidic and Q1 selects for insulin precursor ions with an m/z of about 1162.5±0.5 or 968.5±0.5. Fragmentation of either of these insulin precursor ions generates fragment ions with m/z of about 226.21±0.5, and/or 135.6±0.5. Thus, in embodiments where Q1 selects for one or more insulin precursor ions selected from the group consisting of ions with m/z of about 1162.5±0.5 and 968.5±0.5, Q3 may select one or more fragment ions selected from the group of ions with m/z of about 226.21±0.5, and 135.6±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

Alternate modes of operating a tandem mass spectrometric instrument that may be used in certain embodiments include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

In other embodiments, a high resolution/high accuracy mass analyzer may be used for quantitative analysis of insulin according to methods of the present invention. To achieve acceptable precision for quantitative results, the mass spectrometer must be capable of exhibiting a resolving power (FWHM) of 10,000 or more, with accuracy of about 50 ppm or less for the ions of interest; preferably the mass spectrometer exhibits a resolving power (FWHM) of 18,000 or better, with accuracy of about 5 ppm or less; such as a resolving power (FWHM) of 20,000 or better and accuracy of about 3 ppm or less; such as a resolving power (FWHM) of 25,000 or better and accuracy of about 3 ppm or less. Three exemplary analyzers capable of exhibiting the requisite level of performance for insulin ions are orbitrap mass analyzers, certain TOF mass analyzers, and Fourier transform ion cyclotron resonance mass analyzers.

Elements found in biological active molecules, such as carbon, oxygen, and nitrogen, naturally exist in a number of different isotopic forms. For example, most carbon is present as $^{12}C$, but approximately 1% of all naturally occurring carbon is present as $^{13}C$. Thus, some fraction of naturally occurring molecules containing at least one carbon atom will contain at least one $^{13}C$ atom. Inclusion of naturally occurring elemental isotopes in molecules gives rise to multiple molecular isotopic forms. The difference in masses of molecular isotopic forms is at least 1 atomic mass unit (amu). This is because elemental isotopes differ by at least one neutron (mass of one neutron 1 amu). When molecular isotopic forms are ionized to multiply charged states, the mass distinction between the isotopic forms can become difficult to discern because mass spectrometric detection is based on the mass to charge ratio (m/z). For example, two isotopic forms differing in mass by 1 amu that are both ionized to a 5+ state will exhibit differences in their m/z of only 0.2. High resolution/high accuracy mass spectrometers are capable of discerning between isotopic forms of highly multiply charged ions (such as ions with charges of ±2, ±3, ±4, ±5, or higher).

Figure 5A:
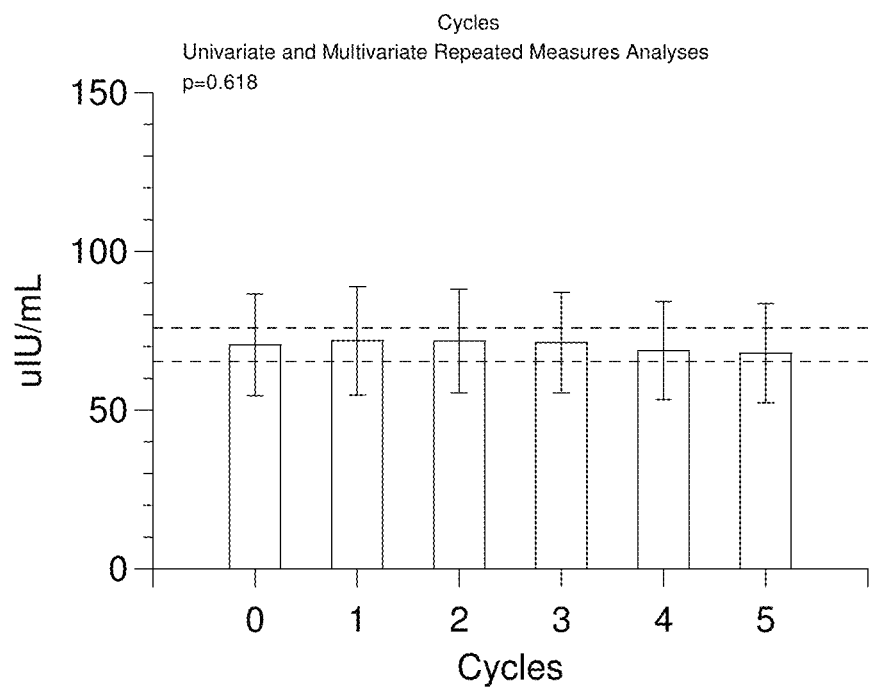
FIGS. 5A-5B show freeze thaw sample stability for insulin (5A) and C-peptide (5B).
Figure 5B:
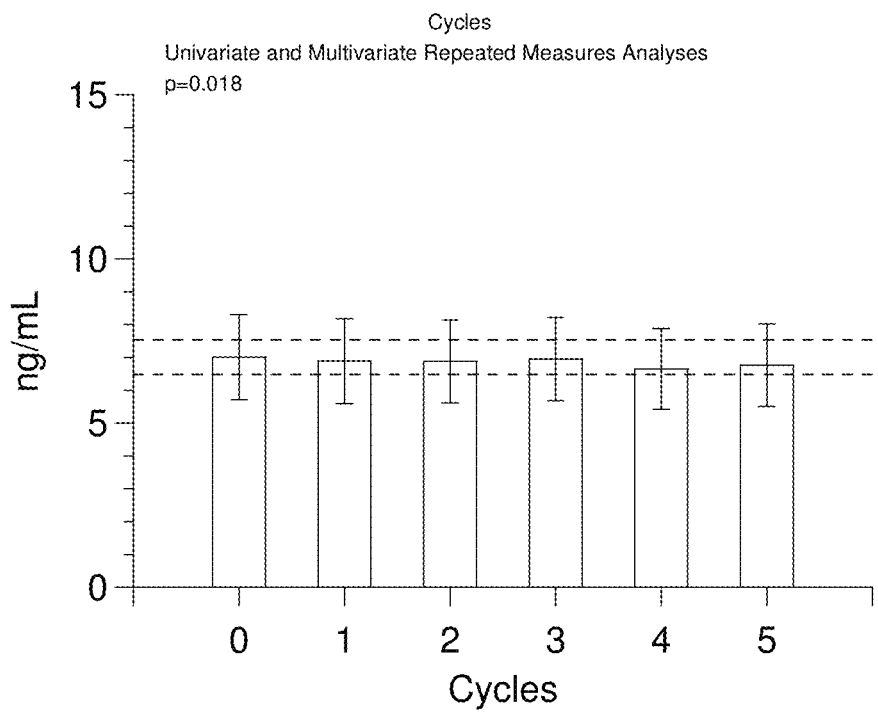
Figure 6A:
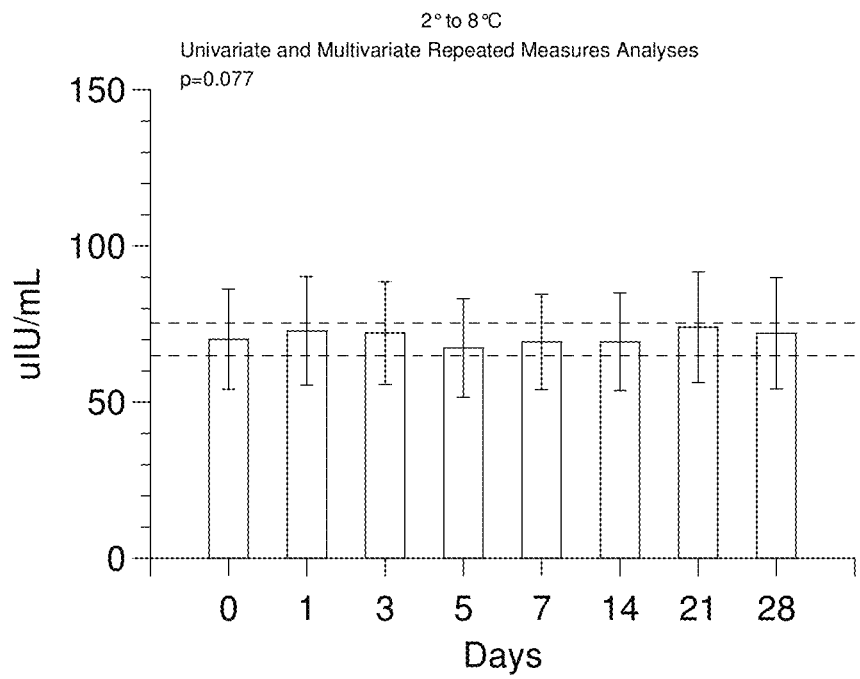
FIGS. 6A-6B show refrigerated temperature sample stability for insulin (6A) and C-peptide (6B).
Figure 6B:
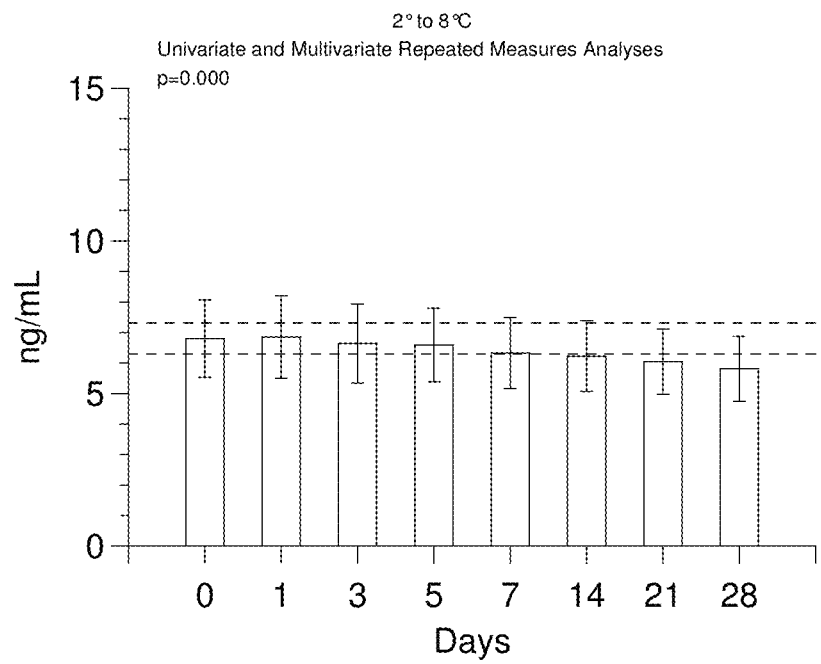

Due to naturally occurring elemental isotopes, multiple isotopic forms typically exist for every molecular ion (each of which may give rise to a separately detectable spectrometric peak if analyzed with a sensitive enough mass spectrometric instrument). The m/z ratios and relative abundances of multiple isotopic forms collectively comprise an isotopic signature for a molecular ion. In some embodiments, the m/z ratios and relative abundances for two or more molecular isotopic forms may be utilized to confirm the identity of a molecular ion under investigation. In some embodiments, the mass spectrometric peak from one or more isotopic forms is used to quantitate a molecular ion. In some related embodiments, a single mass spectrometric peak from one isotopic form is used to quantitate a molecular ion. In other related embodiments, a plurality of isotopic peaks are used to quantitate a molecular ion. In these later embodiments, the plurality of isotopic peaks may be subject to any appropriate mathematical treatment. Several mathematical treatments are known in the art and include, but are not limited to summing the area under multiple peaks, or averaging the response from multiple peaks. Exemplary spectra demonstrating multiple isotopic forms of 5+ and 6+ insulin ions are seen in FIGS. 4-6. As seen in FIG. 5A-B, peaks from various isotopic forms of the 5+ insulin ion are seen at about 1161.72, 1161.92, 1162.12, 1162.32, 1162.52, 1162.72, 1162.92, 1163.12, and 1163.32. As seen in FIG. 6A-B, peaks from various isotopic forms of the 6+ insulin ion are seen at about 968.28, 968.45, 968.62, 968.79, 968.95, 969.12, 969.28, 968.45, and 969.61. Note, however, that the precise masses observed for isotopic variants of any ion may vary slightly because of instrumental variance.

In some embodiments, the relative abundance of one or more ion is measured with a high resolution/high accuracy mass spectrometer in order to qualitatively assess the amount of insulin in the sample. In some embodiments, the one or more ions measured by high resolution/high accuracy mass spectrometry are multiply charged insulin ions. These multiply charged ions may include one or more of ions with a m/z within the ranges of about 1453±0.8 (i.e., one or more monoisotopic peaks from a 4+ ion), and/or 1162±1 (i.e., one or more monoisotopic peaks from a 5+ ion), and/or about 968.8±1.5 (i.e., one or more monoisotopic peaks from a 6+ ion).

Use of high resolution orbitrap analyzers has been reported for qualitative and quantitative analyses of various analytes. See, e.g., U.S. Patent Application Pub. No. 2008/0118932 (filed Nov. 9, 2007); Bredehoft, et al., Rapid Commun. Mass Spectrom., 2008, 22:477-485; Le Breton, et al., Rapid Commun. Mass Spectrom., 2008, 22:3130-36; Thevis, et al., Mass Spectrom. Reviews, 2008, 27:35-50; Thomas, et al., J. Mass Spectrom., 2008, 43:908-15; Schenk, et al., BMC Medical Genomics, 2008, 1:41; and Olsen, et al., Nature Methods, 2007, 4:709-12.

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of insulin. Methods of generating and using such standard curves are well known in the art and one of ordinary skill is capable of selecting an appropriate internal standard. For example, in preferred embodiments one or more forms of isotopically labeled insulin may be used as internal standards. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2$H), $^{13}$C, and $^{15}$N. One or more isotopic labels can be incorporated at one or more positions in the molecule and one or more kinds of isotopic labels can be used on the same isotopically labeled molecule.

In other embodiments, insulin may be subjected to a chemical treatment to generate insulin's constituent chains prior to mass spectrometric analysis. Insulin's B-chain may be separated by any chemical treatment known in the art to cause disulfide reduction. For example, insulin may be treated with TCEP (tris(2-carboxyethyl)phosphine) to reduce insulin's disulfide bridges and separate the A chain and B chain.

The B-chains may then be subject to any one or more of the purification steps described above for purification of insulin. In preferred embodiments, B-chains are subject to purification by HPLC prior to mass spectrometric analysis.

Once purified, B-chains are then subjected to an ionization source. As with insulin, the skilled artisan will understand that the choice of ionization method may be determined based on the analyte to be measured, type of sample, the type of detector, the choice of positive versus negative mode, etc. Insulin B-chains may be ionized in positive or negative mode. In preferred embodiments, insulin B-chains are ionized by ESI in positive mode.

Ionization of insulin B-chains may result in multiply charged B-chain precursor ions (such as precursor ions of 3+, 4+, 5+, etc.). For example, positive electrospray ionization of insulin B-chain molecules may generate 3+, 4+, and 5+ charged B-chain precursor ions with m/z of 1144.2±0.5, 858.3±0.5, and 686.8±0.5, respectively. Similar to insulin, the identity and quantity of the multiply charged species generated from ionization of insulin B-chains is affected by the ionization conditions employed. In preferred embodiments, insulin B-chains are ionized under acidic conditions.

In embodiments where insulin B-chains are subject to tandem mass spectrometric analysis, Q1 may select for one or more insulin B-chain precursor ions with an m/z of about 1144.2±0.5, 858.3±0.5, and 686.8±0.5. Fragmentation of these three insulin B-chain precursor ions may generate fragment ions with m/z of about 825.4±0.5, 768.5±0.5, 753.2±0.5, 345.0±0.5, and 226.2±0.5. Thus, in embodiments where Q1 selects for one or more insulin B-chain precursor ions selected from the group consisting of ions with m/z of about 1144.2±0.5, 858.3±0.5, and 686.8±0.5, Q3 may select one or more fragment ions selected from the group of ions with m/z of about 825.4±0.5, 768.5±0.5, 753.2±0.5, 345.0±0.5, and 226.2±0.5; preferably selected from the group of ions with m/z of about 345.0±0.5 and 226.2±0.5. In certain embodiments, the relative abundance of a single fragment ion from a single precursor ion may be measured. Alternatively, the relative abundances of two or more fragment ions from a single precursor ion may be measured. In these embodiments, the relative abundance of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

Quantitation of Insulin by Quantitation of Chemically Modified Insulin B Chain by Mass Spectrometry In alternative embodiments, insulin B-chains may be subjected to one or more chemical modification steps prior to ionization and/or purification. For example, once separated, insulin B-chain molecules may undergo carbamidomethylation to fully alkylate constituent cysteines. For example, carbamidomthylation may be achieved by subjecting insulin B-chain to react with iodoacetamide after reduction with DTT (1,4-Dithiothreitol). Carbamidomethylation of an insulin B-chain results in the alkylation of 2 cysteines, causing a mass increase of about 114.04 amu (about 57.02 per cysteine).

Once purified, chemically modified (e.g., alkylated) B-chains are subjected to an ionization source. As with insulin, the skilled artisan will understand that the choice of ionization method may be determined based on the analyte to be measured, type of sample, the type of detector, the choice of positive versus negative mode, etc. Alkylated insulin B-chains may be ionized in positive or negative mode. In preferred embodiments, alkylated insulin B-chains are ionized by ESI in positive mode.

Ionization of alkylated insulin B-chains may result in multiply charged alkylated B-chain precursor ions (such as precursor ions of 3+, 4+, 5+, etc.). For example, positive electrospray ionization of alkylated insulin B-chain molecules may generate 3+, 4+, and 5+ charged alkylated B-chain precursor ions with m/z of 1181.9±0.5, 886.9±0.5, and 709.8±0.5, respectively. Similar to insulin, the identity and quantity of the multiply charged species generated from ionization of alkylated insulin B-chains is affected by the ionization conditions employed. In preferred embodiments, alkylated insulin B-chains are ionized under acidic conditions.

In embodiments where alkylated insulin B-chains are subject to tandem mass spectrometric analysis, Q1 may select for one or more insulin B-chain precursor ions with an m/z of about 1181.9±0.5, 886.9±0.5, and 709.8±0.5. Fragmentation of these three alkylated insulin B-chain precursor ions may generate fragment ions with m/z of about 345.0±0.5 and 226.2±0.5. Thus, in embodiments where Q1 selects for one or more alkylated insulin B-chain precursor ions selected from the group consisting of ions with m/z of about 1144.2±0.5, 858.3±0.5, and 686.8±0.5, Q3 may select one or more fragment ions selected from the group of ions with m/z of about 345.0±0.5 and 226.2±0.5. In certain embodiments, the relative abundance of a single fragment ion from a single precursor ion may be measured. Alternatively, the relative abundances of two or more fragment ions from a single precursor ion may be measured. In these embodiments, the relative abundances of each fragment ion may be subjected to any known mathematical treatment to quantitatively assess insulin originally in the sample. In other embodiments, one or more fragment ions from two or more precursor ions may be measured and utilized as above to qualitatively assess insulin originally in the sample.

One or more steps of any of the above described methods may be performed using automated machines. In certain embodiments, one or more purification steps are performed on-line, and more preferably all of the purification and mass spectrometry steps may be performed in an on-line fashion.

The following Examples serve to illustrate the invention. These Examples are in no way intended to limit the scope of the methods.

EXAMPLES

Example 1: Sample Preparation

Human Insulin USP Lot J0J250 was dissolved and diluted in 0.1% formic acid and found to have a peptide content of 75% by quantitative amino acid analysis corresponding to a concentration of 1.3 mg/mL or 35 IU/mL. This solution was further diluted 1 in 5 with 0.1% formic acid, then immediately diluted 1 in 50 with SP1040 stripped serum and allowed to stand for 30 min with intermittent inversion/vortexing.

Human C-peptide Bachem Lot 1012763 was dissolved and diluted in 0.1% formic and found to have a peptide content of 55% by quantitative amino acid analysis corresponding to a concentration of 0.28 mg/mL. This solution was further diluted 1 in 10 with 0.1% formic acid, then immediately diluted 1 in 50 with SP1040 stripped serum and allowed to stand for 30 min with intermittent inversion/vortexing.

The insulin and C-peptide stocks in SP1040 stripped serum were added to 3 separate 50 mL polypropylene tubes labeled QC High, QC Medium and QC Low. Sufficient volume of each peptide solution was added to each tube to bring the final volume to 50 mL and the final calculated concentrations to QH: Insulin 188 uIU/mL, C-peptide 7.70 ng/mL; QM: Insulin 47 uIU/mL, C-peptide 2.07 ng/mL; QL: Insulin 14 uIU/mL, C-peptide 0.48 ng/mL.

After thorough mixing by gentle inversion, the QC pools were distributed as 1.5 mL aliquots in labeled 1.5 mL Eppendorf tubes and stored at −60 to −90° C. until use.

Example 1: Immunocapture

In this assay, serum was first delipidated and then insulin and C-peptide were immunocaptured using antibodies immobilized on magnetic beads. The beads were subjected to a rigorous washing regime to remove non-specifically bound material and the peptides were subsequently eluted from the beads with acidified acetonitrile in water. An aliquot of Trizma base was added to enhance stability of the peptides in the elution plate. Insulin and C-peptide are unstable at low concentration in a purified, or partially purified state undergoing adsorptive losses and "disappear" from solution. Consequently, once prepared, the elution plate should be run within 5 hours, preferably immediately after preparation, for maximum sensitivity. Elution plates should not be frozen. The processes of calibrator preparation, internal standard addition, delipidation, bead deposition, immunocapture, washing and eluting the peptides from the beads were automated, using a Hamilton STAR® robotic liquid handler. Manual steps involved initial dilution of calibrator stocks, transfer to the centrifuge post-delipidation and bead preparation.

Example 2: Liquid Chromatography and Mass Spectrometry

The elution plate was transferred from the deck of the Hamilton robot to the autosampler of a ThermoFisher TurboFlow Aria TX4 HTLC system and immediately run. The sample was injected onto a hydrophilic/lipophilic balanced (HLB) capture column where insulin and C-peptide were further enriched from background contaminants. After washing, a plug of transfer solvent was used to liberate the peptides from the extraction cartridge and transferred them to a reversed phase analytical column. An acetonitrile gradient chromatographically resolved insulin and C-peptide from the remaining background contaminants and each other.

The flow of solvent from the HPLC column was directed to the heated electrospray source of an Agilent 6490 mass spectrometer. In the mass spectrometer, only the ions with the desired mass to charge ratio were allowed to pass through the Quadrupole 1 (Q1) area into the collision chamber (Q2). Then the accelerated ions collided with neutral argon gas molecules to become small fragments. Finally, in Q3 only the selected ions were chosen to reach the detector (see Table 1 below). The intensity of the signal at the detector was proportional to the number of molecules entering the mass spectrometer. Peak area ratios were then calculated for a set of known calibrators and calibration curves are established. The calibration equation can then be used to determine the concentration of insulin and C-peptide in patient samples.

TABLE 1

Nominal fragment ion transition m/z values (+/− 0.1 Dalton) for the analysis of Insulin and C-peptide and their internal standards. Quantifier product ions are underlined.

| Analyte | Charge | Parent m/z | Product Ions m/z |
|---|---|---|---|
| Human insulin | +6 | 968.7 | 136.0, <u>226.1</u>, 345.2 |
| Bovine insulin | +6 | 956.8 | <u>136.0</u>, 226.1, 315.2 |
| C-peptide | +3 | 1007.7 | <u>533.3, 646.4</u>, 927.5 |
| C-peptide heavy IS | +3 | 1009.5 | <u>540.3, 653.4</u>, 934.5 |

Example 3: Intra-Assay and Inter-Assay Precision

The intra-assay precision is defined as the reproducibility of a measurement within an assay and was generated from assaying 5 replicates from QCL, QCM and QCH. The coefficient of variation (CV) for 5 replicates of a sample was used to determine if the reproducibility is acceptable 15%). Statistics performed on the results for a run determined that the reproducibility (CV) for the QC's ranged from 6.2 to 11.5% for insulin and 5.1 to 6.3% C-peptide (Table 2). Intra-assay precision can also be calculated across all assays (see 930TP5319: Assay Validation Calculator). For insulin within run CV ranged from 4.7 to 9.6% and C-peptide within run CVs ranged from 4.7 to 7.0%.

Table 2a: Intra-Assay Precision: Insulin

| Controls | Low | Mid | High |
|---|---|---|---|
| 1 | 13.8 | 38.6 | 166.0 |
| 2 | 13.7 | 42.3 | 166.5 |
| 3 | 11.6 | 39.9 | 193.8 |
| 4 | 11.2 | 37.8 | 177.9 |
| 5 | 10.8 | 35.8 | 164.8 |
| Mean (uIU/mL) | 12.2 | 38.9 | 173.8 |
| SD | 1.4 | 2.4 | 12.3 |
| CV | 11.5% | 6.2% | 7.1% |

Table 2b: Intra-Assay Precision: C-peptide

| Controls | Low | Mid | High |
|---|---|---|---|
| 1 | 0.49 | 1.76 | 7.09 |
| 2 | 0.43 | 1.85 | 6.81 |
| 3 | 0.51 | 1.91 | 7.12 |
| 4 | 0.48 | 1.81 | 7.16 |
| 5 | 0.44 | 1.84 | 6.64 |
| Mean (ng/mL) | 0.47 | 1.83 | 6.96 |
| SD | 0.03 | 0.05 | 0.23 |
| CV | 7.0% | 2.9% | 3.3% |

The inter-assay variation is defined as the reproducibility of measurements between assays. QCL, QCM and QCH were evaluated over 5 days. The inter-assay variation (% CV) for the pools ranged from 7.3-11.3% for insulin and 6.2 to 9.0% for C-peptide. All QC pools for insulin and C-peptide met the requirement for acceptable reproducibility of 15% CV (Table 3).

TABLE 3

Inter-Assay Precision

Table 3a: QCL Insulin
Insulin Low Control (14.4 uIU/mL)

| #/Day | Day 1 | Day 2 | Day 3 | Day 4 | Day 5 |
|---|---|---|---|---|---|
| 1 | 13.8 | 13.4 | 15.7 | 12.3 | 13.3 |
| 2 | 13.7 | 13.1 | 13.8 | 12.5 | 17.7 |
| 3 | 11.6 | 14.2 | 14.4 | 13.1 | 15.1 |
| 4 | 11.2 | 12.8 | 11.5 | 12.9 | 13.3 |
| 5 | 10.8 | 11.9 | 14.4 | 13.0 | 14.8 |
| Mean | 12.2 | 13.1 | 14.0 | 12.8 | 14.9 |
| SD | 1.4 | 0.8 | 1.5 | 0.3 | 1.8 |
| CV | 11.5% | 6.3% | 10.9% | 2.5% | 12.1% |

Overall Mean 13.4 (uIU/mL)
Overall SD 1.5
Overall CV 11.3%

Table 3b: QCL C-peptide
C-peptide Low Control (0.48 ng/mL)

| #/Day | Day 1 | Day 2 | Day 3 | Day 4 | Day 5 |
|---|---|---|---|---|---|
| 1 | 0.49 | 0.48 | 0.44 | 0.41 | 0.48 |
| 2 | 0.43 | 0.47 | 0.43 | 0.49 | 0.47 |
| 3 | 0.51 | 0.51 | 0.42 | 0.45 | 0.54 |
| 4 | 0.48 | 0.48 | 0.50 | 0.46 | 0.55 |
| 5 | 0.44 | 0.50 | 0.41 | 0.43 | 0.50 |

TABLE 3-continued

Inter-Assay Precision

| | | | | | |
|---|---|---|---|---|---|
| Mean | 0.47 | 0.49 | 0.44 | 0.45 | 0.51 |
| SD | 0.03 | 0.02 | 0.03 | 0.03 | 0.03 |
| CV | 7.0% | 3.3% | 7.5% | 7.2% | 6.7% |

Overall Mean 0.47
(ng/mL)
Overall SD 0.04
Overall CV 8.1%

Table 3c: QCM Insulin
Insulin Medium Control (47.0 uIU/mL)

| #/Day | Day 1 | Day 2 | Day 3 | Day 4 | Day 5 |
|---|---|---|---|---|---|
| 1 | 38.6 | 43.6 | 44.6 | 36.2 | 39.9 |
| 2 | 42.3 | 41.8 | 47.6 | 41.4 | 39.4 |
| 3 | 39.9 | 42.5 | 47.6 | 40.5 | 42.8 |
| 4 | 37.8 | 43.7 | 43.2 | 40.6 | 43.3 |
| 5 | 35.8 | 41.3 | 46.5 | 42.0 | 39.6 |
| Mean | 38.9 | 42.6 | 45.9 | 40.1 | 41.0 |
| SD | 2.4 | 1.1 | 1.9 | 2.3 | 1.9 |
| CV | 6.2% | 2.5% | 4.2% | 5.6% | 4.5% |

Overall Mean 41.7
(uIU/mL)
Overall SD 3.1
Overall CV 7.3%

Table 3d: QCM C-peptide
C-peptide Medium Control (2.07 ng/mL)

| #/Day | Day 1 | Day 2 | Day 3 | Day 4 | Day 5 |
|---|---|---|---|---|---|
| 1 | 1.76 | 2.05 | 1.81 | 1.86 | 1.97 |
| 2 | 1.85 | 1.98 | 2.00 | 1.82 | 2.17 |
| 3 | 1.91 | 2.04 | 1.71 | 1.74 | 1.93 |
| 4 | 1.81 | 2.06 | 2.00 | 1.94 | 2.13 |
| 5 | 1.84 | 1.96 | 1.93 | 1.99 | 2.04 |
| Mean | 1.83 | 2.02 | 1.89 | 1.87 | 2.05 |
| SD | 0.05 | 0.04 | 0.13 | 0.10 | 0.10 |
| CV | 2.9% | 2.2% | 6.7% | 5.2% | 5.1% |

Overall Mean 1.93
(ng/mL)
Overall SD 0.12
Overall CV 6.2%

Table 3e: QCH Insulin
Insulin High Control (188.2 uIU/mL)

| #/Day | Day 1 | Day 2 | Day 3 | Day 4 | Day 5 |
|---|---|---|---|---|---|
| 1 | 166.0 | 173.4 | 164.9 | 156.0 | 178.9 |
| 2 | 166.5 | 168.6 | 165.8 | 142.3 | 182.1 |
| 3 | 193.8 | 193.8 | 173.9 | 165.2 | 185.1 |
| 4 | 177.9 | 167.4 | 178.8 | 196.3 | 179.4 |
| 5 | 164.8 | 172.2 | 170.0 | 162.6 | 178.5 |
| Mean | 173.8 | 175.1 | 170.7 | 164.5 | 180.8 |
| SD | 12.3 | 10.7 | 5.8 | 19.9 | 2.8 |
| CV | 7.1% | 6.1% | 3.4% | 12.1% | 1.5% |

Overall Mean 173.0
(uIU/mL)
Overall SD 12.1
Overall CV 7.0%

Table 3f: QCH C-peptide
C-peptide High Control (7.70 ng/mL)

| #/Day | Day 1 | Day 2 | Day 3 | Day 4 | Day 5 |
|---|---|---|---|---|---|
| 1 | 7.09 | 7.37 | 7.03 | 6.31 | 7.46 |
| 2 | 6.81 | 7.99 | 7.80 | 5.05 | 8.14 |
| 3 | 7.12 | 7.73 | 6.87 | 7.18 | 7.83 |
| 4 | 7.16 | 7.20 | 7.56 | 7.50 | 8.01 |
| 5 | 6.64 | 7.60 | 7.50 | 6.68 | 7.66 |

TABLE 3-continued

Inter-Assay Precision

| | | | | | |
|---|---|---|---|---|---|
| Mean | 6.96 | 7.58 | 7.35 | 6.55 | 7.82 |
| SD | 0.23 | 0.31 | 0.39 | 0.95 | 0.27 |
| CV | 3.3% | 4.1% | 5.3% | 14.5% | 3.5% |

Overall Mean 7.25
(ng/mL)
Overall SD 0.65
Overall CV 9.0%

Example 4: Analytical Sensitivity (Detection Limits)

Limit of Blank (LOB): The LOB is the point at which a measured value is larger than the uncertainty associated with it and is defined arbitrarily as 2 standard deviations (SD) from the zero concentration. Selectivity is the ability of an analytical method to differentiate and quantify the analyte in the presence of other components in the sample. For selectivity, analyses of blank samples of the appropriate biological matrix (stripped serum) were obtained, tested for interference and selectivity ensured at lower limit of quantification. A blank was measured 20 times and the resulting area ratios were back calculated (Table 4).

The LOB was determined to be 0.9 uIU/mL for insulin and 0.06 ng/mL for C-peptide.

Limit of Detection (LOD): The LOD is the point at which a measured value is larger than the uncertainty associated with it and is defined arbitrarily as 4 standard deviations (SD) from the Zero concentration. Selectivity is the ability of an analytical method to differentiate and quantify the analyte in the presence of other components in the sample. For selectivity, analyses of blank samples of the appropriate biological matrix (stripped serum) were obtained, tested for interference and selectivity ensured at lower limit of quantification. A blank was measured 20 times and the resulting area ratios were back calculated (Table 4).

The LOD was determined to be 1.5 uIU/mL for insulin and 0.10 ng/mL for C-peptide.

TABLE 4

Limit of Detection (LOD) and Limit of Blank (LOB)

a: Insulin

| Replicate | Calc. Conc. (uIU/mL) |
|---|---|
| 1 | 0.6 |
| 2 | 0.6 |
| 3 | 0.5 |
| 4 | 0.9 |
| 5 | 0.4 |
| 6 | 0.2 |
| 7 | 0.4 |
| 8 | 0.1 |
| 9 | 0.0 |
| 10 | 1.0 |
| 11 | 0.3 |
| 12 | 0.0 |
| 13 | 0.4 |
| 14 | 0.2 |
| 15 | 0.0 |
| 16 | 0.5 |
| 17 | 0.0 |
| 18 | 0.0 |
| 19 | 0.0 |
| 20 | 0.2 |

TABLE 4-continued

Limit of Detection (LOD) and Limit of Blank (LOB)

| | |
|---|---|
| Mean | 0.3 |
| SD | 0.3 |
| SD × 2 | 0.6 |
| SD × 4 | 1.2 |
| LOB | 0.9 |
| LOD | 1.5 | b: C-peptide

| Replicate | Calc. Conc. (ng/mL) |
|---|---|
| 1 | 0.03 |
| 2 | 0.08 |
| 3 | 0.03 |
| 4 | 0.05 |
| 5 | 0.02 |
| 6 | 0.01 |
| 7 | 0.01 |
| 8 | 0.02 |
| 9 | 0.00 |
| 10 | 0.00 |
| 11 | 0.02 |
| 12 | 0.04 |
| 13 | 0.00 |
| 14 | 0.00 |
| 15 | 0.00 |
| 16 | 0.02 |
| 17 | 0.04 |
| 18 | 0.03 |
| 19 | 0.03 |
| 20 | 0.03 |
| Mean | 0.02 |
| SD | 0.02 |
| SD × 2 | 0.04 |
| SD × 4 | 0.08 |
| LOB | 0.06 |
| LOD | 0.10 |

Limit of Quantitation (LOQ): The LOQ is the point where measurements become quantitatively meaningful. The insulin and C-peptide responses at this LOQ are identifiable, discrete and reproducible with a precision of 20% and an accuracy of 80% to 120%. The LOQ was determined by assaying five different samples at concentration close to the expected LOQ (1.25, 2.5, 5, 10, and 20 uIU/mL for insulin and 0.11, 0.22, 0.44, 0.85, 0.17 ng/ml for C-peptide) then evaluating the intra-assay reproducibility in seven runs and inter-assay reproducibility in a further 8 runs (Table 5). FIGS. 1a and b show the relationship between Insulin level and % CV for insulin and C-peptide, respectively. Estimated from the graphs in FIG. 1, 2.5 uIU/mL and 0.11 ng/mL for insulin and C-peptide, respectively are the lowest concentrations that yields acceptable performance where the 95% confidence interval for the CV remains below 20%.

The LOQ was established to be 2.5 or 3 uIU/mL for insulin and 0.11 ng/mL for C-peptide.

TABLE 5

Limit of Quantitation (LOQ)

a: Insulin

| | Calculated Concentration (uIU/mL) | | | | |
|---|---|---|---|---|---|
| Replicate | A | B | C | D | E |
| 1 | 18.8 | 11.0 | 5.1 | 2.4 | 1.2 |
| 2 | 18.4 | 11.4 | 5.4 | 3.9 | 1.2 |
| 3 | 19.5 | 9.6 | 4.4 | 3.0 | 0.8 |
| 4 | 19.3 | 10.4 | 4.0 | 2.5 | 2.4 |
| 5 | 18.8 | 11.1 | 4.9 | 2.3 | 1.0 |
| 6 | 21.7 | 10.9 | 4.7 | 2.6 | 2.4 |
| 7 | 16.6 | 10.2 | 4.9 | 2.2 | 0.3 |
| 1 | 18.5 | 9.0 | 6.0 | 2.9 | 2.0 |
| 1 | 23.6 | 11.3 | 4.9 | 3.3 | 2.5 |
| 1 | 17.4 | 10.0 | 4.7 | 2.1 | 0.6 |
| 1 | 20.0 | 10.1 | 4.3 | 2.0 | 0.8 |
| 1 | 20.6 | 8.9 | 5.3 | 2.4 | 1.4 |
| 1 | 18.8 | 8.8 | 5.8 | 3.0 | 1.0 |
| 1 | 19.7 | 11.3 | 6.2 | 3.1 | 4.3 |
| Exp Conc (uIU/mL) | 20 | 10 | 5 | 2.5 | 1.25 |
| Mean (uIU/mL) | 19.4 | 10.3 | 5.1 | 2.7 | 1.6 |
| SD | 1.8 | 0.9 | 0.6 | 0.5 | 1.1 |
| CV | 9% | 9% | 13% | 20% | 69% |
| Accuracy | 97% | 103% | 101% | 108% | 124% | b: C-peptide

| | Calculated Concentration (ng/mL) | | | | |
|---|---|---|---|---|---|
| Replicate | A | B | C | D | E |
| 1 | 1.59 | 0.80 | 0.41 | 0.22 | 0.12 |
| 2 | 1.65 | 0.88 | 0.42 | 0.23 | 0.08 |
| 3 | 1.66 | 0.85 | 0.40 | 0.20 | 0.11 |
| 4 | 1.72 | 0.88 | 0.42 | 0.22 | 0.08 |
| 5 | 1.59 | 0.87 | 0.46 | 0.22 | 0.12 |
| 6 | 1.69 | 0.84 | 0.39 | 0.21 | 0.13 |
| 7 | 1.72 | 0.81 | 0.42 | 0.20 | 0.13 |
| 1 | 1.70 | 0.87 | 0.44 | 0.19 | 0.13 |
| 1 | 1.50 | 0.80 | 0.46 | 0.26 | 0.16 |
| 1 | 1.53 | 0.70 | 0.33 | 0.18 | 0.10 |
| 1 | 1.59 | 0.85 | 0.43 | 0.19 | 0.10 |
| 1 | 1.47 | 0.75 | 0.46 | 0.24 | 0.14 |
| 1 | 1.65 | 0.85 | 0.46 | 0.25 | 0.13 |
| 1 | 1.92 | 0.87 | 0.45 | 0.25 | 0.15 |
| Exp Conc (ng/mL) | 1.70 | 0.85 | 0.42 | 0.21 | 0.11 |
| Mean (ng/mL) | 1.64 | 0.83 | 0.43 | 0.22 | 0.12 |
| SD | 0.1 | 0.1 | 0.0 | 0.0 | 0.0 |
| CV | 7% | 6% | 9% | 11% | 20% |
| Accuracy | 97% | 98% | 100% | 103% | 114% |

Example 5: Analyte Measurement Range (AMR)

Calibration Verification: Ten spiked stripped serum samples pools (calibrators' concentration are 1.25, 2.5, 5, 10, 20, 40, 80, 160, 240 and 320 uIU/mL for insulin and 0.11, 0.21, 0.43, 0.85, 1.70, 3.40, 6.80, 13.60, 20.40 and 27.20 ng/mL) were prepared and analyzed 18 times on 13 separate days.

A weighted (1/X) quadratic regression (ignoring origin) from the 18 curves yielded coefficient correlations of 0.989 or greater for insulin and 0.992 or greater for C-peptide, with an accuracy of ±20% revealing a linear range of 5 to 320 uIU/mL for insulin and 0.11 to 27.20 ng/mL for C-peptide (Table 6). Example calibration curves are given in FIG. 2.

TABLE 6

Calibration Verification

Table 6a Insulin

| Assay Date | \multicolumn{10}{c}{Insulin Target Concentration uIU/mL} | $R^2$ |
|---|---|---|---|---|---|---|---|---|---|---|---|
|  | 1.25 | 2.5 | 5.0 | 10.0 | 20.0 | 40.0 | 80.0 | 160.0 | 240.0 | 320.0 |  |
| Aug. 7, 2014 | 2.0 | 2.8 | 3.1 | 8.5 | 16.9 | 38.5 | 73.3 | 184.0 | 249.6 | 299.6 | 0.9913 |
| Aug. 11, 2014 | 1.2 | 2.3 | 5.9 | 9.3 | 19.9 | 40.4 | 76.6 | 181.1 | 207.8 | 333.8 | 0.9891 |
| Aug. 11, 2014 | 1.6 | 2.2 | 6.2 | 8.5 | 16.5 | 34.2 | 82.9 | 171.1 | 248.7 | 306.7 | 0.9952 |
| Aug. 13, 2014 | 1.1 | 2.4 | 5.1 | 11.0 | 18.7 | 40.0 | 86.3 | 166.4 | 212.7 | 334.7 | 0.9991 |
| Aug. 18 2014 | 2.0 | 1.1 | 4.3 | 11.8 | 21.4 | 33.0 | 76.7 | 176.3 | 235.1 | 317.0 | 0.9940 |
| Aug. 19, 2014 | 0.5 | 3.3 | 5.6 | 10.2 | 22.8 | 37.0 | 87.9 | 152.0 | 228.0 | 330.5 | 0.9968 |
| Aug. 26, 2014 | 1.9 | 2.7 | 3.0 | 10.5 | 18.8 | 30.5 | 80.2 | 174.0 | 245.9 | 310.7 | 0.9942 |
| Aug. 28, 2014 | 2.0 | 2.1 | 3.8 | 8.6 | 20.7 | 32.5 | 83.5 | 168.5 | 246.6 | 310.5 | 0.9955 |
| Sep. 2, 2014 | 1.0 | 2.5 | 5.4 | 11.1 | 22.5 | 36.6 | 74.6 | 160.3 | 252.5 | 312.2 | 0.9975 |
| Sep. 2, 2014 | 1.5 | 2.3 | 3.9 | 10.4 | 23.0 | 35.6 | 86.5 | 153.3 | 241.2 | 321.1 | 0.9977 |
| Sep. 5, 2014 | 1.9 | 1.2 | 5.0 | 10.1 | 18.5 | 43.5 | 78.3 | 164.6 | 230.3 | 325.3 | 0.9972 |
| Sep. 9, 2014 | 1.1 | 3.1 | 4.5 | 9.3 | 20.6 | 42.5 | 75.6 | 158.1 | 249.5 | 314.5 | 0.9986 |
| Sep. 11, 2014 | 1.6 | 2.2 | 4.7 | 9.3 | 18.5 | 41.0 | 72.8 | 170.9 | 248.1 | 309.5 | 0.9972 |
| Sep. 11, 2014 | 1.2 | 2.3 | 5.4 | 9.2 | 21.6 | 40.8 | 80.8 | 159.8 | 230.3 | 327.3 | 0.9991 |
| Sep. 12, 2014 | 1.8 | 1.6 | 5.6 | 9.2 | 19.1 | 34.3 | 86.2 | 155.3 | 256.0 | 309.7 | 0.9957 |
| Sep. 12, 2014 | 1.1 | 3.0 | 5.7 | 8.5 | 17.8 | 39.4 | 76.4 | 172.8 | 237.0 | 316.9 | 0.9976 |
| Sep. 25, 2014 | 1.5 | 2.2 | 4.9 | 9.6 | 20.9 | 35.0 | 78.8 | 169.5 | 240.3 | 315.9 | 0.9983 |
| Sep. 25, 2014 | 2.2 | 0.8 | 4.3 | 9.9 | 19.1 | 43.0 | 89.0 | 150.3 | 234.0 | 326.3 | 0.9956 |
| Mean | 1.52 | 2.2 | 4.8 | 9.7 | 19.9 | 37.7 | 80.4 | 166.0 | 238.5 | 317.9 |  |
| SD | 0.4 | 0.7 | 0.9 | 1.0 | 2.0 | 3.9 | 5.2 | 10.0 | 13.2 | 9.9 |  |
| CV | 28.8 | 30.7 | 19.4 | 10.0 | 9.8 | 10.4 | 6.5 | 6.0 | 5.5 | 3.1 |  |
| Accuracy | 121.4 | 89.1 | 95.9 | 97.3 | 99.3 | 94.1 | 100.4 | 103.8 | 99.4 | 99.3 |  |
| Diff (Target-Mean) | 0.27 | −0.27 | −0.21 | −0.27 | −0.14 | −2.3 | 0.4 | 6.0 | −1.5 | −2.1 |  |
| TEa/4 | 1.25 | 1.25 | 1.25 | 1.25 | 1.25 | 2.5 | 5.0 | 10.0 | 15.0 | 20.0 |  |

Linear from 5-320 uIU/mL

Table 6b C-peptide

| Assay Date | \multicolumn{9}{c}{C peptide Target ng/mL} | $R^2$ |
|---|---|---|---|---|---|---|---|---|---|---|
|  | 0.11 | 0.21 | 0.43 | 0.85 | 1.70 | 3.40 | 6.80 | 13.60 | 20.40 | 27.20 |
| Aug. 7, 2014 | 0.13 | 0.22 | 0.43 | 0.74 | 1.55 | 3.87 | 6.43 | 13.33 | 21.46 | 26.57 | 0.9973 |
| Aug. 11, 2014 | 0.12 | 0.19 | 0.44 | 0.87 | 1.71 | 3.25 | 7.11 | 13.52 | 20.09 | 27.41 | 0.9995 |
| Aug. 11, 2014 | 0.13 | 0.23 | 0.40 | 0.75 | 1.60 | 3.34 | 6.74 | 14.12 | 20.58 | 26.83 | 0.9992 |
| Aug. 13, 2014 | 0.12 | 0.22 | 0.41 | 0.80 | 1.59 | 3.61 | 6.68 | 13.36 | 21.15 | 26.77 | 0.9929 |
| Aug. 18, 2014 | 0.12 | 0.23 | 0.42 | 0.90 | 1.65 | 2.99 | 6.48 | 14.64 | 20.76 | 26.53 | 0.9975 |
| Aug. 19, 2014 | 0.09 | 0.25 | 0.44 | 0.93 | 1.65 | 3.19 | 6.60 | 13.65 | 21.55 | 27.37 | 0.9986 |
| Aug. 26, 2014 | 0.13 | 0.23 | 0.36 | 0.85 | 1.57 | 3.21 | 7.40 | 13.70 | 19.73 | 27.54 | 0.9943 |
| Aug. 28, 2014 | 0.13 | 0.22 | 0.41 | 0.83 | 1.64 | 2.83 | 7.06 | 13.97 | 21.42 | 26.18 | 0.9971 |
| Sep. 2, 2014 | 0.12 | 0.22 | 0.44 | 0.85 | 1.65 | 3.02 | 6.72 | 14.13 | 21.25 | 26.30 | 0.9982 |
| Sep. 2, 2014 | 0.13 | 0.23 | 0.42 | 0.76 | 1.44 | 3.48 | 6.88 | 14.27 | 19.86 | 27.24 | 0.9984 |
| Sep. 5, 2014 | 0.10 | 0.22 | 0.45 | 0.88 | 1.62 | 3.41 | 6.90 | 13.73 | 19.90 | 27.50 | 0.9997 |
| Sep. 9, 2014 | 0.12 | 0.21 | 0.41 | 0.85 | 1.62 | 3.51 | 6.71 | 13.06 | 21.75 | 26.46 | 0.9980 |
| Sep. 11, 2014 | 0.14 | 0.22 | 0.40 | 0.78 | 1.53 | 3.34 | 6.66 | 13.93 | 21.65 | 26.07 | 0.9980 |
| Sep. 11, 2014 | 0.12 | 0.23 | 0.46 | 0.77 | 1.53 | 3.09 | 6.92 | 14.41 | 20.28 | 26.89 | 0.9983 |
| Sep. 12, 2014 | 0.10 | 0.24 | 0.44 | 0.82 | 1.68 | 3.28 | 6.97 | 13.58 | 20.45 | 27.15 | 0.9997 |
| Sep. 12, 2014 | 0.12 | 0.23 | 0.43 | 0.80 | 1.57 | 3.56 | 6.73 | 13.90 | 20.08 | 27.30 | 0.9995 |
| Sep. 25, 2014 | 0.10 | 0.23 | 0.45 | 0.88 | 1.75 | 2.96 | 7.12 | 13.77 | 20.26 | 27.19 | 0.9989 |
| Sep. 25, 2014 | 0.13 | 0.22 | 0.40 | 0.77 | 1.72 | 3.36 | 7.04 | 13.01 | 21.41 | 26.66 | 0.9986 |
| Mean | 0.12 | 0.22 | 0.42 | 0.82 | 1.61 | 3.29 | 6.84 | 13.78 | 20.76 | 26.89 |  |
| SD | 0.01 | 0.01 | 0.03 | 0.06 | 0.08 | 0.26 | 0.25 | 0.44 | 0.70 | 0.47 |  |
| CV | 10.5 | 5.6 | 6.0 | 6.8 | 4.7 | 7.9 | 3.6 | 3.2 | 3.4 | 1.7 |  |
| Accuracy | 113.3 | 105.3 | 99.6 | 96.7 | 95.0 | 96.9 | 100.6 | 101.3 | 101.8 | 98.8 |  |
| Diff (Target-Mean) | 0.01 | 0.01 | 0.00 | −0.03 | −0.09 | −0.11 | 0.04 | 0.18 | 0.36 | −0.31 |  |
| TEa/4 | 0.05 | 0.05 | 0.05 | 0.06 | 0.13 | 0.26 | 0.51 | 1.02 | 1.53 | 2.04 |  |

Linear from 0.11-27.20 ng/mL

Example 6: Accuracy

Recovery Study: For insulin the TEa was set at 25% or 5 uIU/mL. For C-peptide the TEa was set at 30% or 0.2 ng/mL. An acceptable accuracy of TEa/3 has been set for both peptides for this validation.

Recovery of known standards: Known amounts of USP insulin and Bachem C-peptide were spiked into stripped serum and analyzed in 5 replicates over 5 days.

For insulin, the results were 92.9% and 91.9% overall accuracy at spike levels of 14 and 188 uIU/mL, respectively and were within TEa/3 (Table 7a).

TABLE 7

Recoveries of USP insulin and Bachem C-peptide spiked into stripped serum a: Insulin

| Replicate | Obs. Conc. (uIU/mL) | Obs. Conc. (uIU/mL) |
|---|---|---|
| 1 | 13.8 | 166.0 |
| 2 | 13.7 | 166.5 |
| 3 | 11.6 | 193.8 |
| 4 | 11.2 | 177.9 |
| 5 | 10.8 | 164.8 |

TABLE 7-continued

Recoveries of USP insulin and Bachem C-peptide spiked into stripped serum
a: Insulin

| Replicate | Obs. Conc. (uIU/mL) | Obs. Conc. (uIU/mL) |
|---|---|---|
| 6 | 13.4 | 173.4 |
| 7 | 13.1 | 168.6 |
| 8 | 14.2 | 193.8 |
| 9 | 12.8 | 167.4 |
| 10 | 11.9 | 172.2 |
| 11 | 15.7 | 164.9 |
| 12 | 13.8 | 165.8 |
| 13 | 14.4 | 173.9 |
| 14 | 11.5 | 178.8 |
| 15 | 14.4 | 170.0 |
| 16 | 12.3 | 156.0 |
| 17 | 12.5 | 142.3 |
| 18 | 13.1 | 165.2 |
| 19 | 12.9 | 196.3 |
| 20 | 13.0 | 162.6 |
| 21 | 13.3 | 178.9 |
| 22 | 17.7 | 182.1 |
| 23 | 15.1 | 185.1 |
| 24 | 13.3 | 179.4 |
| 25 | 14.8 | 178.5 |
| Mean | 13.4 | 173.0 |
| SD | 1.5 | 12.1 |
| CV | 11.3 | 7.0 |
| Exp Conc | 14 | 188 |
| Accuracy | 92.9 | 92.0 |
| Diff (Target − Mean) | 1.0 | 15.0 |
| TEa/4 | 0.9 | 11.8 |
| TEa/3 | 1.2 | 15.7 |

For C-peptide, the results were 98.3 and 94.2% overall accuracy at a spike levels of 0.48 and 7.70 ng/mL, respectively and were within TEa/3 (Table 7b).

TABLE 7b

| | C-peptide | |
|---|---|---|
| Replicate | Obs. Conc. (ng/mL) | Obs. Conc. (ng/mL) |
| 1 | 0.49 | 7.09 |
| 2 | 0.43 | 6.81 |

TABLE 7b-continued

| | C-peptide | |
|---|---|---|
| Replicate | Obs. Conc. (ng/mL) | Obs. Conc. (ng/mL) |
| 3 | 0.51 | 7.12 |
| 4 | 0.48 | 7.16 |
| 5 | 0.44 | 6.64 |
| 6 | 0.48 | 7.37 |
| 7 | 0.47 | 7.99 |
| 8 | 0.51 | 7.73 |
| 9 | 0.48 | 7.20 |
| 10 | 0.50 | 7.60 |
| 11 | 0.44 | 7.03 |
| 12 | 0.43 | 7.80 |
| 13 | 0.42 | 6.87 |
| 14 | 0.50 | 7.56 |
| 15 | 0.41 | 7.50 |
| 16 | 0.41 | 6.31 |
| 17 | 0.49 | 5.05 |
| 18 | 0.45 | 7.18 |
| 19 | 0.46 | 7.50 |
| 20 | 0.43 | 6.68 |
| 21 | 0.48 | 7.46 |
| 22 | 0.47 | 8.14 |
| 23 | 0.54 | 7.83 |
| 24 | 0.55 | 8.01 |
| 25 | 0.50 | 7.66 |
| Mean | 0.47 | 7.3 |
| SD | 0.0 | 0.7 |
| CV | 8.1 | 9.0 |
| Exp Conc | 0.48 | 7.7 |
| Accuracy | 98.3 | 94.2 |
| Diff (Target − Mean) | 0.01 | 0.4 |
| TEa/4 | 0.03 | 0.48 |
| TEa/3 | 0.04 | 0.64 |

Spike and Recovery from Patient Sera: A recovery study was performed by taking a patient serum with known low levels of insulin and C-peptide and spiking with known levels of insulin at 10, 20 and 40 uIU/mL and C-peptide at 1.02, 1.7 and 3.4 ng/mL. Correction for background levels of insulin and C-peptide were accounted for.

Recoveries were calculated for each level and the mean recoveries ranged from 96-106% for insulin and 91-104% for C-peptide within ±10% and a Tea/4 (Tables 7c and 7d).

TABLE 7C

| | Insulin | | | | | | | | |
|---|---|---|---|---|---|---|---|---|---|
| Exp Conc | Calculated Conc-Endogenous (uIU/mL) | | | | | | % | Diff | |
| (uIU/mL) | 1 | 2 | 3 | Mean | SD | CV | Recovery | Target-Mean | TEa/4 |
| 10 | 10.0 | 10.3 | 11.6 | 10.6 | 0.8 | 8% | 106% | −0.6 | 1.25 |
| 20 | 19.4 | 17.6 | 20.5 | 19.2 | 1.5 | 8% | 96% | 0.2 | 1.25 |
| 40 | 40.3 | 40.3 | 34.6 | 38.4 | 3.3 | 9% | 96% | 1.9 | 2.5 |

TABLE 7D

| | C-peptide | | | | | | | | |
|---|---|---|---|---|---|---|---|---|---|
| Exp Conc | Calculated Conc-Endogenous (uIU/mL) | | | | | | % | Diff | |
| (uIU/mL) | 1 | 2 | 3 | Mean | SD | CV | Recovery | Target-Mean | TEa/4 |
| 1.02 | 0.84 | 0.88 | 1.05 | 0.92 | 0.11 | 12% | 91% | −0.08 | 0.08 |
| 1.7 | 1.63 | 1.54 | 1.64 | 1.60 | 0.06 | 3% | 94% | 0.03 | 0.13 |
| 3.4 | 3.34 | 3.53 | 3.70 | 3.52 | 0.18 | 5% | 104% | −0.18 | 0.3 |

Recovery on dilution of high insulin and C-peptide patient sera: Patient sera with high endogenous levels of insulin and C-peptide were diluted with stripped serum and the recoveries were measured as a percentage of the value calculated by dividing the neat levels by the dilution factor. Patient #1 serum had an insulin level of 69.3 uIU/mL and a C-peptide level of 6.37 ng/mL whereas Patient #2 serum had an insulin level of 753.5 uIU/mL (by extrapolation) and a C-peptide level of 20.84 ng/mL. In Table 7 e and f recoveries within ±10% (TEa/3) for both C-peptide and insulin for Patients #1 and 2 are presented.

TABLE 7E

Recovery of endogenous Insulin in patient sera on dilution

| Patient | Dilution Factor | Insulin uIU/mL | | | Diff | | |
|---|---|---|---|---|---|---|---|
| | | Observed | Exp Conc | % Recovery | Cal-Obs | TEa/4 | TEa/3 |
| #1 | none | 69.3 | | | | | |
| #1 | 2.0 | 37.0 | 34.6 | 106.7 | -2.3 | 2.2 | 2.9 |
| #1 | 10.0 | 6.3 | 6.9 | 90.6 | 0.6 | 0.4 | 0.6 |
| #2 | none | 753.5 | | | | | |
| #2 | 2.0 | 400.0 | 376.8 | 106.2 | -23.3 | 23.5 | 31.4 |
| #2 | 10.0 | 78.5 | 75.4 | 104.2 | -3.2 | 4.7 | 6.3 |

TABLE 7F

Recovery of endogenous C-peptide in patient sera on dilution

| Patient | Dilution Factor | C-peptide ng/mL | | | Diff | | |
|---|---|---|---|---|---|---|---|
| | | Observed | Exp Conc | % Recovery | Cal-Obs | TEa/4 | TEa/3 |
| #1 | none | 6.37 | | | | | |
| #1 | 2.0 | 3.08 | 3.19 | 96.7 | 0.11 | 0.24 | 0.27 |
| #1 | 10.0 | 0.61 | 0.64 | 95.0 | 0.03 | 0.05 | 0.05 |
| #2 | none | 20.84 | | | | | |
| #2 | 2.0 | 10.73 | 10.42 | 103.03 | -0.32 | 0.65 | 0.87 |
| #2 | 10.0 | 2.15 | 2.08 | 103.19 | -0.07 | 0.13 | 0.17 |

Split-Sample Comparison Study: Previously tested samples were collected from the C-peptide Immulite 2000 assay, the FDA-approved Beckman Access® ICMA platform for insulin and the in-house LC-MS/MS that measures insulin B chain as a surrogate for intact insulin concentration. The current proposed assay was performed on all samples, and when there was sufficient sample volume, the samples were submitted to the other assays for insulin and C-peptide.

Figures 3A, 3B:
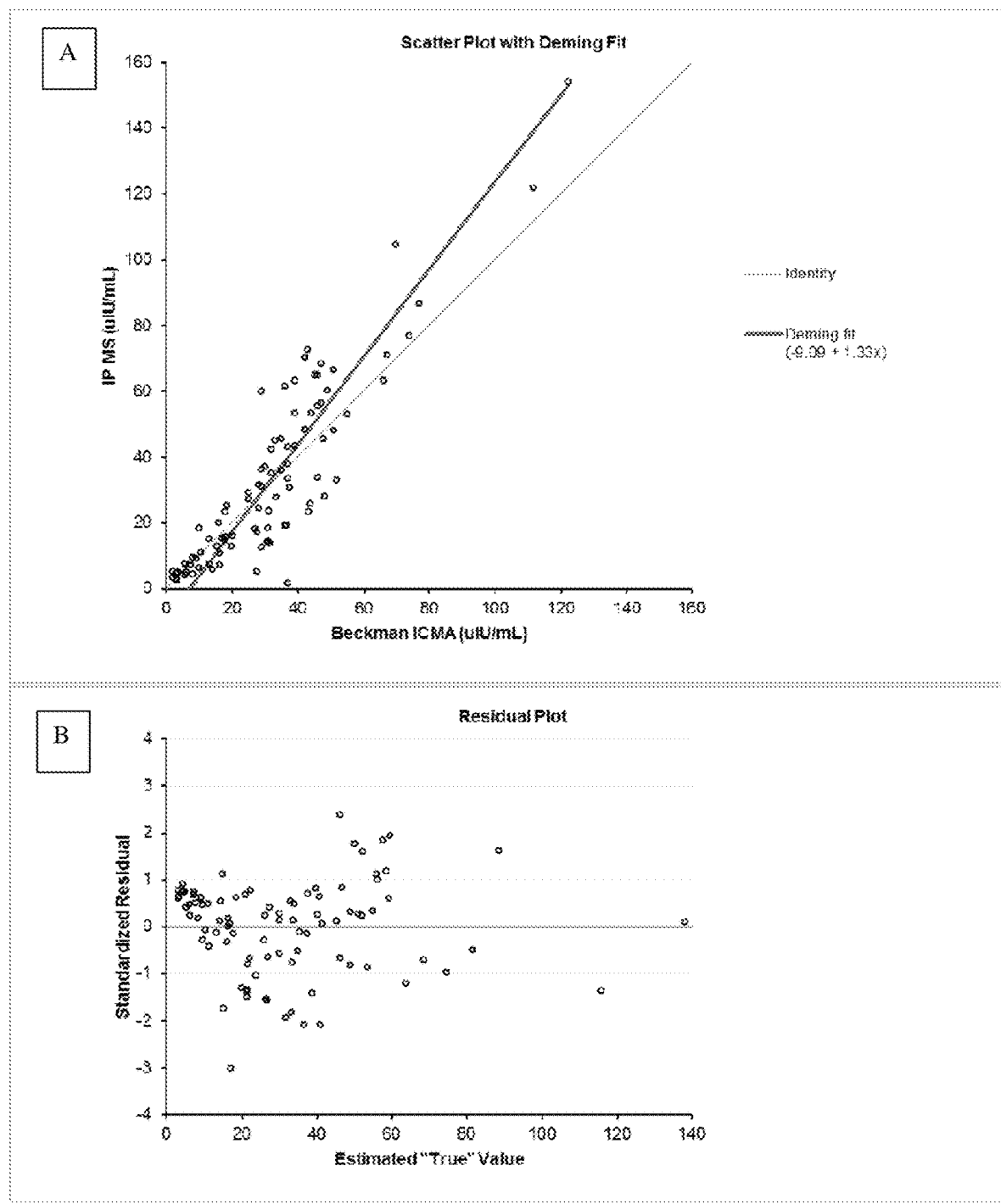
FIGS. 3A-3F show comparison of insulin results for 94 patient samples by Deming regression analysis using different test methods: Immunocapture (IPMS) versus (3A and 3B) Beckman ICMA and (3C and 3D) LC-MS/MS as reference methods. In 3E and 3F a comparison of the current insulin calibrators in the current assay and the Beckman ICMA is presented.
Figures 3C, 3D:
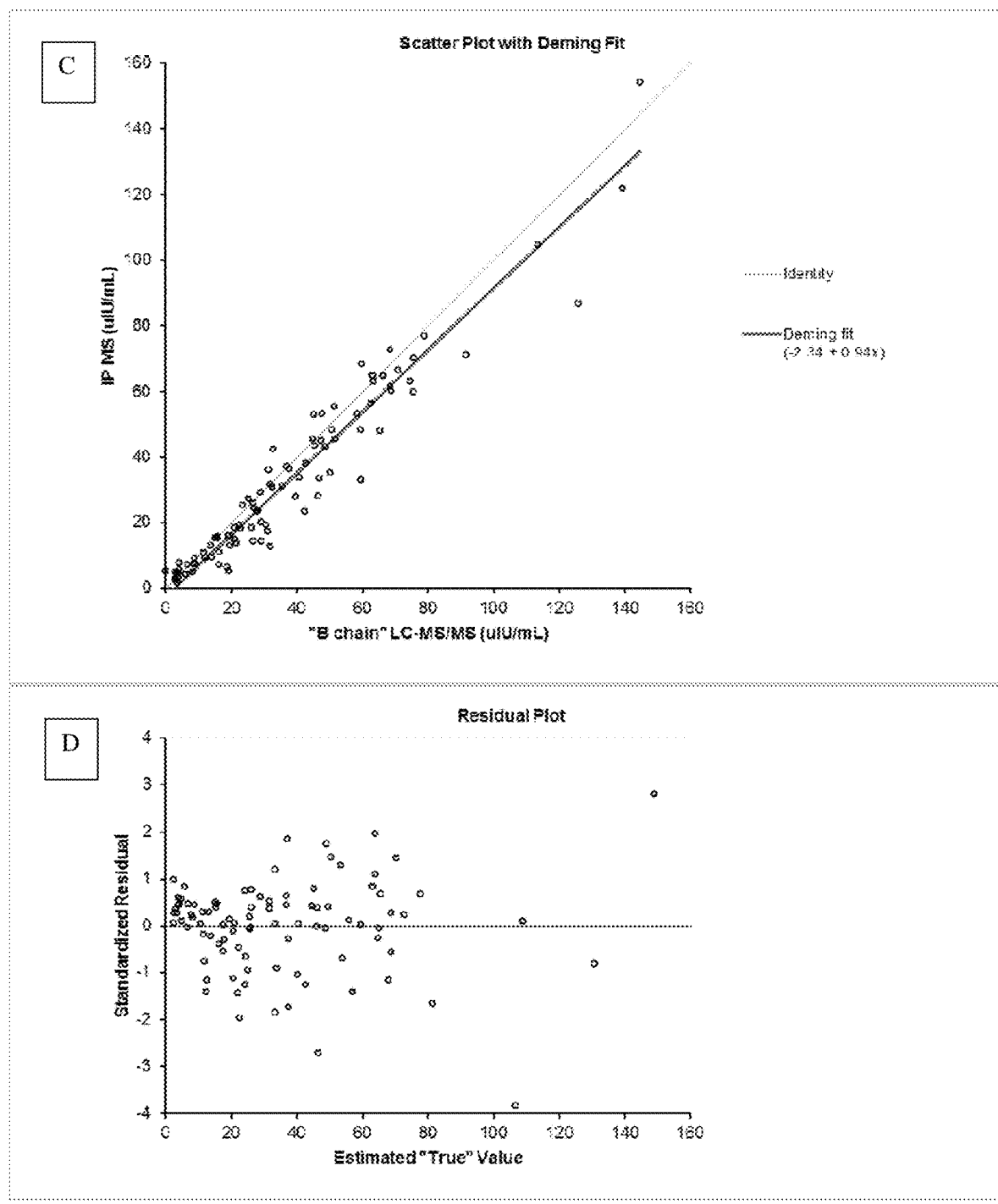
Figures 3E, 3F:
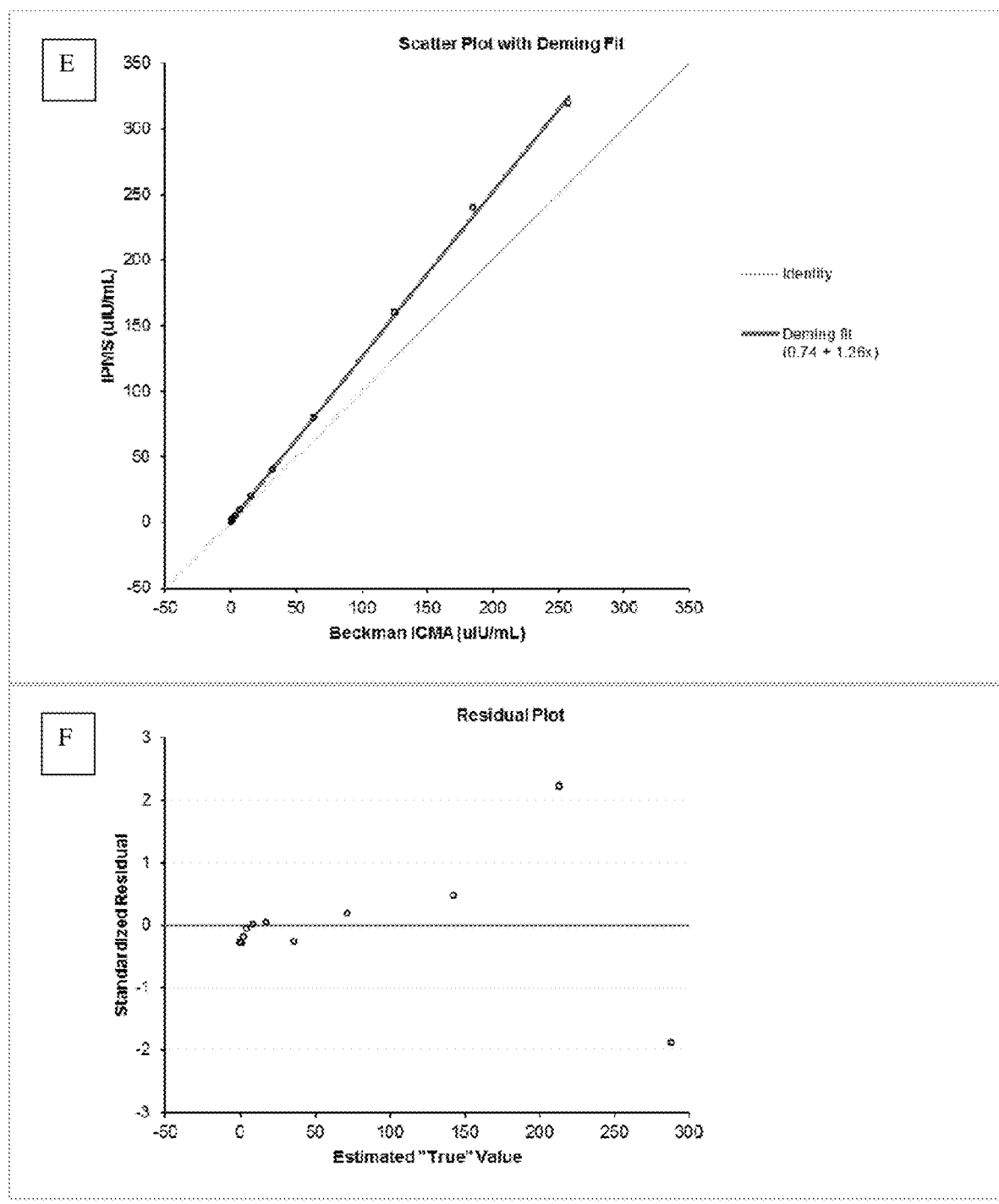

Insulin results from 94 patients were compared by the current assay and the 2 established assays for insulin with the LC-MS/MS "B chain" assay yielding a good correlation (Deming regression, 0.94x-2.34) (FIGS. 3a and 3b). The correlation with the commercial Beckman ICMA platform had a Deming regression of 1.33x-9.09 (FIGS. 3c and 3d). The bias towards the higher values was reflected in the behavior of the current calibrators in the Beckman ICMA assay (Deming Regression 1.26x+0.74 (FIGS. 3e and 3f).

Figures 4A, 4B:
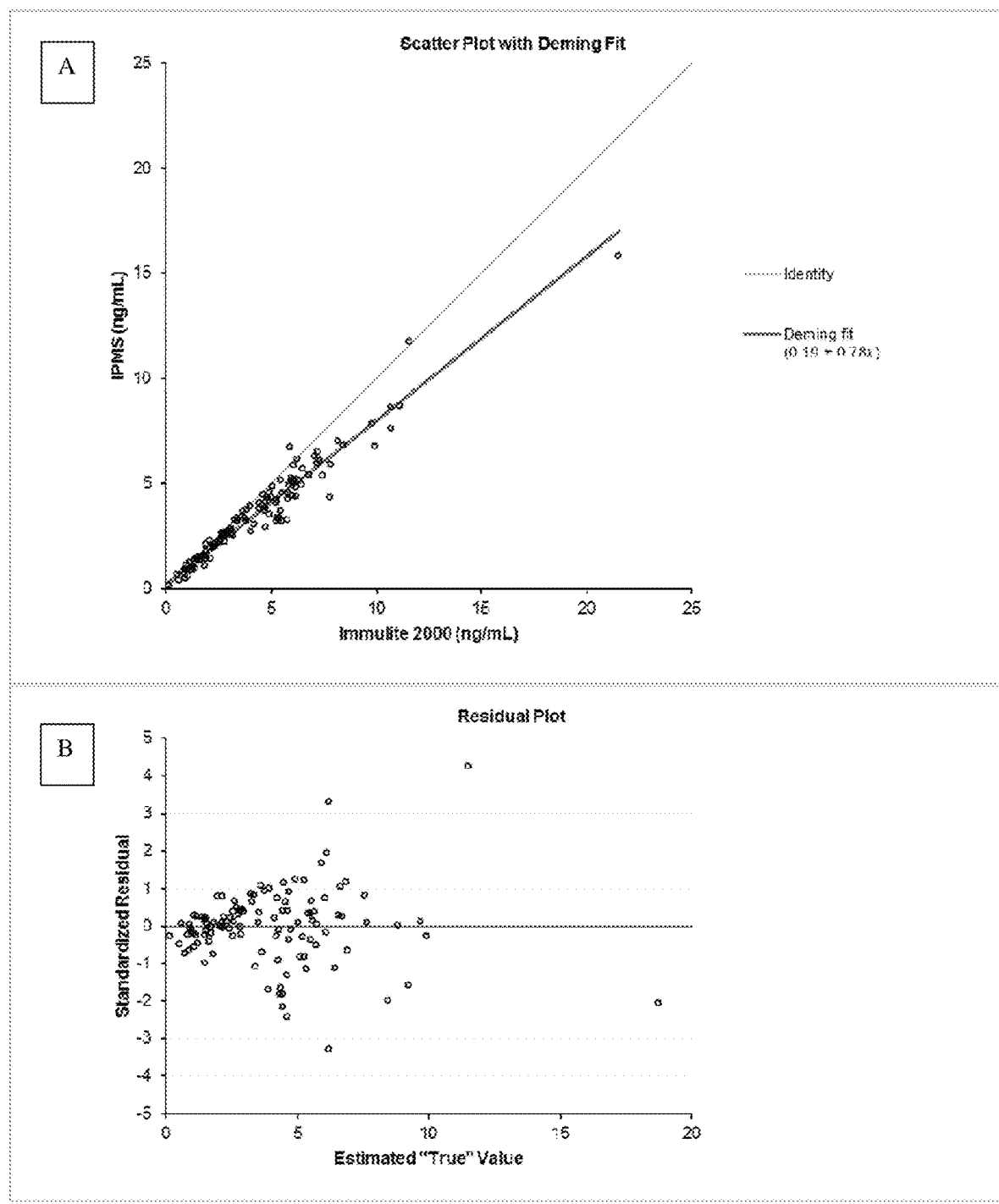
FIGS. 4A-4D show comparison of C-peptide results for 115 patient samples by Deming regression analysis using different test methods: Immunocapture (IPMS) versus (4A and 4B) Immulite 2000 Assay. In 4C and 4D, a comparison of the current C-peptide calibrators in the current assay and the Immulite 2000 assay is presented.
Figures 4C, 4D:
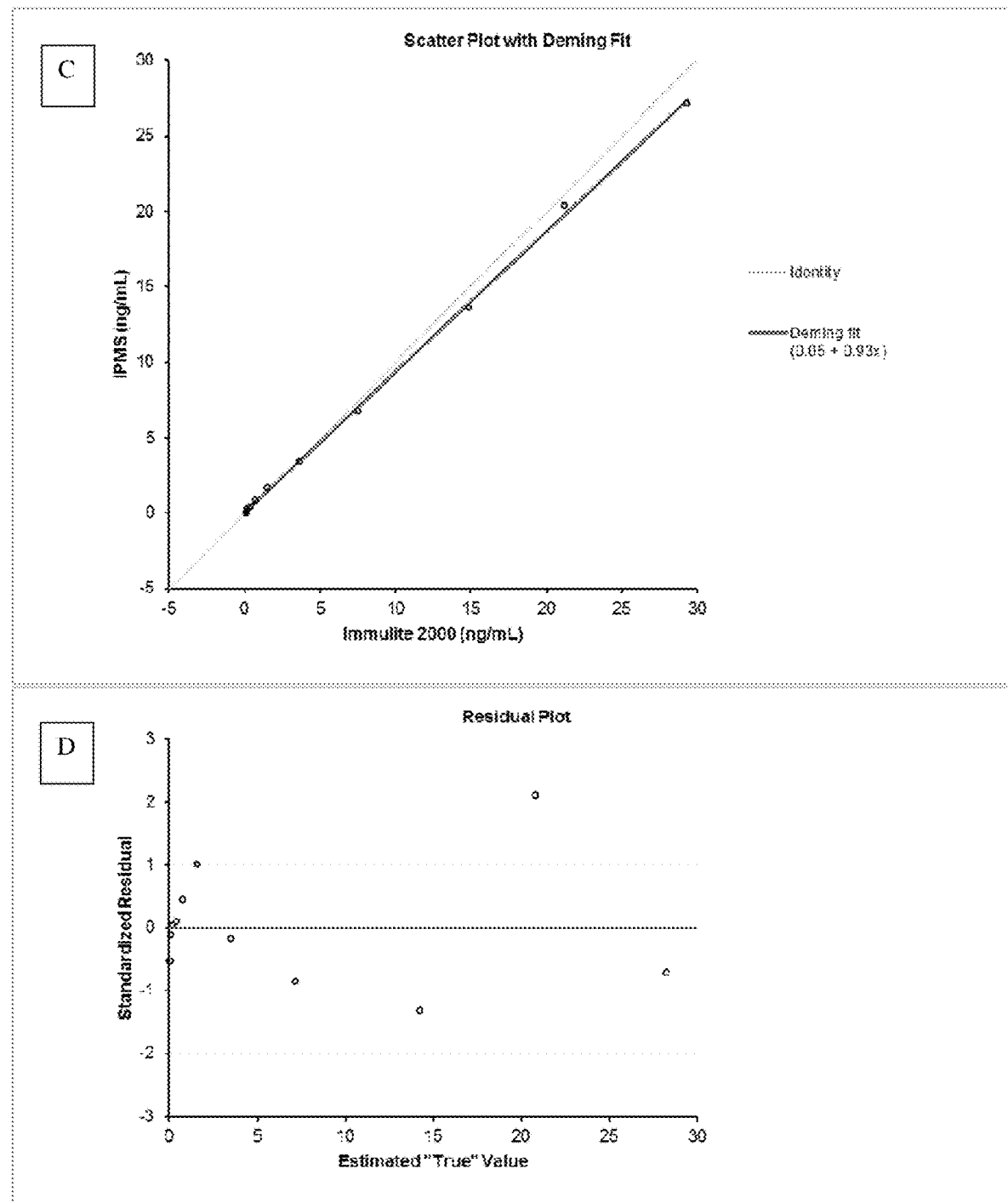

For C-peptide results from 115 patients, the correlation against the C-peptide Immulite 2000 assay (Deming regression, 0.78x+0.19) was strongly biased toward the immunoassay by at least 20% reflecting the specificity of LC-MS/MS only detecting intact C-peptide and not partially processed, truncated or modified forms (FIGS. 4a and 4b). This is supported by the correlation of current proposed assay's C-peptide calibrators in the C-peptide Immulite assay (Deming regression 0.93x+0.08) (FIGS. 4c and 4d).

Example 7: Specimen Stability

Acceptability criteria: A sample is considered stable as long as the average difference between the baseline value and the time/temperature sample value is ≤TEa/4 for that analyte. (Stability tested using the STAEFA temperature ranges).

Freeze/Thaw Sample Stability: Six serum pools were evaluated for freeze/thaw stability of C-peptide and insulin in human serum. Six samples were spiked with known concentrations of the peptides and underwent 5 freeze/thaw cycles (Table 8 and FIG. 5). Samples were frozen in the ultralow freezer (−60 to −90° C.) and thawed to room temperature. The data indicates that both insulin and C-peptide are stable for at least 5 freeze/thaw cycles.

TABLE 8

Freeze Thaw Stability

Table 8a: Insulin

Average Calculated Concentrations (uIU/mL)

| Sample | Baseline | Cycle 1 | Cycle 2 | Cycle 3 | Cycle 4 | Cycle 5 | Mean | SD | CV |
|---|---|---|---|---|---|---|---|---|---|
| Patient 1 | 54.5 | 59.2 | 54.7 | 55.4 | 52.2 | 54.1 | 55.0 | 2.3 | 4% |
| Patient 2 | 47.2 | 44.4 | 49.2 | 47.9 | 49.6 | 45.1 | 47.2 | 2.1 | 4% |
| Patient 3 | 89.5 | 82.7 | 87.0 | 88.7 | 98.4 | 86.7 | 88.8 | 5.2 | 6% |
| Patient 4 | 110.7 | 111.1 | 105.6 | 108.6 | 92.6 | 97.1 | 104.3 | 7.7 | 7% |
| Patient 5 | 101.2 | 114.1 | 113.1 | 105.3 | 101.9 | 106.7 | 107.1 | 5.5 | 5% |
| Patient 6 | 20.1 | 19.4 | 20.8 | 21.6 | 17.6 | 17.7 | 19.5 | 1.6 | 8% |

TABLE 8-continued

Freeze Thaw Stability

% Recovery

| Sample | Cycle 1 | Cycle 2 | Cycle 3 | Cycle 4 | Cycle 5 |
|---|---|---|---|---|---|
| Patient 1 | 109% | 100% | 102% | 96% | 99% |
| Patient 2 | 94% | 104% | 101% | 105% | 96% |
| Patient 3 | 92% | 97% | 99% | 110% | 97% |
| Patient 4 | 100% | 95% | 98% | 84% | 88% |
| Patient 5 | 113% | 112% | 104% | 101% | 105% |
| Patient 6 | 96% | 104% | 107% | 88% | 88% |

Table 8b: C-peptide

Average Calculated Concentrations (ng/mL)

| Sample | Baseline | Cycle 1 | Cycle 2 | Cycle 3 | Cycle 4 | Cycle 5 | Mean | SD | CV |
|---|---|---|---|---|---|---|---|---|---|
| Patient 1 | 7.01 | 7.10 | 6.55 | 6.90 | 6.58 | 6.54 | 6.78 | 0.25 | 4% |
| Patient 2 | 5.49 | 5.14 | 5.44 | 5.34 | 4.99 | 5.35 | 5.29 | 0.19 | 4% |
| Patient 3 | 7.97 | 7.70 | 7.88 | 8.12 | 7.42 | 7.53 | 7.77 | 0.27 | 3% |
| Patient 4 | 10.15 | 9.86 | 9.91 | 9.88 | 9.58 | 10.17 | 9.93 | 0.22 | 2% |
| Patient 5 | 9.23 | 9.33 | 9.20 | 9.19 | 9.03 | 8.75 | 9.12 | 0.21 | 2% |
| Patient 6 | 2.23 | 2.21 | 2.29 | 2.31 | 2.28 | 2.25 | 2.26 | 0.04 | 2% |

% Recovery

| Sample | Cycle 1 | Cycle 2 | Cycle 3 | Cycle 4 | Cycle 5 |
|---|---|---|---|---|---|
| Patient 1 | 101% | 94% | 98% | 94% | 93% |
| Patient 2 | 94% | 99% | 97% | 91% | 97% |
| Patient 3 | 97% | 99% | 102% | 93% | 95% |
| Patient 4 | 97% | 98% | 97% | 94% | 100% |
| Patient 5 | 101% | 100% | 100% | 98% | 95% |
| Patient 6 | 99% | 103% | 103% | 102% | 101% |

Refrigerated Temperature Sample Stability (2 to 8° C.): Six serum pools were evaluated for stability of C-peptide and insulin at refrigerated temperatures between 2 to 8° C. in human serum. Six samples were spiked with known concentrations of the peptides, stored in the refrigerator, and transferred to the ultralow freezer on allotted days (Day 0, 1, 3, 5, 7, 14, 21 and 28). The data indicates that insulin is stable at refrigerated temperatures for at least 28 days whereas C-peptide is stable for up to 7 days under these conditions (Table 9 and FIG. 6).

TABLE 9

Refrigerated Temperature Sample Stability

Table 9a: Insulin

Average Calculated Concentrations (uIU/mL)

| Sample | Baseline | Day 1 | Day 3 | Day 5 | Day 7 | Day 14 | Day 21 | Day 28 | Mean | SD | CV |
|---|---|---|---|---|---|---|---|---|---|---|---|
| Patient 1 | 58.9 | 55.9 | 58.6 | 50.6 | 62.1 | 61.1 | 59.1 | 54.1 | 57.5 | 3.8 | 7% |
| Patient 2 | 45.3 | 44.6 | 45.1 | 43.9 | 44.6 | 42.8 | 48.8 | 45.4 | 45.1 | 1.7 | 4% |

TABLE 9-continued

Refrigerated Temperature Sample Stability

| Patient 3 | 87.5 | 93.6 | 88.7 | 84.3 | 82.6 | 85.0 | 92.5 | 96.0 | 88.8 | 4.8 | 5% |
| Patient 4 | 111.5 | 121.4 | 109.0 | 107.8 | 108.9 | 103.9 | 117.3 | 114.0 | 111.7 | 5.6 | 5% |
| Patient 5 | 99.1 | 100.5 | 110.2 | 98.8 | 97.8 | 103.9 | 109.6 | 107.0 | 103.3 | 5.0 | 5% |
| Patient 6 | 18.5 | 20.8 | 21.1 | 19.0 | 19.6 | 19.2 | 16.9 | 15.8 | 18.9 | 1.8 | 10% |

% Recovery

| Sample | Day 1 | Day 3 | Day 5 | Day 7 | Day 14 | Day 21 | Day 28 |
|---|---|---|---|---|---|---|---|
| Patient 1 | 95% | 100% | 86% | 106% | 104% | 100% | 92% |
| Patient 2 | 98% | 100% | 97% | 99% | 94% | 108% | 100% |
| Patient 3 | 107% | 101% | 96% | 94% | 97% | 106% | 110% |
| Patient 4 | 109% | 98% | 97% | 98% | 93% | 105% | 102% |
| Patient 5 | 101% | 111% | 100% | 99% | 105% | 111% | 108% |
| Patient 6 | 112% | 114% | 102% | 106% | 104% | 91% | 85% |

Table 9b: C-peptide

Average Calculated Concentrations (ng/mL)

| Sample | Baseline | Day 1 | Day 3 | Day 5 | Day 7 | Day 14 | Day 21 | Day 28 | Mean | SD | CV |
|---|---|---|---|---|---|---|---|---|---|---|---|
| Patient 1 | 6.47 | 6.58 | 6.22 | 6.39 | 6.37 | 6.15 | 6.09 | 5.58 | 6.23 | 0.3 | 5% |
| Patient 2 | 5.39 | 5.14 | 4.76 | 5.01 | 4.74 | 4.65 | 4.51 | 4.41 | 4.83 | 0.3 | 7% |
| Patient 3 | 7.62 | 7.90 | 7.74 | 7.70 | 7.24 | 7.08 | 7.12 | 6.41 | 7.35 | 0.5 | 7% |
| Patient 4 | 9.84 | 10.67 | 9.53 | 9.60 | 9.18 | 9.07 | 8.37 | 8.28 | 9.32 | 0.8 | 8% |
| Patient 5 | 9.29 | 8.70 | 9.40 | 8.58 | 8.29 | 8.29 | 8.02 | 8.10 | 8.58 | 0.5 | 6% |
| Patient 6 | 2.19 | 2.13 | 2.17 | 2.26 | 2.14 | 2.10 | 2.16 | 2.07 | 2.15 | 0.1 | 3% |

% Recovery

| Sample | Day 1 | Day 3 | Day 5 | Day 7 | Day 14 | Day 21 | Day 28 |
|---|---|---|---|---|---|---|---|
| Patient 1 | 102% | 96% | 99% | 98% | 95% | 94% | 86% |
| Patient 2 | 95% | 88% | 93% | 88% | 86% | 84% | 82% |
| Patient 3 | 104% | 102% | 101% | 95% | 93% | 93% | 84% |
| Patient 4 | 109% | 97% | 98% | 93% | 92% | 85% | 84% |
| Patient 5 | 94% | 101% | 92% | 89% | 89% | 86% | 87% |
| Patient 6 | 97% | 99% | 103% | 98% | 96% | 99% | 94% |

Figure 7A:
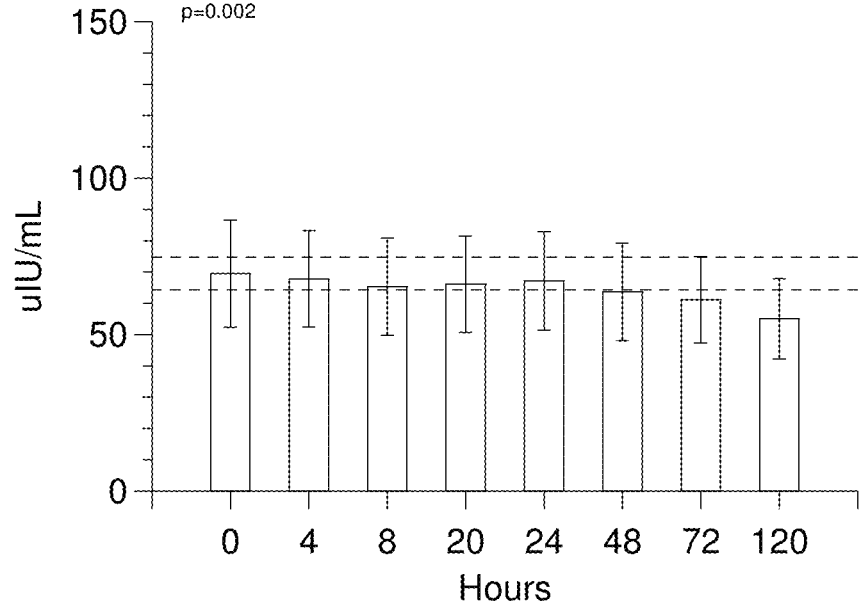
FIGS. 7A-7B show room temperature sample stability for insulin (7A) and C-peptide (7B).
Figure 7B:
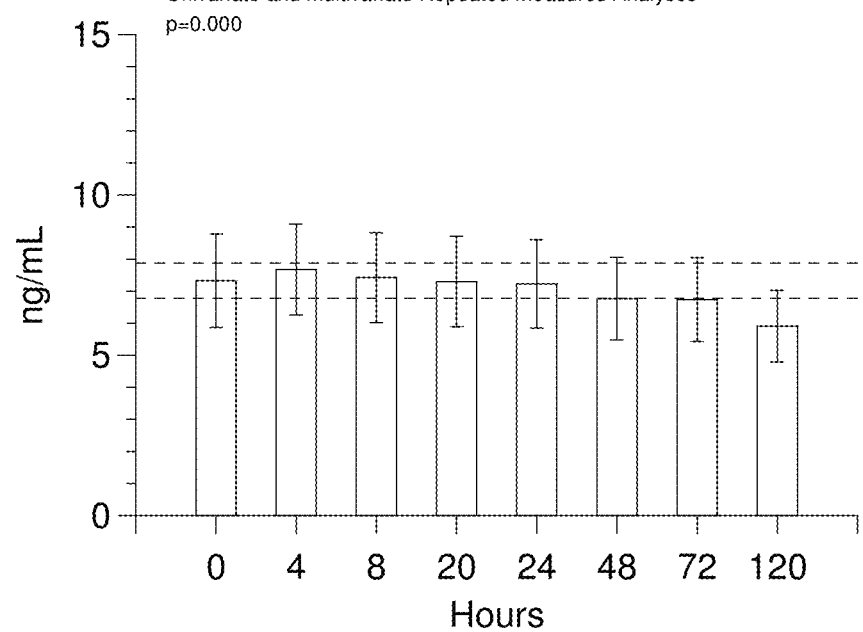

Room Temperature Sample Stability (18 to 26° C.): Six serum pools were evaluated for stability of C-peptide and insulin and at room temperature between 18 to 26° C. in human serum. Six samples were spiked with known concentrations of the peptides, left out at room temperature, and transferred to the ultralow freezer on allotted days over 120 hours. The data indicate that both peptides are stable at room temperature for 24 hours (Table 10 and FIG. 7).

TABLE 10

Room Temperature Sample Stability

Table 10a: Insulin

| Sample | Average Calculated Concentrations (uIU/mL) | | | | | | | | Mean | SD | CV |
|---|---|---|---|---|---|---|---|---|---|---|---|
| | Baseline | 4 h | 8 h | 20 h | 24 h | 48 h | 72 h | 120 h | | | |
| Patient 1 | 50.8 | 54.7 | 48.0 | 58.9 | 58.4 | 55.5 | 56.7 | 45.0 | 53.5 | 5.1 | 9% |
| Patient 2 | 43.8 | 46.9 | 48.6 | 38.7 | 40.4 | 37.7 | 38.3 | 33.3 | 41.0 | 5.1 | 12% |
| Patient 3 | 92.6 | 91.3 | 73.7 | 81.1 | 90.8 | 74.6 | 79.7 | 73.6 | 82.2 | 8.2 | 10% |
| Patient 4 | 103.4 | 97.0 | 104.3 | 100.4 | 100.0 | 92.4 | 93.0 | 87.2 | 97.2 | 6.0 | 6% |
| Patient 5 | 110.0 | 100.7 | 101.3 | 100.3 | 98.0 | 106.9 | 84.8 | 76.4 | 97.3 | 11.2 | 12% |
| Patient 6 | 16.5 | 16.1 | 16.0 | 17.1 | 15.4 | 15.0 | 14.3 | 14.7 | 15.6 | 1.0 | 6% |

| Sample | % Recovery | | | | | | |
|---|---|---|---|---|---|---|---|
| | 4 h | 8 h | 20 h | 24 h | 48 h | 72 h | 120 h |
| Patient 1 | 108% | 94% | 116% | 115% | 109% | 112% | 89% |
| Patient 2 | 107% | 111% | 88% | 92% | 86% | 88% | 76% |
| Patient 3 | 99% | 80% | 88% | 98% | 81% | 86% | 80% |
| Patient 4 | 94% | 101% | 97% | 97% | 89% | 90% | 84% |
| Patient 5 | 91% | 92% | 91% | 89% | 97% | 77% | 69% |
| Patient 6 | 98% | 97% | 104% | 93% | 91% | 87% | 90% |

Table 10b: C-peptide

| Sample | Average Calculated Concentrations (ng/mL) | | | | | | | | Mean | SD | CV |
|---|---|---|---|---|---|---|---|---|---|---|---|
| | Baseline | 4 h | 8 h | 20 h | 24 h | 48 h | 72 h | 120 h | | | |
| Patient 1 | 6.68 | 7.90 | 6.92 | 6.67 | 6.94 | 6.53 | 6.48 | 5.51 | 6.70 | 0.66 | 10% |
| Patient 2 | 5.47 | 5.86 | 5.63 | 5.67 | 5.26 | 4.94 | 4.82 | 4.25 | 5.24 | 0.54 | 10% |
| Patient 3 | 8.36 | 9.23 | 8.25 | 8.41 | 8.48 | 7.98 | 7.78 | 7.20 | 8.21 | 0.59 | 7% |
| Patient 4 | 11.59 | 11.15 | 10.80 | 10.84 | 10.44 | 9.59 | 9.63 | 7.79 | 10.23 | 1.21 | 12% |
| Patient 5 | 9.44 | 9.48 | 10.36 | 9.90 | 9.84 | 9.38 | 9.50 | 8.65 | 9.57 | 0.50 | 5% |
| Patient 6 | 2.42 | 2.43 | 2.57 | 2.32 | 2.40 | 2.21 | 2.20 | 2.05 | 2.32 | 0.16 | 7% |

| Sample | % Recovery | | | | | | |
|---|---|---|---|---|---|---|---|
| | 4 h | 8 h | 20 h | 24 h | 48 h | 72 h | 120 h |
| Patient 1 | 118% | 104% | 100% | 104% | 98% | 97% | 83% |
| Patient 2 | 107% | 103% | 104% | 96% | 90% | 88% | 78% |
| Patient 3 | 110% | 99% | 101% | 101% | 95% | 93% | 86% |
| Patient 4 | 96% | 93% | 94% | 90% | 83% | 83% | 67% |
| Patient 5 | 100% | 110% | 105% | 104% | 99% | 101% | 92% |
| Patient 6 | 100% | 106% | 96% | 99% | 91% | 91% | 85% |

Figure 8A:
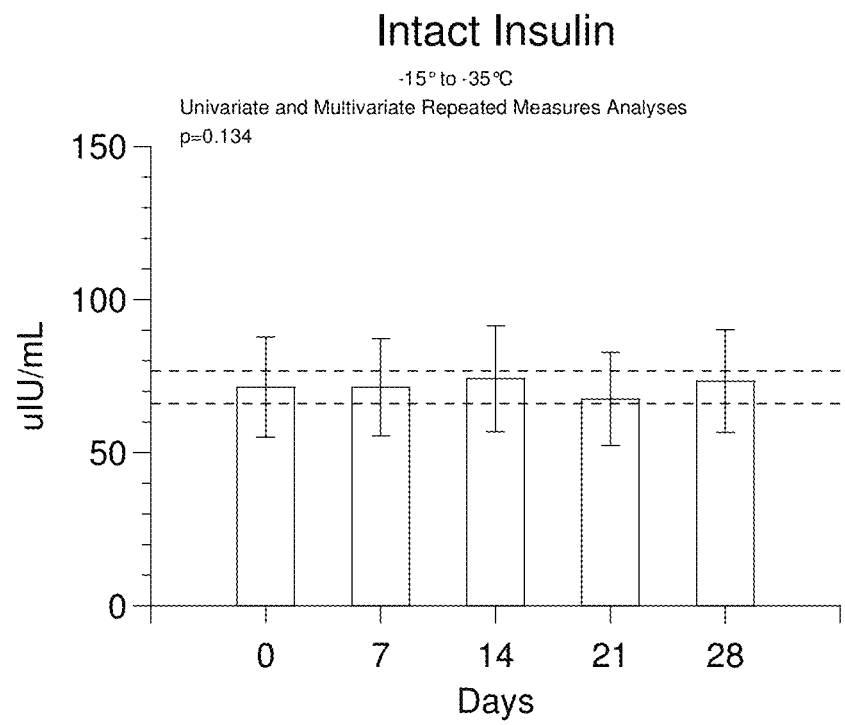
FIGS. 8A-8B show frozen temperature sample stability for insulin (8A) and C-peptide (8B).
Figure 8B:
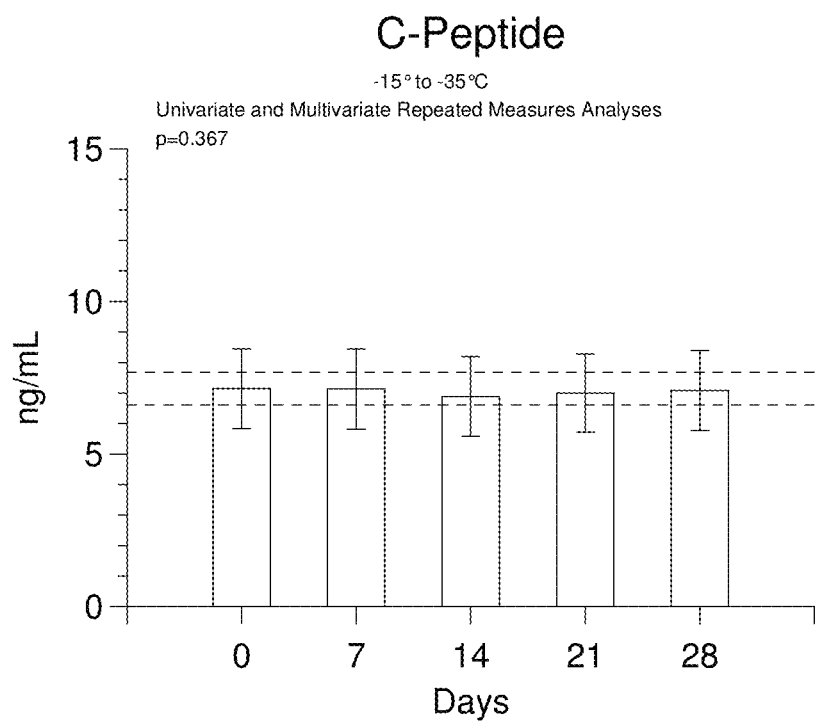

Frozen Temperature Sample Stability (−10 to −30° C.): Six serum pools were evaluated for stability of C-peptide and insulin at frozen temperatures between −10 to 30° C. in human serum. Six samples were spiked with known concentrations of the peptides, stored frozen, and transferred to the ultralow freezer on allotted days (Day 0, 7, 14, 21 and 28). The data indicates that both peptides stable when frozen for at least 28 days (Table 11 and FIG. 8).

TABLE 11

Frozen Temperature Sample Stability

Table 11a: Insulin

Average Calculated Concentrations (uIU/mL)

| Sample | Baseline | Day 7 | Day 14 | Day 21 | Day 28 | Mean | SD | CV |
|---|---|---|---|---|---|---|---|---|
| Patient 1 | 55.7 | 59.0 | 54.9 | 52.6 | 57.3 | 55.9 | 2.4 | 4% |
| Patient 2 | 48.2 | 46.3 | 53.1 | 45.4 | 48.7 | 48.3 | 3.0 | 6% |
| Patient 3 | 91.8 | 97.9 | 89.0 | 84.7 | 94.0 | 91.5 | 5.0 | 5% |
| Patient 4 | 110.7 | 105.3 | 106.2 | 98.5 | 110.3 | 106.2 | 4.9 | 5% |
| Patient 5 | 103.1 | 100.1 | 121.9 | 104.7 | 110.0 | 108.0 | 8.6 | 8% |
| Patient 6 | 18.8 | 19.7 | 20.0 | 19.5 | 19.9 | 19.6 | 0.5 | 2% |

% Recovery

| Sample | Day 7 | Day 14 | Day 21 | Day 28 |
|---|---|---|---|---|
| Patient 1 | 106% | 99% | 94% | 103% |
| Patient 2 | 96% | 110% | 94% | 101% |
| Patient 3 | 107% | 97% | 92% | 102% |
| Patient 4 | 95% | 96% | 89% | 100% |
| Patient 5 | 97% | 118% | 102% | 107% |
| Patient 6 | 105% | 106% | 103% | 106% |

Table 11b: C-peptide

Average Calculated Concentrations (ng/mL)

| Sample | Baseline | Day 7 | Day 14 | Day 21 | Day 28 | Mean | SD | CV |
|---|---|---|---|---|---|---|---|---|
| Patient 1 | 6.87 | 7.29 | 6.16 | 6.71 | 7.06 | 6.82 | 0.43 | 6% |
| Patient 2 | 5.59 | 5.44 | 5.18 | 5.32 | 5.35 | 5.38 | 0.15 | 3% |
| Patient 3 | 8.16 | 7.90 | 8.29 | 8.14 | 7.91 | 8.08 | 0.17 | 2% |
| Patient 4 | 10.16 | 10.40 | 10.38 | 9.97 | 10.43 | 10.27 | 0.20 | 2% |
| Patient 5 | 9.66 | 9.40 | 8.86 | 9.43 | 9.35 | 9.34 | 0.29 | 3% |
| Patient 6 | 2.40 | 2.35 | 2.45 | 2.42 | 2.42 | 2.41 | 0.04 | 2% |

% Recovery

| Sample | Day 7 | Day 14 | Day 21 | Day 28 |
|---|---|---|---|---|
| Patient 1 | 106% | 90% | 98% | 103% |
| Patient 2 | 97% | 93% | 95% | 96% |
| Patient 3 | 97% | 102% | 100% | 97% |
| Patient 4 | 102% | 102% | 98% | 103% |
| Patient 5 | 97% | 92% | 98% | 97% |
| Patient 6 | 98% | 102% | 101% | 101% |

Figure 9A:
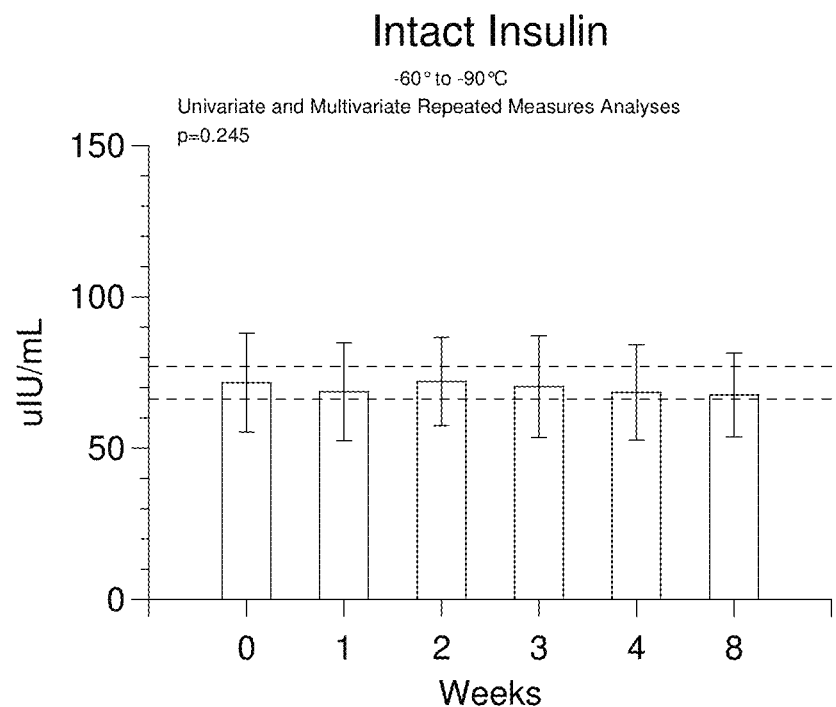
FIGS. 9A-9B show ultra frozen temperature sample stability for insulin (9A) and C-peptide (9B).
Figure 9B:
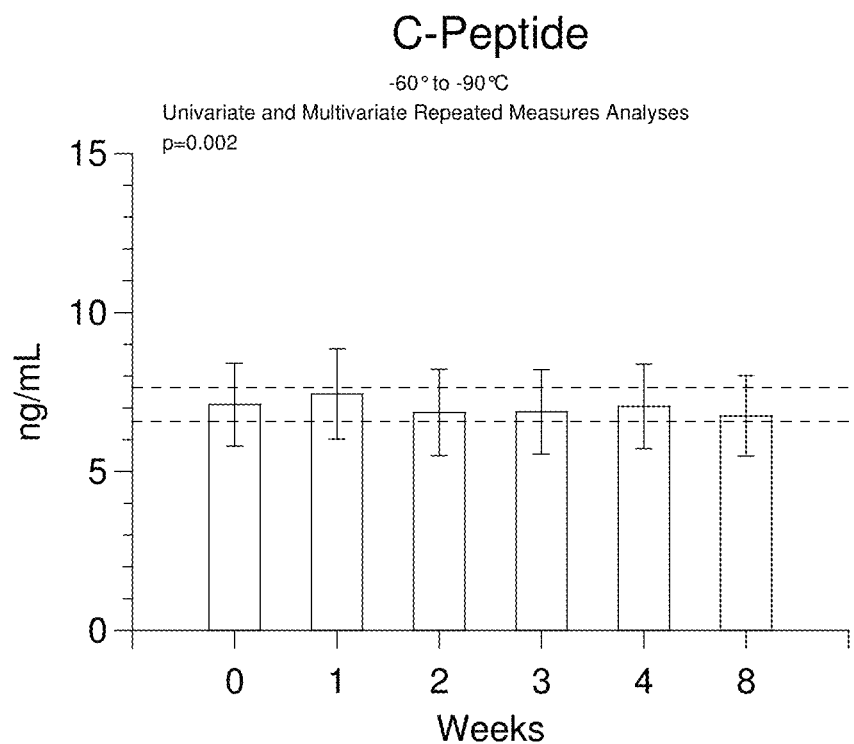
Figure 10A:
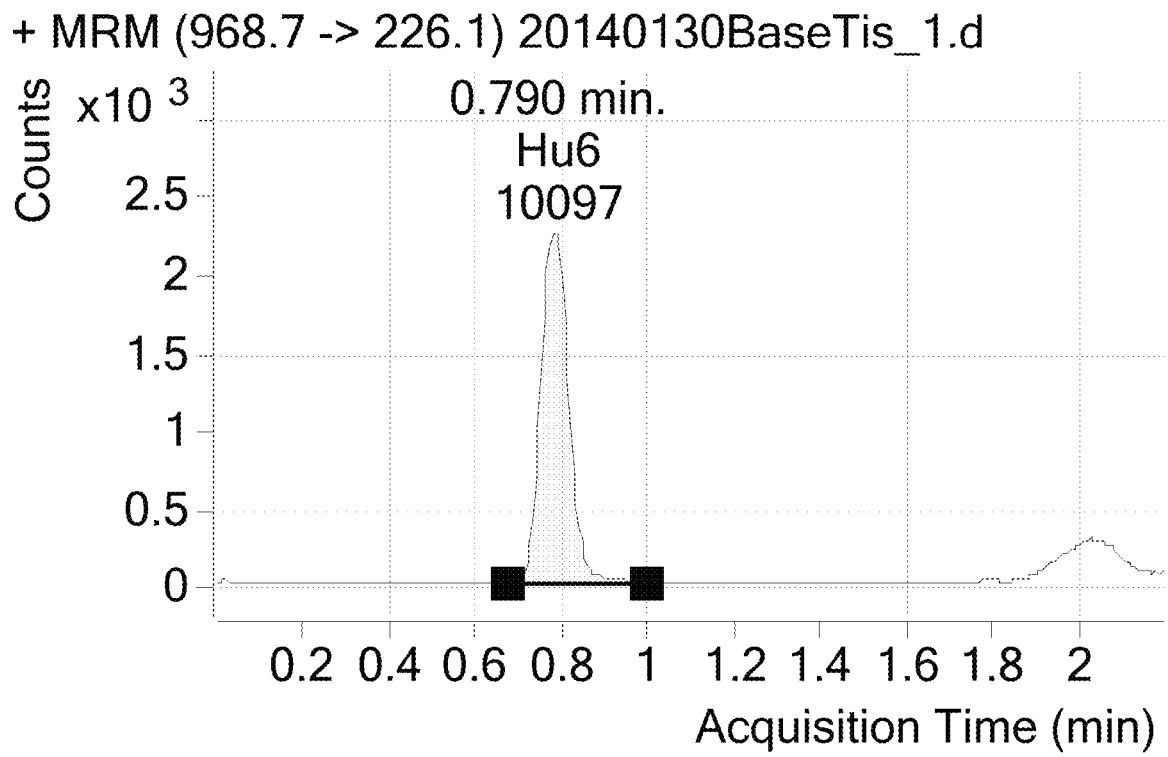
FIGS. 10A-10D show mass spectra of HUMALIN® (10A) in base, (10B) in 0.1 formic acid, 30% ACN, (10C) base extraction, (10D) CLENACITE®/base extraction.
Figure 10B:
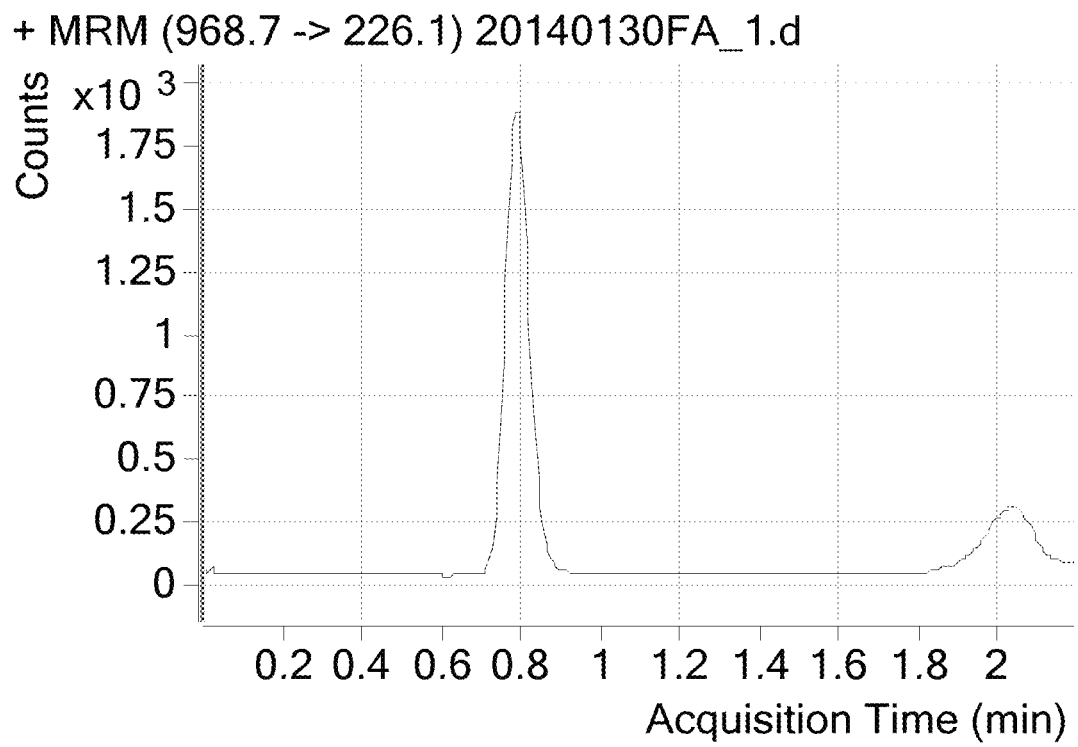
Figure 10C:
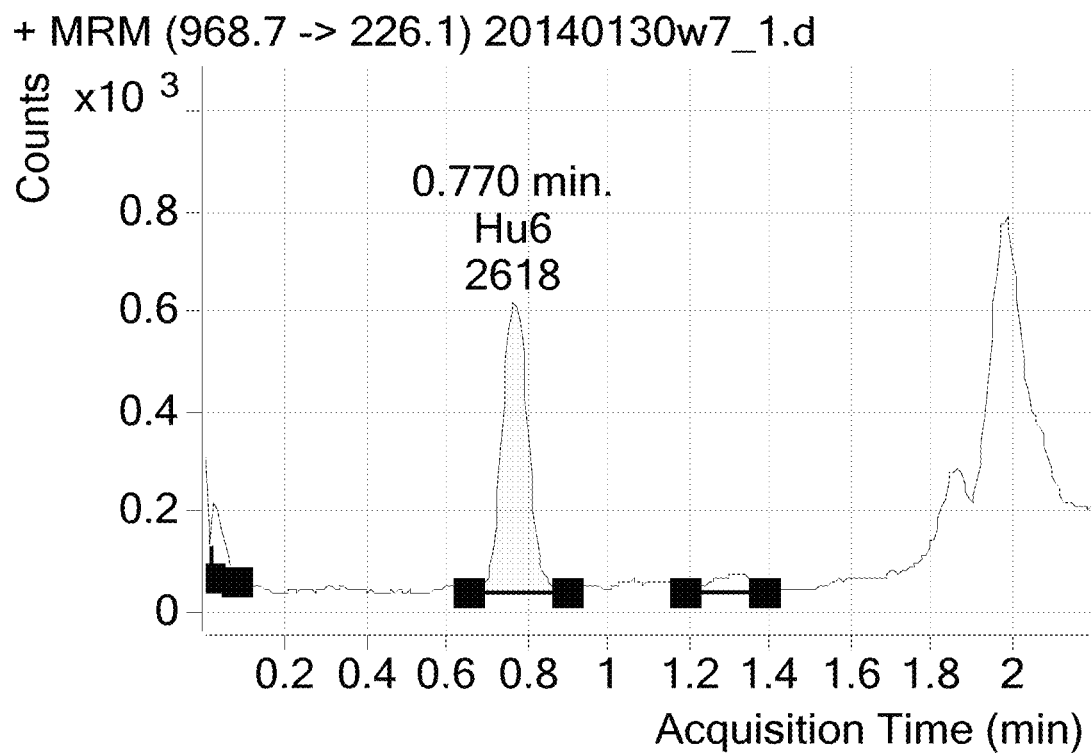
Figure 10D:
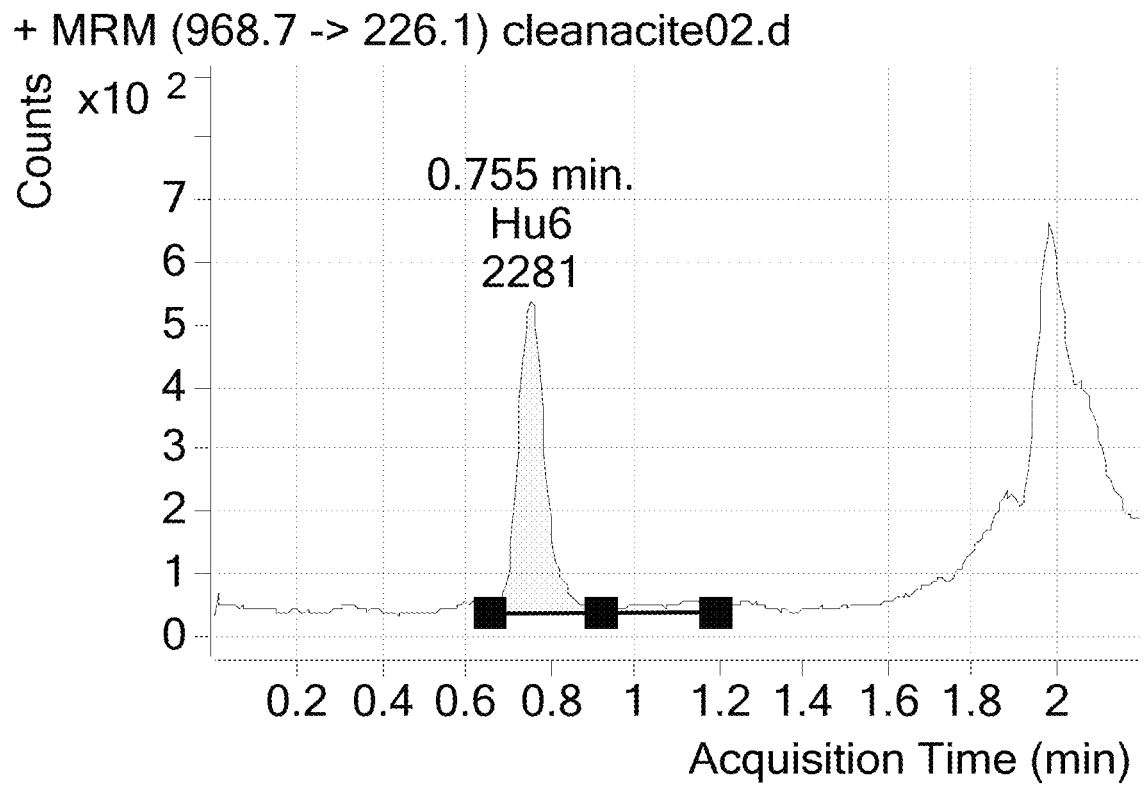
Figure 11:
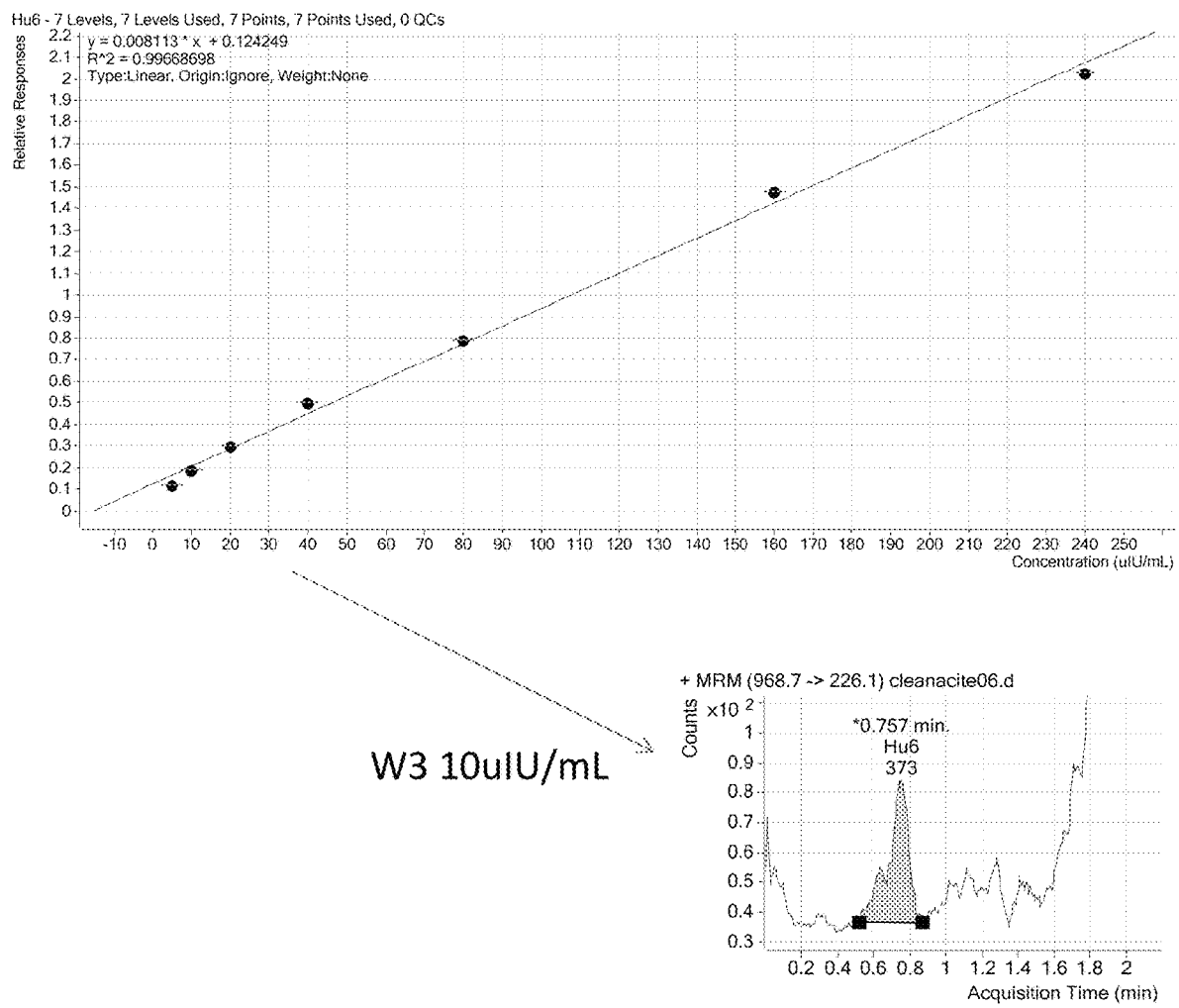
FIG. 11 shows the results of HUMALIN® for CLENACITE®/base extraction.
Figure 12A:
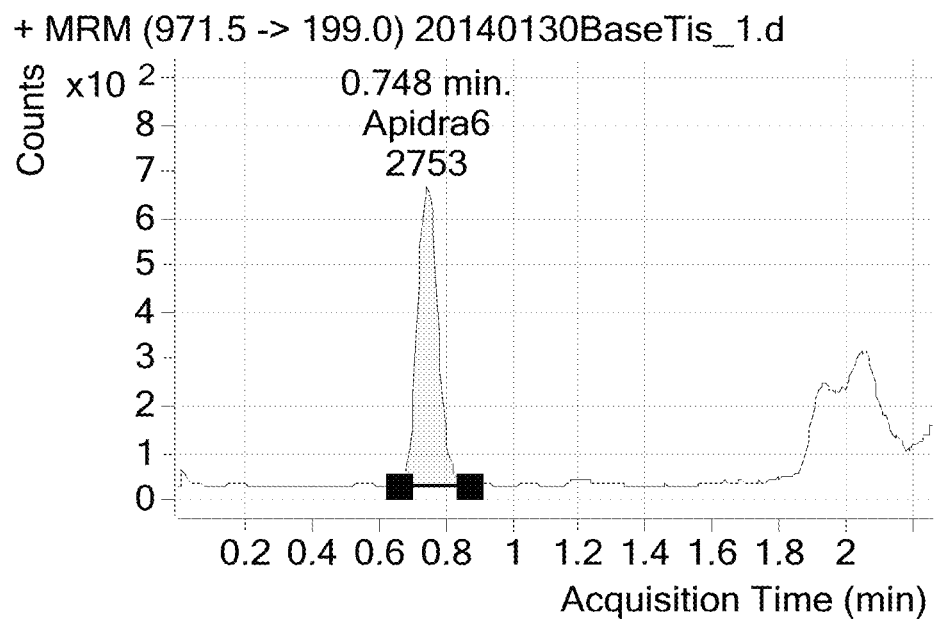
FIGS. 12A-12D show mass spectra of APIDRA® (12A) in base, (12B) in 0.1 formic acid, 30% ACN, (12C) base extraction, (12D) CLENACITE®/base extraction.
Figure 12B:
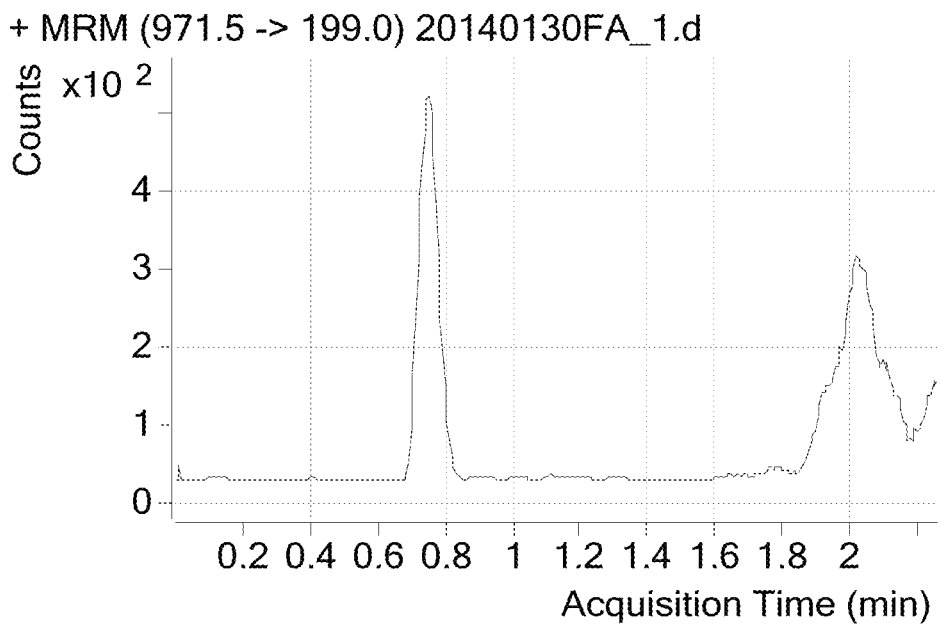
Figure 12C:
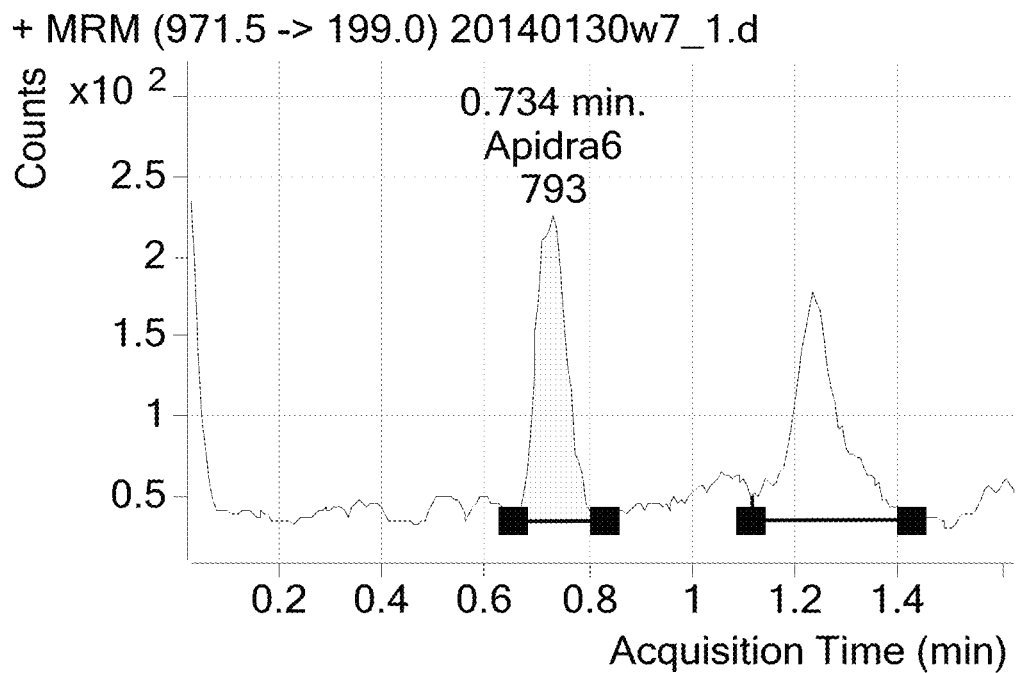
Figure 12D:
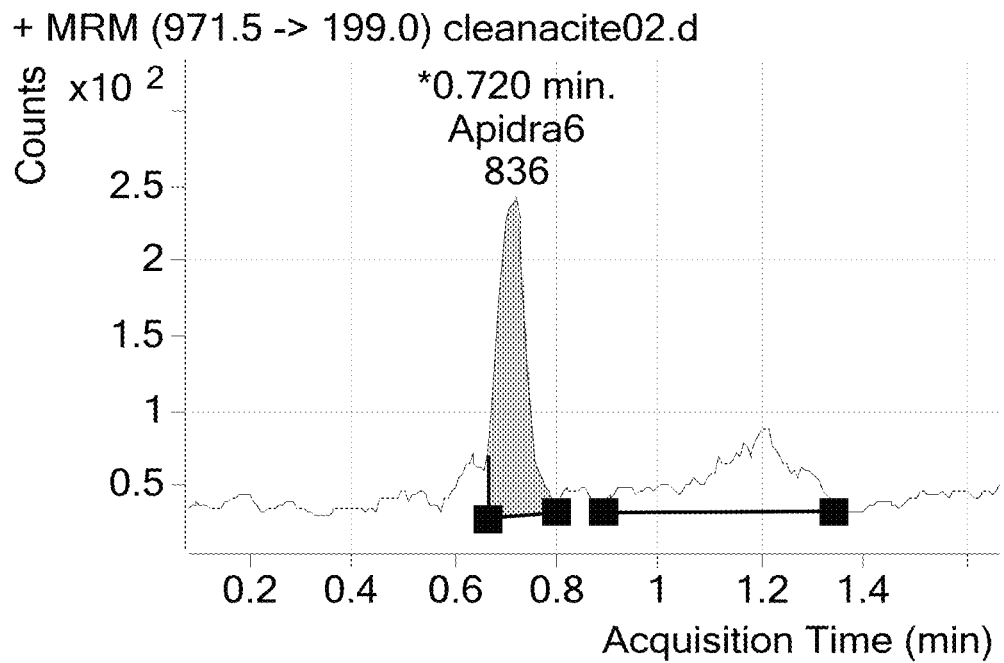
Figure 13:
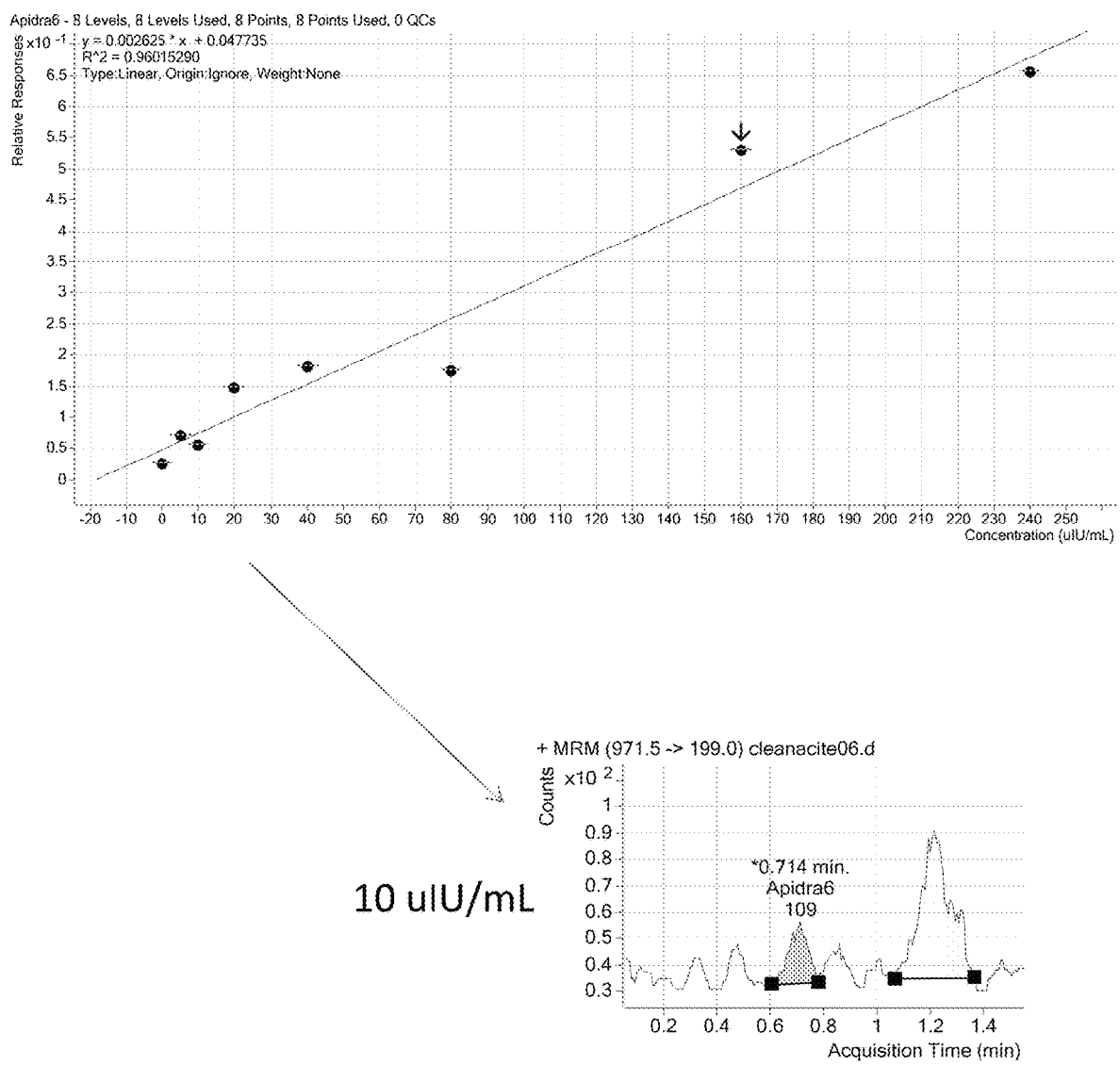
FIG. 13 shows the results of APIDRA® for CLENACITE®/base extraction.
Figure 14A:
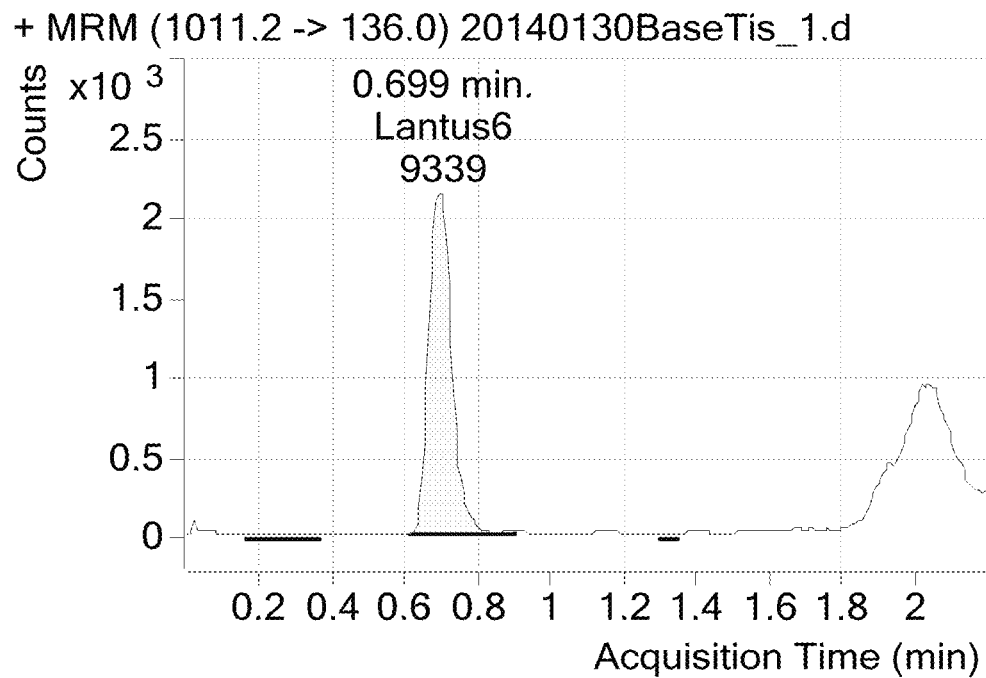
FIGS. 14A-14D show mass spectra of LANTUS® (14A) in base, (14B) in 0.1 formic acid, 30% ACN, (14C) base extraction, (14D) CLENACITE®/base extraction.
Figure 14B:
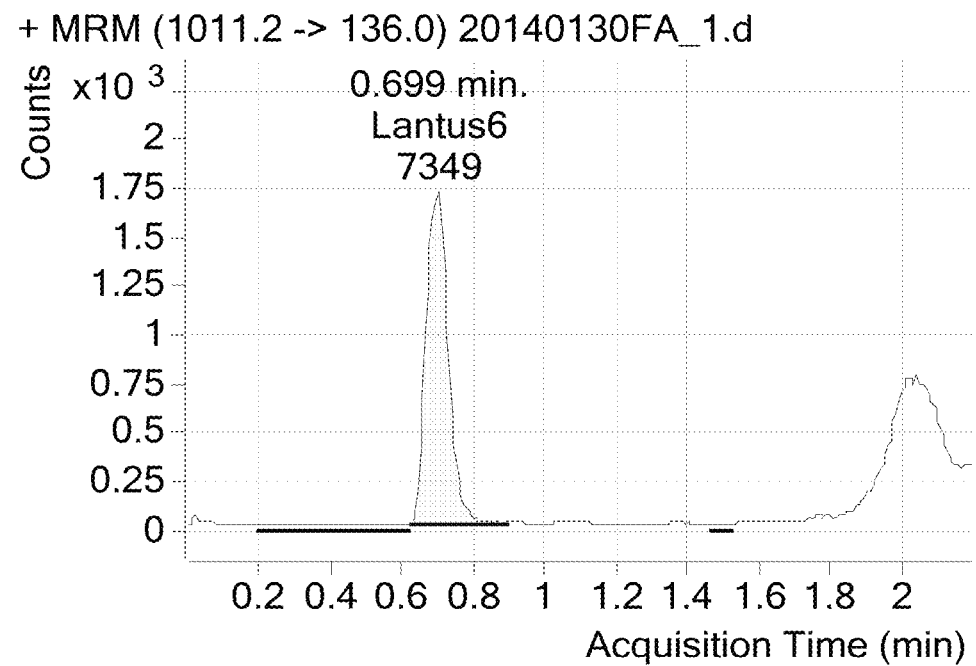
Figure 14C:
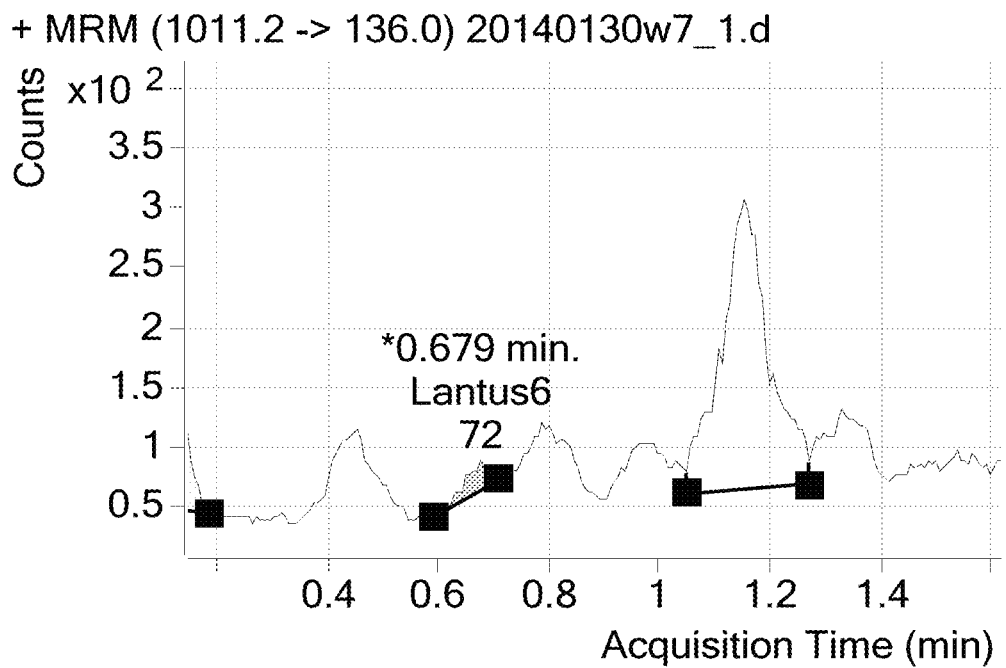
Figure 14D:
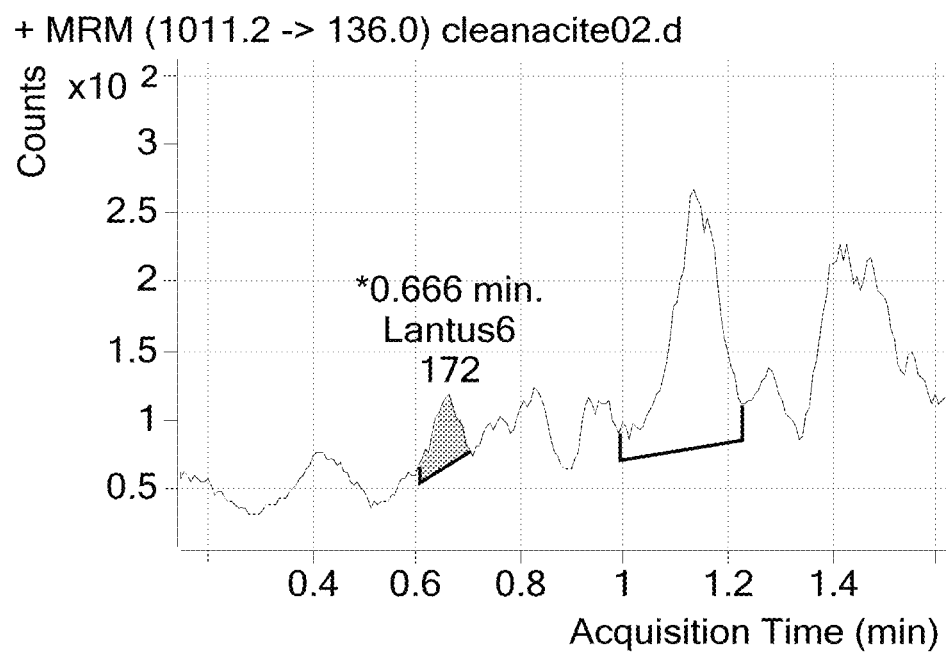
Figure 15A:
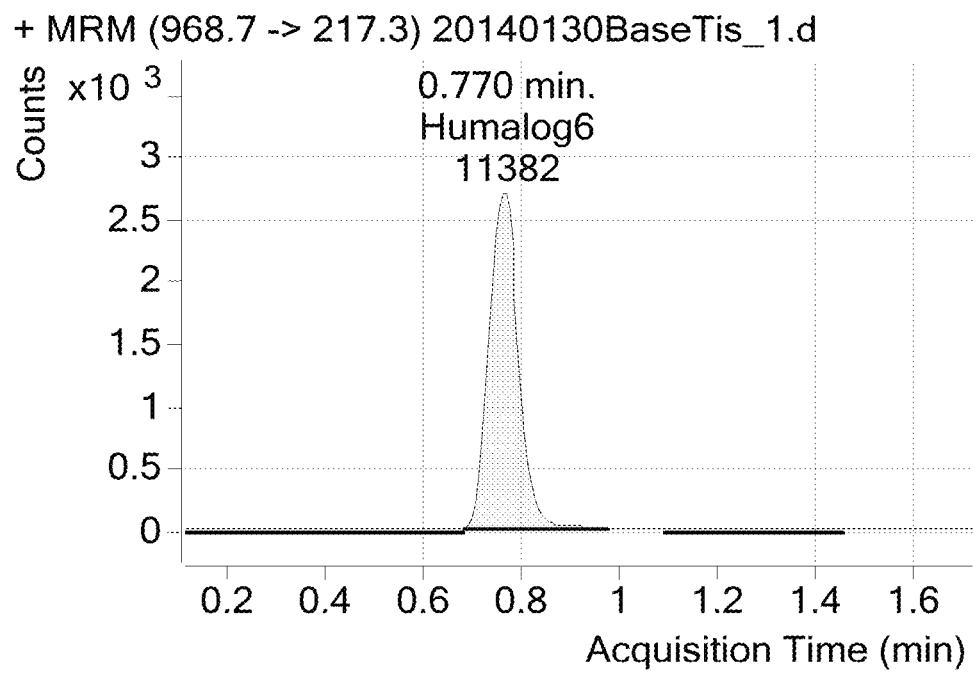
FIGS. 15A-15D show mass spectra of HUMALOG® (15A) in base, (15B) in 0.1 formic acid, 30% ACN, (15C) base extraction, (15D) CLENACITE®/base extraction.
Figure 15B:
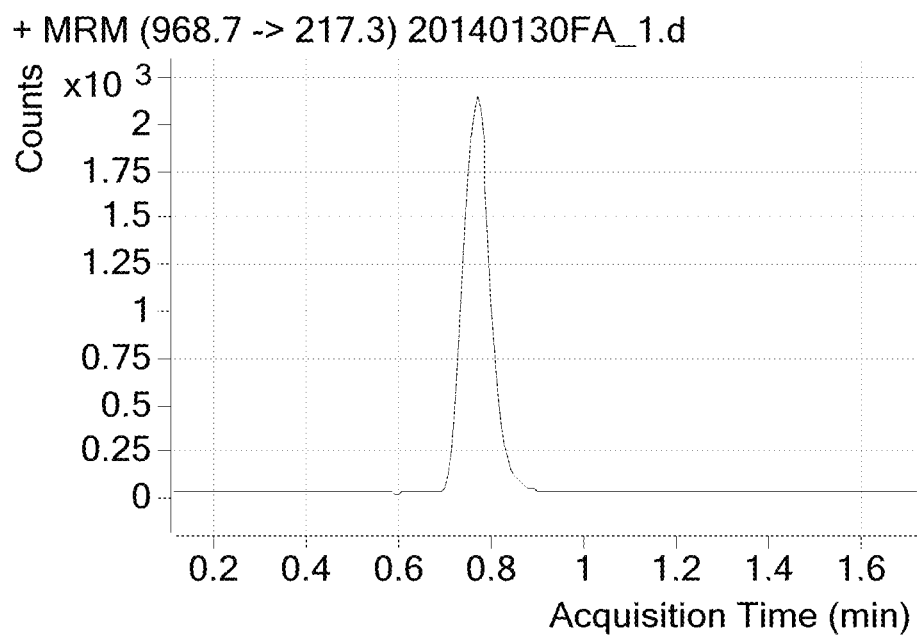
Figure 15C:
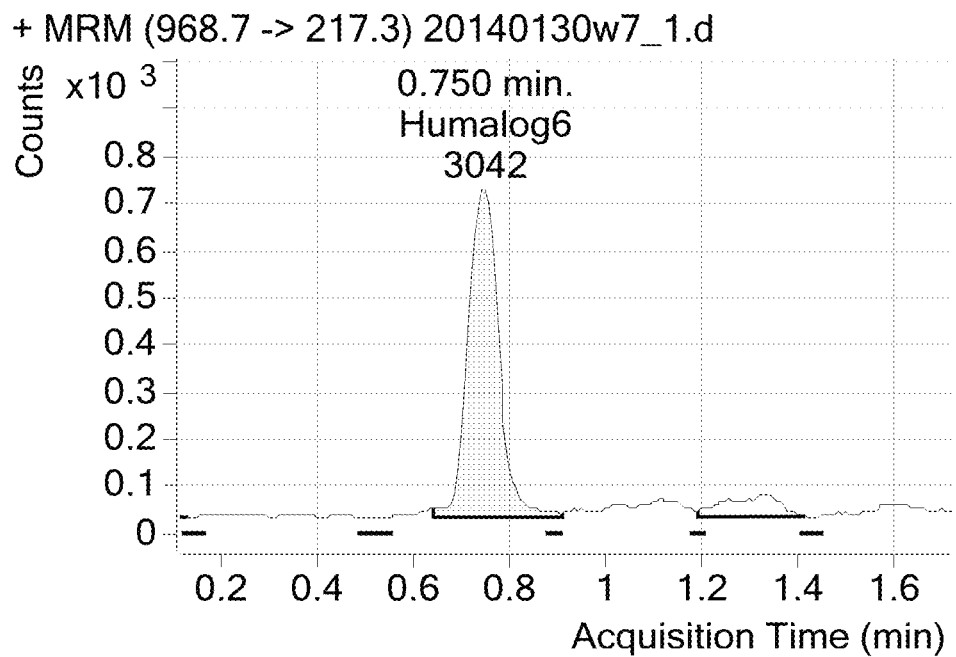
Figure 15D:
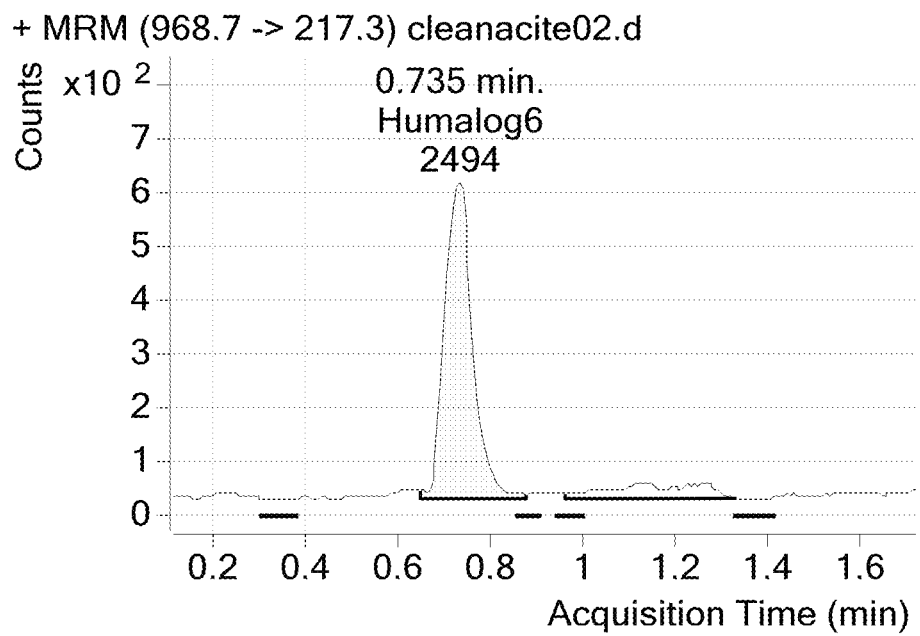
Figure 16:
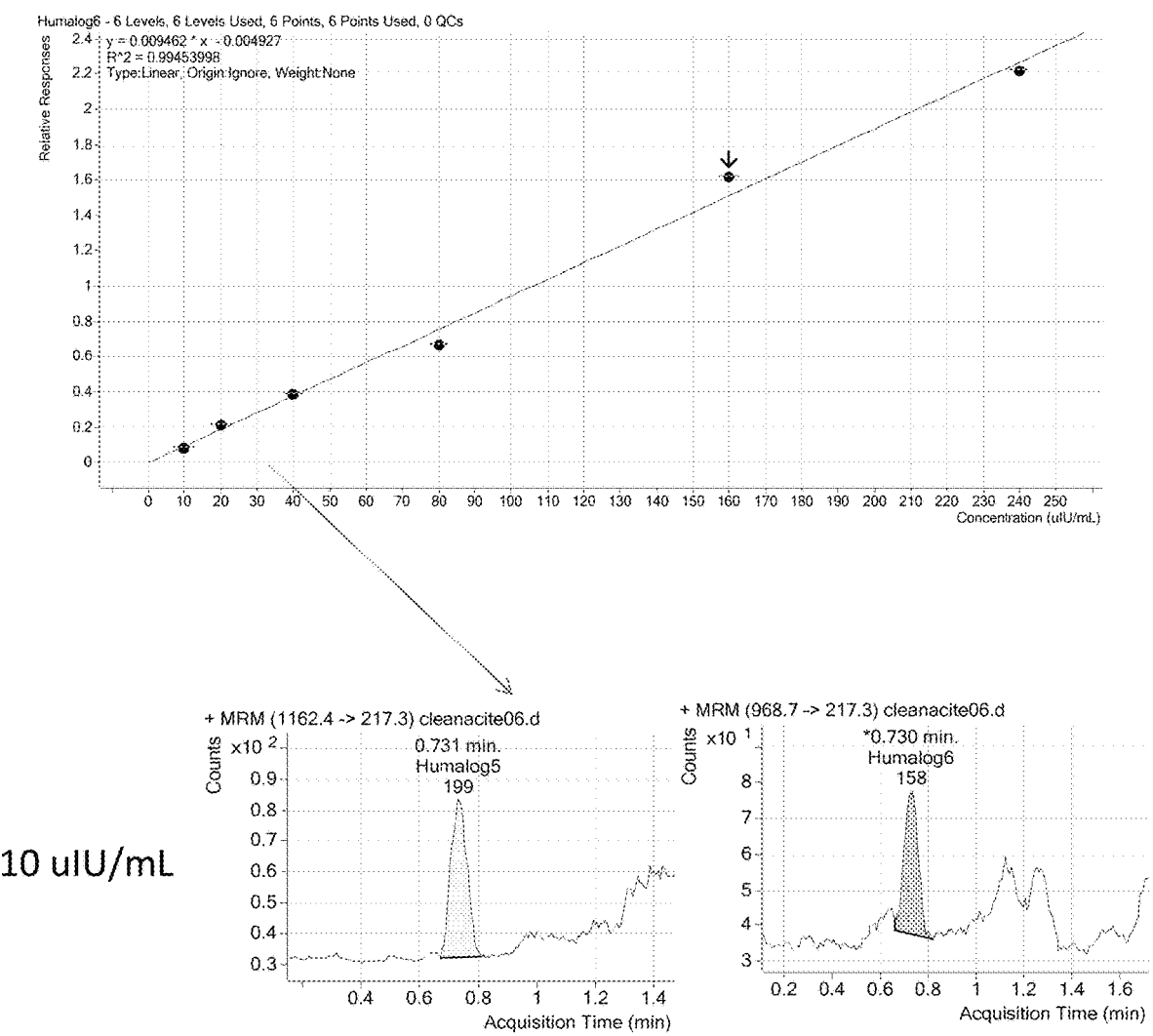
FIG. 16 shows the results of HUMALOG® for CLENACITE®/base extraction.
Figure 17A:
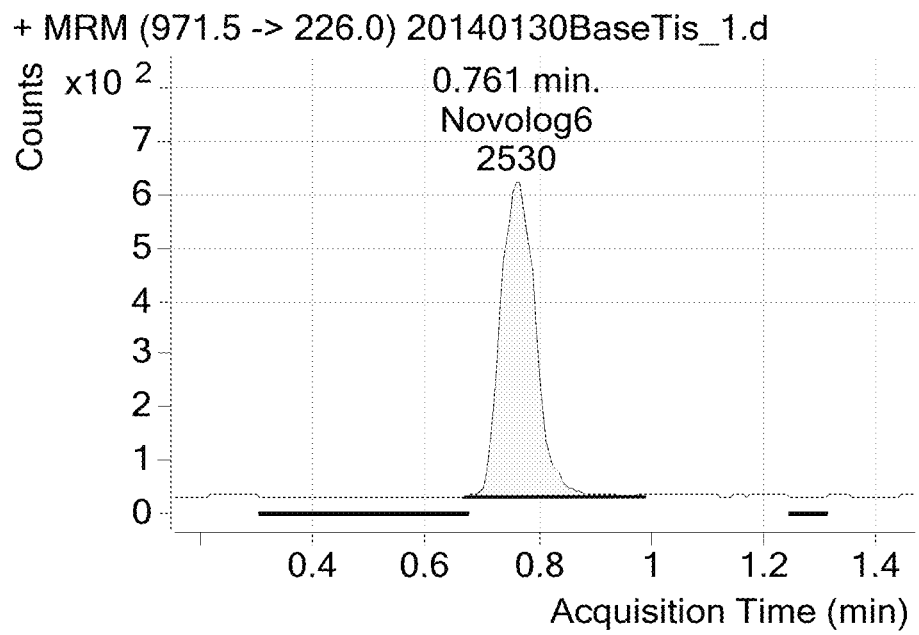
FIGS. 17A-17D show mass spectra of NOVOLOG® (17A) in base, (17B) in 0.1 formic acid, 30% ACN, (17C) base extraction, (17D) CLENACITE®/base extraction.
Figure 17B:
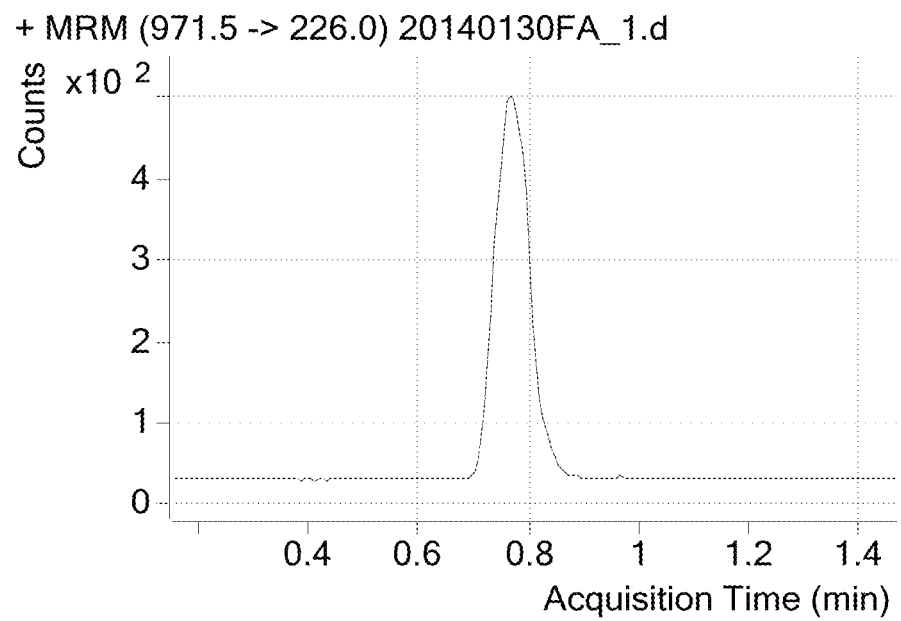
Figure 17C:
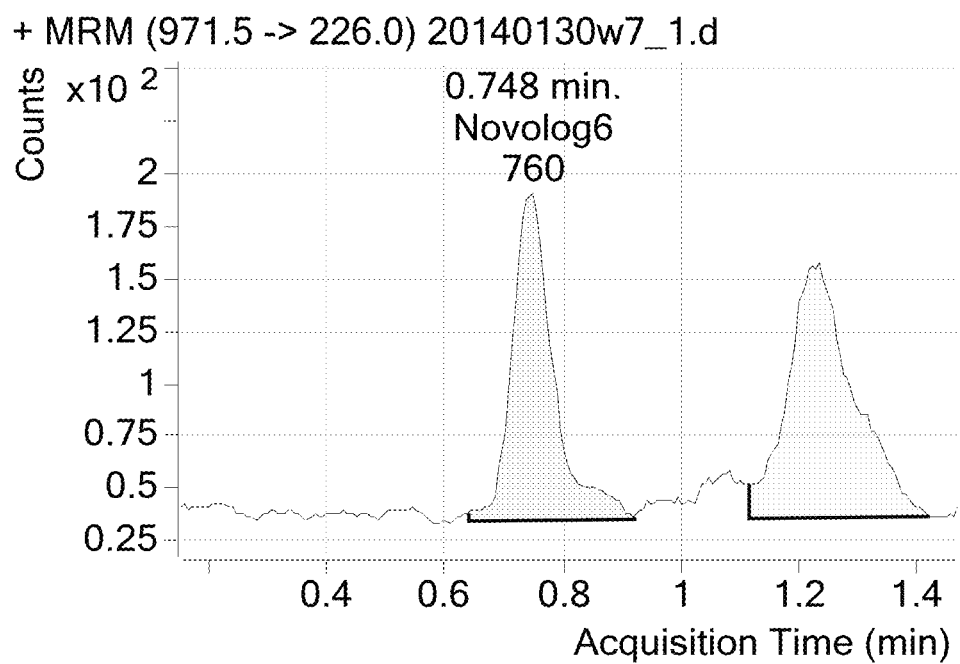
Figure 17D:
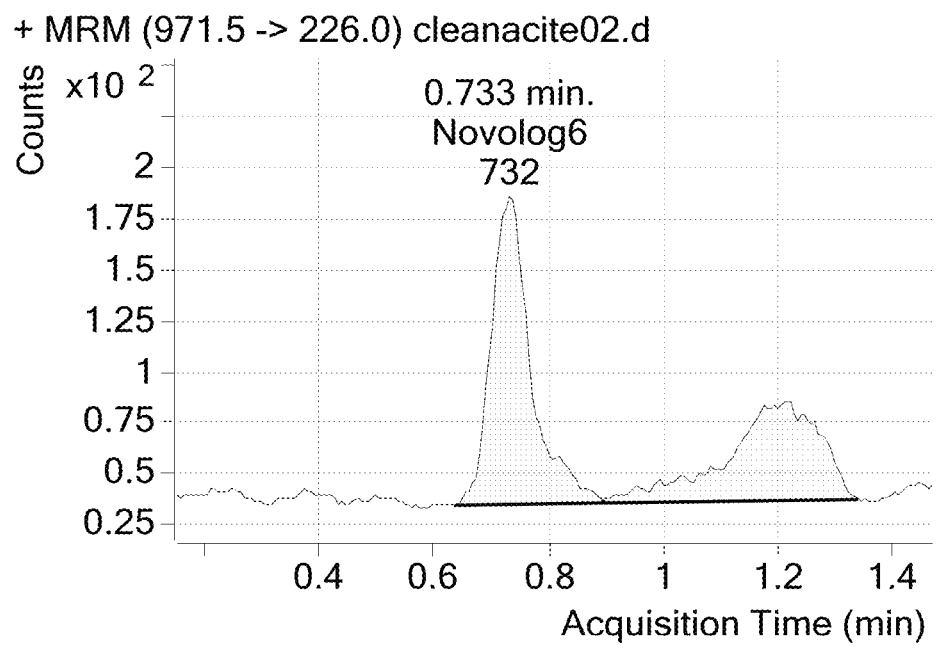
Figure 18:
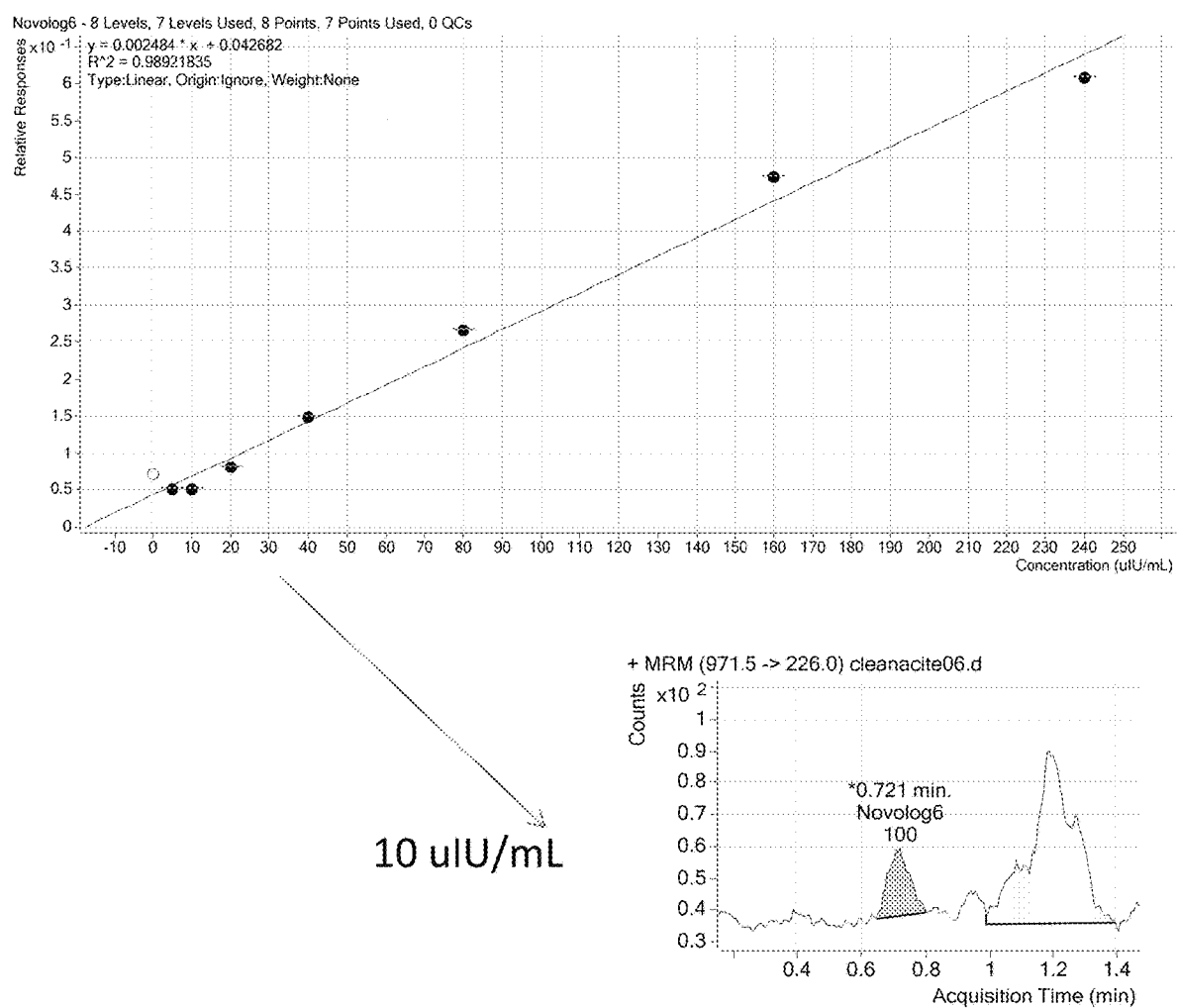
FIG. 18 shows the results of NOVOLOG® for CLENACITE®/base extraction.
Figure 19A:
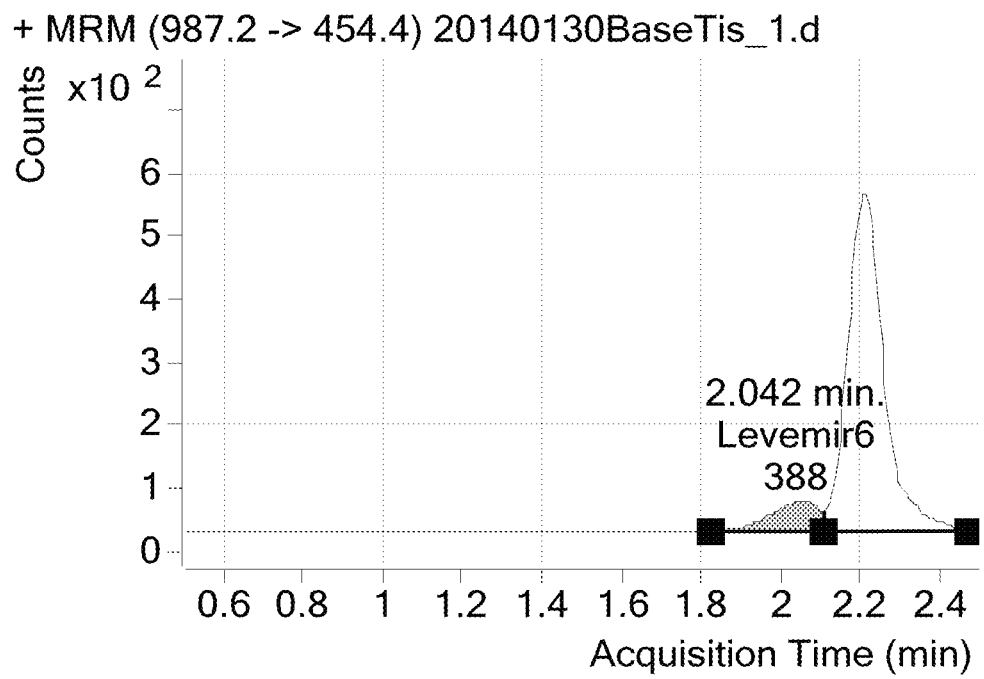
FIGS. 19A-19D show mass spectra of LEVEMIR® (19A) in base, (19B) in 0.1 formic acid, 30% ACN, (19C) base extraction, (19D) CLENACITE®/base extraction.
Figure 19B:
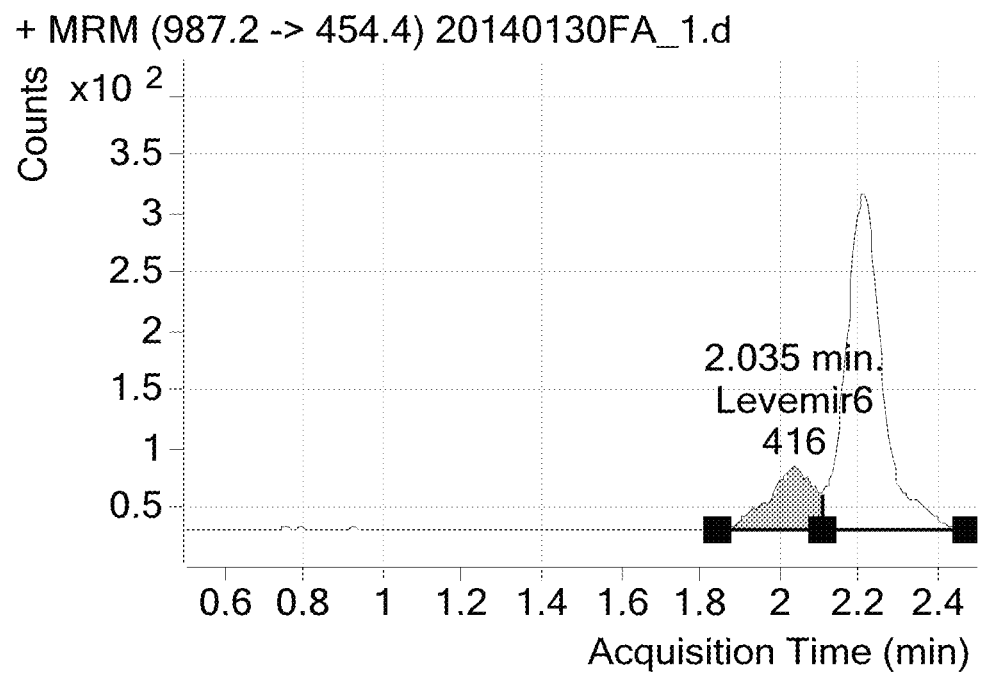
Figure 19C:
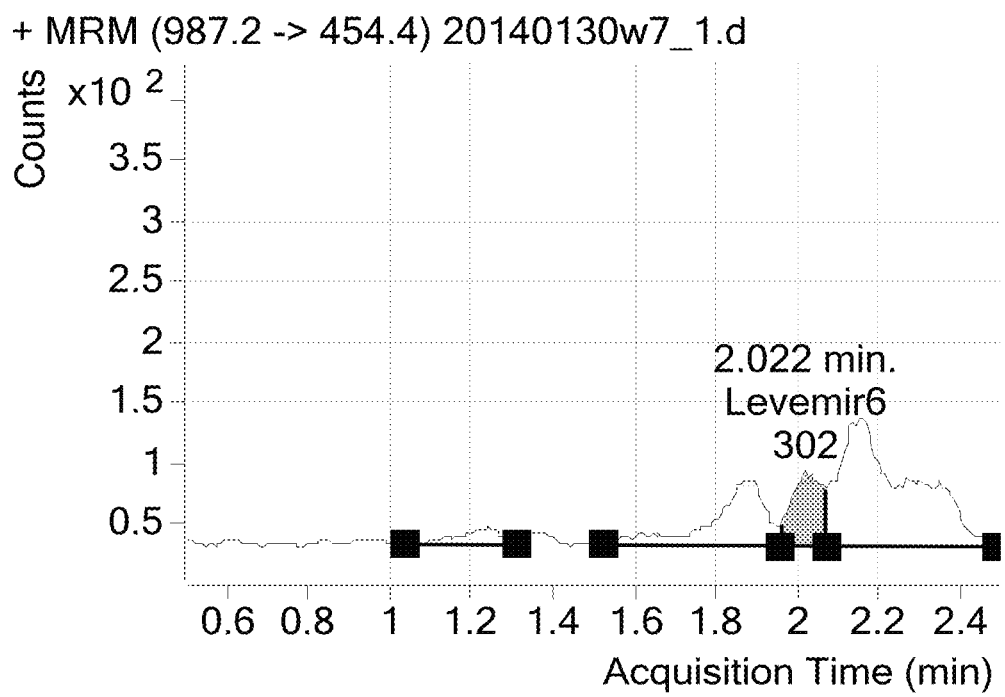
Figure 19D:
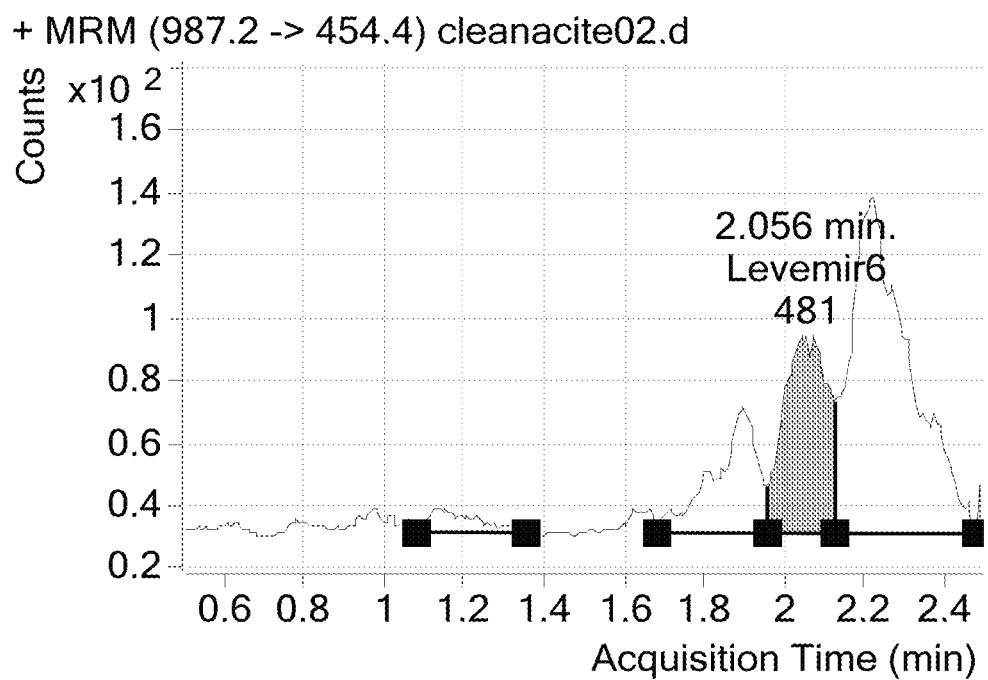
Figure 20:
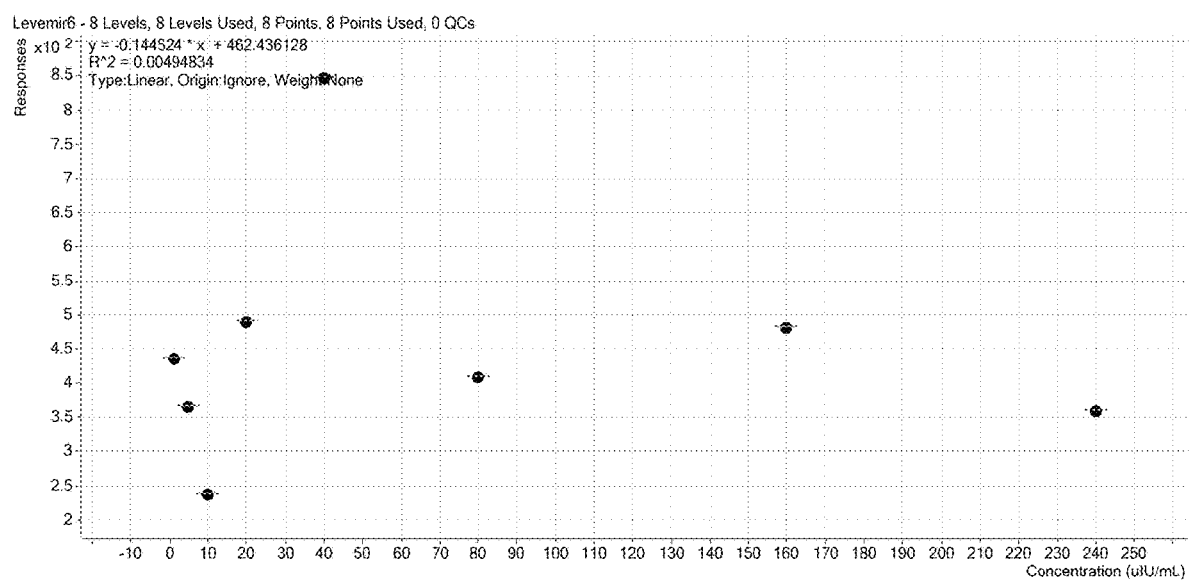
FIG. 20 shows the results of LEVEMIR® for CLENACITE®/base extraction.
Figure 21:
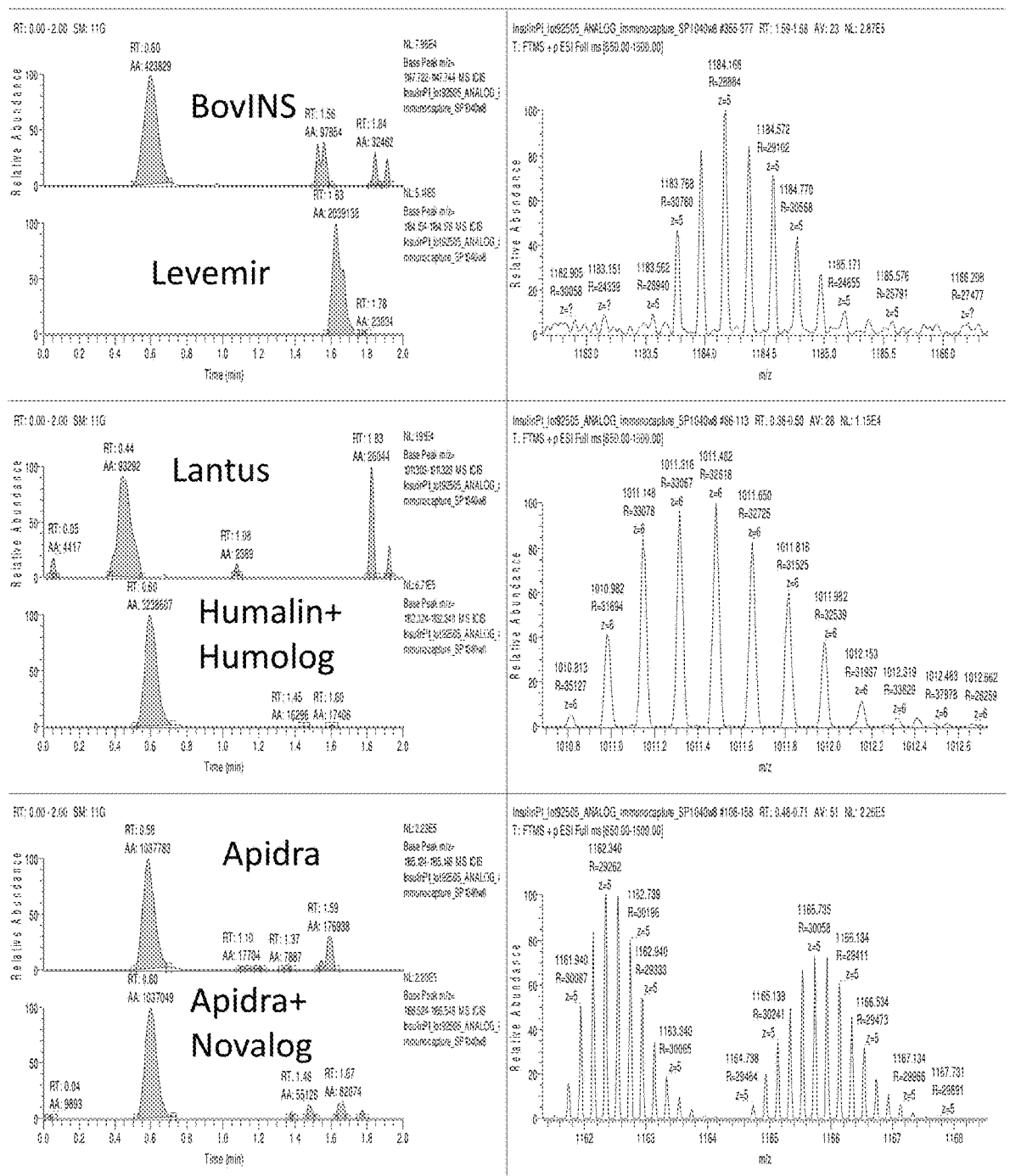
FIG. 21 shows W8 calibrator results for all species of immunocapture insulin analogs using an insulin antibody.
Figure 22:
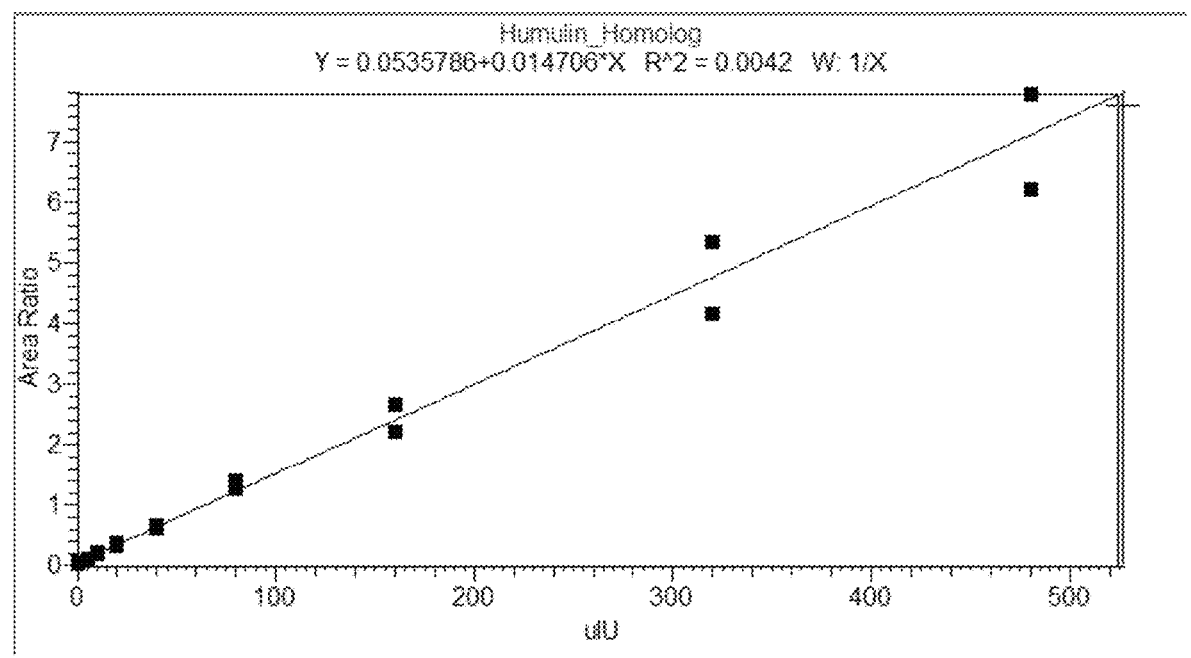
FIG. 22 shows IgG comparison results for humalin homolog.
Figure 23:
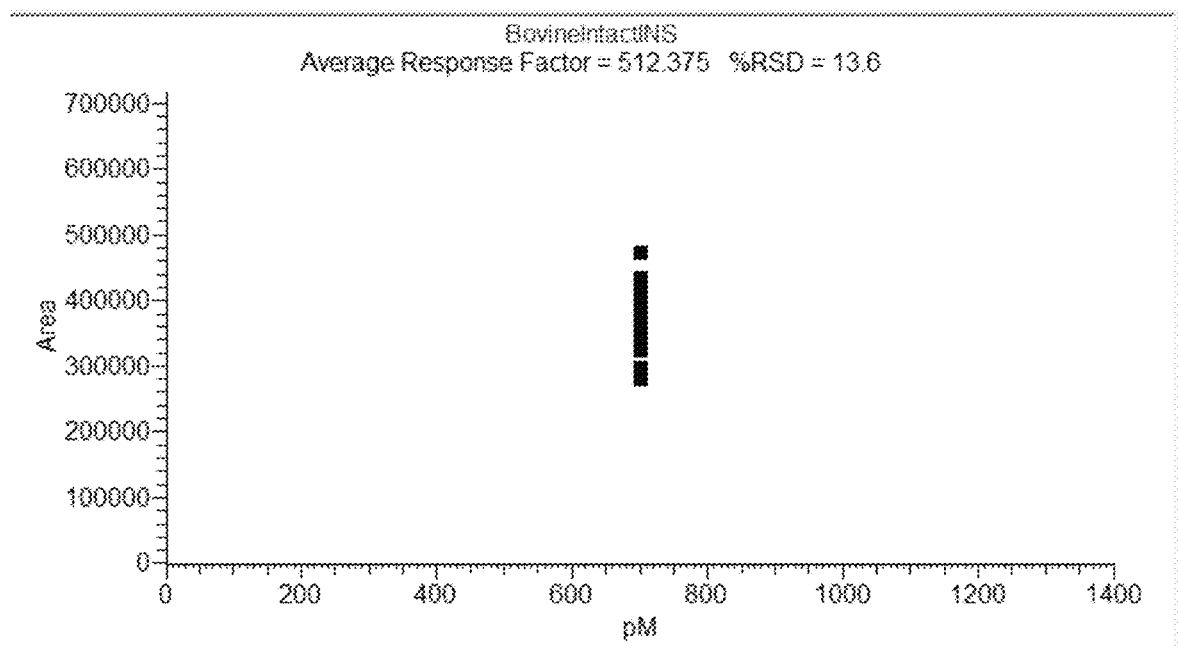
FIG. 23 shows no difference for IgGs for bovine insulin.
Figure 24:
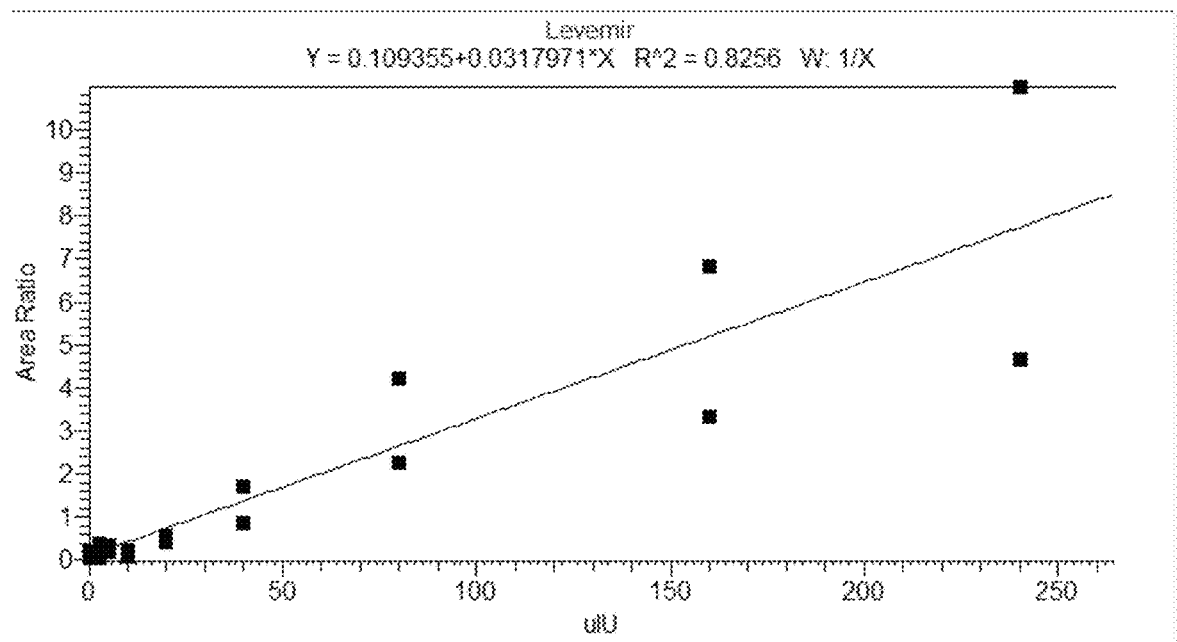
FIG. 24 shows a significant difference for LEVEMIR®: proinsulin IgG provided a favored result.
Figure 25:
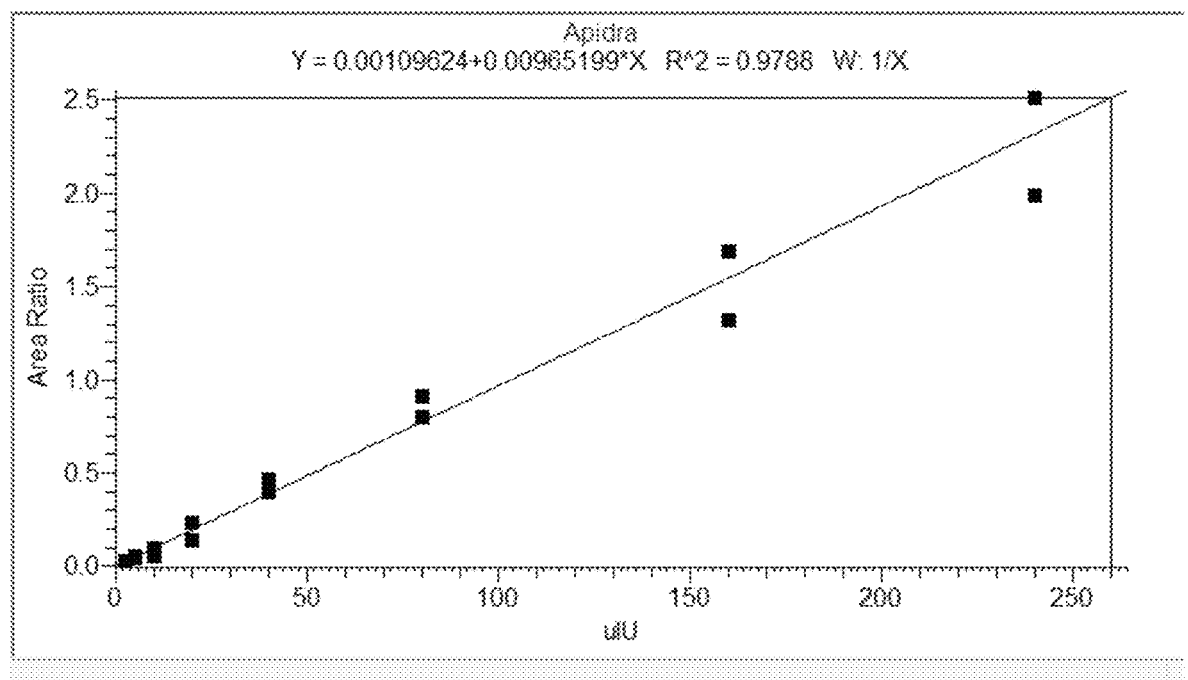
FIG. 25 shows a significant difference for APIDRA®: proinsulin IgG provided a higher response.
Figure 26:
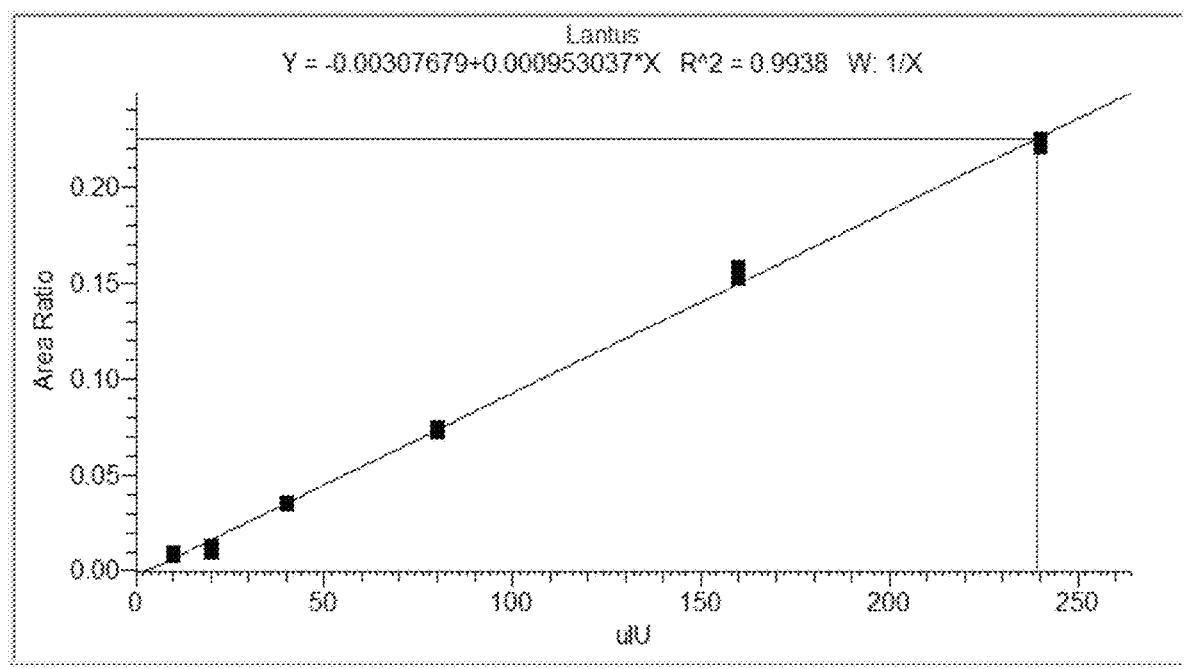
FIG. 26 shows no difference for LANTUS®.
Figure 27:
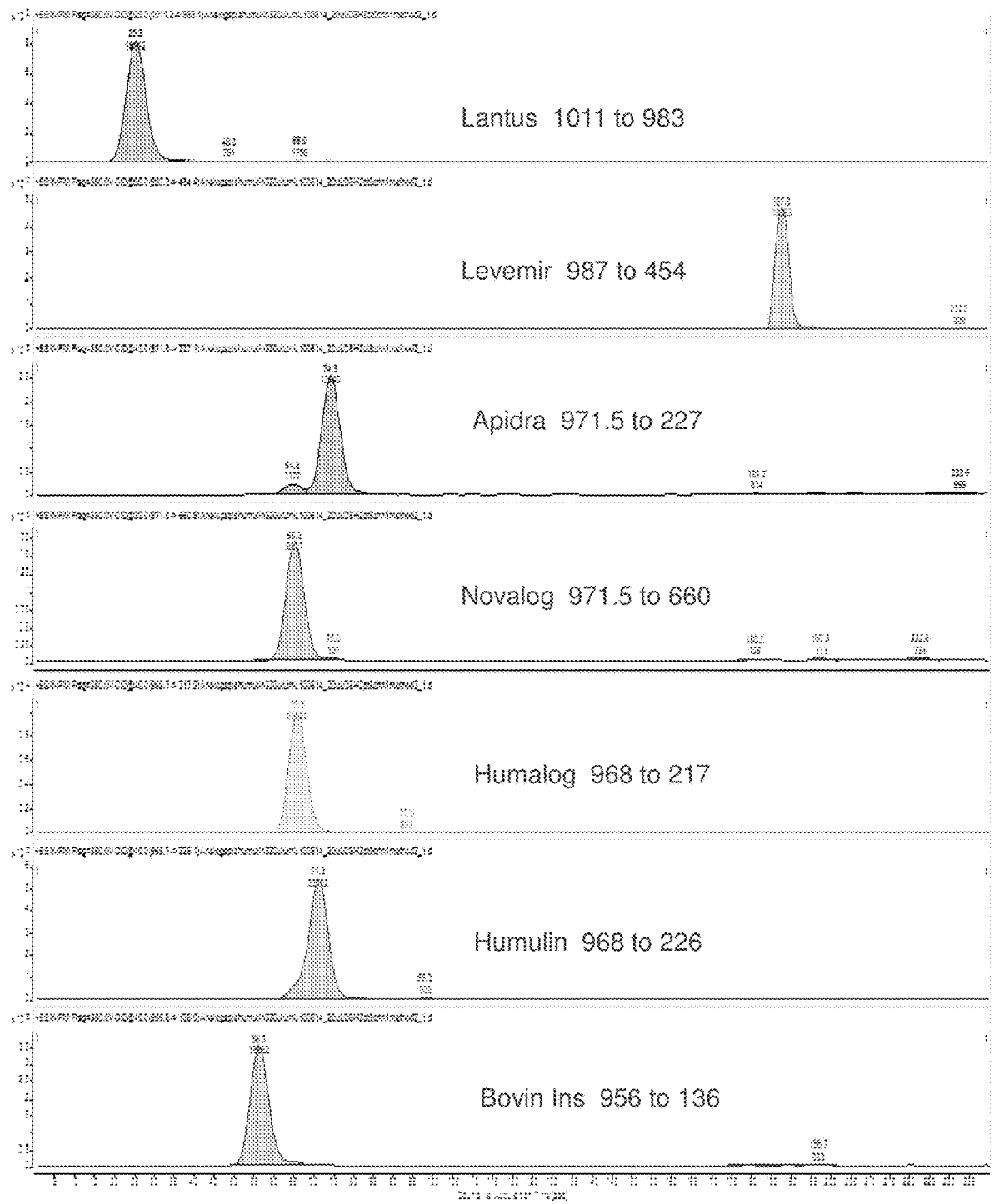
FIG. 27 shows MRMs for insulin drug mixture gradient extended to catch Levemir.
Figure 28:
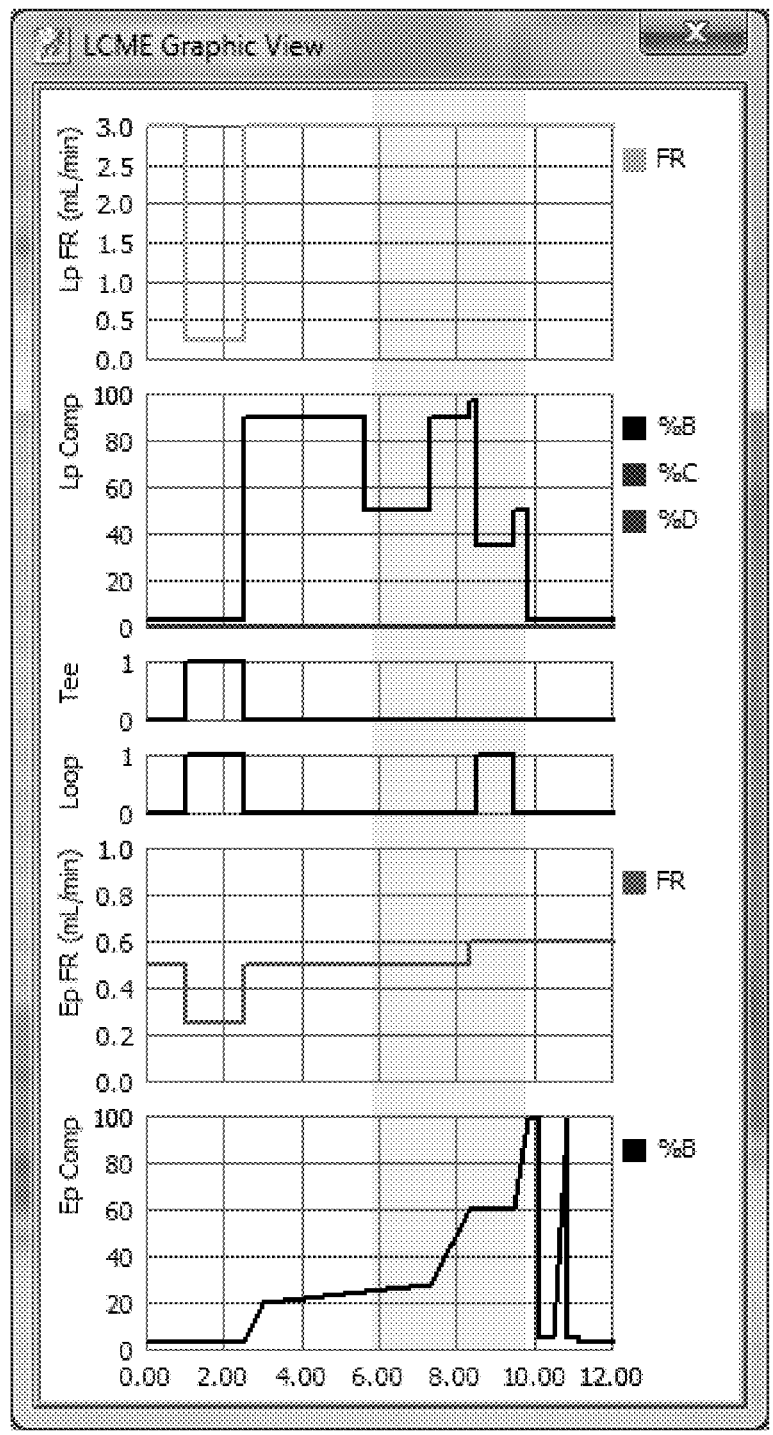
FIG. 28 shows a graphic view of MRMs for insulin drug mixture gradient extended to catch Levemir shown in FIG. 27.
Figure 29:
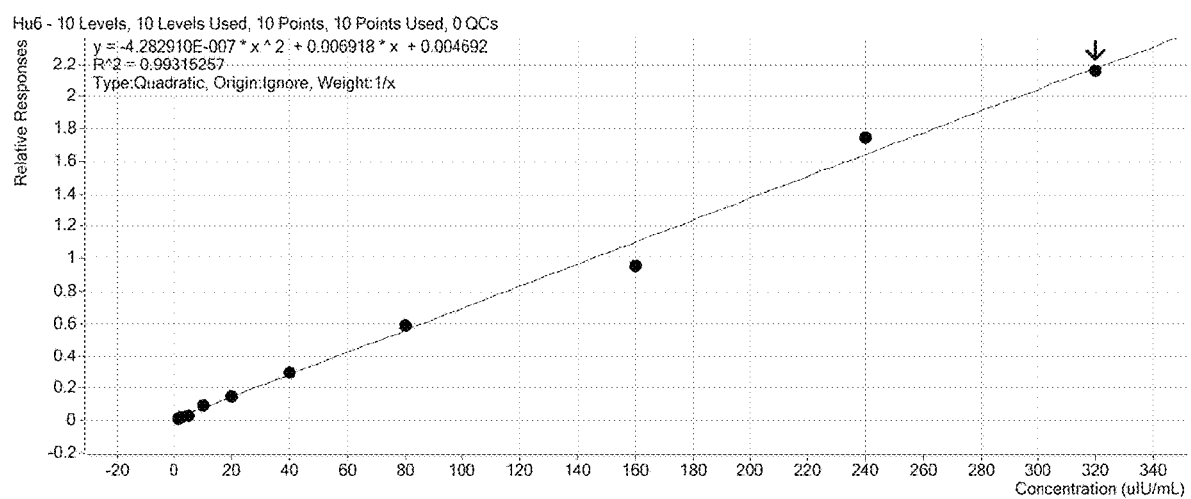
FIG. 29 shows the results of immunocapture of insulin using a B-chain antibody.
Figure 30:
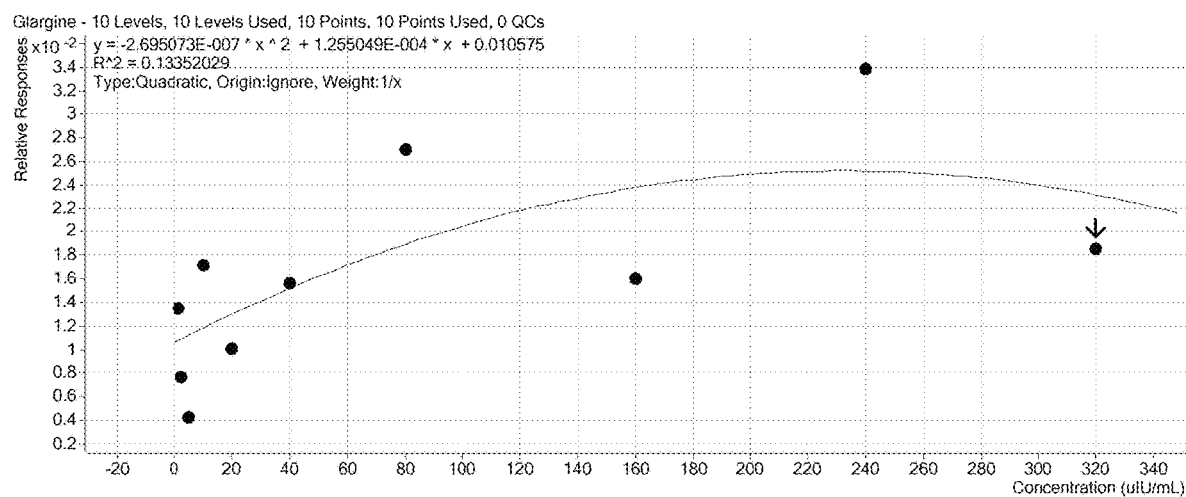
FIG. 30 shows the results of immunocapture of LANTUS® using a B-chain antibody.
Figure 31:
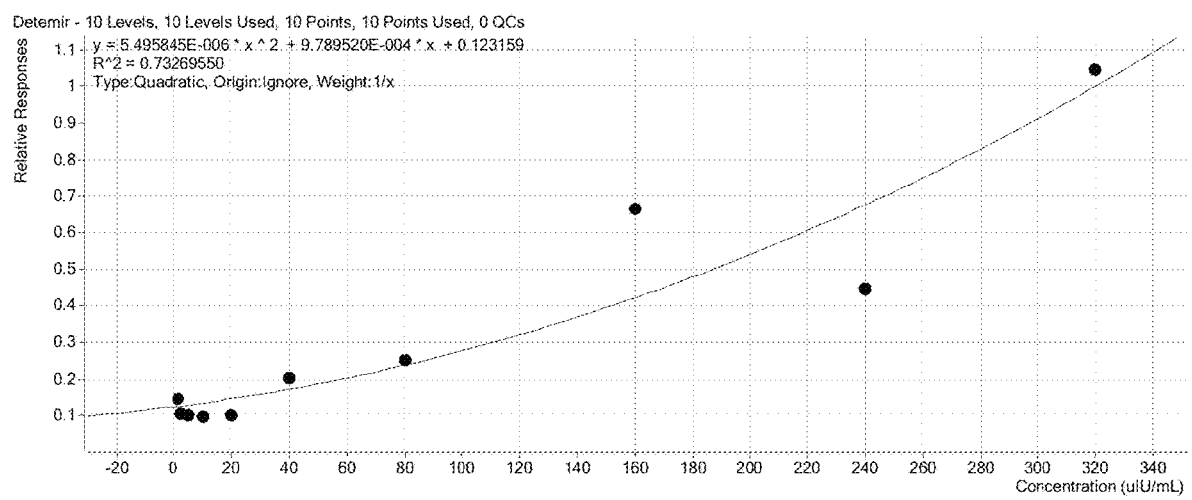
FIG. 31 shows the results of immunocapture of LEVEMIR® using a B-chain antibody.
Figure 32:
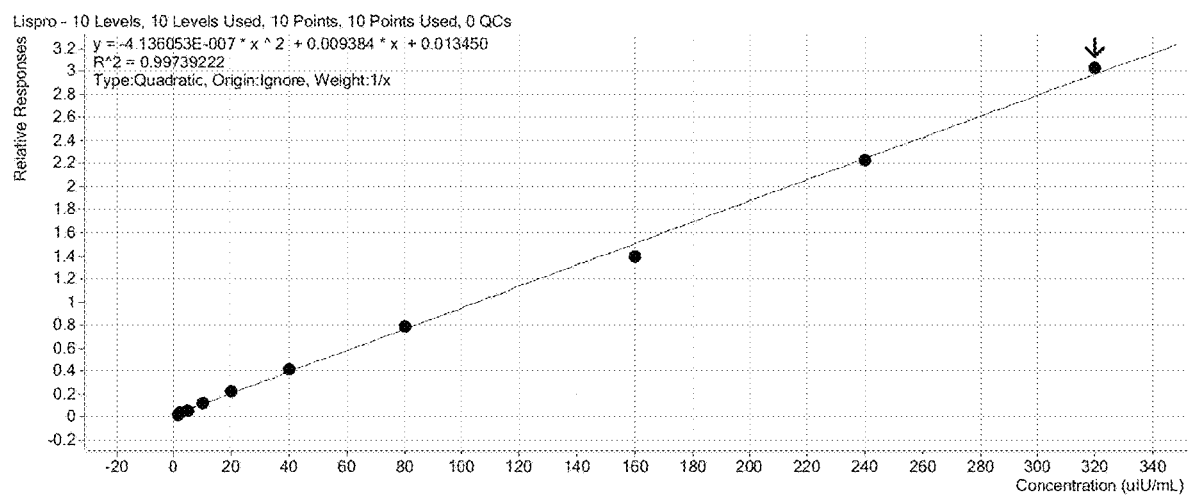
FIG. 32 shows the results of immunocapture of HUMALOG® using a B-chain antibody.
Figure 33:
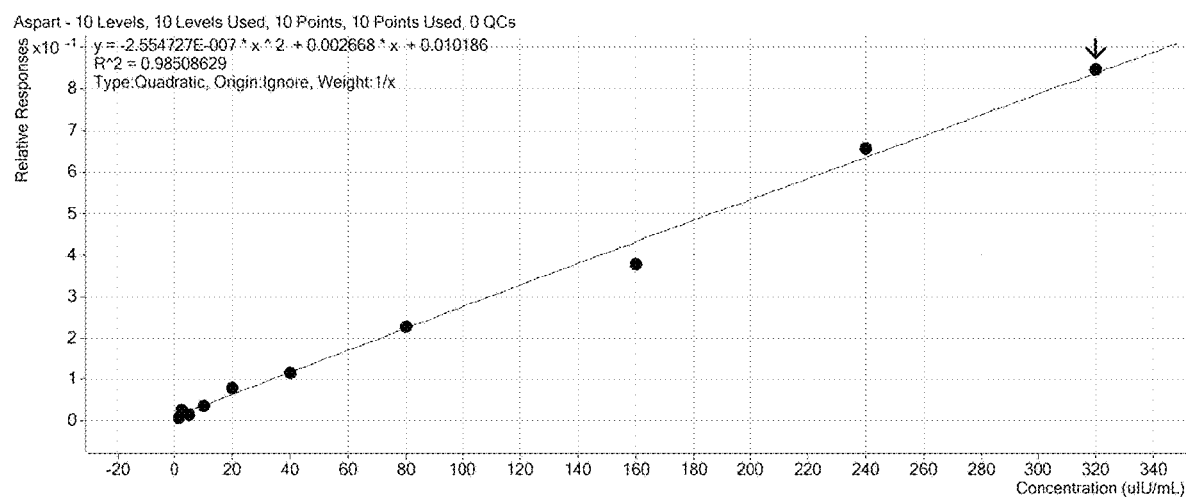
FIG. 33 shows the results of immunocapture of NOVALOG® using a B-chain antibody.
Figure 34:
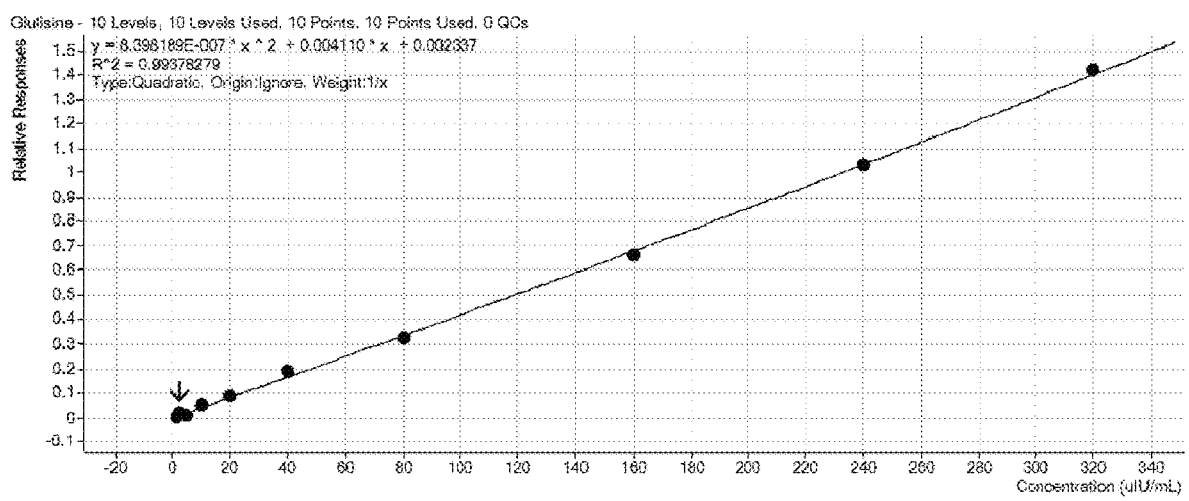
FIG. 34 shows the results of immunocapture of APIDRA® using a B-chain antibody.
Figure 35:
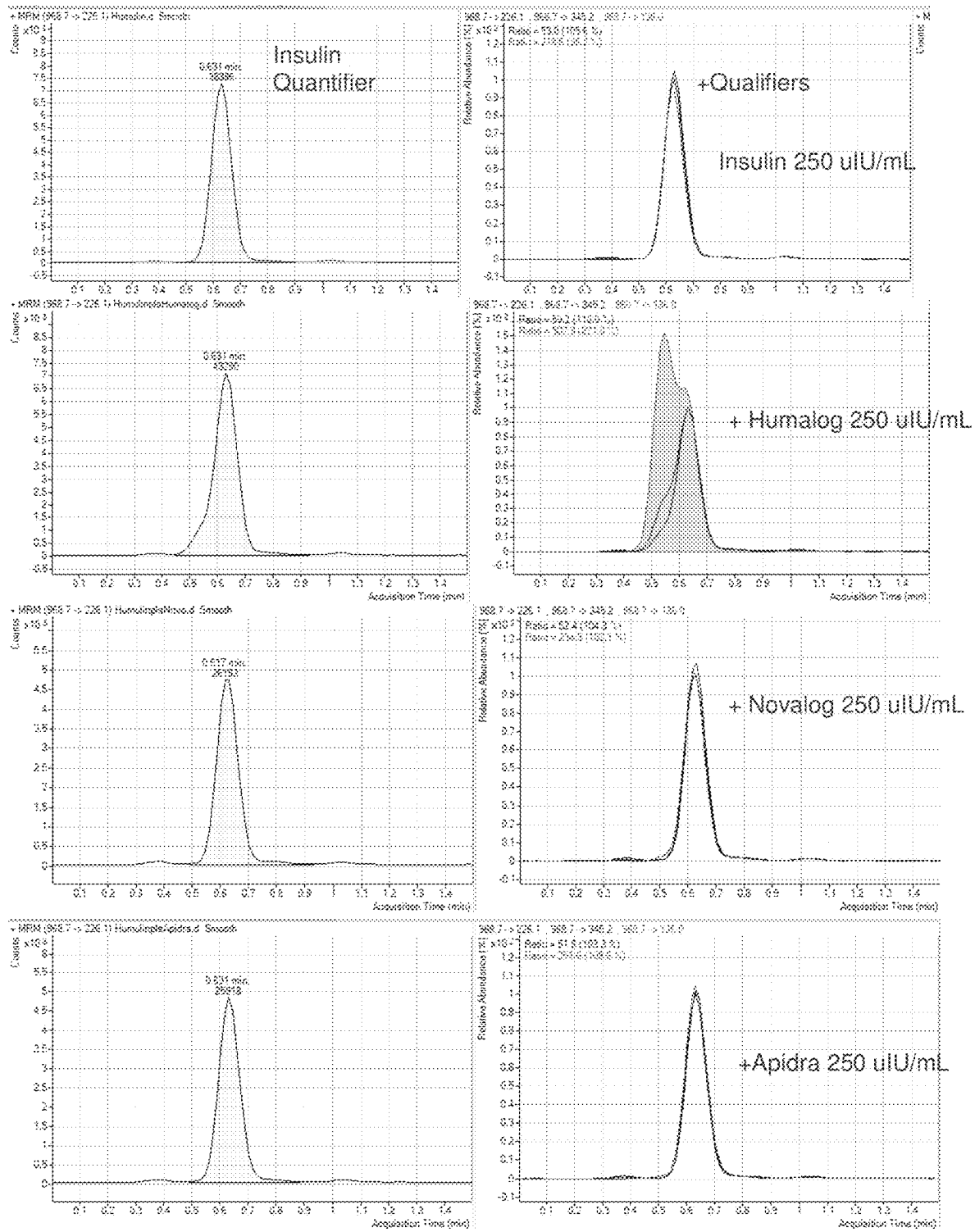
FIG. 35 shows the HUMALOG® source of interference.
Figure 36:
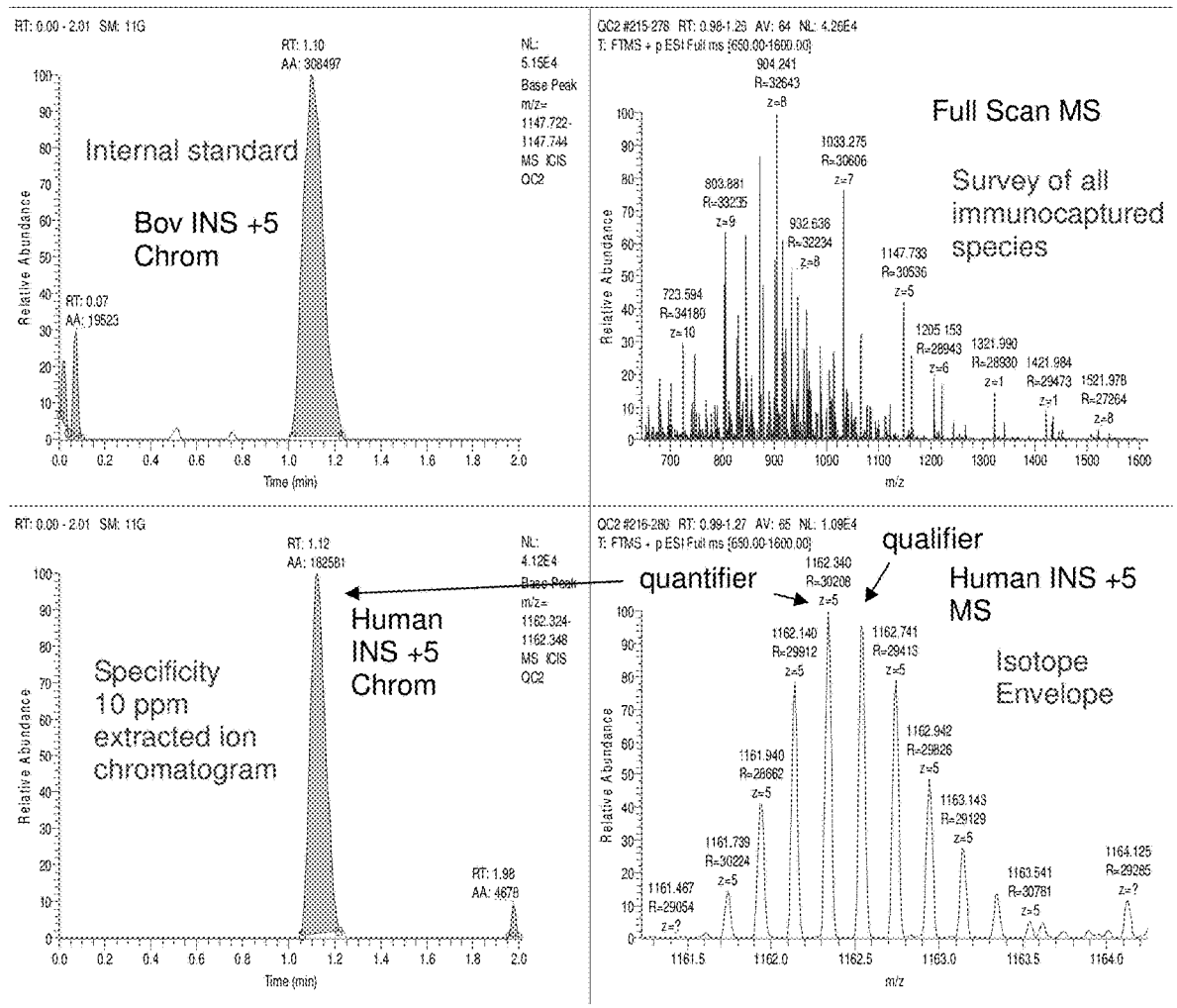
FIG. 36 shows survey and quantitation of immunocaptured species by high resolution LC-MS.
Figure 37:
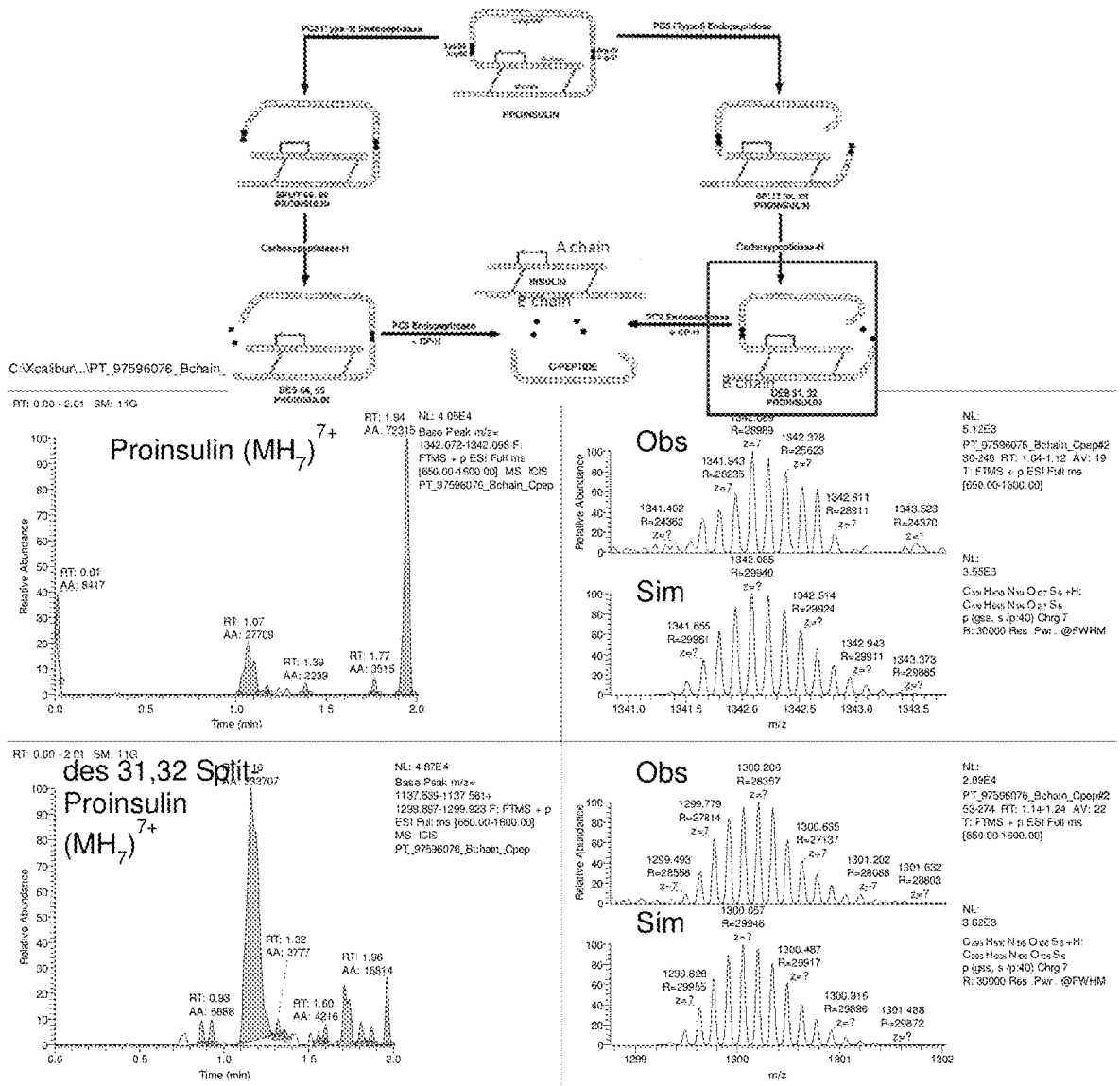
FIG. 37 shows proinsulin/des-31,32 split proinsulin in a patient sample.
Figure 38:
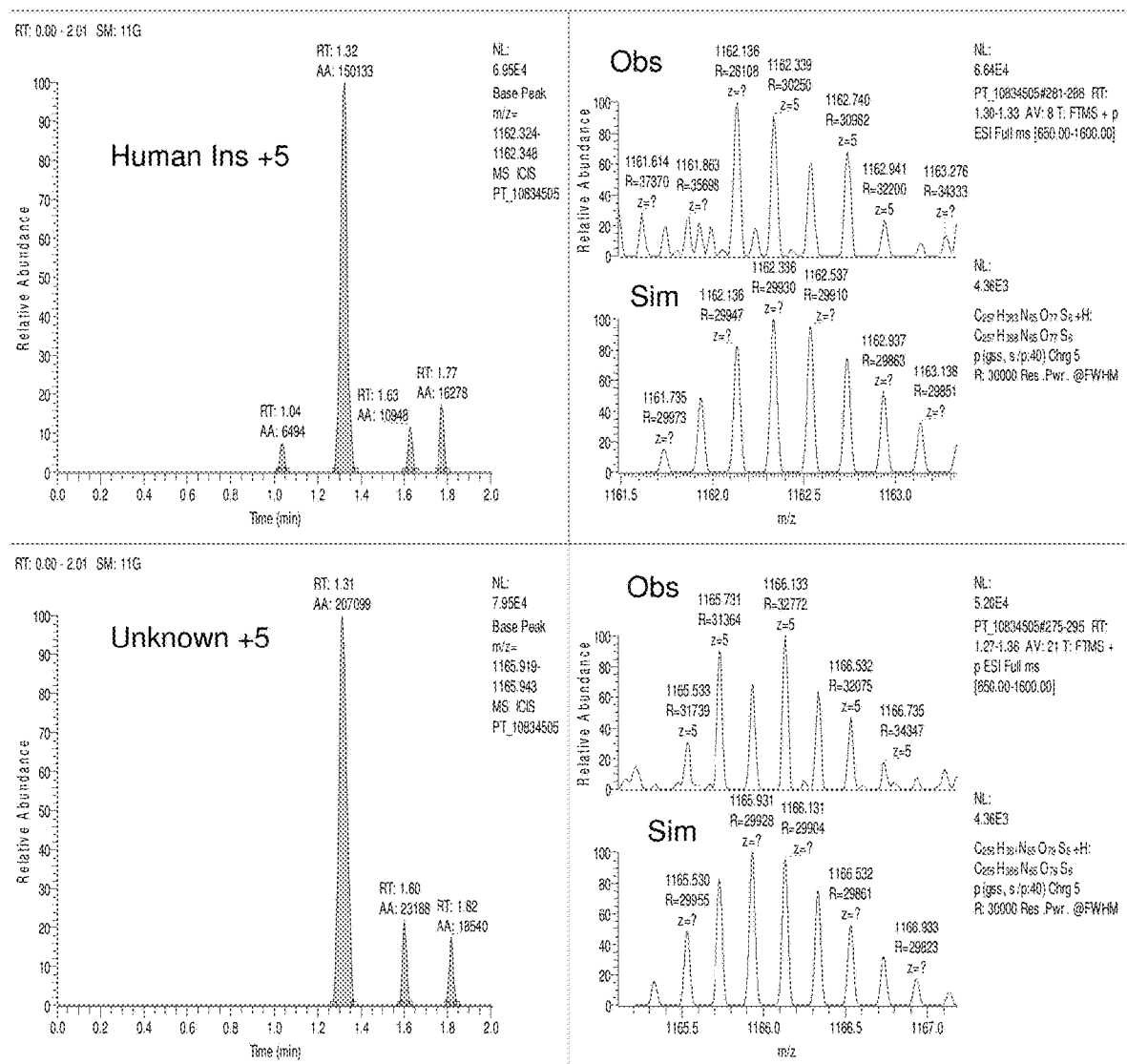
FIG. 38 shows the results of NOVALOG® in a patient sample.
Figure 39:
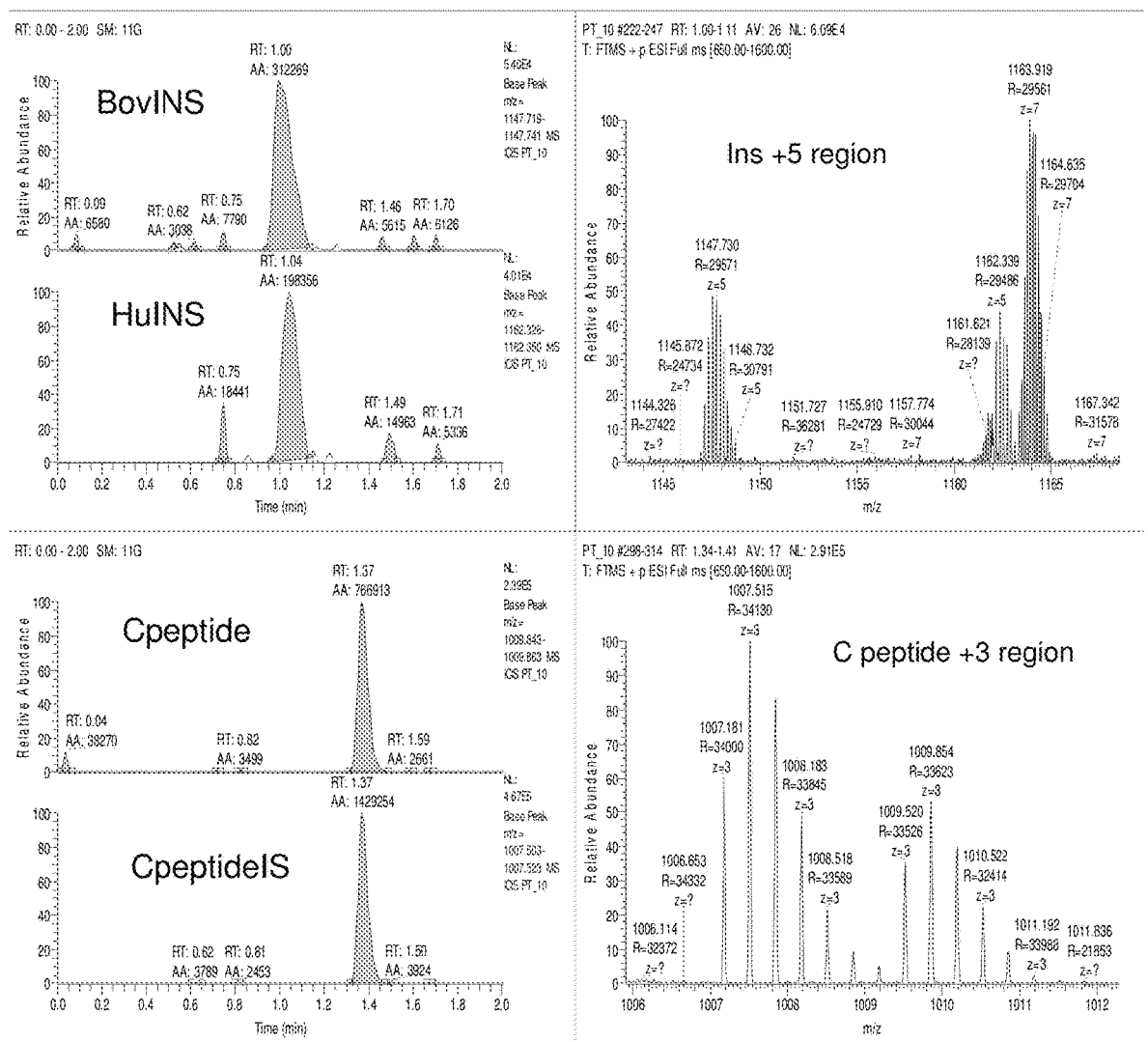
FIGS. 39-40 show simultaneous determination of insulin and C peptide in a patient sample.
Figure 40:
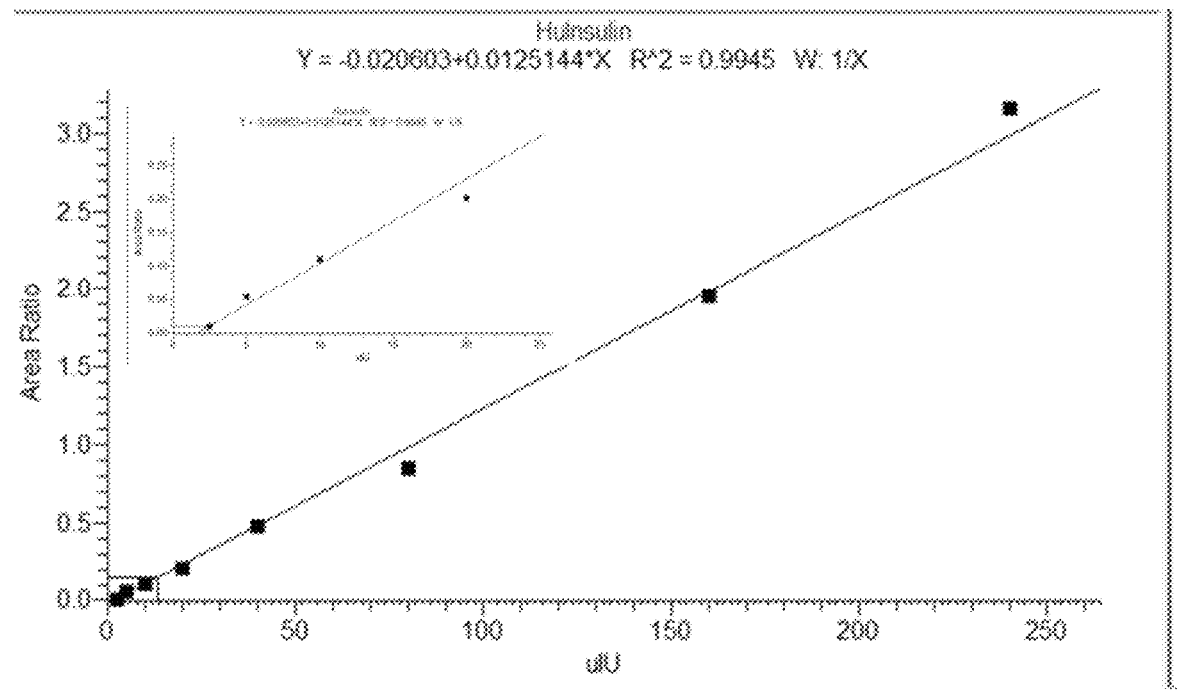
Figure 40:
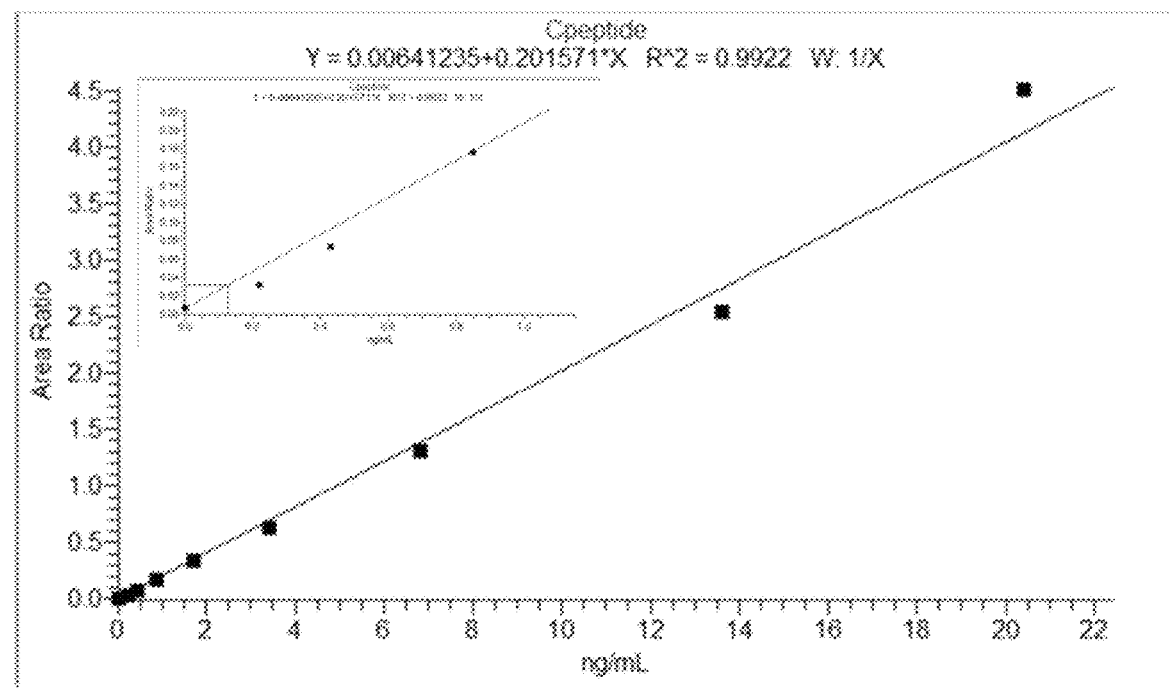
Figure 41:
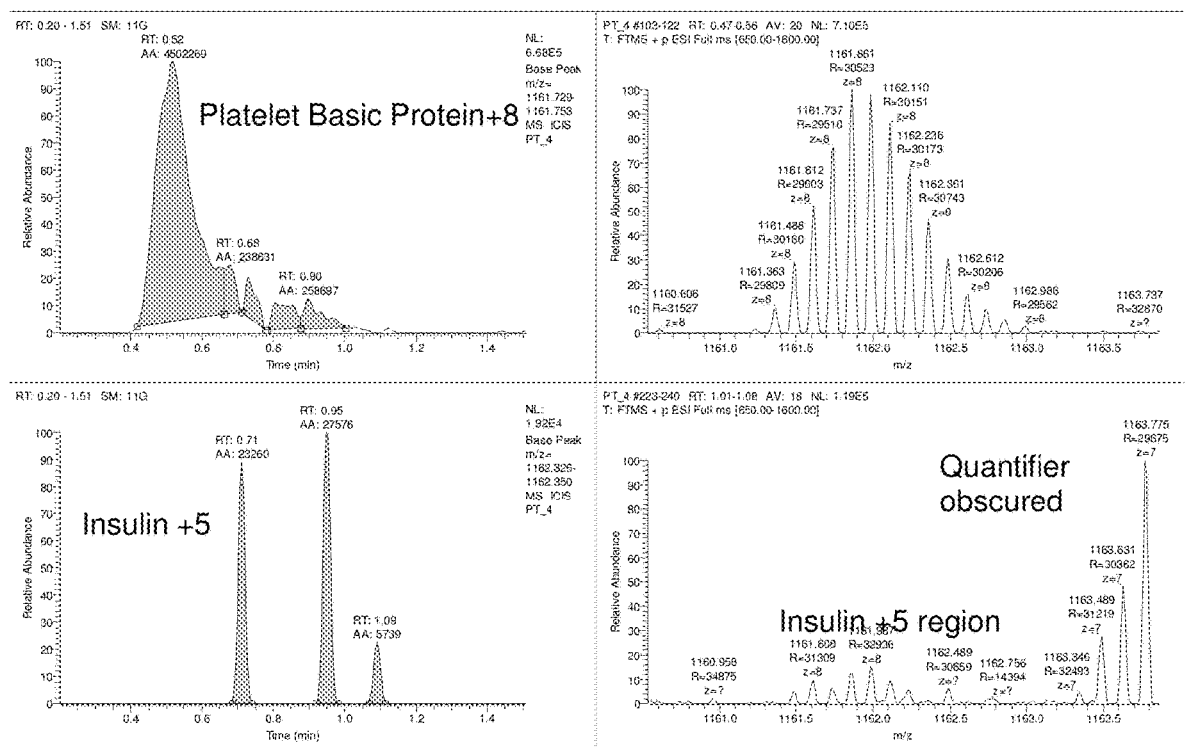
FIG. 41 shows interference from platelet factors in a patient sample.
Figure 42:
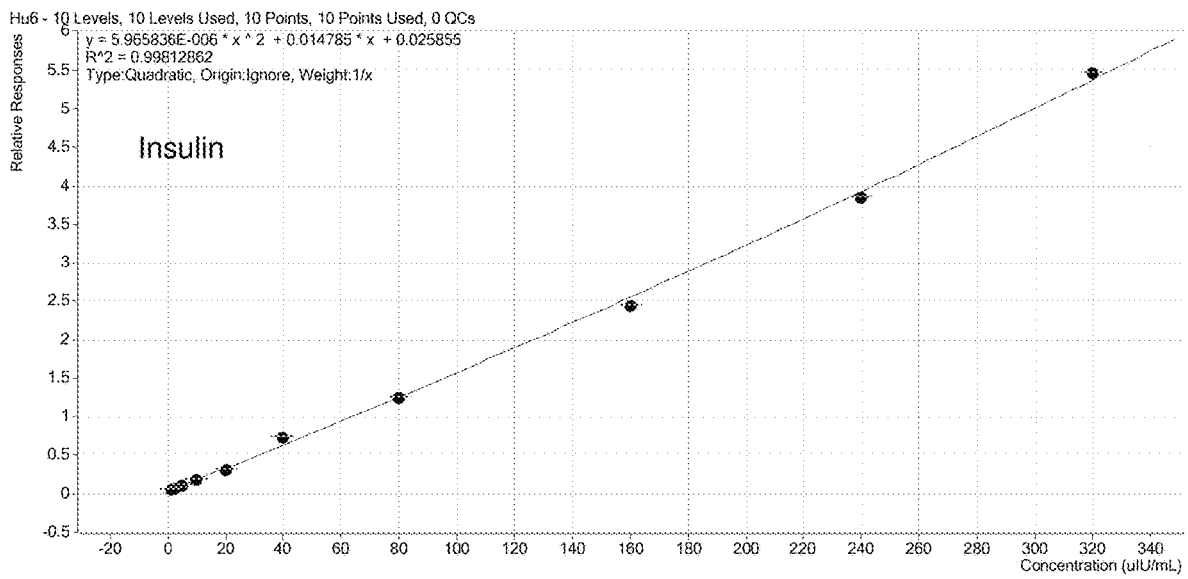
FIG. 42 shows insulin and C peptide STD curves.
Figure 42:
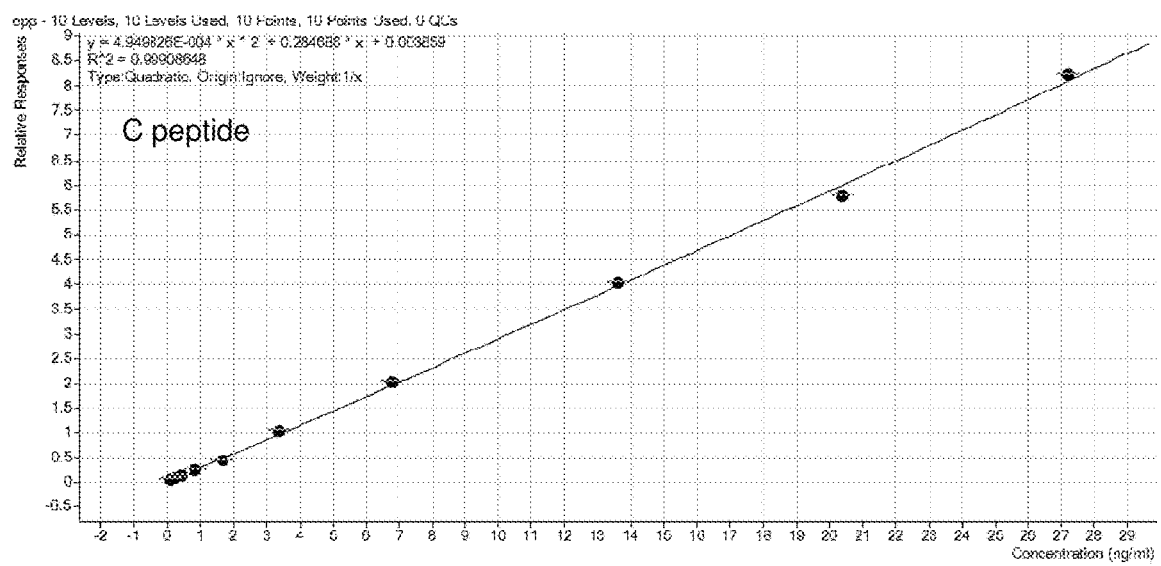
Figure 43A:
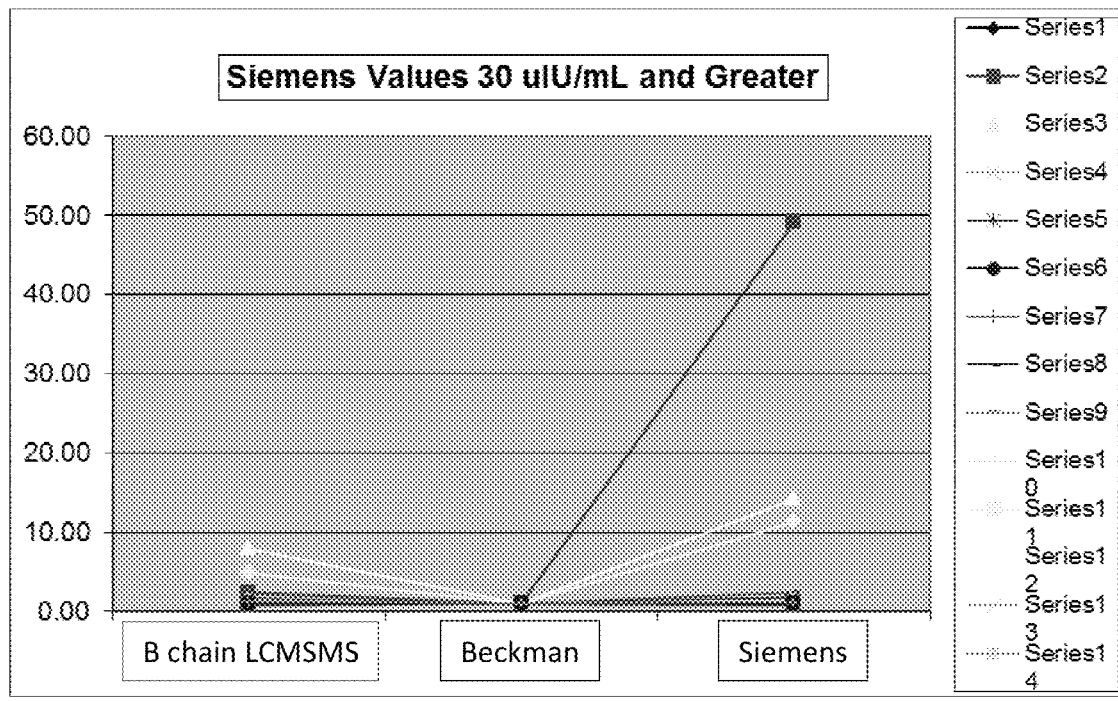
FIGS. 43A-43B show the results of 3 assays measuring insulin.
Figure 43B:
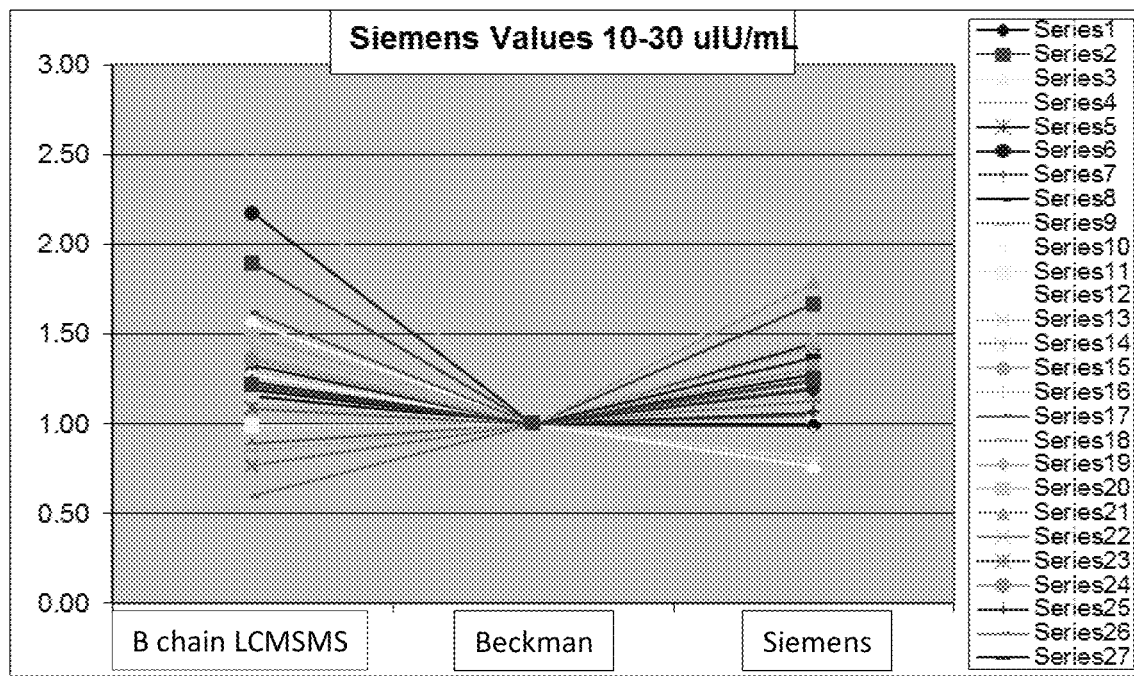
Figure 44:
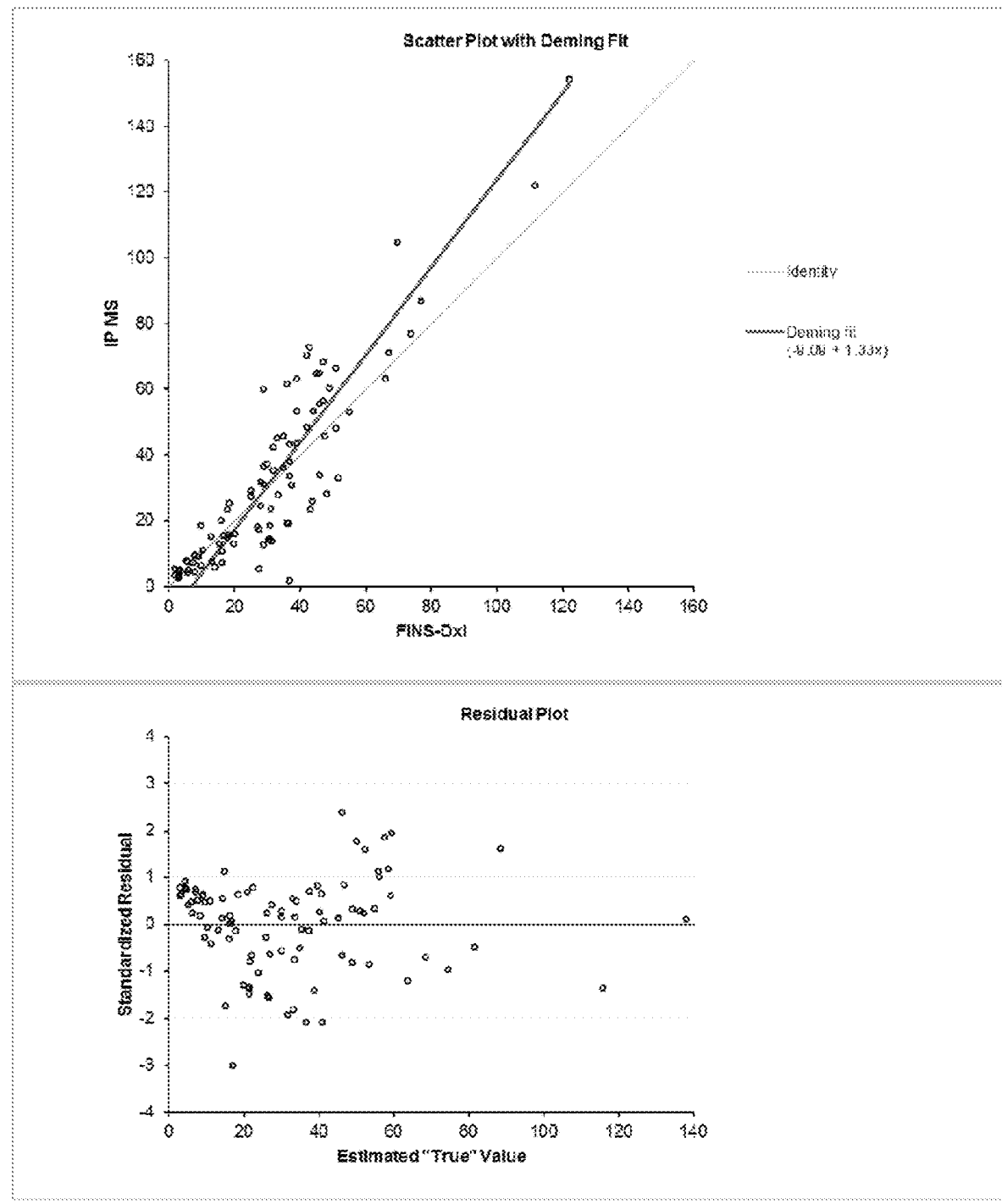
FIGS. 44-45 show insulin correlations (n=94) of immunocapture-mass spectrometry versus Beckman immunoassay and insulin B chain LC-MS/MS.
Figure 45:
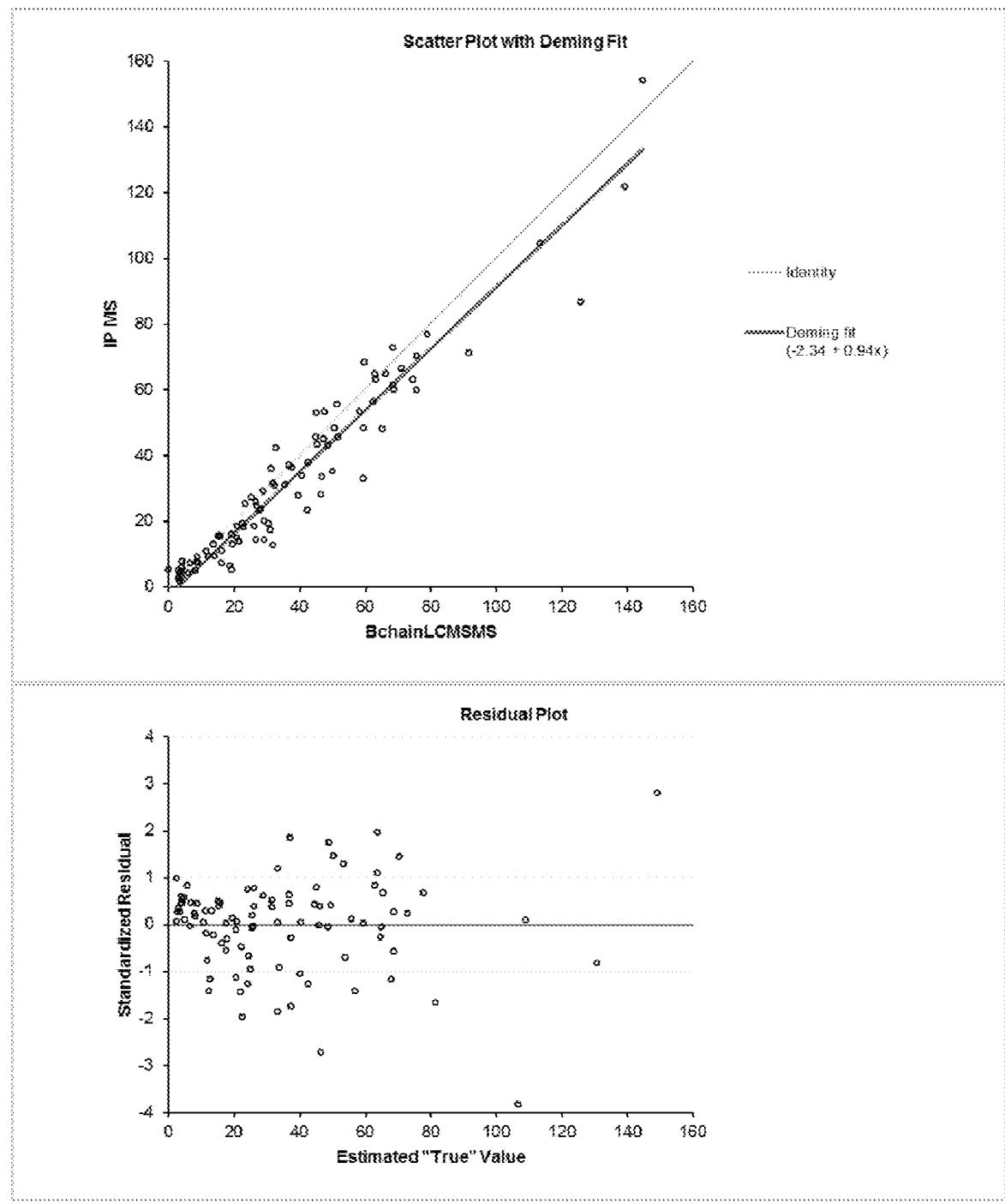
Figure 46:
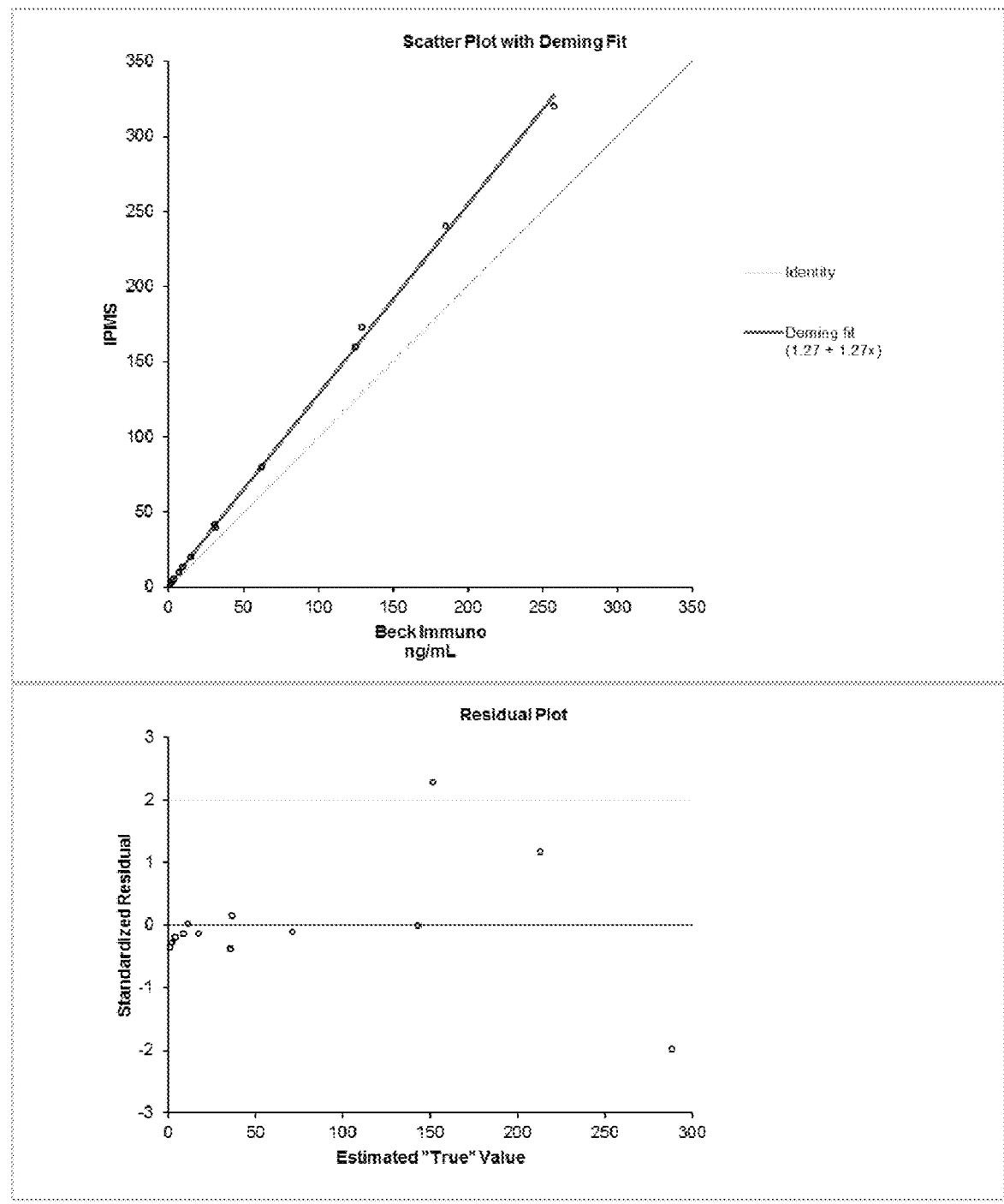
FIGS. 46-47 show calibrators quality controls.
Figure 47:
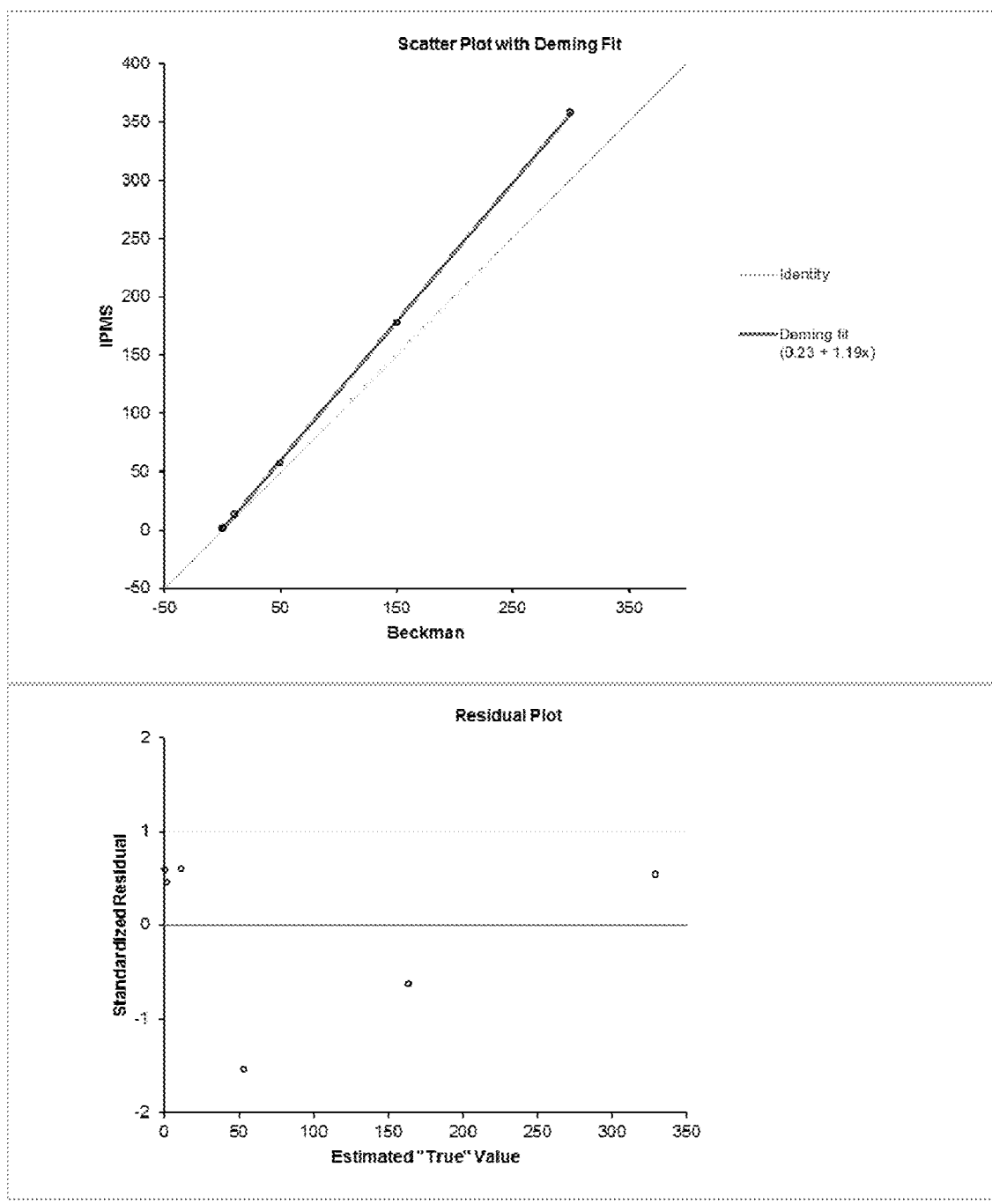

Frozen Temperature Sample Stability: Ultralow (−60 to −90° C.): Six serum pools were evaluated for stability of C-peptide and insulin at frozen temperatures between −60 to 90° C. in human serum. Six samples were spiked with known concentrations of the peptides, immediately frozen on dry ice, and transferred to the ultralow freezer. Tubes were removed from the freezer over 8 weeks. The data indicates that both peptides stable when frozen at ultralow temperatures for at least 8 weeks (Table 12 and FIG. 9).

TABLE 12

Ultralow Frozen Temperature Sample Stability

Table 12a: Insulin

| Sample | Average Calculated Concentrations (uIU/mL) | | | | | | | | |
|---|---|---|---|---|---|---|---|---|---|
| | Baseline | Week 1 | Week 2 | Week 3 | Week 4 | Week 8 | Mean | SD | CV |
| Patient 1 | 56.7 | 50.3 | 57.9 | 56.9 | 54.0 | 57.2 | 55.5 | 2.9 | 5% |
| Patient 2 | 45.9 | 46.2 | 51.0 | 42.5 | 46.4 | 44.4 | 46.1 | 2.8 | 6% |
| Patient 3 | 88.4 | 88.0 | 96.1 | 86.0 | 82.2 | 86.0 | 87.8 | 4.6 | 5% |
| Patient 4 | 114.2 | 107.5 | 105.3 | 114.6 | 108.3 | 101.2 | 108.5 | 5.2 | 5% |
| Patient 5 | 103.4 | 101.8 | 97.0 | 103.1 | 101.2 | 92.8 | 99.9 | 4.1 | 4% |
| Patient 6 | 21.4 | 18.2 | 24.7 | 19.0 | 18.5 | 23.8 | 20.9 | 2.8 | 13% |

| Sample | % Recovery | | | | |
|---|---|---|---|---|---|
| | Week 1 | Week 2 | Week 3 | Week 4 | Week 8 |
| Patient 1 | 89% | 102% | 100% | 95% | 101% |
| Patient 2 | 101% | 111% | 93% | 101% | 97% |
| Patient 3 | 100% | 109% | 97% | 93% | 97% |
| Patient 4 | 94% | 92% | 100% | 95% | 89% |
| Patient 5 | 99% | 94% | 100% | 98% | 90% |
| Patient 6 | 85% | 115% | 89% | 87% | 111% |

Table 12b: C-peptide

| Sample | Average Calculated Concentrations (ng/mL) | | | | | | | | |
|---|---|---|---|---|---|---|---|---|---|
| | Baseline | Week 1 | Week 2 | Week 3 | Week 4 | Week 8 | Mean | SD | CV |
| Patient 1 | 6.92 | 7.09 | 6.54 | 6.32 | 6.86 | 6.37 | 6.68 | 0.32 | 5% |
| Patient 2 | 5.43 | 5.79 | 4.91 | 5.21 | 5.52 | 5.11 | 5.33 | 0.31 | 6% |
| Patient 3 | 8.33 | 8.41 | 7.56 | 7.94 | 7.98 | 8.29 | 8.08 | 0.32 | 4% |
| Patient 4 | 10.20 | 11.23 | 10.66 | 10.21 | 10.31 | 9.42 | 10.34 | 0.60 | 6% |
| Patient 5 | 9.38 | 9.70 | 9.16 | 9.35 | 9.39 | 9.12 | 9.35 | 0.21 | 2% |
| Patient 6 | 2.36 | 2.39 | 2.32 | 2.24 | 2.21 | 2.19 | 2.28 | 0.09 | 4% |

| Sample | % Recovery | | | | |
|---|---|---|---|---|---|
| | Week 1 | Week 2 | Week 3 | Week 4 | Week 8 |
| Patient 1 | 103% | 95% | 91% | 99% | 92% |
| Patient 2 | 107% | 90% | 96% | 102% | 94% |
| Patient 3 | 101% | 91% | 95% | 96% | 100% |
| Patient 4 | 110% | 104% | 100% | 101% | 92% |

TABLE 12-continued

Ultralow Frozen Temperature Sample Stability

| Patient 5 | 103% | 98% | 100% | 100% | 97% |
| Patient 6 | 101% | 98% | 95% | 93% | 93% |

Example 8: Interference Study

Acceptability criteria: The difference due to a potential interfering substance should be ≤TEa/4 to be considered acceptable (Table 13).

Hemolysis Interference: The effects of hemolysis in the assay were evaluated by spiking the low, medium and low QC's with hemolyzed RBC's at low, medium, and high concentrations to represent moderate to grossly hemolyzed serum samples.

For insulin, all levels of hemolysis were found to be unacceptable with progress loss of the insulin peak until it was unquantifiable.

For C-peptide, average recoveries for all QC levels were 98%, 94 and 85% for mild, moderate and highly hemolyzed red blood cells, respectively. Consequently, while the assay can tolerate mild to moderate hemolysis, grossly hemolyzed samples are unacceptable for C-peptide determination.

Lipemia Interference: The effects of lipemia in the assay were evaluated by spiking the low, medium and low QC's with intralipid at low, medium, and high concentrations to represent moderate to grossly lipemic serum samples.

For insulin, average recoveries for all QC levels were 97% to 100%.

For C-peptide the average recoveries were 96 to 99% indicating that the determination of either peptide is not impacted by lipemic interference.

Bilirubin Interference: The effects of icteria in the assay were evaluated by spiking the low, medium and low QC's with bilirubin at low, medium, and high concentrations to represent moderate to grossly icteric serum samples.

For insulin, average recoveries for all QC levels were 96% to 98%.

For C-peptide the average recoveries were 97 to 99% indicating that the determination of either peptide is not impacted by icteric interference.

TABLE 13

Interference

Table 13a: Insulin

Low QC Observed Concentrations (uIU/mL)

| Replicate | Baseline | Hemolysis | | | Lipemic | | | Icterus | | |
| --- | --- | --- | --- | --- | --- | --- | --- | --- | --- | --- |
| | | Mild | Mod | Gross | Mild | Mod | Gross | Mild | Mod | Gross |
| 1 | 12.0 | 8.4 | 7.8 | 0.0 | 11.2 | 13.2 | 13.3 | 11.1 | 11.3 | 9.6 |
| 2 | 13.2 | 7.8 | 7.3 | 0.0 | 9.3 | 11.3 | 11.0 | 12.0 | 10.5 | 10.9 |
| Mean | 12.6 | 8.1 | 7.5 | 0.0 | 10.3 | 12.3 | 12.2 | 11.6 | 10.9 | 10.2 |
| % Recovery | | 64% | 60% | 0% | 81% | 97% | 97% | 92% | 87% | 81% |

Medium QC Observed Concentrations (uIU/mL)

| Replicate | Baseline | Hemolysis | | | Lipemic | | | Icterus | | |
| --- | --- | --- | --- | --- | --- | --- | --- | --- | --- | --- |
| | | Mild | Mod | Gross | Mild | Mod | Gross | Mild | Mod | Gross |
| 1 | 35.6 | 25.8 | 19.8 | 0.0 | 36.8 | 41.3 | 36.5 | 36.1 | 37.5 | 36.6 |
| 2 | 39.9 | 26.2 | 13.3 | 0.0 | 38.0 | 37.9 | 37.3 | 38.5 | 39.7 | 35.7 |
| Mean | 37.8 | 26.0 | 16.6 | 0.0 | 37.4 | 39.6 | 36.9 | 37.3 | 38.6 | 36.1 |
| % Recovery | | 69% | 44% | 0% | 99% | 105% | 98% | 99% | 102% | 96% |

High QC Observed Concentrations (uIU/mL)

| Replicate | Baseline | Hemolysis | | | Lipemic | | | Icterus | | |
| --- | --- | --- | --- | --- | --- | --- | --- | --- | --- | --- |
| | | Mild | Mod | Gross | Mild | Mod | Gross | Mild | Mod | Gross |
| 1 | 149.1 | 126.5 | 78.3 | 0.0 | 176.6 | 134.8 | 157.4 | 145.2 | 171.2 | 191.0 |
| 2 | 156.3 | 113.6 | 83.9 | 0.0 | 158.2 | 162.5 | 150.6 | 161.4 | 150.0 | 150.6 |
| Mean | 152.7 | 120.1 | 81.1 | 0.0 | 167.4 | 148.7 | 154.0 | 153.3 | 160.6 | 170.8 |
| % Recovery | | 79% | 53% | 0% | 110% | 97% | 101% | 100% | 105% | 112% |

Average Recovery All Pools

| % Recovery | | 71% | 52% | 0% | 97% | 100% | 98% | 97% | 98% | 96% |

TABLE 13-continued

Interference

Table 13b: C-peptide

Low QC Observed Concentrations (ng/mL)

| | | Hemolysis | | | Lipemic | | | Icterus | | |
|---|---|---|---|---|---|---|---|---|---|---|
| Replicate | Baseline | Mild | Mod | Gross | Mild | Mod | Gross | Mild | Mod | Gross |
| 1 | 0.48 | 0.43 | 0.47 | 0.41 | 0.44 | 0.40 | 0.42 | 0.46 | 0.43 | 0.46 |
| 2 | 0.46 | 0.46 | 0.47 | 0.40 | 0.42 | 0.45 | 0.41 | 0.40 | 0.42 | 0.42 |
| Mean | 0.47 | 0.45 | 0.47 | 0.41 | 0.43 | 0.43 | 0.41 | 0.43 | 0.42 | 0.44 |
| % Recovery | | 95% | 99% | 86% | 91% | 90% | 88% | 91% | 89% | 93% |

Medium QC Observed Concentrations (ng/mL)

| | | Hemolysis | | | Lipemic | | | Icterus | | |
|---|---|---|---|---|---|---|---|---|---|---|
| Replicate | Baseline | Mild | Mod | Gross | Mild | Mod | Gross | Mild | Mod | Gross |
| 1 | 1.69 | 1.60 | 1.65 | 1.53 | 1.63 | 1.75 | 1.61 | 1.79 | 1.62 | 1.69 |
| 2 | 1.65 | 1.69 | 1.12 | 1.64 | 1.63 | 1.70 | 1.70 | 1.61 | 1.67 | 1.75 |
| Mean | 1.67 | 1.65 | 1.38 | 1.59 | 1.63 | 1.73 | 1.66 | 1.70 | 1.65 | 1.72 |
| % Recovery | | 99% | 83% | 95% | 98% | 103% | 99% | 102% | 99% | 103% |

High QC Observed Concentrations (ng/mL)

| | | Hemolysis | | | Lipemic | | | Icterus | | |
|---|---|---|---|---|---|---|---|---|---|---|
| Replicate | Baseline | Mild | Mod | Gross | Mild | Mod | Gross | Mild | Mod | Gross |
| 1 | 6.13 | 6.07 | 6.11 | 5.70 | 6.01 | 6.69 | 6.19 | 6.24 | 6.53 | 6.17 |
| 2 | 6.11 | 6.39 | 6.23 | 3.24 | 5.65 | 6.02 | 6.07 | 6.27 | 5.91 | 6.35 |
| Mean | 6.12 | 6.23 | 6.17 | 4.47 | 5.83 | 6.35 | 6.13 | 6.25 | 6.22 | 6.26 |
| % Recovery | | 102% | 101% | 73% | 95% | 104% | 100% | 102% | 102% | 102% |

Average Recovery All Pools

| | | | | | | | | | | |
|---|---|---|---|---|---|---|---|---|---|---|
| % Recovery | | 98% | 94% | 85% | 95% | 99% | 96% | 98% | 97% | 99% |

Insulin analogue interference: Several common insulin analogues were tested for possible interference with the assay. Insulin glargine (LANTUS®) was not immunocaptured by the antibodies used and Insulin detemir (LEVEMIR®) eluted well after insulin. This left the three analogues, Insulin aspart (NOVOLOG®), Insulin glulisine (APIDRA®) and Insulin lispro (HUMALOG®) as possible sources of interference. All three were immunocaptured and eluted within the window used to detect human and bovine insulin IS. Consequently all 3 were tested for interference.

A stripped serum blank and stripped serum containing 20 uIU/mL insulin and 1.70 ng/mL C-peptide were separately spiked either with 75 or 150 uIU/mL of each of the 3 analogues, respectively. Insulin and C-peptide levels were then measured in each of these mixtures (Table 13c). Only Insulin lispro caused significant interference above the LOQ in the insulin blank and became worse with increasing concentration. Neither Insulin aspart nor insulin glulisine cause interference at any level. As expected, no analogues interfered with C-peptide determination.

TABLE 13c

Insulin Analogue Interference

| Analogue | Analogue Concentration uIU/mL | Insulin 0 uIU/mL Observed | Insulin 20 uIU/mL Observed | % Recovery |
|---|---|---|---|---|
| Insulin apart | 75.0 | 0.0 | 20.3 | 101.6 |
| Insulin apart | 150.0 | 2.2 | 21.5 | 107.6 |

TABLE 13c-continued

Insulin Analogue Interference

| | | | | |
|---|---|---|---|---|
| Insulin glulisine | 75.0 | 0.5 | 18.6 | 92.9 |
| Insulin glulisine | 150.0 | 0.7 | 19.8 | 98.9 |
| Insulin lispro | 75.0 | 8.8 | 28.4 | 141.9 |
| Insulin lispro | 150.0 | 18.0 | 38.4 | 192.0 |

| Analogue | Analogue Concentration uIU/mL | C-peptide 0 ng/mL Observed | C-peptide 1.7 ng/mL Observed | % Recovery |
|---|---|---|---|---|
| Insulin apart | 75.0 | 0.04 | 1.66 | 97.5 |
| Insulin apart | 150.0 | 0.05 | 1.64 | 96.6 |
| Insulin glulisine | 75.0 | 0.04 | 1.57 | 92.1 |
| Insulin glulisine | 150.0 | 0.04 | 1.55 | 91.1 |
| Insulin lispro | 75.0 | 0.05 | 1.62 | 95.2 |
| Insulin lispro | 150.0 | 0.05 | 1.68 | 98.9 |

Example 9: Carryover

Four matrix blanks were run immediately after four high standards and evaluated for any evidence of carryover on each LC column corresponding to each of the 4 channels on the Aria LC system. The readings of blanks run immediately after the 320 uIU/mL (insulin) and 27.2 ng/mL (C-peptide) high calibrators showed carryover ranging from 0.37 to 0.74% for insulin and 0.25 to 0.39% for C-peptide corresponding to the LOQ or less (Table 16). Consequently, matrix blanks should be run after the high calibrator. Patient samples close to the LOQ should be rerun if they immediately follow an LC column exposed to a patient sample with 320 uIU/mL insulin or 27.2 ng/mL C-peptide or greater.

TABLE 14

Carryover a Insulin

Insulin (uIU/mL)

| | | | | | |
|---|---|---|---|---|---|
| preBlank1 | 0.6 | 0.4 | 0.0 | 0.4 | 0.0 |
| preBlank2 | 0.6 | 0.2 | 1.0 | 0.2 | 0.0 |
| preBlank3 | 0.5 | 0.4 | 0.3 | 0.0 | 0.0 |
| preBlank4 | 0.9 | 0.1 | 0.0 | 0.5 | 0.2 |
| HC1 | 299.6 | 394.5 | 334.7 | 317.0 | 330.5 |
| HC2 | 367.3 | 338.3 | 289.4 | 303.0 | 321.0 |
| HC3 | 352.6 | 336.5 | 285.6 | 303.1 | 323.7 |
| HC4 | 332.5 | 312.9 | 275.2 | 331.1 | 288.7 |
| postBlank5 | 1.5 | 2.8 | 1.9 | 1.7 | 1.3 |
| postBlank6 | 4.0 | 2.4 | 0.8 | 2.6 | 1.7 |
| posyBlank7 | 1.3 | 1.3 | 0.5 | 0.1 | 1.6 |
| postBlank4 | 3.1 | 3.3 | 1.1 | 2.9 | 2.1 |
| Mean preBlank | 0.67 | 0.28 | 0.32 | 0.28 | 0.06 |
| Mean HC | 338.00 | 345.56 | 296.24 | 313.57 | 315.98 |
| Mean postBlank | 2.50 | 2.46 | 1.09 | 1.81 | 1.68 |
| Carryover % | 0.74% | 0.71% | 0.37% | 0.58% | 0.53% | b: C-peptide

C-peptide (ng/mL)

| | | | | | |
|---|---|---|---|---|---|
| preBlank1 | 0.03 | 0.02 | 0.00 | 0.00 | 0.04 |
| preBlank2 | 0.08 | 0.01 | 0.00 | 0.00 | 0.03 |
| preBlank3 | 0.03 | 0.01 | 0.02 | 0.00 | 0.03 |
| preBlank4 | 0.05 | 0.02 | 0.04 | 0.02 | 0.03 |
| HC1 | 26.57 | 29.14 | 26.77 | 26.53 | 27.37 |
| HC2 | 29.09 | 27.48 | 26.48 | 23.90 | 26.19 |
| HC3 | 27.55 | 29.35 | 26.48 | 24.72 | 27.78 |
| HC4 | 25.93 | 29.29 | 29.11 | 25.35 | 27.96 |
| postBlank5 | 0.11 | 0.10 | 0.07 | 0.08 | 0.13 |
| postBlank6 | 0.12 | 0.11 | 0.07 | 0.06 | 0.10 |
| posyBlank7 | 0.09 | 0.06 | 0.05 | 0.05 | 0.08 |
| postBlank4 | 0.10 | 0.10 | 0.10 | 0.06 | 0.09 |
| Mean preBlank | 0.05 | 0.01 | 0.02 | 0.01 | 0.03 |
| Mean HC | 27.28 | 28.81 | 27.21 | 25.12 | 27.33 |
| Mean postBlank | 0.11 | 0.09 | 0.07 | 0.06 | 0.10 |
| Carryover % | 0.39% | 0.32% | 0.27% | 0.25% | 0.37% |

Example 10: Reference Intervals

All subjects consented to being healthy, ambulatory, non-medicated individuals who were drawn fasted and had a fasted glucose value of <100 mg/dL and a BMI outside the healthy range (less than 18.5, greater than 25).
Insulin: 15.3 uIU/mL or less (N=51)
C peptide: 0.61-2.40 ng/mL (N=52)

Example 10: Specimen

The insulin and C-peptide multiplex assay was validated for human serum collected in red top (no gel) tubes. In order to evaluate the difference between the samples collected in different container types, seventeen patient pools were collected in four tube types (red top serum, SST, EDTA plasma and sodium heparin plasma) and insulin and C-peptide levels were determined as shown in Table 16. The data were analyzed by pairwise t tests and Deming and Linear regression.

TABLE 16

Sample Type Comparison a: Insulin

Insulin (uIU/mL)

| Patient | Red Top Serum | SST | EDTA Plasma | Sodium Heparin Plasma |
|---|---|---|---|---|
| #1 | 5.2 | 6.5 | 2.8 | 4.1 |
| #2 | 9.8 | 10.6 | 9.7 | 9.2 |
| #3 | 15.2 | 13.1 | 9.1 | 8.3 |
| #4 | 10.3 | 10.0 | 11.0 | 9.7 |
| #5 | 4.0 | 4.8 | 6.9 | 6.5 |
| #6 | 15.8 | 20.6 | 27.6 | 25.6 |
| #7 | 7.7 | 8.0 | 6.5 | 6.1 |
| #8 | 4.1 | 4.0 | 4.4 | 6.5 |
| #9 | 18.4 | 22.8 | 26.2 | 22.8 |
| #10 | 91.6 | 88.6 | 77.6 | 90.3 |
| #11 | 10.5 | 6.9 | 9.2 | 9.3 |
| #12 | 6.5 | 5.3 | 6.4 | 6.4 |
| #13 | <2.5 | 5.2 | 3.9 | 3.2 |
| #14 | 14.5 | 19.9 | 16.6 | 17.7 |
| #15 | 17.7 | 19.0 | 20.2 | 21.7 |
| #16 | 8.1 | 10.8 | 13.1 | 9.2 |
| #17 | 13.7 | 16.8 | 9.6 | 13.7 |
| 2-tailed p | | 0.12 | 0.79 | 0.29 |

| Sample Type | (n) | $R^2$ | Slope | y-intercept |
|---|---|---|---|---|
| Serum vs EDTA Linear Regression | 17 | 0.93 | 0.8357 | 2.83 |
| Serum vs EDTA Deming Regression | 17 | | 0.86 | 2.46 |
| Serum vs Sodium Heparin Linear Regression | 17 | 0.97 | 0.9813 | 1.223 |
| Serum vs Sodium Heparin Deming Regression | 17 | | 1.00 | 1.00 |
| Serum vs SST Linear Regression | 17 | 0.98 | 0.9577 | 1.721 |
| Serum vs SST Deming Regression | 17 | | 0.97 | 1.60 | b C-peptide

C-peptide (ng/mL)

| Patient | Red Top Serum | SST | EDTA Plasma | Sodium Heparin Plasma |
|---|---|---|---|---|
| #1 | 1.26 | 1.19 | 1.30 | 1.22 |
| #2 | 1.84 | 1.95 | 1.88 | 1.81 |
| #3 | 1.48 | 1.60 | 1.47 | 1.49 |
| #4 | 2.06 | 1.77 | 2.06 | 2.06 |
| #5 | 0.91 | 0.87 | 0.89 | 0.92 |
| #6 | 2.77 | 2.52 | 2.86 | 2.68 |
| #7 | 1.04 | 1.13 | 1.00 | 1.07 |
| #8 | 0.78 | 0.86 | 0.80 | 0.76 |
| #9 | 3.40 | 3.40 | 3.32 | 3.47 |
| #10 | 6.97 | 6.26 | 7.00 | 6.93 |
| #11 | 1.66 | 1.71 | 1.66 | 1.66 |
| #12 | 1.39 | 1.41 | 1.39 | 1.40 |
| #13 | 0.80 | 0.84 | 0.81 | 0.78 |
| #14 | 2.61 | 2.59 | 2.73 | 2.50 |
| #15 | 4.50 | 4.14 | 4.33 | 4.67 |
| #16 | 1.68 | 1.70 | 1.60 | 1.75 |
| #17 | 2.00 | 2.14 | 1.78 | 2.21 |
| 2-tailed p | | 0.26 | 0.49 | 0.49 |

| Sample Type | (n) | $R^2$ | Slope | y-intercept |
|---|---|---|---|---|
| Serum vs EDTA Linear Regression | 17 | 1.00 | 0.9957 | −0.004735 |
| Serum vs EDTA Deming Regression | 17 | | 1.00 | −0.01 |
| Serum vs Sodium Heparin Linear Regression | 17 | 1.00 | 1.004 | 0.004735 |

TABLE 16-continued

| Sample Type Comparison | | | | |
|---|---|---|---|---|
| Serum vs Sodium Heparin Deming Regression | 17 | | 1.01 | 0.00 |
| Serum vs SST Linear Regression | 17 | 0.99 | 0.8822 | 0.1949 |
| Serum vs SST Deming Regression | 17 | | 0.88 | 0.19 |

Analysis of the data suggests that all tube types tested are acceptable for C-peptide.

For insulin, regression analysis suggested that EDTA plasma tubes yield different results to the other tube types and should not be used. Furthermore, heparin plasma, which yielded statistically identical results to red top tubes, should be avoided, if possible—many of the heparin samples exhibited viscosity incompatible with the robotic liquid handling, necessitating manual transfer to the sample plate from the tubes.

TABLE 17

| Summary of results for insulin | |
|---|---|
| Specimen Type | Serum Red Top (no gel) & SST are acceptable. Plasma is unacceptable |
| Intra Assay Precision | 4.7-9.6% |
| Inter Assay Precision | 7.0-11.3% |
| Method Comparison | The Deming regression results: Intact Insulin versus B-chain LC-MS/MS: (n = 94, y = 0.94 + 2.34) Intact Insulin versus Beckman Access ® ICMA platform (n = 94, y = 1.33x − 9.09). |
| Recovery Study | Average range of recovery for insulin spiked patient samples was 96-106% at 10, 20 and 40 uIU/mL, respectively |
| Analytical Sensitivity (Limit of Detection) | LOB = 0.9 uIU/mL LOD = 1.5 uIU/mL |
| Analytical Sensitivity (Limit of Quantitation) | 2.5 uIU/mL. Assay will report in whole numbers; LOQ = 3 uIU/mL. |
| Analytical Specificity (Cross Reactivity) | Humulin (Recombinant Human Insulin) (100%) |
| Analytical Specificity (Interference) | Hemolysis, Humalog (insulin lispro) |
| Linearity | 5-320 uIU/mL |
| Analytical Measurement Range (AMR) | 3-320 uIU/mL (3200 uIU/mL allowable on dilution) |
| Clinical Reportable Range (CRR) | 3-320 uIU/mL |
| Reference Interval Range | 15 uIU/mL or less |
| Carryover | ≥320 uIU/mL (0.55% or 1.7 uIU/mL after High Calibrator) |

TABLE 18

| Summary of results for C-peptide | |
|---|---|
| Specimen Type | Red Top, SST and EDTA Plasma are acceptable. Sodium Heparin Plasma is unacceptable |
| Intra Assay Precision | 4.7-7.0% |
| Inter Assay Precision | 6.2-9.0% |
| Method Comparison | The Deming regression results: versus C-peptide Siemen (DPC) Immulite 2000: (n = 115, y = 0.78x + 0.19) |
| Recovery Study | Average range of recovery for C-peptide spiked into patient samples was 91 to 104% at 1.02, 1.70 and 3.40 ng/mL, respectively |
| Analytical Sensitivity (Limit of Detection) | LOB = 0.06 ng/mL LOD = 0.10 ng/mL |
| Analytical Sensitivity (Limit of Quantitation) | 0.11 ng/mL |
| Analytical Specificity (Cross Reactivity) | none |
| Analytical Specificity (Interference) | Gross Hemolysis (Slight or moderate hemolysis is acceptable) |
| Linearity | 0.11-27.2 ng/mL |
| Analytical Measurement Range (AMR) | 0.11-27.2 ng/mL (272 ng/mL allowable on dilution) |
| Clinical Reportable Range (CRR) | 0.11-27.2 ng/mL |
| Reference Interval Range | 0.61-2.40 ng/mL (N = 52) |
| Carryover | ≥27.2 ng/mL (0.30% or 0.08 ng/mL after High Calibrator) |

Example 11: Insulin Analog Immunocapture Assay 6 insulin analogs spiked in Tris base were used to check the response (160 uIU/mL). 6 insulin analogs spiked in formic acid (FA) buffer were used to check the response (160 uIU/mL). 6 insulin analogs spiked in stripped serum sp1040; performed the preparations for the insulin standards with concentrations of (w0, w1 ... w8=0, 2.5, 5, 10, 20, 40, 80, 160 and 240 uIU/mL). 150 ul of stripped serum were mixed with 350 ul BASE/EtOH. 150 ul of cleanacite treated stripped serum were mixed with 350 ul BASE/EtOH.

The samples were run with HLB-Jupiter 3 um liquid chromatography columns.

All 6 analogs are observed as the following m/z. Table 18:

| | m/z | time | parent ion | products | | |
|---|---|---|---|---|---|---|
| lantus | 1012.2 | 0.70 | 1011.2 | 136 | 1179 | 175 |
| Levemir | 937.2 | 2.00 | 987.2 | 454.4 | 357.2 | |
| Novalog | 971.5 | 0.77 | 971.5 | 219 | 226 | 660.8 |
| Apidra | 971.5 | 0.76 | 971.5 | 199 | 346.2 | 328.2 |
| Humalog | 968.7 | 0.77 | 1162.4 | 217.3 | | |
| | | | 968.7 | 217.3 | | |

-continued

|   | m/z | time | parent ion | products |
|---|---|---|---|---|
| Huinsulin | 968.8 | 0.79 | 968.7 | 226.1 |
|   |   | 0.79 | 1162.4 | 226.1 |
| Boy | 956.8 | 0.80 | 956.8 | 315 |
|   |   |   | 1147.9 | 226 |

The results for each of the insulin analogs are provided in FIGS. 10-20.

Example 11: Insulin B-Chain Assay

A patient presented with anomalous results for insulin (very high on Siemens immunoassay, very high on LC-MSMS insulin assay; confirmed by follow up testing. Subsequent investigations detected no explanation. Subjected to third assay (Beckmann immunoassay) which gave normal results.

TABLE 19 insulin levels in a patient determined by different methods

| Date | | Result (noramal range) |
|---|---|---|
| Dec. 18, 2013 | Glucose | 90 |
|   | C-peptide | 1.17 (0.8-3.10) |
| Jan. 9, 2013 | Insulin (Siemens) | 188 uIU/mL (17.7) |
| Jan. 22, 2013 | C-peptide | 1.26 ng/mL (0.8-3.10) |
|   | Insulin, LC/MS/MS | 84.8 uIU/mL (<13.7) |
|   | Insulin free (Beckman) | 5.4 uIU/mL (1.5-14.9) |
|   | Proinsulin | <7.5 pmol/L (≤18.8) |
|   | Insulin autoantibody | <0.4 U/mL (<0.4) |

TABLE 20 insulin levels in a patient determined by different methods
Additional Work on Original Index Case

| Date | B chain LC-MS/MS | Beckman Total | IP-LC-MS/MS |
|---|---|---|---|
| Feb. 18, 2014 | 71.2 | 3.4 | 3.57 |

A survey of patient discards revealed a significant discordance between the results obtained using Siemens, Beckmann, and B-chain LC-MSMS insulin assay. Queries to Beckman and Siemens revealed that the assays were configured such that the Beckman assay employed a B chain capture and an A chain readout antibody; the Siemens uses a B chain capture, but a mixture of A and B chain readout antibodies—This information led to the inference that excess B chains were in the circulation, causing—at least in part—the discordances.

TABLE 21 details of quantitation methods

| Assay | Type | Immunoassay details |
|---|---|---|
| Siemens | Immunoassay | B-chain antibody capture; B-chain and A chain specific antibody readout |
| Beckman | Immunoassay | B-chain antibody capture A chain specific antibody readout |
| LCMSMS | B chain specific LCMSMS, following reduction and HTLC | Not applicable |

A larger comprehensive tests revealed that this occurred in significant number of instances—~50% difference in as many as 30%; alterations 50 to >10-fold differences in ~4% of samples. Work was initiated to create a whole molecule assay; results obtained using this assay revealed that the results were more in line with the Beckmann than the Siemens or B-chain LC-MSMS insulin assay, when discordances were present—consistent with an excess of B Chains in circulation. With consent of initial patient (WIRB approved protocol), samples obtained and analyzed revealed that the initial discordances were maintained ~1 year later. Results using the whole molecule insulin assay gave normal results, while the Siemens and LC-MSMS B chain assays gave elevated levels.

TABLE 22

Comparison of immunoassays

|   | Insulin, Fasting (Siemens) | Out of Range | Rslt Dte | Total Insulin performed on the Beckman Coulter Dxl |
|---|---|---|---|---|
|   | >300 | H | Mar. 15, 2013 | 293.2 |
| * | >300 | H | Mar. 13, 2013 | 6.1 |
| * | >300 | H | Mar. 26, 2013 | 245.9 |
|   | >300 | H | Mar. 12, 2013 | >305.0 |
|   | 213 | H | Mar. 13, 2013 | 141.6 |
|   | 159 | H | Mar. 12, 2013 | 142.8 |
|   | 142 | H | Mar. 13, 2013 | 94.2 |
|   | 129 | H | Mar. 12, 2013 | 124.7 |
|   | 127 | H | Mar. 12, 2013 | 132.9 |
|   | 108 | H | Mar. 11, 2013 | 112.7 |
|   | 102 | H | Mar. 12, 2013 | 74.9 |
|   | 91 | H | Mar. 12, 2013 | 6.4 |
|   | 87 | H | Mar. 13, 2013 | 40.9 |
|   | 76 | H | Mar. 15, 2013 | 66.5 |
|   | 75 | H | Mar. 12, 2013 | 76.6 |
|   | 74 | H | Mar. 12, 2013 | 77.9 |
|   | 68 | H | Mar. 15, 2013 | 28.8 |
|   | 68 | H | Mar. 11, 2013 | 48.0 |
|   | 64 | H | Mar. 15, 2013 | 64.1 |

Figure 48:
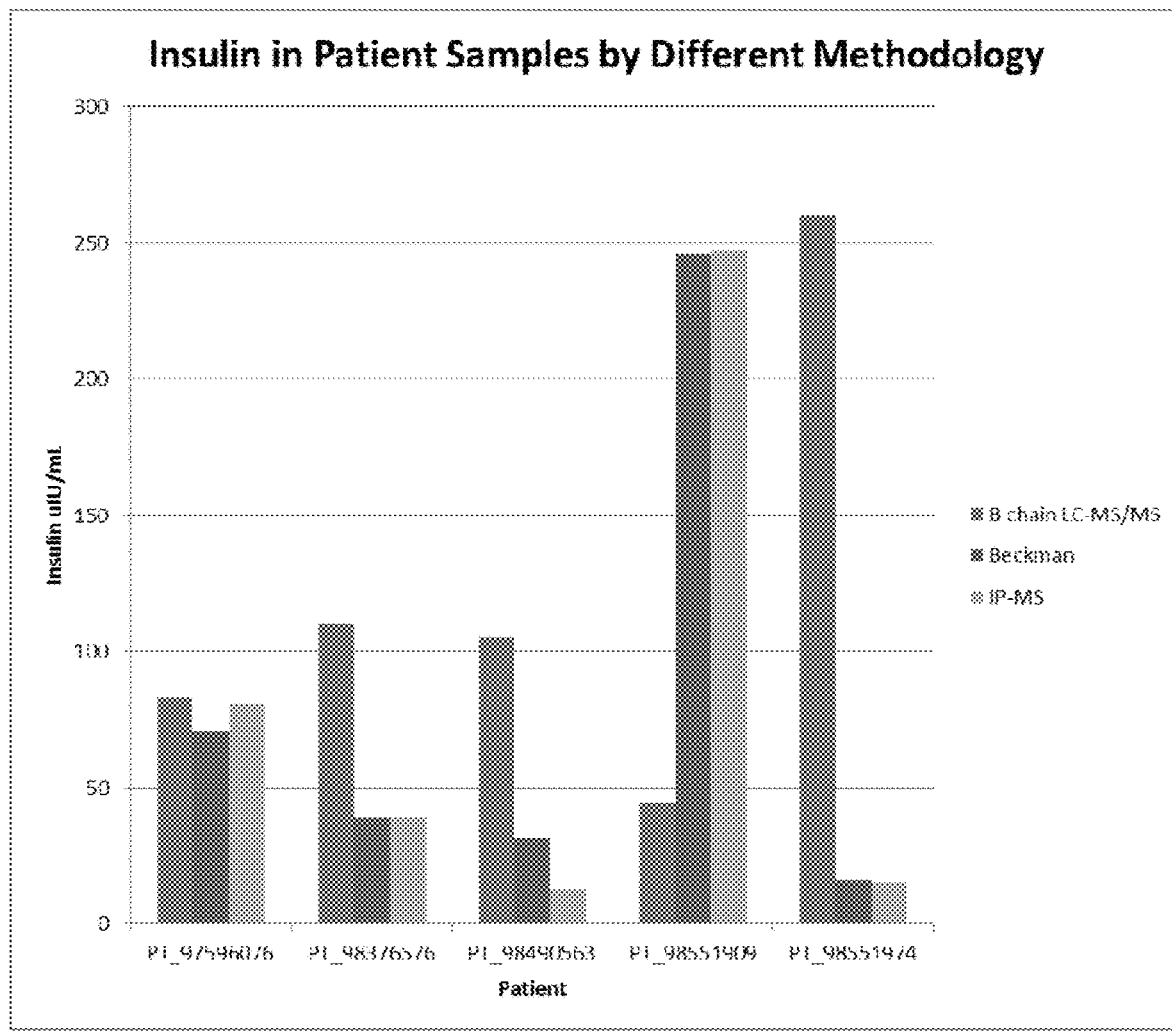
FIG. 48 shows quantitation by three different insulin B chain assays for 5 patient samples, LC-MS/MS (left bars), Beckman immunoassay (middle bars), immunocapture-mass spectrometry (right bars).

A comparison of 5 representative patient samples provided the following results, which are graphically represented in FIG. 48:

TABLE 23

| Patient | B chain LC-MS/MS | Beckman | IP-MS |
|---|---|---|---|
| PT_97596076 | 83 | 70.7 | 81.0 |
| PT_98376576 | 110 | 38.7 | 38.8 |
| PT_98490563 | 105 | 31.4 | 12.5 |
| PT_98551909 | 44 | 245.7 | 246.9 |
| PT_98551974 | 260 | 16.0 | 14.7 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of insulin and insulin B-chain in a sample by mass spectrometry, the method comprising:
    (a) subjecting insulin and insulin B-chain from a sample to an ionization source under conditions suitable to generate one or more insulin ions and one or more insulin B-chain ions detectable by mass spectrometry, wherein said one or more insulin ions comprise an insulin precursor ion having a mass to charge ratio (m/z) of 968.9±0.5 and wherein said one or more insulin B-chain ions comprise an insulin B chain precursor ion selected from the group consisting of ions with a mass to charge ratio (m/z) of 1144.2±0.5, 858.3±0.5, and 686.8±0.5; and
    (b) determining the amount of one or more insulin ions and one or more insulin B-chain ions by mass spectrometry,
    wherein the amount of the ions is used to determine the amount of insulin and insulin B-chain in the sample.

2. The method of claim 1, wherein the amount of insulin and insulin B-chain in the sample is used to determine the ratio of insulin and insulin B-chain.

3. The method of claim 1, wherein said step (b) comprises determining the amount of one or more insulin fragment ions selected from the group consisting of ions with m/z of 136.0±0.5, 226.1±0.5, and 345.2±0.5.

4. The method of claim 1, wherein said insulin B chain is not chemically modified prior to ionization.

5. The method of claim 1, wherein said step (b) comprises determining the amount of one or more fragment ions selected from the group consisting of ions with mass to charge ratios (m/z) of 345.0±0.5 and 226.2±0.5.

6. The method of claim 1, wherein said insulin B chain is chemically modified prior to ionization.

7. The method of claim 1, wherein said chemical modification comprises alkylating said insulin B chains.

8. The method of claim 1, wherein said one or more ions comprise an alkylated insulin B chain precursor ion selected from the group consisting of ions with a mass to charge ratio (m/z) of 1181.9±0.5, 886.9±0.5, and 709.8±0.5.

9. The method of claim 1, wherein said one or more ions comprise one or more fragment ions selected from the group of ions with mass to charge ratios (m/z) of 345.0±0.5 and 226.2±0.5.

10. The method of claim 1, wherein said biological sample comprises a plasma or serum sample.

11. The method of claim 1, wherein said ionization source is an electrospray (ESI) ionization source.

12. The method of claim 1, wherein said sample is subjected to acidic conditions prior to mass spectrometry.

13. The method of claim 12, wherein subjecting said sample to acidic conditions comprises subjecting said sample to formic acid.

14. The method of claim 1, wherein said sample is subjected to basic conditions prior to mass spectrometry.

15. The method of claim 14, wherein subjecting said sample to basic conditions comprises subjecting said sample to trizma and/or ethanol.

16. The method of claim 1, wherein the sample is delipidated prior to quantitation by mass spectrometry.

17. The method of claim 1, further comprising purifying the sample prior to mass spectrometry.

18. The method of claim 17, wherein said purifying comprises subjecting the sample to liquid chromatography.

19. The method of claim 18, wherein liquid chromatography comprises high performance liquid chromatography (HPLC) or high turbulence liquid chromatograph (HTLC).

20. The method of claim 18, wherein said purifying comprises subjecting a sample to solid phase extraction (SPE).

21. The method of claim 1, wherein the mass spectrometry is tandem mass spectrometry, high resolution mass spectrometry, or high resolution/high accuracy mass spectrometry.

22. The method of claim 1, wherein ionization is electrospray ionization (ESI).

23. The method of claim 1, wherein ionization is in positive ion mode.

24. The method of claim 1, wherein internal standards for insulin and insulin B-chain are added to the sample.

25. The method of claim 1, wherein the amount of insulin and insulin B-chain in the sample is used to determine the ratio of insulin to insulin B-chain.

26. A method for determining the amount of insulin and insulin B-chain in a sample by mass spectrometry, the method comprising:
    (a) subjecting a sample to an enrichment process to obtain a fraction enriched in insulin and insulin B-chain;
    (b) subjecting the enriched insulin and insulin B-chain to an ionization source under conditions suitable to generate one or more insulin ions and one or more insulin B-chain ions detectable by mass spectrometry, wherein said one or more insulin ions comprise an insulin precursor ion has a mass to charge ratio (m/z) of 968.9±0.5 and wherein said one or more insulin B-chain ions comprise an insulin B chain precursor ion selected from the group consisting of ions with a mass to charge ratio (m/z) of 1144.2±0.5, 858.3±0.5, and 686.8±0.5; and
    (c) determining the amount of one or more insulin ions and one or more insulin B-chain ions by mass spectrometry.

27. The method of claim 26, wherein the enrichment process comprises immunocapture of insulin and insulin B-chain.

28. The method of claim 27, wherein the immunocapture comprises using anti-insulin antibodies and anti-insulin B-chain antibodies.

29. The method of claim 28, wherein the antibodies are monoclonal antibodies.

30. The method of claim 29, wherein the antibodies IgG.

31. The method of claim 28, wherein the anti-insulin antibodies and anti-insulin B-chain antibodies are immobilized on magnetic beads.

32. The method of claim 27, wherein insulin and insulin B-chain immunocaptured on magnetic beads are washed and eluted.

33. The method of claim 26, wherein said biological sample comprises a plasma or serum sample.

34. The method of claim 26, wherein said ionization source is an electrospray (ESI) ionization source.

35. The method of claim 26, wherein said sample is subjected to acidic conditions prior to mass spectrometry.

36. The method of claim 35, wherein subjecting said sample to acidic conditions comprises subjecting said sample to formic acid.

37. The method of claim 26, wherein said sample is subjected to basic conditions prior to mass spectrometry.

38. The method of claim 37, wherein subjecting said sample to basic conditions comprises subjecting said sample to trizma and/or ethanol.

39. The method of claim 26, wherein the sample is delipidated prior to quantitation by mass spectrometry.

40. The method of claim 26, further comprising purifying the sample prior to mass spectrometry.

41. The method of claim 40, wherein said purifying comprises subjecting the sample to liquid chromatography.

42. The method of claim 41, wherein liquid chromatography comprises high performance liquid chromatography (HPLC) or high turbulence liquid chromatograph (HTLC).

43. The method of claim 40, wherein said purifying comprises subjecting a sample to solid phase extraction (SPE).

44. The method of claim 26, wherein the mass spectrometry is tandem mass spectrometry, high resolution mass spectrometry, or high resolution/high accuracy mass spectrometry.

45. The method of claim 26, wherein ionization is electrospray ionization (ESI).

46. The method of claim 26, wherein ionization is in positive ion mode.

47. The method of claim 26, wherein internal standards for insulin and insulin B-chain are added to the sample.

48. The method of claim 26, wherein the amount of the one or more ions determined is used to determine the amount of insulin and insulin B-chain in the sample.

49. The method of claim 48, wherein the amount of insulin and C-peptide in the sample is used to determine the ratio of insulin to insulin B-chain.

50. A method for diagnosing glycemic disorders or insulin resistant syndromes in diabetic and pre-diabetic patients comprising determining the amount of insulin and insulin B-chain as in claim 26.

* * * * *